United States Patent
Butz et al.

(10) Patent No.: US 10,851,144 B2
(45) Date of Patent: Dec. 1, 2020

(54) INTERLEUKIN-2 MUTEINS FOR THE EXPANSION OF T-REGULATORY CELLS

(71) Applicant: AMGEN INC., Thousand Oaks, CA (US)

(72) Inventors: Eric Alan Butz, Seattle, WA (US); Christy Ann Thomson, Port Moody (CA); Marc Alain Gavin, Seattle, WA (US); Ian Nevin Foltz, Burnaby (CA); Dong Xia, Redmond, WA (US); Dina N. Alcorn, Federal Way, WA (US); Ai Ching Lim, San Carlos, CA (US); Randal Robert Ketchum, Snohomish, WA (US); Kathy Manchulenko, Port Coquitlam (CA); Laura Sekirov, Vancouver (CA); Kelly Ann Berry, Port Coquitlam (CA); Cyr Clovis Chua De Imus, Kenmore, WA (US); Neeraj Jagdish Agrawal, Thousand Oaks, CA (US); Gunasekaran Kannan, Daly City, CA (US); Li Li, Sammamish, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 15/565,376

(22) PCT Filed: May 4, 2016

(86) PCT No.: PCT/US2016/030843
§ 371 (c)(1),
(2) Date: Oct. 9, 2017

(87) PCT Pub. No.: WO2016/164937
PCT Pub. Date: Oct. 13, 2016

(65) Prior Publication Data
US 2020/0024319 A1    Jan. 23, 2020

(51) Int. Cl.
*C07K 14/55* (2006.01)
*A61P 37/00* (2006.01)
*A61K 38/20* (2006.01)
*C07K 16/24* (2006.01)

(52) U.S. Cl.
CPC .......... *C07K 14/55* (2013.01); *A61K 38/2013* (2013.01); *A61P 37/00* (2018.01); *C07K 16/246* (2013.01); *C07K 2317/21* (2013.01); *C07K 2317/41* (2013.01); *C07K 2317/524* (2013.01); *C07K 2317/76* (2013.01); *C07K 2317/92* (2013.01); *C07K 2317/94* (2013.01); *C07K 2319/30* (2013.01)

(58) Field of Classification Search
CPC .................................................... C07K 14/55
See application file for complete search history.

(56) References Cited

U.S. PATENT DOCUMENTS

| | | |
|---|---|---|
| 3,691,016 A | 9/1972 | Patel |
| 3,773,919 A | 11/1973 | Boswell |
| 3,969,287 A | 7/1976 | Jaworek et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,301,144 A | 11/1981 | Iwashita et al. |
| 4,330,440 A | 5/1982 | Ayers et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,496,689 A | 1/1985 | Mitra |
| 4,596,556 A | 6/1986 | Morrow et al. |
| 4,640,835 A | 2/1987 | Shimizu et al. |
| 4,670,417 A | 6/1987 | Iwasaki et al. |
| 4,790,824 A | 12/1988 | Morrow et al. |
| 4,791,192 A | 12/1988 | Nakagawa et al. |
| 4,941,880 A | 7/1990 | Burns |
| 4,968,607 A | 11/1990 | Dower et al. |
| RE33,653 E | 7/1991 | Mark et al. |
| 5,064,413 A | 11/1991 | McKinnon et al. |

(Continued)

FOREIGN PATENT DOCUMENTS

| DE | 10 2008 023820 A1 | 11/2009 |
|---|---|---|
| EP | 0036676 A1 | 9/1981 |

(Continued)

OTHER PUBLICATIONS

Boyman et al., "Selective Stimulation of T Cell Subsets with Antibody-Cytokine Immune Complexes", Science, 311:1924-1927, 2006.
Chaput et al., Identification of CD8+CD25+PoxP3+ Suppressive T Cells in Colorectal Cancer Tissue, Gut (2008), 58(4):520-529.
Collins et al., "Identification of specific residues of human interleukin 2 that affect binding to the 70-kDa subunit (p70) of the interleukin 2 receptor", Proc. Natl. Acad. Sci. USA, 85:7709-7713, 1988.

(Continued)

*Primary Examiner* — Prema M Mertz
(74) *Attorney, Agent, or Firm* — Lawrence B. Kong

(57) ABSTRACT

Provided herein are IL-2 muteins, IL-2 mutein Fc-fusion molecules, anti-IL-2 antibodies, and complexes comprising an anti IL-2 antibody bound to an IL-2 cytokine that preferentially expand and activate T regulatory cells and are amenable to large scale production. Also provided herein are variant human IgG1 Fc molecules lacking or with highly reduced effector function and high stability despite lacking glycosylation at N297. Also provided herein are linker peptides that are glycosylated when expressed in mammalian cells. Also provided herein are methods of making and using the compositions of the present invention.

10 Claims, 110 Drawing Sheets

Specification includes a Sequence Listing.

(56) References Cited

U.S. PATENT DOCUMENTS

| | | | |
|---|---|---|---|
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,677,425 | A | 10/1997 | Bodmer et al. |
| 6,037,525 | A | 3/2000 | Thompson et al. |
| 6,177,612 | B1 | 1/2001 | Jordan et al. |
| 6,239,328 | B1 | 5/2001 | Thompson |
| 6,245,974 | B1 | 6/2001 | Michalowski et al. |
| 6,348,192 | B1 | 2/2002 | Chan et al. |
| 6,388,066 | B1 | 5/2002 | Bruce et al. |
| 6,737,056 | B1 | 5/2004 | Presta |
| 6,927,043 | B2 | 8/2005 | Chan et al. |
| 6,955,807 | B1 | 10/2005 | Shanafelt et al. |
| 7,091,321 | B2 | 8/2006 | Gillies et al. |
| 7,105,653 | B2 | 9/2006 | Shanafelt et al. |
| 7,129,062 | B2 | 10/2006 | Mermod et al. |
| 7,259,010 | B2 | 8/2007 | Kim et al. |
| 7,317,091 | B2 | 1/2008 | Lazar et al. |
| 7,326,567 | B2 | 2/2008 | Saha |
| 7,371,371 | B2 | 5/2008 | Epstein et al. |
| 7,422,874 | B2 | 9/2008 | Kim et al. |
| 7,507,406 | B2 | 3/2009 | Gillies et al. |
| 7,514,073 | B2 | 4/2009 | Epstein et al. |
| 7,569,215 | B2 | 8/2009 | Wittrup et al. |
| 7,695,963 | B2 | 4/2010 | Agulnick et al. |
| 7,790,415 | B2 | 9/2010 | Gillies et al. |
| 7,803,361 | B2 | 9/2010 | Epstein et al. |
| 7,888,071 | B2 | 2/2011 | Gillies et al. |
| 8,124,066 | B2 | 2/2012 | Epstein et al. |
| 8,592,562 | B2 | 11/2013 | Kannan et al. |
| 2006/0269515 | A1 | 11/2006 | Denis-Mize et al. |
| 2007/0161087 | A1 | 7/2007 | Glaesner et al. |
| 2009/0171562 | A1 | 7/2009 | Shimada |
| 2010/0286374 | A1 | 11/2010 | Kannan et al. |
| 2011/0091412 | A1 | 4/2011 | Wittrup et al. |
| 2011/0150826 | A1 | 6/2011 | Paulsen et al. |
| 2011/0274650 | A1 | 11/2011 | Gavin et al. |
| 2013/0011401 | A1 | 1/2013 | Huber et al. |

FOREIGN PATENT DOCUMENTS

| | | |
|---|---|---|
| EP | 0058481 B2 | 8/1982 |
| EP | 0088046 A3 | 7/1983 |
| EP | 0133988 A2 | 3/1985 |
| EP | 0143949 B1 | 6/1985 |
| EP | 0460846 B1 | 11/1991 |
| EP | 506124 A1 | 3/1992 |
| EP | 1252192 B1 | 8/2006 |
| EP | 2288372 B1 | 2/2012 |
| WO | 1987/005330 | 9/1987 |
| WO | 1988/007054 | 9/1988 |
| WO | 1990/000565 A1 | 1/1990 |
| WO | 1993/15722 | 8/1993 |
| WO | 2002/046227 A2 | 6/2002 |
| WO | 2003/086444 A1 | 10/2003 |
| WO | 2004/082681 A1 | 9/2004 |
| WO | 2004/099249 A2 | 11/2004 |
| WO | 2005/000892 A2 | 1/2005 |
| WO | 2005/086751 A2 | 9/2005 |
| WO | 2005/086798 A2 | 9/2005 |
| WO | 2006/034488 A2 | 3/2006 |
| WO | 2006/138181 A2 | 12/2006 |
| WO | 2007/095643 A2 | 8/2007 |
| WO | 2007/100770 A2 | 9/2007 |
| WO | 2008/062158 A2 | 5/2008 |
| WO | 2008/106116 A2 | 9/2008 |
| WO | 2008/112325 A2 | 9/2008 |
| WO | 2009/061853 A2 | 5/2009 |
| WO | 2009/089004 A1 | 7/2009 |
| WO | 2009/135615 A2 | 11/2009 |
| WO | 2010/017220 A1 | 2/2010 |
| WO | 2010/085495 A1 | 7/2010 |
| WO | 2011/063348 A1 | 5/2011 |
| WO | 2011/076781 A1 | 6/2011 |
| WO | 2012/075037 A1 | 6/2012 |
| WO | 2012/123381 A1 | 9/2012 |
| WO | 2012/125850 A1 | 9/2012 |
| WO | 2013/093809 A1 | 6/2013 |
| WO | 2013/119716 A1 | 8/2013 |
| WO | 2013/177062 A2 | 11/2013 |
| WO | 2014/145016 A2 | 9/2014 |
| WO | 2014/153063 A1 | 9/2014 |
| WO | 2014/153111 A2 | 9/2014 |
| WO | 2016/014428 A2 | 1/2016 |
| WO | 2016/025385 A1 | 2/2016 |

OTHER PUBLICATIONS

Fell et al., Genetic construction and characterization of a fusion protein consisting of a chimeric F(ab') with specificity for carcinomas and human IL-2, Apr. 1991, J. Immunol, vol. 146(7); 2446-52.

Finkelman et al., "Anti-Cytokine Antibodies as Carrier Proteins", J. Immunol. 151(3):1235-1244, 1993.

Fujii et al., Activation of Stat5 by interleukin 2 requires a carboxyl-terminal region of the interleukin 2 receptor beta chain but is not essential for the proliferative signal transmission, 1995, PNAS 92:5482-5486.

Gillessen et al., A phase I dose-escalation study of the immunocytokine EMD 521873 (Selectikine) in patients with advanced solid tumours, Jan. 2013, Eur J Cancer, vol. 49(1); 35-44.

Gillies et al. Biological activity and in vivo clearance of antitumor antibody/cytokine fusion proteins, May/Jun. 1993, Bioconjug Chem, vol. 4(3); 230-5.

Gillies et al., A low-toxicity IL-2-based immunocytokine retains antitumor activity despite its high degree of IL-2 receptor selectivity, Jun. 2011, Clin. Cancer Res., vol. 17(11); 3673-85.

Gillies et al., Antibody-targeted interleukin 2 stimulates T-cell killing of autologous tumor cells, Feb. 1992, Proc Natl Acad Sci U.S.A., vol. 89(4); 1428-32.

Gillies et al., Improved circulating half-life and efficacy of an antibody-interleukin 2 immunocytokine based on reduced intracellular proteolysis, Jan. 2002, Clin. Cancer Res, vol. 8(1); 210-6.

Hartmann, Gunther, "Technology evaluation: BAY-50-4798, Bayer", Current Opinion in Molecular Therapeutics, 6(2):221-227 + 684, 2004.

Hoyer et al., Interleukin-2 in the development and control of inflammatory disease, Immunol. Rev. (2008), 226:19-28.

Hristodorov et al., With or Without Sugar? (A)glycosylation of Therapeutic Antibodies, Mol. Biotechnol (2013) 54:1056-1068.

Jung et al., Aglycosylated IgG variants expressed in bacteria that selectively bind FcγRI potentiate tumor cell killing by monocyte-dendritic cells, PNAS (2010), 107:604-609.

Kendra et al., Pharmacokinetics and stability of the ch14.18-interleukin-2 fusion protein in mice, Aug. 1999, Cancer Immunol Immunother, vol. 48(5), 219-29.

King et al., Phase I clinical trial of the immunocytokine EMD 273063 in melanoma patients, Nov. 2004, J. Clin. Oncol., vol. 22(22); 4463-73.

Ko et al., Safety, pharmacokinetics, and biological pharmacodynamics of the immunocytokine EMD 273066 (huKS-IL2): results of a phase I trial in patients with prostate cancer, May/Jun. 2004, J Immunother, vol. 27(3); 233-239.

Koreth et al., "Interleukin-2 and Regulatory T Cells in Graft-versus-Host Disease", The New England Journal of Medicine, 365(22):2055-2066, 2011.

Lan et al., "The regulatory, inflammatory, and T cell programming roles of interleukin-2 (IL-2)," J Autoimmun 31:7-12, 2008.

Laurent et al., T-cell activation by treatment of cancer patients with EMD 521873 (Selectikine), an IL-2/anti-DNA fusion protein, Jan. 2013, vol. 11, 5.

Liston et al., Tracing the action of IL-2 in tolerance to islet-specific antigen, Immunol. & Cell Bio. (2007), 85:4:338-342.

Liu et al., Engineered Interleukin-2 Antagonists for the Inhibition of Regulatory T Cells, J. Immunol. (2009), 32(9):887-894.

Malek, "The biology of interleukin-2," Annu Rev Immunol 26:453-479, 2008.

Margolin et al., Phase I trial of BAY 50-4798, an interleukin-2-specific agonist in advanced melanoma and renal cancer, Jun. 2007, Clin. Cancer Res, vol. 13(11), 3312-9.

(56) References Cited

OTHER PUBLICATIONS

Matthews et al., BAY 50-4798, a novel, high-affinity receptor-specific recombinant interleukin-2 analog, induces dose-dependent increases in CD25 expression and proliferation among unstimulated, human peripheral blood mononuclear cells in vitro, Dec. 2004, Clin. Immunol., vol. 113(3); 248-55.
Nagase et al., Despite increased CD4+Foxp3+ cells within the infection site, BALB/c IL-4 receptor-deficient mice reveal CD4+ Foxp3-negative T cells as a source ofIL-1 0 in Leishmania major susceptibility, 2007, J Immunol, 179:2435-2444.
Passerini et al., STAT5-signaling cytokines regulate the expression of FOXP3 in CD4+CD25+ regulatory T cells and CD4+CD25− effector T cells, Intl. Immunol. (2008), 20:3:421-431.
Rao et al., High-affinity CD25-binding IL-2 mutants potently stimulate persistent T cell growth, 2005, Biochemistry 44:10696-10701.
Sasaoki et al., Deamidation at asparagine-88 in recombinant human interleukin 2,1992, Chem Pharm Bull 40(4):976-980.
Shanafelt et al., A T-cell-selective interleukin 2 mutein exhibits potent antitumor activity and is well tolerated in vivo, Nov. 2000, Nat. Biotechnol., vol. 18(11); 1197-1202.
Siegmund et al., Unique Phenotype of Human Tonsillar and In-Vitro-Induced FOXP3 CD8 T Cells, *J. Immunol.* (2009), 182:2124-2130.
Spangler et al., Insights into Cytokine-Receptor Interactions from Cytokine Engineering, Annual Review of Immunology (2015), 33(1):139-167.
Stauber et al., Crystal Structure of the IL-2 Signaling Complex: Paradigm for Heterotrimeric Cytokine Receptor, Proceedings of the Natl. Acad. of Sci. (2006), 103(8):2788-2793.
Steppan et al., Reduced secondary cytokine induction by BAY 50-4798, a high-affinity receptor-specific interleukin-2 analog, Mar. 2006, J. Interferon Cytokine Res., vol. 26(3); 171-8.
Stork et al., *N-Glycosylation as Novel Strategy to Improve Pharmacokinetic Properties of Bispecific Single-Chain Diabodies*, The Journal of Biological Chemistry (2008), 283:12:7804-7812.
Tang et al., Central role of defective interleukin-2 production in the triggering of islet autoimmune destruction, 2008, Immunity 28:687-697.
Thanos et al., "Hot-Spot mimicry of a cytokine receptor by a small molecule", PNAS, 103(42):15422-15427, 2006.
Wozniak-Knopp et al., Stabilization of the FC fragment of human IgG1 by engineered intradomain disulfide bonds, Jan. 17, 2012, PloS One 7(1): e30083.
Adames et al., The c-myc Oncogene Driven by Immunoglobulin Enhancers Induces Lymphoid Malignancy in Transgenic Mice, Nature (1985), 318:533-538.
Aldrich et al., EASE Vectors for Rapid Stable Expression of Recombinant Antibodies, Biotechnol. Prog. (2003), 19(5):1433-1438.
Alexander et al., Expression of the c-myc Oncogene Under Control of an Immunoglobulin Enhancer in Eμ-myc Transgenic Mice, Mol. Cell. Biol. (1987), 7:1436-1444.
Altschul et al., Basic Local Alignment Search Tool, J. Mol. Biol. (1990), 215:403-410.
Altschul et al., Gapped BLAST and PSI-BLAST: a new generation of protein database search programs, Nucleic Acids Res. (1997), 25(17):3389-3402.
Altschul et al., Local Alignment Statistics, Methods in Enzymology (1996), 266:460-480.
Aplin et al., Preparation, Properties, and Applications of Carbohydrate Conjugates of Proteins and Lipids, CRC Crit. Rev. Biochem. (1981), 10(4):259-306.
Arakawa et al., Protein-Solvent Interactions in Pharmaceutical Formulations, Pharm. Res. (1991), 8(3):285-291.
Banks et al., Integrated Modeling Program, Applied Chemical Theory (IMPACT), J. Comp. Chem. (2005), 26:1752-1780.
Benoist and Chambon, In Vivo Sequence Requirements of the SV40 Early Promotor Region, Nature (1981), 290(5804):304-310.
Bluestone et al., IL-2: Change Structure . . . Change Function, Immunity (2015), 42:779-781.

Cosman et al., Cloning, Sequence and Expression of Human Interleukin-2 Receptor, Nature (1984), 312:768-771.
Creighton et al., Proteins: Structure and Molecular Properties, W.H. Freeman & Co., San Francisco (1983), 70-86.
Deboer et al., The tac Promoter: A Functional Hybrid Derived from the trp and lac Promoters, Proc. Natl. Acad. Sci. USA (1983), 80:21-25.
Devereux et al., A comprehensive set of sequence analysis programs for the VAX, Nucl. Acid Res. (1984), 12(1):387-395.
Du et al., Improved folding yields of a model protein using protein disulfide isomerase, Pharm. Res. (1998), 15:1808-1815.
Duskin et al, Relationship of the Structure and Biological Activity of the Natural Homologues of Tunicamycin*, J. Biol. Chem. (1982) 257(6):3105-3109.
Edge et al., Deglycosylation of Glycoproteins by Trifluoromethanesulfonic Acid, Anal. Biochem. (1981), 118:131-137.
Eppstein et al., Biological Activity of Liposome-Encapsulated Murine Interferon γ is Mediated by a Cell Membrane Receptor, PNAS (1985), 82:3688-3692.
Feng et al., Progressive sequence alignment as a prerequisite to correct phylogenic tress, J. Mol. Evol. (1987), 25(4):351-360.
George et al., Current Methods in Sequence Comparison and Analysis, Macromolecule Sequencing and Synthesis, Selected Methods and Applications (1988), 127-149.
Gluzman et al., SV40-Transformed Simian Cells Support the Replication of Early SV40 Mutants, Cell (1981) 23(1):175-182.
Grosschedel et al., Introduction of a μ Immunoglobulin Gene into the Mouse Germ Line: Specific Expression in Lymphoid Cells and Synthesis of Functional Antibody, Cell (1984), 38(3):647-658.
Hakimuddin et al., A Chemical Method for the Deglycosylation of Proteins, Arch. Biochem. Biophys. (1987), 259(1):52-57.
Hammer et al., Diversity of Alpha-Fetoprotein Gene Expression in Mice is Generated by a Combination of Separate Enhancer Elements, Science (1987), 253:53-58.
Hanahan et al., Heritable Formation of Pancreatic Beta-Cell Tumours in Transgenic Mice Expressing Recombinant Insulin/Simian Virus 40 Oncogenes, Nature (1985), 315:115-122.
Higgins et al., Fast and sensitive multiple sequence alignments on a microcomputer, CABIOS Comm (1989) 5(2):151-153.
Innis et al., PCR Protocols—A Guide to Methods and Applications, Polymerase Chain Reaction (Current Communications in Molecular Biology), Academic Press, Inc. (1990), 6(7):229.
Karlin et al., Applications and Statistics for Multiple High-Scoring Segments in Molecular Sequences, Proc. Natl. Acad. Sci. U.S.A. (1993), 90:5873-5777.
Kelsey et al., Species- and Tissue-Specific Expression of Human Alpha 1-Antitrypsin in Transgenic Mice, Genes and Devel. (1987), 1:161-171.
Kendrick et al., Physical Stabilization of Proteins in Aqueous Solution, Pharmaceutical Biotechnology (2002), 13:61-84.
Kollias et al., Regulated Expression of Human Aγ-, β-, and Hybrid γβ-Globin Genes in Transgenic Mice: Manipulation of the Developmental Expression Patterns, Cell (1986), 46:89-94.
Krumlauf et al., Developmental Regulation of Alpha-Fetoprotein Genes in Transgenic Mice, Mol. Cell. Biol. (1985), 5:1639-1648.
Langer et al., Biocompatibility of Polymeric Delivery Systems for Macromolecules, J. Biomed. Mater. Res. (1981), 15:267-277.
Langer et al., Controlled Release of Macromolecules, Chem. Tech. (1982), 12:98-105.
Leder et al., Consequences of Widespread Deregulation of the c-myc Gene in Transgenic Mice: Multiple Neoplasms and Normal Development, Cell (1986), 45:485-495.
Luckow and Summers, Trends in the Development of Baculovirus Expression Vectors, Bio/Technology (1988), 6(1):47-55.
Macdonald et al., Expression of the Pancreatic Elastase I Gene in Transgenic Mice, Hepatology (1987), 7(1):425-515.
Mason et al., The Hypogonadal Mouse: Reproductive Functions Restored by Gene Therapy, Science (1986), 234:1372-1378.
McMahan et al., A Novel IL-1 Receptor, Cloned from B Cells by Mammalian Expression, is Expressed in Many Cell Types, EMBO J. (1991), 10(10):2821-2832.

(56) References Cited

OTHER PUBLICATIONS

Mogram et al., Developmental Regulation of a Cloned Adult β-Globin Gene in Transgenic Mice, Nature (1985), 315:338-340.
Needleman et al., A General Method Applicable to the Search for Similarities in the Amino Acid Sequence of Two Proteins, J. Mol. Biol. (1970), 48:443-453.
Ornitz et al., Elastase I Promoter Directs Expression of Human Growth Hormone and SV40 T Antigen Genes to Pancreatic Acinar Cells in Transgenic Mice, Cold Spring Harbor Symp. Quant. Biol. (1985), 50:399-409.
Pearson et al., Improved tools for biological sequence comparison, Proc. Nat. Acad. Sci. U.S.A. (1988), 85:2444-2448.
Pinkert et al., An Albumin Enhancer Located 10 kb Upstream Functions along with its Promoter to Direct Efficient, Liver-Specific Expression in Transgenic Mice, Genes and Devel. (1987), 1:268-276.
Prinster et al., Regulation of Metallothionein-Thymidine Kinase Fusion Plasmids Injected into Mouse Eggs, Nature (1982), 296:39-42.
Randolph et al., Surfactant-Protein Interactions, Pharm. Biotehcnol. (2002), 13:159-175.
Rasmussen et al., Isolation, Characterization and Recombinant Protein in Veggie-CHO: A Serum-Free CHO Host Cell Line, Cytotechnology (1998), 28(1-3):31-42.
Readhead et al., Expression of a Myelin Basic Protein Gene in Transgenic Shiverer Mice: Correction of the Dysmyelinating Phenotype, Cell (1987), 48:703-712.
Saiki et al., Primer-Directed Enzymatic Amplification of DNA with a Thermostable DNA Polymerase, Science (1988) 239:487-491.
Sani et al., Tissue-Specific Expression of Rat Myosin Light-Chain 2 Gene in Transgenic Mice, Nature (1985), 314:283-286.
Sehouli et al., Epigenetic quantification of tumor-infiltrating T-lymphocytes, Epigenetics (2011), 6(2):236-246.
Sidman et al., Controlled Release of Macromolecules and Pharmaceuticals from Synthetic Polypeptides Based on Glutamic Acid, Biopolymers (1983), 2:547-556.
Smith et al., Comparison of Biosequences, Adv. Appl. Math. (1981), 2:482-489.
Strohl, Optimization of Fc-mediated effector functions of monoclonal antibodies, Curr. Opin. Biotech. (2009), 20(6):685-691.
Summers and Smith, Texas Agricultural Experiment Station Bulletin No. 1555 (1987).
Swift et al., Tissue-Specific Expression of the Rat Pancreatic Elastase I Gene in Transgenic Mice, Cell (1984), 38:639-646.
Thornsen et al., Promoter-Regulatory Region of the Major Immediate Early Gene of Human Cytomegalovirus, Proc. Natl. Acad. Sci. USA (1984), 81:659-663.
Thotakura et al., Enzymatic Deglycosylation of Glycoproteins, Meth. Enzymol. (1987) 138:350-359.
Villa-Kamaroff et al., A Bacterial Clone Synthesizing Proinsulin, Proc. Natl. Acad. Sci. USA (1978), 75:3727-3731.
Wagner et al., Nucleotide Sequence of the Thymidine Kinase Gene of Herpes Simplex Virus Type 1, Proc. Natl. Acad. Sci. USA (1981), 78:1444-1445.
Wang et al., Structure of the Quaternary Complex of Interleukin-2 with Its α, β, and $\gamma_2$ Receptors, Science (2005), 310(5751):1159-1163.
Yamamoto et al., Identification of a Functional Promoter in the Long Terminal Repeat of Rous Sarcoma Virus, Cell (1980), 22:787-797.
Rojas et al., "Deciphering the Molecular Bases of the Biological Effects of Antibodies Against Interleukin-2: a Versatile Platform for Fine Epitope Mapping", Immunobiology (2013), 218(1):105-113.

FIG. 2A
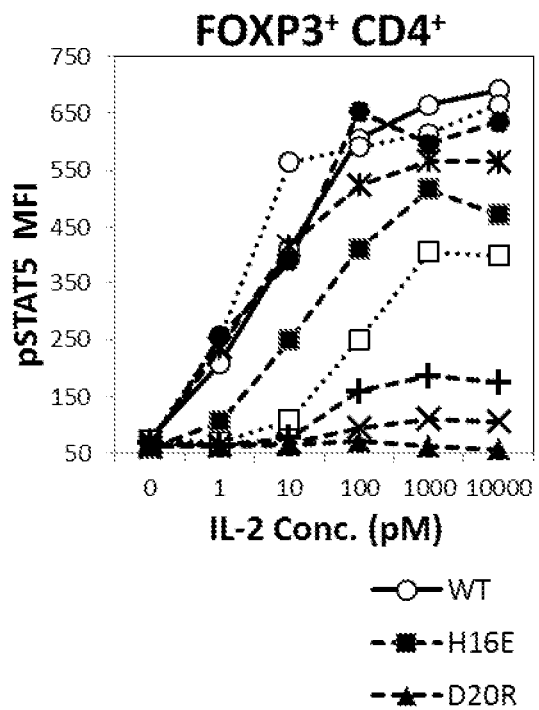
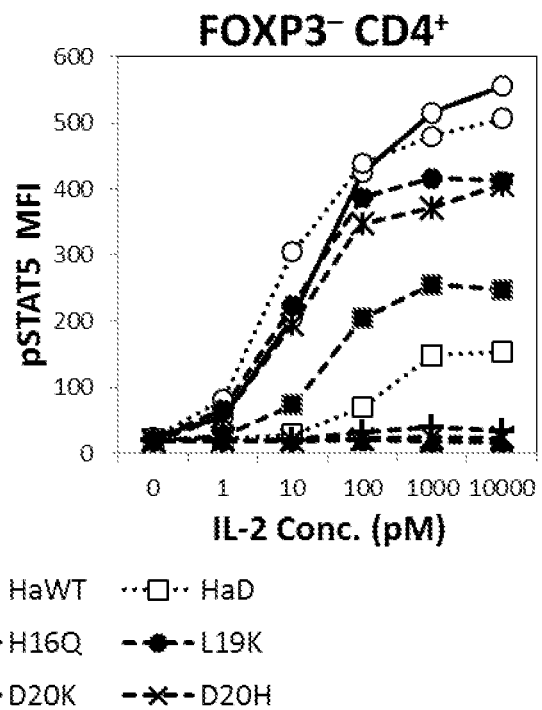
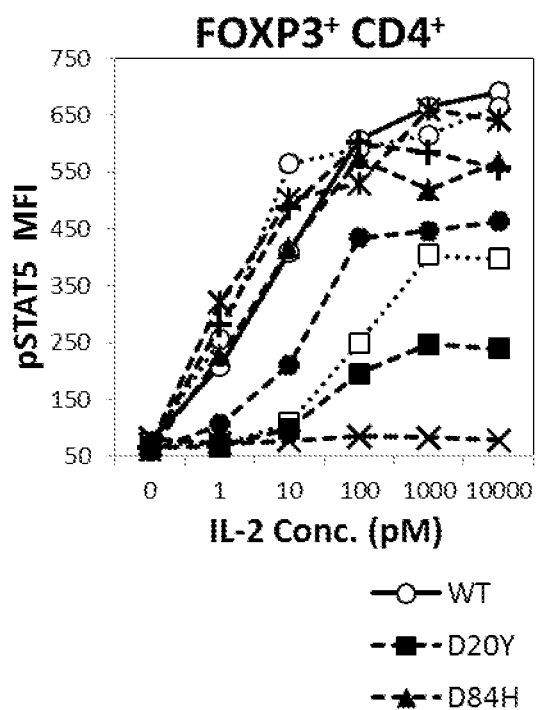
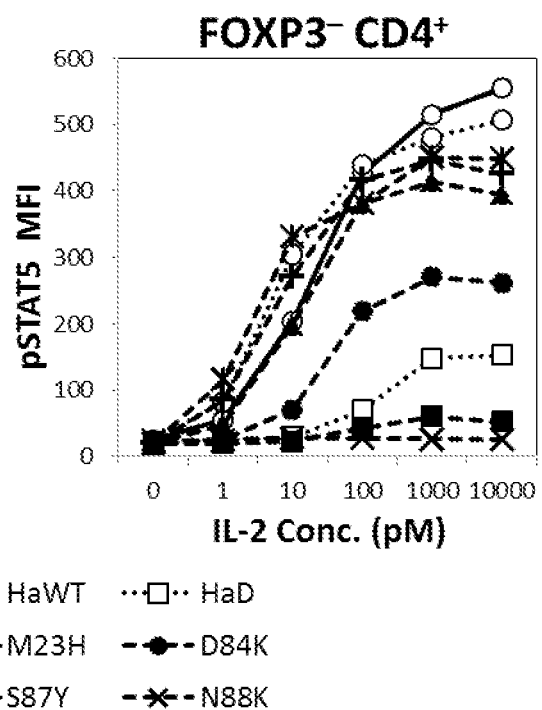

FIG. 2B
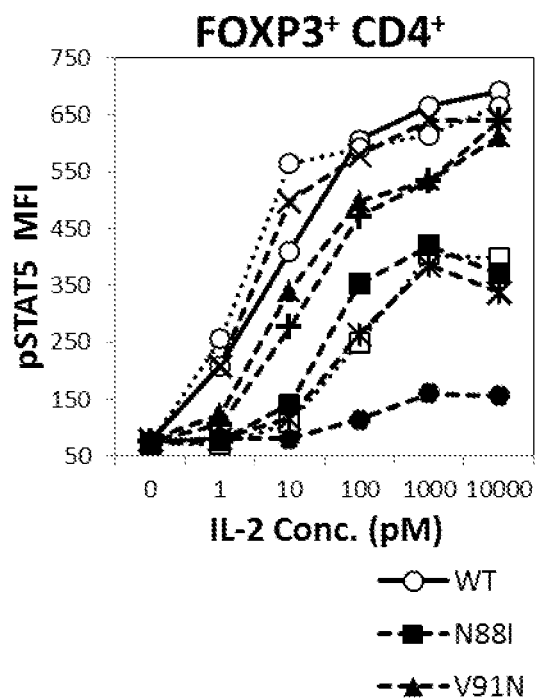
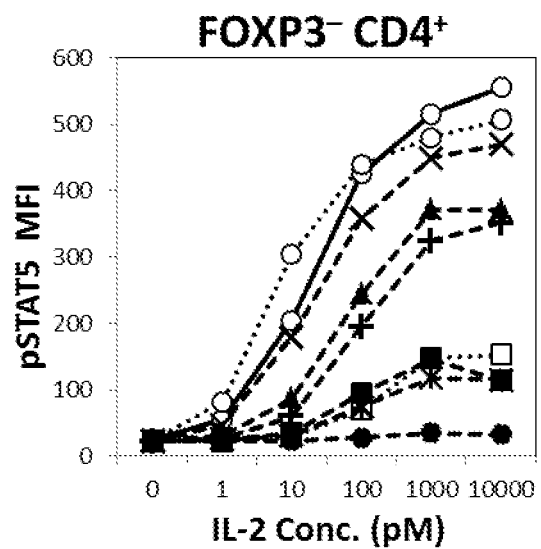
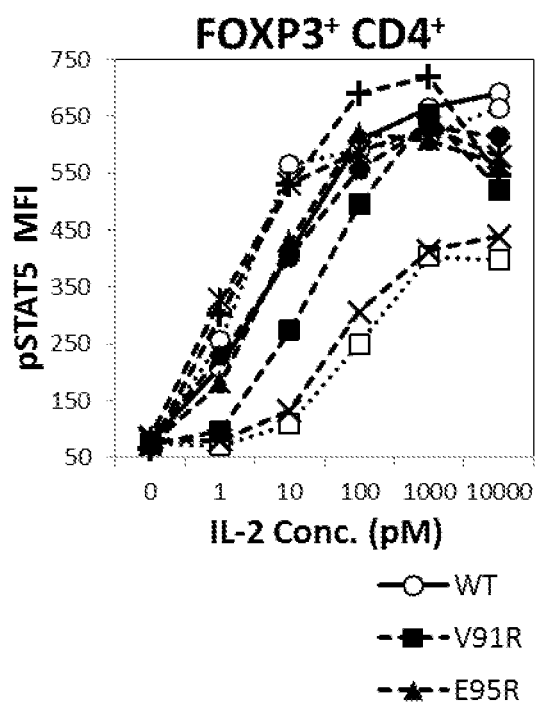
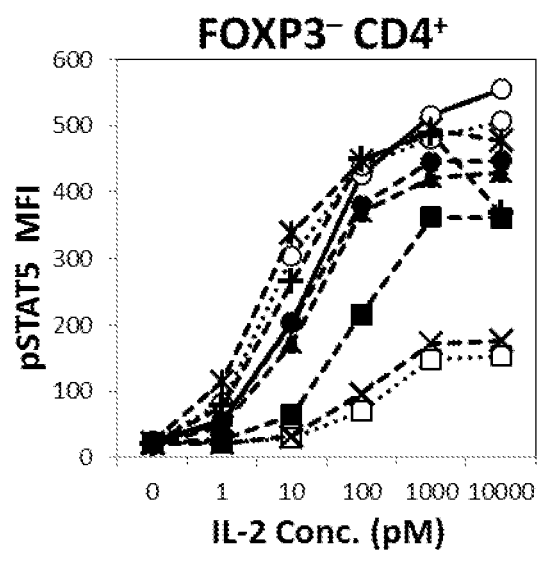

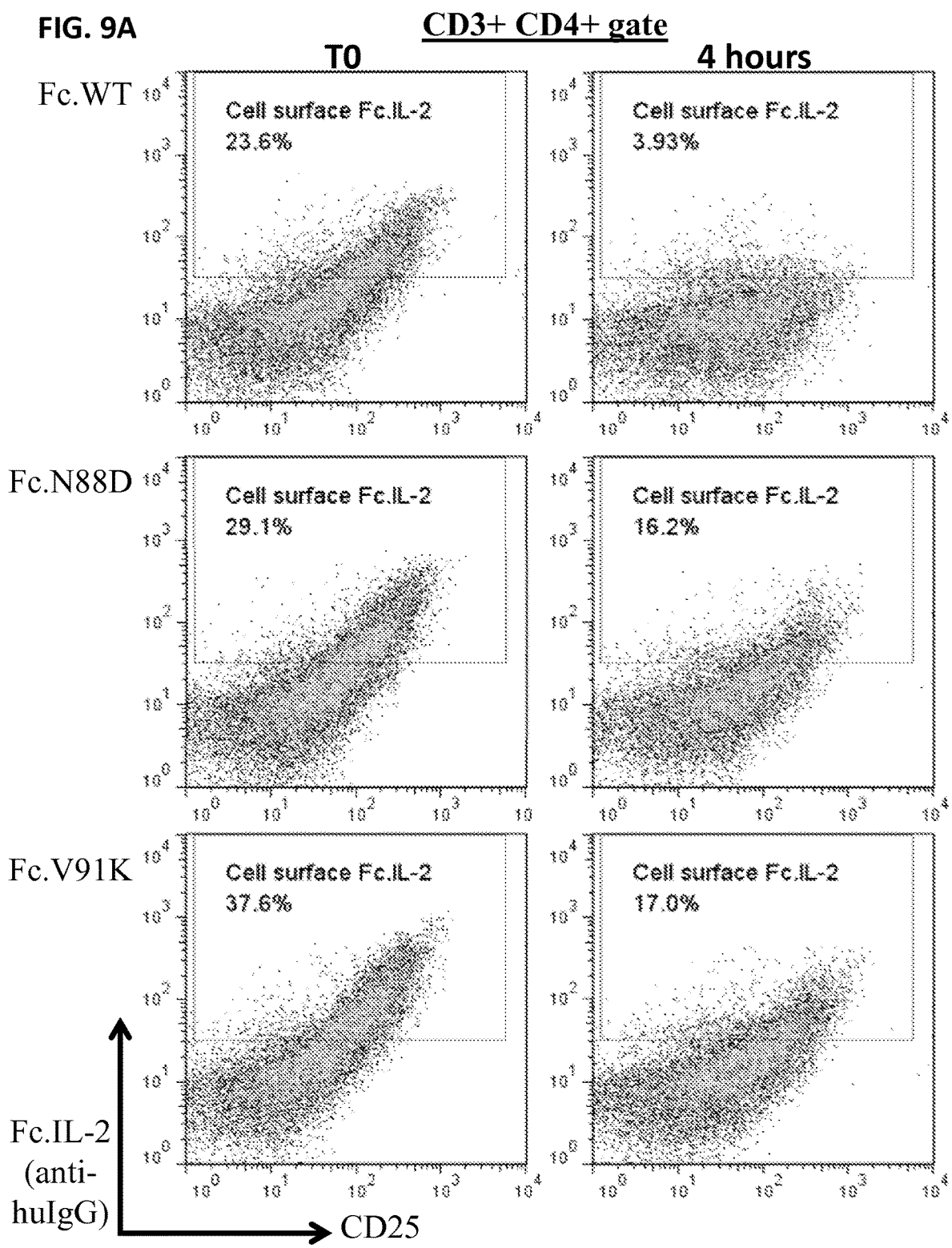

FIG. 14

| | L12 | Q13 | E15 | H16 | L19 | D20 | M23 | R81 | D84 | S87 | N88 | V91 | I92 | L94 | E95 |
|---|---|---|---|---|---|---|---|---|---|---|---|---|---|---|---|
| A | 1.18 | 0.82 | 1.26 | 2.51 | 2.05 | 1.61 | 0.68 | 1.61 | 1.53 | -0.1 | 2.13 | 1.22 | 1.04 | 0.21 | 0.68 |
| D | 0.49 | 0.81 | 0.99 | 2.39 | 1.7 | 0 | 0.41 | 1.19 | 0 | -0.4 | 1.1 | 0.52 | 0.29 | -0.2 | 0.15 |
| E | 0.93 | -0.1 | 0 | 1.01 | 1.58 | 0.49 | 0.01 | 0.93 | 2.4 | -0.4 | 2.15 | 1.89 | 0.75 | -0.9 | -0 |
| F | 0.1 | 0.86 | -0.5 | 0.97 | -0.9 | 1.6 | 0.2 | -0 | 0.98 | -1.5 | 1.3 | -0.6 | 0.18 | -0 | -0.5 |
| G | 1.36 | 1.08 | 1.51 | 3.06 | 2.73 | 1.83 | 0.82 | 1.62 | 2.11 | 0.19 | 2.78 | 1.88 | 1.29 | 0.32 | 1.11 |
| H | -0.1 | -0 | 0.29 | 0.42 | 0.18 | 0.55 | 0.39 | 0.52 | 1.64 | -0.3 | 1.69 | 0.5 | -0.1 | 0.04 | 0.84 |
| I | -0.1 | 0.45 | 0.06 | 0.91 | 0.73 | 0.74 | -0.1 | 1.01 | 1.76 | -0.9 | 0.25 | 0.98 | 0 | -0.6 | 0.48 |
| K | 1.19 | 0.25 | 0.85 | 3.98 | -0.3 | 1.56 | 0.22 | 1.04 | 2.66 | 0.01 | 3.72 | 2.7 | 1.57 | 0.59 | 0.73 |
| L | 0 | 0.33 | -0.1 | 1.47 | 0 | 0.57 | 0.14 | 1.11 | 1.16 | -0.8 | 0.29 | 0.74 | -0.3 | 0 | 0.12 |
| M | 1.09 | -0.1 | 0.41 | 1.86 | 1.2 | 0.96 | 0 | 0.9 | 2.04 | -1 | 2.17 | 1.09 | 0.72 | 0.09 | 0.64 |
| N | 0.26 | 0.66 | 0.68 | 1.59 | 1.31 | 0.16 | 0.26 | 1.38 | 0.66 | -0.5 | 0 | 0.32 | 0.89 | -0.3 | 0.5 |
| P | 0.89 | 0.24 | 1.01 | 2.18 | 0.97 | 0.86 | 0.34 | 1.36 | 1.18 | -0.5 | 0.89 | 0.28 | 0.33 | -0.1 | 0.08 |
| Q | 1.27 | -0 | 0.21 | 0.94 | 0.98 | 0.61 | -0.2 | 1.11 | 2.41 | -0.2 | 1.46 | 0.73 | -0.3 | 0.08 | 0.51 |
| R | 1.04 | -0.2 | 0.48 | 2.69 | 1.17 | 1.33 | 1.19 | 0 | 1.69 | 1.15 | 2.19 | 1.23 | 1.8 | 0.47 | 1.03 |
| S | 1.35 | 0.85 | 1.3 | 2.73 | 2.33 | 1.25 | 0.89 | 1.71 | 2.06 | 0 | 2.19 | 1.54 | 0.8 | 0.24 | 0.68 |
| T | 1.11 | 0.6 | 0.88 | 1.91 | 1.58 | 1.16 | 0.67 | 1.69 | 2.3 | -0.2 | 1.17 | 0.72 | 0.53 | 0.07 | 0.6 |
| V | 0.77 | 0.75 | 0.45 | 1.76 | 1.64 | 1.22 | 0.28 | 1.34 | 0.69 | -0.3 | 2.2 | -0 | 0.54 | -0.1 | 0.31 |
| W | -1.4 | 0.47 | -0.7 | -0.6 | -2.4 | 3.88 | 0.08 | -0.7 | 0.33 | -0 | 2.88 | -0.5 | -0.3 | -0.2 | -0.4 |
| Y | 0.25 | 0.62 | -0.2 | 1.55 | -1.8 | 0.96 | 0.06 | -0.3 | 0.82 | -0.6 | 1.07 | -0.4 | -0.3 | -0 | 0.63 |

FIG. 15

| | L12 | Q13 | E15 | H16 | L19 | D20 | M23 | R81 | D84 | S87 | N88 | V91 | I92 | L94 | E95 |
|---|---|---|---|---|---|---|---|---|---|---|---|---|---|---|---|
| A | 2.9 | 3.4 | 4.8 | 12.1 | 7.0 | 6.0 | 3.5 | 5.4 | 8.1 | 1.4 | 11.7 | 8.4 | 5.6 | -0.3 | 6.5 |
| D | 5.9 | 8.2 | 8.6 | 21.0 | 17.8 | | 5.6 | 6.9 | | -3.4 | 14.4 | 13.5 | 9.8 | 0.1 | 3.6 |
| E | 6.9 | 2.5 | | 13.7 | 12.1 | 19.0 | 4.1 | 4.3 | 1.6 | -0.4 | 20.4 | 4.4 | 8.6 | -1.2 | |
| F | -3.0 | -1.5 | 0.0 | -3.9 | -0.2 | 13.4 | 2.0 | 3.3 | 2.3 | -7.7 | 26.4 | 0.3 | 4.1 | -0.2 | 3.4 |
| G | 3.2 | 4.8 | 6.4 | 15.1 | 9.8 | 6.8 | 3.8 | 5.5 | 9.8 | 2.1 | 13.5 | 12.8 | 7.5 | -0.1 | 8.6 |
| H | 4.4 | 1.1 | -2.2 | | 5.9 | 12.3 | 3.2 | 3.3 | 4.9 | -5.9 | 21.3 | 4.2 | | -0.2 | 2.8 |
| I | 1.2 | 3.9 | 2.2 | 2.9 | 1.9 | 4.6 | 0.9 | 2.5 | 6.0 | -1.8 | 12.7 | 1.2 | | | 4.1 |
| K | | 2.0 | 7.9 | 8.1 | | 25.8 | 1.6 | 3.7 | 14.4 | 4.7 | 24.1 | 9.3 | 12.0 | 1.3 | 8.6 |
| L | -4.2 | -1.1 | -3.5 | 3.1 | -1.7 | 5.1 | 1.4 | 2.2 | 2.8 | -2.3 | 1.9 | 0.5 | -3.0 | 0.0 | 3.4 |
| M | -1.5 | -0.6 | -4.7 | -4.0 | -3.2 | 4.0 | | -2.2 | 7.0 | -6.0 | -0.9 | -4.6 | -1.9 | -0.3 | -2.4 |
| N | -1.0 | 2.8 | 6.4 | 7.7 | 5.9 | -0.4 | 2.3 | 5.3 | 4.7 | -1.9 | | 4.2 | -7.4 | -0.2 | 6.9 |
| P | 2.4 | 2.6 | 3.9 | 7.1 | 7.0 | 7.5 | 3.1 | 4.7 | 6.9 | 0.2 | 13.1 | 4.0 | -1.8 | 0.1 | 5.9 |
| Q | 1.9 | 0.2 | -2.2 | 1.1 | 4.4 | 3.1 | 0.5 | 0.8 | 8.7 | -2.7 | 3.0 | -0.5 | 2.1 | 1.3 | 1.4 |
| R | -14.9 | 2.2 | -0.8 | 6.6 | -7.4 | 16.6 | 3.4 | | 10.9 | 3.4 | 5.4 | 4.0 | -5.7 | -0.3 | 4.7 |
| S | 2.1 | 0.3 | 4.5 | 10.6 | 6.1 | 2.4 | 3.2 | 5.6 | 6.2 | 0.1 | 9.0 | 6.7 | -4.5 | -0.2 | 6.5 |
| T | 0.9 | 0.1 | 2.3 | 5.1 | 7.3 | 5.0 | 2.3 | 4.6 | 4.9 | 0.4 | 8.2 | 4.3 | 5.2 | 0.1 | 4.2 |
| V | 1.3 | -2.1 | 2.1 | 7.8 | 3.9 | 4.2 | 2.0 | 4.8 | 5.9 | -13.1 | 5.6 | | 3.9 | -0.3 | 5.7 |
| W | -0.5 | -1.9 | -7.8 | 8.9 | 3.6 | 39.6 | 2.9 | 3.6 | -0.5 | | 36.8 | -0.9 | 1.4 | -4.7 | -1.2 |
| Y | -6.0 | | 1.0 | -3.2 | 4.9 | 37.4 | 1.7 | 2.0 | 4.4 | -13.2 | 27.0 | -0.6 | 2.9 | -0.2 | 3.7 |

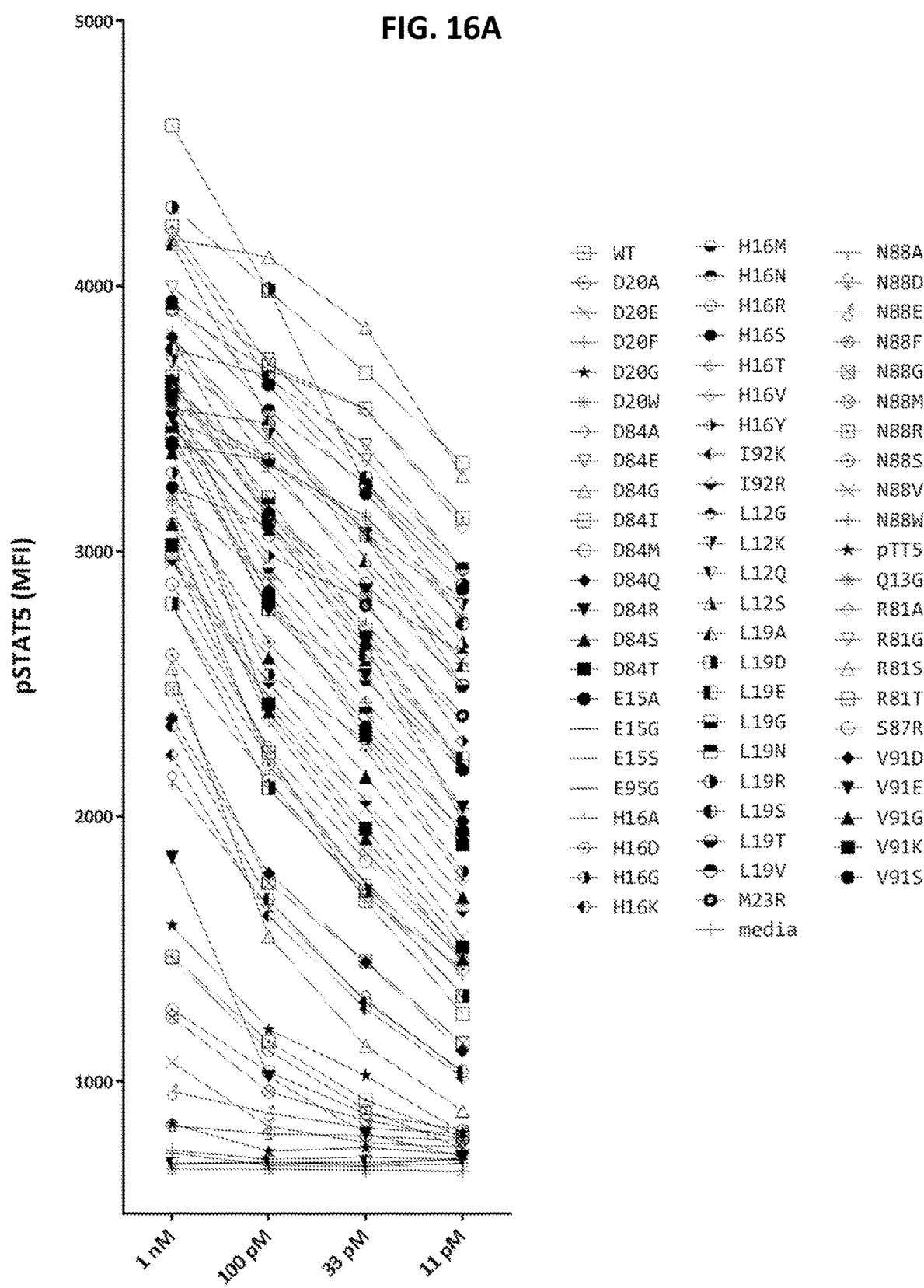

FIG. 16B
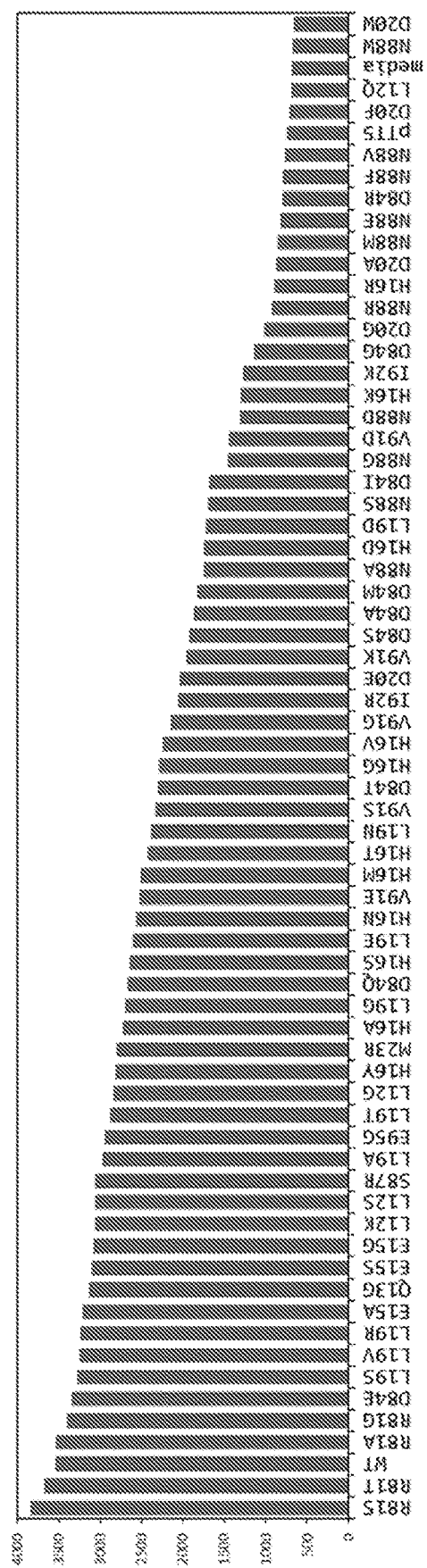
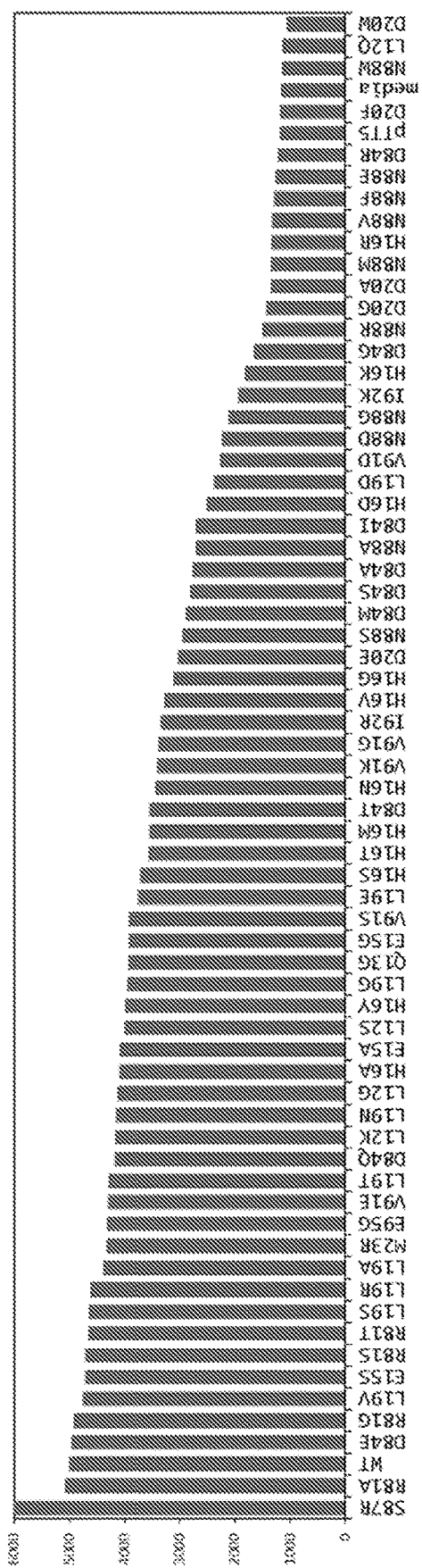

FIG. 18A FOXP3⁻ CD4⁺ proliferation
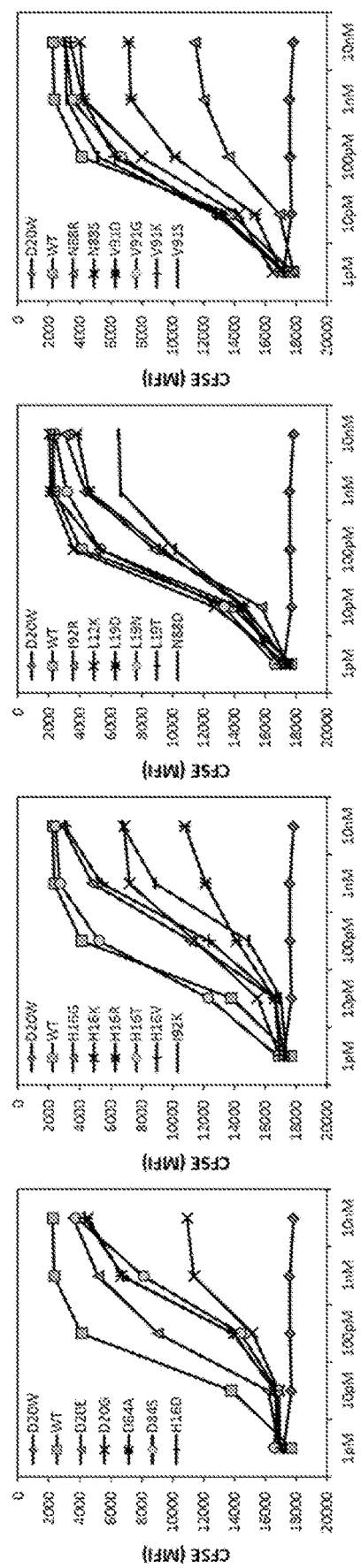
FIG. 18B FOXP3⁻ CD8⁺ proliferation
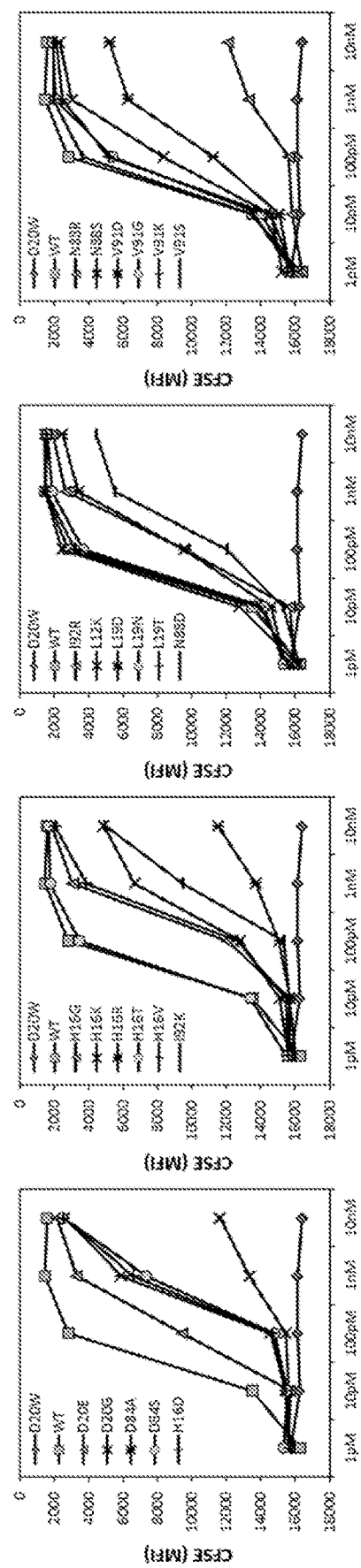

FIG. 18C FOXP3+ HELIOS+ CD4+ proliferation
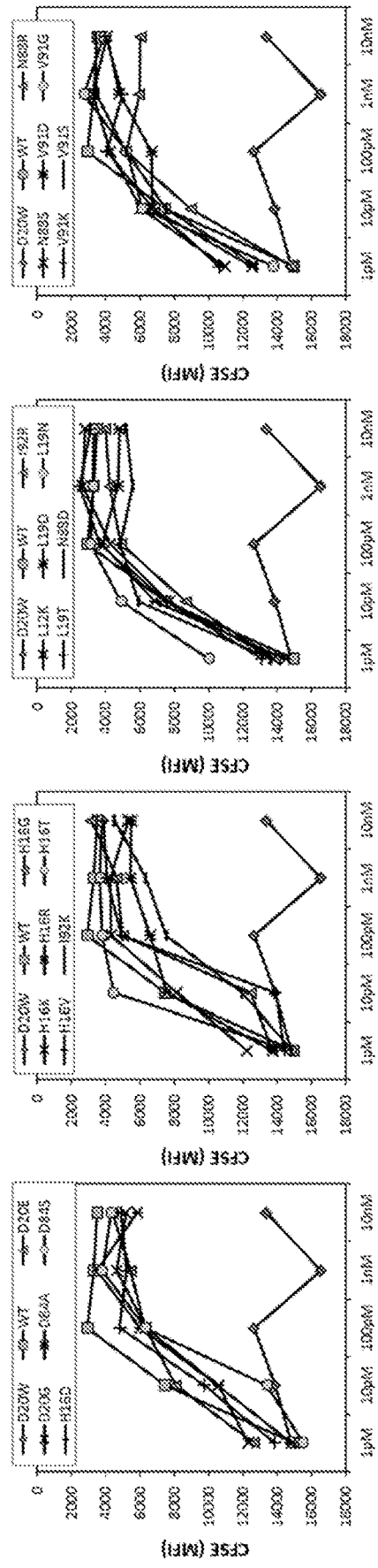
FIG. 18D FOXP3 MFI in FOXP3+ HELIOS+ CD4+
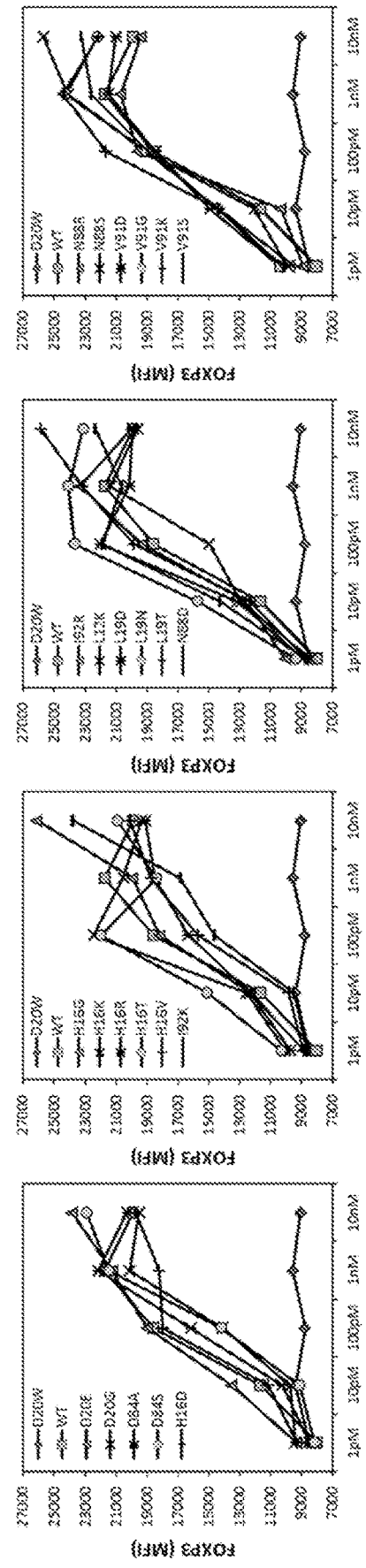

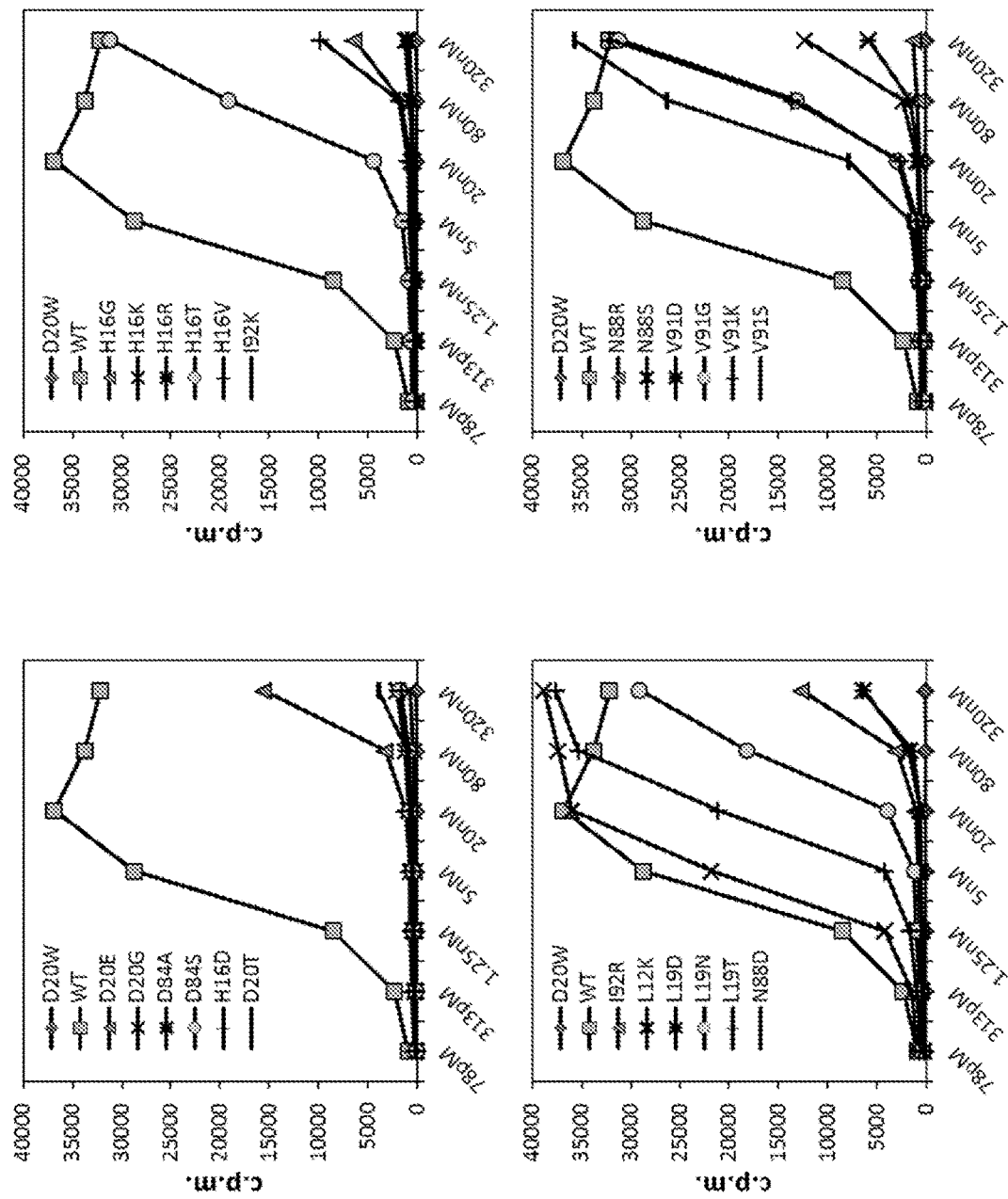
FIG. 19 NK proliferation

FIG. 21
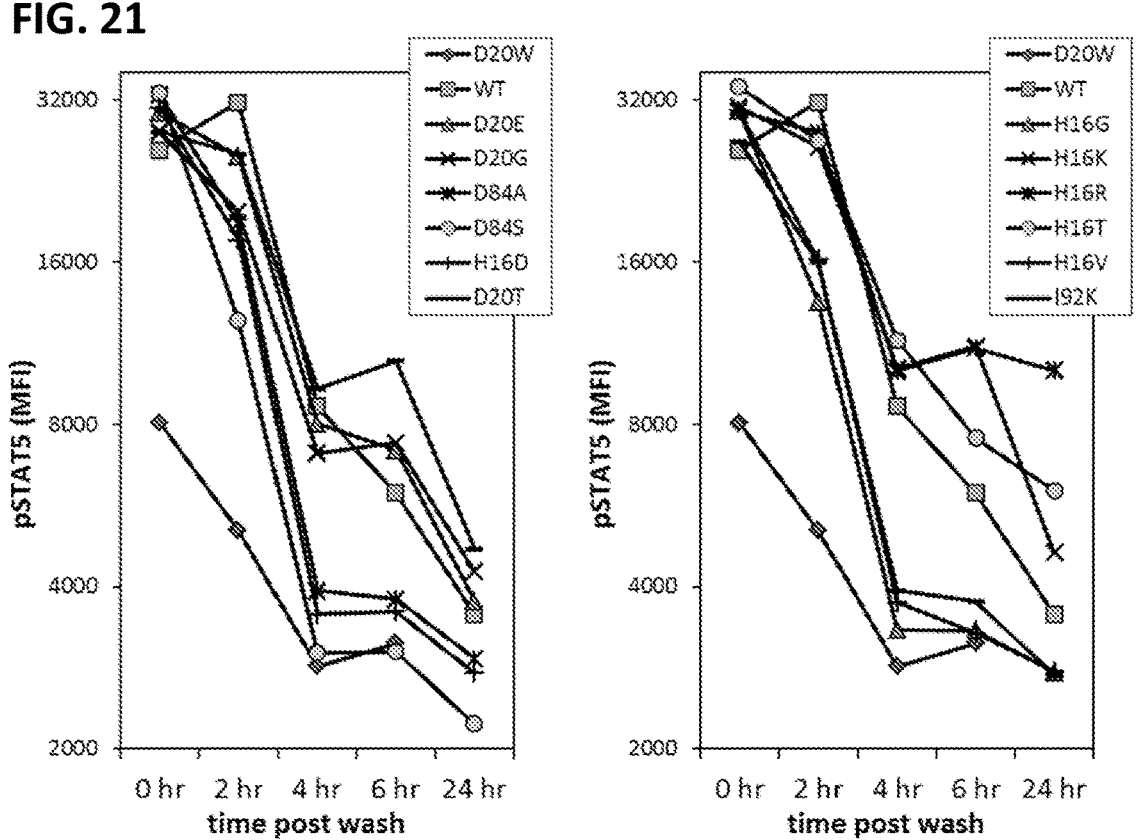
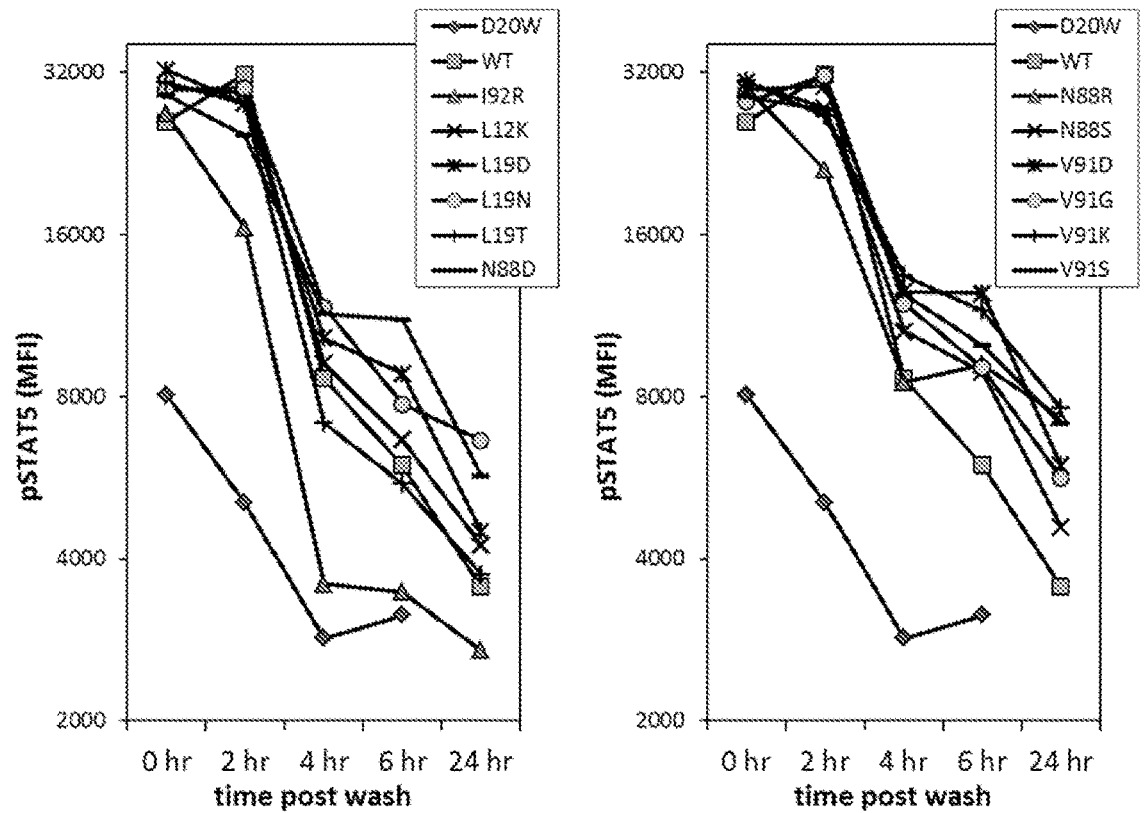

FIG. 24A Fc(N297G_delK)::G4S::IL-2(L12G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQGQLEHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L12K, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQKQLEHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L12Q, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQQQLEHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L12S, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQSQLEHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24B

IgG1Fc(N297G_delK)::G4S::huIL-2(Q13G, C125A)

MDMRVPAQLLGLLLLWLRGARC *DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG*<u>GG
GGS</u>APTSSSTKKTQLGLEHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(E15A, C125A)

MDMRVPAQLLGLLLLWLRGARC*DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG* <u>GG
GGS</u>APTSSSTKKTQLQLAHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(E15G, C125A)

MDMRVPAQLLGLLLLWLRGARC*DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG*<u>GG
GGS</u>APTSSSTKKTQLQLGHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(E15S, C125A)

MDMRVPAQLLGLLLLWLRGARC*DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG*<u>GG
GGS</u>APTSSSTKKTQLQLSHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24C

IgG1Fc(N297G_delK)::G4S::huIL-2(H16A, C125A)

MDMRVPAQLLGLLLLWLRGARC *DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG*GG
GGSAPTSSSTKKTQLQLEALLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16D, C125A)

MDMRVPAQLLGLLLLWLRGARC*DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG* GG
GGSAPTSSSTKKTQLQLEDLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16G, C125A)

MDMRVPAQLLGLLLLWLRGARC*DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG*GG
GGSAPTSSSTKKTQLQLEGLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16K, C125A)

MDMRVPAQLLGLLLLWLRGARC*DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG*GG
GGSAPTSSSTKKTQLQLEKLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24D IgG1Fc(N297G_delK)::G4S::huIL-2(H16M, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEMLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16N, C125A)

MDMRVPAQLLGLLLLWLRGARC DKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLENLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16R, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLERLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16S, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLESLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24E IgG1Fc(N297G_delK)::G4S::huIL-2(H16T, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLETLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16V, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEVLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(H16Y, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEYLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L19A, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLADLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24F  IgG1Fc(N297G_delK)::G4S::huIL-2(L19D, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLDDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L19E, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLEDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L19G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLGDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L19N, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLNDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24G

IgG1Fc(N297G_delK)::G4S::huIL-2(L19R, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLRDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L19S, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLSDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L19T, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLTDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(L19V, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLVDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24H IgG1Fc(N297G_delK)::G4S::huIL-2(D20A, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLALQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(D20E, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLELQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(D20F, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLFLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(D20G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLGLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

FIG. 24I  IgG1Fc(N297G_delK)::G4S::huIL-2(D20W, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLWLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(M23R, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQRILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFAQSIISTLT

IgG1Fc(N297G_delK)::G4S::huIL-2(R81A, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLAPRDLISNINVIVLELK
GSETTFMCEYADETATIVEFLNRWITFAQSIISTLT

IgG1Fc(N297G_delK)::G4S::huIL-2(R81G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLGPRDLISNINVIVLELK
GSETTFMCEYADETATIVEFLNRWITFAQSIISTLT

FIG. 24J  IgG1Fc(N297G_delK)::G4S::huIL-2(R81S, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLSPRDLISNINVIVLELK
GSETTFMCEYADETATIVEFLNRWITFAQSIISTLT

IgG1Fc(N297G_delK)::G4S::huIL-2(R81T, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLTPRDLISNINVIVLELK
GSETTFMCEYADETATIVEFLNRWITFAQSIISTLT

IgG1Fc(N297G_delK)::G4S::huIL-2(D84A, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG <u>GG
GGS</u>APTSSSTKKTQLQLEHLLLDLQMILNGINNYKNPKLTRMLTFKFYMP
KKATELKHLQCLEEELKPLEEVLNLAQSKNFHLRPRALISNINVIVLELK
GSETTFMCEYADETATIVEFLNRWITFAQSIISTLT

IgG1Fc(N297G_delK)::G4S::huIL-2(D84E, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRELISNINVIVLELK
GSETTFMCEYADETATIVEFLNRWITFAQSIISTLT

FIG. 24K IgG1Fc(N297G_delK)::G4S::huIL-2(D84G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRGLISNINVIVLELK
GSETTFMCEYADETATIVEFLNRWITFAQSIISTLT

IgG1Fc(N297G_delK)::G4S::huIL-2(D84I, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRILISNINVIVLELK
GSETTFMCEYADETATIVEFLNRWITFAQSIISTLT

IgG1Fc(N297G_delK)::G4S::huIL-2(D84M, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRMLISNINVIVLELK
GSETTFMCEYADETATIVEFLNRWITFAQSIISTLT

IgG1Fc(N297G_delK)::G4S::huIL-2(D84Q, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRQLISNINVIVLELK
GSETTFMCEYADETATIVEFLNRWITFAQSIISTLT

FIG. 24L IgG1Fc(N297G_delK)::G4S::huIL-2(D84R, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRRLISNINVIVLELK
GSETTFMCEYADETATIVEFLNRWITFAQSIISTLT

IgG1Fc(N297G_delK)::G4S::huIL-2(D84S, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRSLISNINVIVLELK
GSETTFMCEYADETATIVEFLNRWITFAQSIISTLT

IgG1Fc(N297G_delK)::G4S::huIL-2(D84T, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRTLISNINVIVLELK
GSETTFMCEYADETATIVEFLNRWITFAQSIISTLT

IgG1Fc(N297G_delK)::G4S::huIL-2(S87R, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLIRNINVIVLELK
GSETTFMCEYADETATIVEFLNRWITFAQSIISTLT

FIG. 24M IgG1Fc(N297G_delK)::G4S::huIL-2(N88A, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISAINVIVLELK
GSETTFMCEYADETATIVEFLNRWITFAQSIISTLT

IgG1Fc(N297G_delK)::G4S::huIL-2(N88E, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISEINVIVLELK
GSETTFMCEYADETATIVEFLNRWITFAQSIISTLT

IgG1Fc(N297G_delK)::G4S::huIL-2(N88F, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISFINVIVLELK
GSETTFMCEYADETATIVEFLNRWITFAQSIISTLT

IgG1Fc(N297G_delK)::G4S::huIL-2(N88G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISGINVIVLELK
GSETTFMCEYADETATIVEFLNRWITFAQSIISTLT

FIG. 24N  IgG1Fc(N297G_delK)::G4S::huIL-2(N88M, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISMINVIVLELK
GSETTFMCEYADETATIVEFLNRWITFAQSIISTLT

IgG1Fc(N297G_delK)::G4S::huIL-2(N88S, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISSINVIVLELK
GSETTFMCEYADETATIVEFLNRWITFAQSIISTLT

IgG1Fc(N297G_delK)::G4S::huIL-2(N88V, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISVINVIVLELK
GSETTFMCEYADETATIVEFLNRWITFAQSIISTLT

IgG1Fc(N297G_delK)::G4S::huIL-2(N88W, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG
GGS</u>APTSSSTKKTQLQLEHLLLDLQMILNGINNYKNPKLTRMLTFKFYMP
KKATELKHLQCLEEELKPLEEVLNLAQSKNFHLRPRDLISWINVIVLELK
GSETTFMCEYADETATIVEFLNRWITFAQSIISTLT

FIG. 24O

IgG1Fc(N297G_delK)::G4S::huIL-2(V91D, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLDLQMILNGINNYKNPKLTRMLTFKFYMP
KKATELKHLQCLEEELKPLEEVLNLAQSKNFHLRPRDLISNINDIVLELK
GSETTFMCEYADETATIVEFLNRWITFAQSIISTLT

IgG1Fc(N297G_delK)::G4S::huIL-2(V91E, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLDLQMILNGINNYKNPKLTRMLTFKFYMP
KKATELKHLQCLEEELKPLEEVLNLAQSKNFHLRPRDLISNINEIVLELK
GSETTFMCEYADETATIVEFLNRWITFAQSIISTLT

IgG1Fc(N297G_delK)::G4S::huIL-2(V91G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLDLQMILNGINNYKNPKLTRMLTFKFYMP
KKATELKHLQCLEEELKPLEEVLNLAQSKNFHLRPRDLISNINGIVLELK
GSETTFMCEYADETATIVEFLNRWITFAQSIISTLT

IgG1Fc(N297G_delK)::G4S::huIL-2(V91S, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLDLQMILNGINNYKNPKLTRMLTFKFYMP
KKATELKHLQCLEEELKPLEEVLNLAQSKNFHLRPRDLISNINSIVLELK
GSETTFMCEYADETATIVEFLNRWITFAQSIISTLT

FIG. 24P  IgG1Fc(N297G_delK)::G4S::huIL-2(I92K, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLDLQMILNGINNYKNPKLTRMLTFKFYMP
KKATELKHLQCLEEELKPLEEVLNLAQSKNFHLRPRDLISNINVKVLELK
GSETTFMCEYADETATIVEFLNRWITFAQSIISTLT

IgG1Fc(N297G_delK)::G4S::huIL-2(I92R, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLDLQMILNGINNYKNPKLTRMLTFKFYMP
KKATELKHLQCLEEELKPLEEVLNLAQSKNFHLRPRDLISNINVRVLELK
GSETTFMCEYADETATIVEFLNRWITFAQSIISTLT

IgG1Fc(N297G_delK)::G4S::huIL-2(E95G, C125A)

MDMRVPAQLLGLLLLWLRGARCDKTHTCPPCPAPELLGGPSVFLFPPKPK
DTLMISRTPEVTCVVVDVSHEDPEVKFNWYVDGVEVHNAKTKPREEQYGS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG<u>GG</u>
<u>GGS</u>APTSSSTKKTQLQLEHLLLDLQMILNGINNYKNPKLTRMLTFKFYMP
KKATELKHLQCLEEELKPLEEVLNLAQSKNFHLRPRDLISNINVIVLGLK
GSETTFMCEYADETATIVEFLNRWITFAQSIISTLT

FIG. 25A

Fc(N297G_delK)::G4S::IL-2(L12G, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttcccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagcccteccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaaGGGcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(L12K, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttcccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagcccteccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaaAAGcaatt

FIG. 25B ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttttatgtgtgagtacgctgacgagactgctactat
cgttgagttttttgaatcggtggatcacttttgctcaatccatcatctcca
ctttgact IgG1Fc(N297G_delK)::G4S::huIL-2(L12Q, C125A)

atggacatgagagtgcctgcacagctgctgggcctgctgctgctgtggct
gagaggcgccagatgcgacaaaactcacacatgcccaccgtgcccagcac
ctgaactcctgggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaaCAGcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttttatgtgtgagtacgctgacgagactgctactat
cgttgagttttttgaatcggtggatcacttttgctcaatccatcatctcca
ctttgact IgG1Fc(N297G_delK)::G4S::huIL-2(L12S, C125A)

atggacatgagagtgcctgcacagctgctgggcctgctgctgctgtggct
gagaggcgccagatgcgacaaaactcacacatgcccaccgtgcccagcac
ctgaactcctgggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc

FIG. 25C acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaaTCGcaatt
ggagcacttgttgttggacttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact

IgG1Fc(N297G_delK)::G4S::huIL-2(Q13G, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgGGAtt
ggagcacttgttgttggacttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact

FIG. 25D

IgG1Fc(N297G_delK)::G4S::huIL-2(E15A, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
gGCGcacttgttgttggacttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactacttttatgtgtgagtacgctgacgagactgctactat
cgttgagttttgaatcggtggatcacttttgctcaatccatcatctcca
ctttgact IgG1Fc(N297G_delK)::G4S::huIL-2(E15G, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
gGGGcacttgttgttggacttgcaaatgatcttgaatggtatcaataatt

FIG. 25E

```
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(E15S, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
gTCGcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(H16A, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
```

FIG. 25F tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagGCCttgttgttggacttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(H16D, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagGACttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact

FIG. 25G

IgG1Fc(N297G_delK)::G4S::huIL-2(H16G, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagGGCttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(H16K, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagAAGttgttgttggacttgcaaatgatcttgaatggtatcaataatt

FIG. 25H

```
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactacttttatgtgtgagtacgctgacgagactgctactat
cgttgagttttgaatcggtggatcacttttgctcaatccatcatctcca
ctttgact
```

IgG1Fc(N297G_delK)::G4S::huIL-2(H16M, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagATGttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactacttttatgtgtgagtacgctgacgagactgctactat
cgttgagttttgaatcggtggatcacttttgctcaatccatcatctcca
ctttgact
```

IgG1Fc(N297G_delK)::G4S::huIL-2(H16N, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
```

FIG. 25I tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagAACttgttgttggacttgcaaatgatcttgaatggtatcataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(H16R, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagCGCttgttgttggacttgcaaatgatcttgaatggtatcataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact

FIG. 25J

IgG1Fc(N297G_delK)::G4S::huIL-2(H16S, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagAGCttgttgttggacttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(H16T, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagACCttgttgttggacttgcaaatgatcttgaatggtatcaataatt

FIG. 25K acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(H16V, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagcccca
tcgagaaaaccatctccaaagccaaagggcagccccgagaaccacaggtg
tacaccctgccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagGTCttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(H16Y, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa

FIG. 25L

```
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagTACttgttgttggacttgcaaatgatcttgaatggtatcaataatt
acaagaatccaaagttgactcggatgttgactttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(L19A, C125A)

```
atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgGCGgacttgcaaatgatcttgaatggtatcaataatt
acaagaatccaaagttgactcggatgttgactttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

FIG. 25M

IgG1Fc(N297G_delK)::G4S::huIL-2(L19D, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgGATgacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(L19E, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgGAGacttgcaaatgatcttgaatggtatcaataatt

FIG. 25N acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactacttttatgtgtgagtacgctgacgagactgctactat
cgttgagttttgaatcggtggatcacttttgctcaatccatcatctcca
ctttgact IgG1Fc(N297G_delK)::G4S::huIL-2(L19G, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgGGGgacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactacttttatgtgtgagtacgctgacgagactgctactat
cgttgagttttgaatcggtggatcacttttgctcaatccatcatctcca
ctttgact IgG1Fc(N297G_delK)::G4S::huIL-2(L19N, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa

FIG. 25O tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgAATgacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(L19R, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgCGGgacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact

FIG. 25P

IgG1Fc(N297G_delK)::G4S::huIL-2(L19S, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgTCGgacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(L19T, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgACGgacttgcaaatgatcttgaatggtatcaataatt

FIG. 25Q

```
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttttatgtgtgagtacgctgacgagactgctactat
cgttgagttttgaatcggtggatcacttttgctcaatccatcatctcca
ctttgact
```

IgG1Fc(N297G_delK)::G4S::huIL-2(L19V, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgGTGgacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttttatgtgtgagtacgctgacgagactgctactat
cgttgagttttgaatcggtggatcacttttgctcaatccatcatctcca
ctttgact
```

IgG1Fc(N297G_delK)::G4S::huIL-2(D20A, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
```

FIG. 25R

```
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttgGCCttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(D20E, C125A)

```
atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttgGAGttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

FIG. 25S

IgG1Fc(N297G_delK)::G4S::huIL-2(D20F, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagcccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttgTTCttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D20G, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagcccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttgGGCttgcaaatgatcttgaatggtatcaataatt

FIG. 25T acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D20W, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttgTGGttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(M23R, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa

FIG. 25U

```
tggcaaggagtacaagtgcaaggtctccaacaaagccctcccagccccca
tcgagaaaaccatctccaaagccaagggcagccccgagaaccacaggtg
tacaccctgccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaAGGatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(R81A, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgG
CGccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact
```

FIG. 25V

IgG1Fc(N297G_delK)::G4S::huIL-2(R81G, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgG
GGccacgggacttgatctccaatatcaatgtgatcgttttggagttgaag
ggttccgagactacttttatgtgtgagtacgctgacgagactgctactat
cgttgagttttgaatcggtggatcacttttgctcaatccatcatctcca
ctttgact IgG1Fc(N297G_delK)::G4S::huIL-2(R81S, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt

FIG. 25W acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgT
CGccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(R81T, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgA
CGccacgggacttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D84A, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa

FIG. 25X tggcaaggagtacaagtgcaaggtctccaacaaagccctcccagcccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggGCCttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D84E, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagcccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggGAGttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact

FIG. 25Y

IgG1Fc(N297G_delK)::G4S::huIL-2(D84G, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggGGCttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D84I, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt

FIG. 25Z acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggATCttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D84M, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggATGttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D84Q, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggggaggagcagtacggcagc
acgtaccgtgtggtcagcgtcctcaccgtcctgcaccaggactggctgaa

FIG. 25AA tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggCAGttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D84R, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggCGCttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact

FIG. 25BB

IgG1Fc(N297G_delK)::G4S::huIL-2(D84S, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggAGCttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(D84T, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt

FIG. 25CC acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacggACCttgatctccaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(S87R, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatcCGCaatatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(N88A, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa

FIG. 25DD

```
tggcaaggagtacaagtgcaaggtctccaacaaagccctcccagccccca
tcgagaaaaccatctccaaagccaagggcagccccgagaaccacaggtg
tacaccctgccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccGCTatcaatgtgatcgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(N88E, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccGAGatcaatgtgatcgttttggagttgaag
ggttccgagactactttatgtgtgagtacgctgacgagactgctactat
cgttgagttttgaatcggtggatcacttttgctcaatccatcatctcca
ctttgact
```

FIG. 25EE

IgG1Fc(N297G_delK)::G4S::huIL-2(N88F, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccTTTatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(N88G, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt

FIG. 25FF acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccGGTatcaatgtgatcgttttggagttgaag
ggttccgagactacttttatgtgtgagtacgctgacgagactgctactat
cgttgagttttgaatcggtggatcacttttgctcaatccatcatctcca
ctttgact IgG1Fc(N297G_delK)::G4S::huIL-2(N88M, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccATGatcaatgtgatcgttttggagttgaag
ggttccgagactacttttatgtgtgagtacgctgacgagactgctactat
cgttgagttttgaatcggtggatcacttttgctcaatccatcatctcca
ctttgact IgG1Fc(N297G_delK)::G4S::huIL-2(N88S, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggaggagcagtacggcagc
acgtaccgtgtggtcagcgtcctcaccgtcctgcaccaggactggctgaa

FIG. 25GG tggcaaggagtacaagtgcaaggtctccaacaaagccctcccagcccca
tcgagaaaaccatctccaaagccaaagggcagccccgagaaccacaggtg
tacaccctgccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccAGTatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(N88V, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagcccca
tcgagaaaaccatctccaaagccaaagggcagccccgagaaccacaggtg
tacaccctgccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccGTTatcaatgtgatcgttttggagttgaag
ggttccgagactactttatgtgtgagtacgctgacgagactgctactat
cgttgagttttgaatcggtggatcacttttgctcaatccatcatctcca
ctttgact

FIG. 25HH

IgG1Fc(N297G_delK)::G4S::huIL-2(N88W, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccTGGatcaatgtgatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(V91D, C125A)

atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt

FIG. 25II ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatGATatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(V91E, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgagctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatGAGatcgttttggagttgaag
ggttccgagactactttatgtgtgagtacgctgacgagactgctactat
cgttgagttttgaatcggtggatcacttttgctcaatccatcatctcca
ctttgact IgG1Fc(N297G_delK)::G4S::huIL-2(V91G, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg

FIG. 25JJ

```
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatGGGatcgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(V91S, C125A)

```
atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatTCGatcgttttggagttgaag
ggttccgagactactttatgtgtgagtacgctgacgagactgctactat
```

FIG. 25KK cgttgagttttttgaatcggtggatcacttttgctcaatccatcatctcca
ctttgact

IgG1Fc(N297G_delK)::G4S::huIL-2(I92K, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
agaaggctactgagttgaagcacttgcaatgtttggaggaggagttgaa
gccattggaggaggttttgaatttggctcaatccaagaattttcacttgc
ggccacgggacttgatctccaatatcaatgtgAAGgttttggagttgaag
ggttccgagactactttatgtgtgagtacgctgacgagactgctactat
cgttgagttttttgaatcggtggatcacttttgctcaatccatcatctcca
ctttgact IgG1Fc(N297G_delK)::G4S::huIL-2(I92R, C125A)

atggacatgagagtgcctgcacagctgctgggcctgctgctgctgtggct
gagaggcgccagatgcgacaaaactcacacatgcccaccgtgcccagcac
ctgaactcctggggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcgggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg

FIG. 25LL

```
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgAGAgttttggagttgaag
ggttccgagactactttatgtgtgagtacgctgacgagactgctactat
cgttgagttttgaatcggtggatcacttttgctcaatccatcatctcca
ctttgact
```

IgG1Fc(N297G_delK)::G4S::huIL-2(E95G, C125A)

```
atggacatgagagtgcctgcacagctgctgggcctgctgctgctgtggct
gagaggcgccagatgcgacaaaactcacacatgcccaccgtgcccagcac
ctgaactcctgggggaccgtcagtcttcctcttccccccaaaacccaag
gacaccctcatgatctcccggacccctgaggtcacatgcgtggtggtgga
cgtgagccacgaagaccctgaggtcaagttcaactggtacgtggacggcg
tggaggtgcataatgccaagacaaagccgcggaggagcagtacggcagc
acgtaccgtgtggtcagcgtcctcaccgtcctgcaccaggactggctgaa
tggcaaggagtacaagtgcaaggtctccaacaaagccctcccagccccca
tcgagaaaaccatctccaaagccaagggcagccccgagaaccacaggtg
tacaccctgcccccatcccgggaggagatgaccaagaaccaggtcagcct
gacctgcctggtcaaaggcttctatcccagcgacatcgccgtggagtggg
agagcaatgggcagccggagaacaactacaagaccacgcctcccgtgctg
gactccgacggctccttcttcctctatagcaagctcaccgtggacaagag
caggtggcagcaggggaacgtcttctcatgctccgtgatgcatgaggctc
tgcacaaccactacacgcagaagagcctctccctgtctccgggtggaggt
ggtggaagcgctccaacttcctcctccactaagaagactcaattgcaatt
ggagcacttgttgttggacttgcaaatgatcttgaatggtatcaataatt
acaagaatccaaagttgactcggatgttgacttttaagttttacatgcca
aagaaggctactgagttgaagcacttgcaatgtttggaggaggagttgaa
gccattggaggaggttttgaatttggctcaatccaagaattttcacttgc
ggccacgggacttgatctccaatatcaatgtgatcgttttgGGGttgaag
ggttccgagactactttatgtgtgagtacgctgacgagactgctactat
cgttgagttttgaatcggtggatcacttttgctcaatccatcatctcca
ctttgact
```

FIG. 26  Light Chain Variable Domain Amino Acid Sequences

FIG. 27A

Light Chain Nucleic Acid Sequences

9D6

GATATTGTGATGACCCAGACTCCACTCTCCTTGCCCGTCACCCCTGGAGAGCCGGCCTCCATCTCCTGCAGGTCTAG
TCAGAGCCTCTTAGATAGTGATGAGGGAAACACCTATTTGGACTGGTACCTGCAGAAGCCAGGGCAGTCTCCACA
GCTCCTGATCTATACGCTTTCCTATCGGGCCTCTGGAGTCCCAGACAGGTTCAGTGGCACTGGGTCAGACACTGAT
TTCACACTGAAAATCAGCAGGGTGGAGGCTGAGGATGTTGGAGTTTATTACTGCATGCAACGTATAGAGTTTCCTC
TCACTTTCGGCGGAGGGACCAAGGTGGAGATCAAACGA

2C3

GAAATTGTATTGACGCAGTCTCCAGGCACCCTGTCTTTGTCTCCAGGGGAAAGAGCCACCCTCTCCTGCAGGGCCA
GTCAGAGTTTTAGCAGCAGCTACTTAGTCTGGTACCAGCAGAAACCTGGCCAGGCTCCCAGGCTCCTCATCTATGG
TGCATCCAGCAGGGCCACTGGCATCCCAGACAGGTTCGGTGGCAGTGGGTCTGGGACAGACTTCACTCTCACCAT
CAGCAGACTGGAGCCTGAAGATTTTGCAGTGTATTACTGTCAGCAGTATGGTAGCTCACCTCTCACTTTCGGCGGA
GGGACCAAGGTGGAGATCAAACGA

14C9

GATATTGTGCTGACCCAGACTCCACTCTCCTCACCTGTCACCCTTGGACAGCCGGCCTCCATCTCCTGCAGGTCTAG
TCATCACCTCATACACAGTGATGGAAACACCTACTTGAGTTGGCTTCAGCAGAGGCCAGGCCAGCCTCCAAGACTC
CTAATTTATAAGATTTCTAACCGGTTCTCTGGGGTCCCAGACAGATTCACTGGCAGTGGGACAGGGACAGATTTCA
CACTGAAAATCAGCAGGGTGGAAGCTGGGGATGTCGGGGTTTATTACTGCATGCAAACTACACAATTTCCGACGT
TCGGCCAAGGGACCAAGGTGGAAATCAAACGA

8B12

GATATTGTGATGACCCAGACTCCACTCTCCTCACCTGTCACCCTTGGACAGCCGGCCTCCATCTCCTGCAGGTCCAG
TCAAAACCTCGTTCAAAGTGATGGAAACACCTACTTGAGTTGGCTTCACCAGAGGCCAGGCCAGCCTCCAAGACTC
CTAATTTATAAGATTTCTAACCGGTTCTCTGGGGTCCCAGACAGATTCAGTGGCAGTGGGGCAGGGACAGATTTCA
CACTGAAAATCAGCAGGGTGGAAGCTGAGGATGTCGGGGTTTATTTCTGCATGCAAACTACACAATTTCCGACGTT
CGGCCAAGGGACCAAGGTGGAAATCAAACGA

GATATTGTGATGACCCAGACTCCACTCTCCTCACCTGTCACCCTTGGACAGCCGGCCTCCATTTCCTGCAGGTCTAG
TCAAATCCTCGTAAACAGTGATGGAAACACCTACTTGAGTTGGCTTCACCAGAGGCCAGGCCAGCCTCCAAGACTC
CTAATTTATAAGATTTCTAACCGGTTCTCTGGGGTCCCAGACAGATTCAGTGGCAGTGGGGCAGGGACAGATTTCA
CACTGAAAATCAGCAGGGTGGAAGCTGAGGATGTCGGGGTTTATTACTGCATGCAAACTACACAATTTCCGACGT
TCGGCCAAGGGACCAAGGTGGAAATCAAACGA

16E1

GATATTGTGATGACCCAGACTCCACTCTCCTCACCTGTCACCCTTGGACAGCCGGCCTCCATCTCCTGCAGGTCTAG
TCAAAGCCTCGTACGCAGTGATGGAAACACCTACTTGAGTTGGCTTCACCAGAGGCCAGGCCAGCCTCCAAGACT
CCTAATTTATAAGATTTCTAACCGGTTCTCTGGGGTCCCAGACAGATTCAGTGGCAGTGGGGCAGGGACAGATTTC
ACACTGAAAATCAGCAGGGTGGAAGCTGAGGATGTCGGGGTTTATTACTGCATGCAAACTACACAATTTCCGACG
TTCGGCCAAGGGACCAAGGTGGAAATCAAACGA

13A1

GATATTGTGATGACCCAGACTCCACTCTCCTCACCTGTCACCCTTGGACAGCCGGCCTCCATCTCCTGCAGGTCTAG
TCACAGCCTCGTACACAGTGATGGACACACCTACTTGAGTTGGCTTCAGCAGAGGCCAGGCCAGCCTCCAAGACTC
CTACTTTATAAGATTTCTAACCGGTTCTCTGGGGTCCCAGACAGATTCAGTGGCAGTGGGGCAGGGACAGATTTCA
CACTGAAAATCAGCAGGGTGGAAGCTGAGGATGTCGGGGTTTATTACTGCATGCAAACTACACAATTTCCCACTTT
CGGCGGAGGGACCAAGGTGGAGATCAAACGA

8F10

GATATTGCGATGAGTCAGTCTCCACTCTCCCTGCCCGTCACCCCTGGAGAGCCGGCCTCCATGTCATGCAGGTCTA
GTCAGAGCCTCCTGCATAGTAATGGATTCAACTATTTGGATTGGTACCTGCAGAAGCCAGGGCAGTCTCCACAGGT
CCTGATCCATTTGGGTTCTGATCGGGCCTCCGGGGTCCCTGACAGGTTCAGTGGCAGTGGATCAGGCACAGATTTT
ACATTGAAAATCAGCAGAGTGGAGGCTGAGGATGTTGGAATTTATTACTGCATGCAAGCTCTACAAACTCCTCTCA
CTTTCGGCGGAGGGACCAAGGTGGAGATCAAACGA

GATATTGTGATGACTCAGTCTCCACTCTCCCTGCCCGTCACCCCTGGAGAGCCGGCCTCCATCTCCTGCAGGTCTAG
TCAGAGCCTCCTACATAGTAATGGATTCAACTATTTGGATTGGTTCCTGCAGAAGCCAGGACAGTCTCCACAGCCC
CTGATCTATTTGGGTTCTGATCGGGCCTCCGGGGTCCCTGACAGGTTCAGTGGCAGTGGATCAGGCACAGATTTTA
CACTGAAAATCAGCAGAGTGGAGGCTGAGGATGTTGGGGTTTATTACTGCATGCAAGCTCTACAAACTCCGCTCA
CTTTCGGCGGAGGGACCAAGGTGGAGATCAAACGA

9B12

GATATTGTGATGACTCAGTCTCCACTCTCCCTGCCCGTCACCCCTGGAGAGCCGGCCTCCATCTCCTGCAGGTCTAG
TCAGAGCCTCCTGCATAGTAATGGATTCAACTATTTGGATTGGTACCTGCAGAAGCCAGGGCAGTCTCCACAGCTC
CTGATCTATTTGGGTTCTGATCGGGCCTCCGGGGTCCCTGACAGGTTCAGTGGCAGTGGATCAGGCACAGATTTTA
CACTGAAAATCAGCAGAGTGGAGGCTGAGGATGTTGGGGTTTATTACTGCATGCAAGCTCTACAAACTCCGCTCA
CTTTCGGCGGAGGGACCAAGGTGGAGATCAAACGA

3H5

GATATTGTGATGACCCAGACTCCACTCTCCTCACCTGTCACCCTTGGACAGCCGGCCTCCATATCCTGCAGGTCCAG
TCAAAGCCTCGTAAACATTGATGGAAGTACCCACTTGAGTTGGCTTCAGCAGAGGCCAGGCCAGCCTCCAAGACT
CCTAATTTATAAGATTTCTAACCGGTTCTCTGGGGTCCCAGACAGATTCAGTGGCAGTGGGGCAGGGACAGATTTC
ACACTGAAGATCAGCAGGGTGGAAGCTGAGGATGTCGGGGTTTATTACTGCATGCAAACTACACAATTCCCCACC
TTCGGCCAAGGGACACGACTGGAGATTAAACGA

18A6

GAAATTGTGATGACCCAGACTCCACTCTCCTCACCTGTCACCCTTGGACAGCCGGCCTCCATTTCCTGCAGGTCTAG
TCAAAGCCTCGTTCAGAGTGATGGAATCACCTACTTGAGTTGGCTTCAGCAGAGGCCAGGCCAGCCTCCAAGACTC
CTAATTTATAAGATTTCTAACCGGTTCTCTGGGGTCCCAGACAGATTCAGTGGCAGTGGGGCAGGGACAGATTTCA
CACTGAAAATCAGCAGGGTGGAAGCTGAGGATGTCGGGGTTTATTACTGCATGCAAACTACACAATTTCCGACGT
TCGGCCAAGGGACCAAGGTGGAAATCAAACGA

GATATTGTGATGACCCAGACTCCACTCTCCTCACCTGTCACCCTTGGACAGCCGGCCTCCATCTCCTGCAGGTCTAG
TCAAAGCCTCGTAAACAGTGATGGAAACACCTACTTGAATTGGCTTCAGCAGAGGCCAGGCCAGCCTCCAAGACT
CCTAATTTATAAGATTTCTAACCGGTTCTCTGGGGTCCCAGACAGATTCAGTGGCAGTGGGGCAGGGACAGATTTC
ACACTGAAAATCAGCAGGGTGGAAGCTGAGGATGTCGGGGTTTATTACTGCATGCAAGCTACACAATTTCCGACG
TTCGGCCAAGGGACCAAGGTGGAAATCAAACGA

10H7

GATATTGTGATGACCCAGACTCCACTCTCCTCACCTGTCACCCTTGGACAGCCGGCCTCCATCTCCTGCAGGTCCAG
TCACAACCTCGTACGCAGTGATGGAAACACCTACTTGAGTTGGCTTCAGCAGAGGCCAGGCCAGCCTCCAAGACT
CCTAATTTATAAGATTTCTAACCGGTTCTCTGGGGTCCCAGACAGATTCAGTGGCAGTGGGGCAGGGACAGATTTC
ACACTGAAAATCAGCAGGGTGGGAGCTGAGGATGTCGGGGTTTATTACTGCATGCAAGCTACACAATTTCCCACC
TTCGGCCAAGGGACGCGACTGGAGATTAAACGA

15A10

AATATTGTGATGACCCAGACTCCACTCTCCTCACCTGTCACCCTTGGACAGCCGGCCTCCATCTCCTGCAGGTCTAG
TCAAAGCCTCGTACAAACTGATGGAAACACATATTTGAGTTGGCTTCAGCAGAGGCCAGGCCAGCCTCCAAGACC
CCTAATTTATAAGATTTCTAACCGGTTTTCTGGGGTCCCAGACAGATTCAGTGGCAGTGGGGCAGGGACAGATTTC
ACACTGAAAATCAGCAGGGTGGAAGCTGAGGATGTCGGGGTTTATTACTGCATGCAAGTAACACAATTTCCCACC
TTCGGCCAAGGGACACGACTGGAGATTAAACGA

12D2

GATATTGTGATGACCCAGACTCCACTCTCCTCACCTGTCACCCTTGGACAGCCGGCCTCCATCTCCTGTAGGTCTAG
TCATAACCTCATACACAGTGATGGAAACACCTACTTGAGTTGGCTTCACCAGAGGCCAGGCCAGCCTCCAAGACTC
CTAATTTATAAGATTTCTAACCGGTTCTCTGGGGTCCCGGACAGATTCAGTGGCAGTGGGGCAGGGACAGATTTCA
CACTGAAAATCAGCAGGGTGGAAGCTGAGGATGTCGGGGTTTATTACTGCATGCAAACTTCACAGTTTCCCACTTT
CGGCGGAGGGACCAAGGTGGAGATCAAACGA

GATATTGTGATGACCCAGACTCCACTCTCCTCACCTGTCACCCTTGGACAGCCGGCCTCCATCTCCTGCAGGTCTAG
TCATAACCTCCTACACAGTGATGGAAACACCTACTTGAGTTGGCTTCAGCAGAGGCCAGGCCAGCCTCCAAGACTC
CTAATTTATGAGATTTCTAACCGGTTCTCTGGGGTCCCAGACAGATTCAGTGGCAGTGGGGCAGGGACAGATTTCA
CACTGAAAATCAGCAGGGTGGAAGCTGAGGATGTCGGGGTTTATTACTGCATGCAAGTTACACAATTTCCCACTTT
CGGCGGCGGGACCAAGGTGGAGATCAAACGA

17D3

GAAATTGTGTTGACGCAGTCTCCAGGCACCCTGTCTTTGTCTCCAGGGGAAAGAGCCACCCTCTCCTGCAGGGCCA
GTCAGAGTGTTAGCAGCAGCTACTTAGCCTGGTACCAGCAGAAACCTGGCCAGGCTCCCAGGCTCCTCATCTATGG
TGCATCCAGCAGGGCCACTGGCATCCCAGACAGGTTCAGTGGCAGTGGGTCTGGGACAGACTTCACTCTCACCAT
CAGCAGACTGGAGCCTGAAGATTTTGCAGTGTATTACTGTCAGCAGTATGGTAGCTCACCGCTCACTTTCGGCGGA
GGGACCAAGGTGGAGATCAAACGA

15G11

GAAATTGTGTTGACGCAGTCTCCAGGCACCCTGTCTTTGTCTCCAGGGGAAAGAGCCACCCTCTCCTGTAGGGCCA
GTCAGAGTGTTAGCAGCAGGTACTTAGCCTGGTACCAGCAGAAACCTGGCCAGGCTCCCAGGCTCCTCATCCATG
GTCCATTCAGCAGGGCCACTGGCATCCCAGACAGGTTCAGTGGCAGTGGGTCTGGGACAGATTTCACTCTCACCAT
CAGCAGACTGGAGCCTGAAGATTTTGCAGTGTATTACTGTCAGCAGTATGGTAATTCATCGATCACCTTCGGCCAA
GGGACACGACTGGAGATTAAACGA

14D7

GACATCCAGATGACCCAGTCTCCATCCTCCCTGTCTGCATCTGTAGGAGACAGAGTCACCATCACTTGCCGGGCAA
GTCAGACCATTAGCAGTTATTTAAATTGGTATCAGCAGAAACCAGGGAAAGCCCCTAAGGTCCTGATCTATGCTGC
ATCCAGTTTCCAAAGTGGGGTCCCATCAAGGTTCAGTGGCAGTGGATCTGGGACAGATTTCACTCTCACCATCAGC
AGTCTGCAACCTGAAGATTTTGCAACTTACTACTGTCAACAGAGTCACTATATCCCTCGGACGTTCGGCCAAGGGA
CCAAGGTGGAAATCAAACGA

TCCTATGAGCTGACACAGCCACCCTCGGTGTCAGTGTCCCCAGGACAAACGGCCAGGATCGCCTGCTCTGGAGAT
GCATTGCCAAGAAAATTTGCTTATTGGTACCAGCAGAAGTCAGGCCAGGCCCCTGTGCTGGTCATCTCTGAGGACA
GCAGACGACCCTCCGGGATCCCTGAGAGATTCTCTGGCTCCAGCTCAGGGACAATGGCCACCTTGACTATCAGTG
GGGCCCAGGTGGAGGATGAAGCTGACTACTACTGTTTCTCAACAGACAGCAGTGCTAATCATAGGGTATTCGGCG
GAGGGACCAAGCTGACCGTCCTAGGT

17D9

GACATCCAGATGACCCAGTCTCCATCCTCCCTGTCTGCATCTGTAGGAGACAGAGTCACCATCACTTGCCGGGCAA
GTCAGGACATTAGAAATGATTTAGGCTGGTATCAGCAGAAACCAGGGAAAGCCCCTAAGCGCCTGATCTATGCTG
CATCCAGTTTGCAAAGTGGGGTCCCATCAAGGTTCAGCGGCAGTGGATCTGGGACAGAATTCACTCTCACAATCG
GCAGCCTGCAGCCTGAAGATTTTACAACTTATTACTGTCTACAGCATAATAGTTACCCGCTCACTTTCGGCGGAGG
GACCAAGGTGGAGATCAAACGA

21F8

GACATCCAGATGACCCAGTCTCCATCCTCCCTGTCTGCATCTGTAGGAGACAGAGTCACCATCACTTGCCGGGCAA
GTCAGGGCATTAGAGATGATTTAGGCTGGTATCAGCAGAAACCAGGGAAAGCCCCTAAGCGCCTGATCTATATTG
CAACCAGTTTGCAAAGTGGGGTCCCATCAAGGTTCAGCGGCAGTGGATCTGGGACAGAATTCACTCTCACAATCA
GCAGCCTGCAGCCTGAAGATTTTGCAACTTATTACTGTCTACAGCATATTAGTTACCCGTGGACGTTCGGCCAAGG
GACCAAGGTGGAAATCAAACGA

22B9

GACATCCAGATGACCCAGTCTCCATCCTCCCTGTCTGCATCTGTAGGAGACAGAGTCACCATCACTTGCCGGGCAA
GTCAGGACATCAGAGATGATTTAGGCTGGTATCAGCAGAAACCAGGGAAAGCCCCTAAGCGCCTGATCTATGTTG
CATCCAGTTTGCAAAGTGGGGTCCCATCAAGGTTCAGCGGCAGTGGATCTGGGACAGAATTCACTCTCACAATCA
GCAGCCTGCAGCCTGAAGATTTTGCAACTTATTACTGTCTACAGCATATTAGTTACCCGTGGACGTTCGGCCAAGG
GACCAAGGTGGAAATCAAACGA

GACATCCAGATGACCCAGTCTCCATCCTCCCTGTCTGCATCTGTAGGAGACAGAGTCACCATCACTTGCCGGGCAA
GTCAGGACATTAGAGATGATTTAGGCTGGTATCAGCAGAAACCAGGGAAAGCCCCTAAGCGCCTGATCTATGTTG
TATCCAGTTTGCAAAGTGGGGTCCCATCAAGGTTCAGCGGCAGTGGATCTGGGACAGAGTTCACTCTCACAATCA
GCAGCCTGCAGCCTGAAGATTTTGCAACTTATTACTGTCTACAGCATAATGGTTACCCGTGGACGTTCGGCCAAGG
GACCAAGGTGGAAATCAAACGA

14A6

GACATCCAGATGACCCAGTCTCCATCCTCCCTGTCTGCATCTGTAGGAGACAGAGTCACCATCACTTGCCGGGCAA
GTCAGGGCATTGGAGATGATTTAGGCTGGTATCAGCAGAAGCCAGGAAAAGCCCCTCAGCGCCTGATCTATTCTG
CATCCAGTTTGCCAAGTGGGGTCCCATCAAGGTTCAGCGGCAGTGGATCTGGGACAGAATTCACTCTCACAATCA
GCAGCCTGCAGCCTGAAGATTTTGCAACTTATTACTGTCTACAGCATAATAGTTACCCTCGCAGTTTTGGCCAGGG
GACCAAGCTGGAGATCAGACGA

11D6

GACATCCAGATGACCCAGTCTCCATCCTCCCTGTCTGCATCTGTAGGAGACAGAGTCACCATCACTTGCCGGGCAA
GTCAGGACATTGAACATGATTTAGGCTGGTATCAGCAGAAACCAGGGAAAGCCCCTAAGCGCCTGATCTATGCTG
CATCCACTTTGCCAAGTGGGGTCCCATCAAGGTTCAGCGGCAGTGGATCTGGGACAGAATTCACTCTCACAATCAG
CAGCCTGCAGCCTGAAGATTTTGCAACTTATTACTGTCTACAGCATAATAGTTTCCCTCGCAGTTTTGGCCAGGGGA
CCCAGCTGGAGATCAAACGA

10A9

GATATTGTGATGACCCAGACTCCACTCTCCCTGCCCGTCACCCCTGGAGAGCCGGCCTCCATCTCCTGCAGGTCTAC
TCAGAGCCTCTTGGATGGTGATGATGGAAACACCCTTTTGGACTGGTACCTGCAGAAGCCAGGGCAGTCTCCACA
GCTCCTGATCTATACGCTTTCCTATCGGGCCTCTGGAGTCCCAGACAGGTTCAGTGGCAGTGGGTCAGGCACTGAT
TTCACACTGAAAATCAGCAGGGTGGAGGCTGAGGATGTTGGAGTTTATTACTGCATGCAACGTTTAGAGTTTCCTC
TCACTTTCGGCGGAGGGACCAAGGTGGAGATCAAACGA

GACATTGTGATGACCCAGACTCCACTCTCCTTGCCCGTCACCCCTGGAGAGCCGGCCTCCATCTCCTGCAGGTCTAG
TCAGAGCCTCTTGGATAGTGATGAAGGAAACACCTTTTTGGATTGGTACCTGCAGAAGCCAGGGCAGCCTCCACA
GCTCCTGATCTATACGCTTTCCTATCGGGCCTCTGGAGTCCCAGACAGGTTCAGTGGCAGTGGGTCAGGCACTGAT
TTCACACTGAAAATCAGCAGGGTGGAGGCTGAGGATGTTGGAGTTTATTACTGCATGCAACGTATAGAGTTTCCTC
TCACTTTCGGCGGAGGGACCAAGGTGGAGATCAAACGA

14G7

GACATCCAGATGACCCAGTCTCCATCCTCCCTGTCTGCATCTGTAGGAGACAGAGTCACCATCACTTGCCAGGCGA
GTCAGGACATTAGCAACTATTTAAATTGGTATCAGCAGAAACCAGGGAAAGCCCCTAAGCTCCTGATCTACGATGC
ATCCAATTTGGAAACAGGGGTCCCATCAAGGTTCAGTGGAAGTGGATCTGAGACAGATTTTACTTTCACCATCAGC
AGCCTGCAGCCTGAAGATATTGCAACATATTACTGTCAACAGTATGAAAATCTCCCATTCACTTTCGGCCCTGGGAC
CAAAGTGGATATCAAACGA

5H3

TCCTATGAGCTGACACAGCCACCCTCGGTGTCAGTGTCCCCAGGACAGACGGCCAGGATCACCTGCTCTGGAGAT
GCATTGCCAAGGCAATATGCTTATTGGTACCAGCAGAAGCCAGGCCAGGCCCCTATGCTGGTGATATATAAAGAC
AGTGAGAGGCCCTCAGGGATCCCTGAGCGATTCTCTGGCTCCAGCTCAGGGACAACAGTCACGTTGACCATCAGT
GGAGTCCAGGCAGAAGACGAGGCTGACTATTACTGTCAATCAGCAGACAGCAGTGGTACTTATGTGGTATTCGGC
GGAGGGACCAAGCTGACCGTCCTAGGT

2B12

TCCTATGAGCTGACACAGCCACCCTCGGTGTCAGTGTCCCCAGGACAAACGGCCAGGATCACCTGCTCTGGAGAT
GCATTGCCAAGAAAATATGCTTATTGGTACCAGCAGAAGTCAGGCCAGGCCCCTGTGCTGGTCATCTATGAGGAC
AGCAAACGACCCTCCGGGATCCCTGAGAGATTCTCTGGCTCCAGCTCAGGGACAATGGCCACCTTGACTATCAGTG
GGGCCCAGGTGGAGGACGAAGCTGACTACTACTGTTACTCAACAGACAGCAGTGGTAATCATTATGTCTTCGGAA
CTGGGACCAAGGTCACCGTCCTAGGT

GACATCCAGATGACCCAGTCTCCATCCTCCCTGTCTGCATCTGTAGGAGACAGAGTCACCATCACTTGCCAGGCGA
GTCAGGACATTAGCAACTATTTAAATTGGTATCAGCAGAAACCAGGGAAAGCCCCTAAGTTCCTGATCTACGATGC
ATCCAATTTGGAAACAGGGGTCCCATCAAGGTTCAGTGGAAGTGGATCTGGGACAGATTTTTTTTTCACCATCAGC
AACCTGCAGCCTGAAGATATTGCAACATATTTCTGTCAACAGGATGATAATCTCCCATTCACTTTCGGCCCTGGGAC
CAAAGTGGATATCAAACGA

26C12

GACATCCAGATGACCCAGTCTCCATCCTCCCTGTCTGCATCTGTAGGAGACAGAGTCACCATCACTTGCCAGGCGA
GTCAGGACATTAGCAACTATTTAAATTGGTATCAGCAGAAACCAGGGAAAGCCCCTAAACTCCTGATCTACGATGC
ATCCAATTTGGAAACAGGGGTCCCATCAAGGTTCAGTGGAAGTGGATCTGGGACAGATTTTACTTTCACCATCAGC
AGCCTGCAGCCTGAAGATATTGCAACATTTTACTGTCAACAGTATGATAATCTCCCATTCACTTTCGGCCCTGGGAC
CAAAGTGGATATCAAACGA

2H11

TCCTATGAGCTGACACAGCCACCCTCGGTGTCAGTGTCCCCAGGACAAACGGCCAGGATCACCTGCTCTGGAGAT
GCATTGCCAAGAAAATTTGCTTATTGGTACCAGCAGAAGTCAGGCCAGGCCCCTGTGCTGGTCATCTATGAGGAC
AGGAAACGACCCTCCGGGATCCCTGAGAGATTCTCTGGCTCCAGCTCAGGGACAATGGCCACCTTGACTATCAGT
GGGGCCCAGGTGGAGGATGAAGCTGACTACTACTGTTACTCAACAGACCGCAGTGGTGATCATGTGGTATTCGGC
GGAGGGACCAAGCTGACCGTCCTAGGT

18H9

GACATCCAGATGACCCAGTCTCCATCTTCCGTGTCTGCATCTGTAGGAGACAGAGTCACCATCACTTGTCGGGCGA
GTCAGGGTATTAGCAACTGGTTAGTCTGGTATCAGCAGAAACCAGGGAAACCCCCTAAACTCCTGATCTATGCTGC
ATCCAGTTTGCAAAATGGGGTCCCATCAAGATTCAGCGGCAGTGGATCTGGGACAGATTTCACTCTCACCATCAGC
AGCCTGCAGACTGAAGATTTTGCAACTTACTATTGTCAACAGGCTCTCAGTTTCCCGTGGACGTTCGGCCCAGGGA
CCAAGGTGGAAGTCAAACGA

FIG. 28 Heavy Chain Variable Domain Amino Acid Sequences

FIG. 29A

Heavy Chain Nucleic Acid Sequences

9D6

GAGGTGCAGTTGGTGCAGTCTGGAGCAGAGGTGAAAAAGCCCGGGGAGTCTCTGAAGATCTCCTGTAAGGGTTC
TGGATACAGGTTTACCAGCTACTGGATCGGCTGGGTGCGCCAGATGCCCGGGAAAGGCCTGGAGTGGATGGGGA
TCATCCATCCTGGTGACTCTGATACCAGATACAGCCCGTCCTTCCAAGGCCAGGTCACCATCTCAGCCGACAAGTCC
ATCAGCACCGCCTACCTGCAGTGGAGCAGCCTGAAGGCCTCGGACACTGCCATATATTACTGTACGAGACAGGGT
AGAAGCTTCTACTACTACGGTATGGACGTCTGGGGCCAAGGGACCACGGTCACCGTCTCCTCA

2C3

GAGGTGCAGCTGGTGCAGTCTGGAGCAGAGGTGAAAAAGCCCGGGGAGTCTCTGAAGATCTCCTGTAAGGGTTC
TGGATACAGGTTTACCAGCTACTGGATCGGCTGGGTGCGCCAGATGCCCGGGAAAGGCCTGGAGTGGATGGGGA
TCATCTATCCTGGTGACTCTGATACCAGATACAGCCCGTCCTTCCAAGGCCAGGTCACCATCTCAGCCGACAAGTCC
ATCAGCGCCGCCTACCTGCAGTGGAGCAGCCTGAAGGCCTCGGACACCGCCATGTATTACTGTGCGAGACAACAA
GTGGCTGGTATGTTGGACTACTGGGGCCAGGGAACCCTGGTCACCGTCTCCTCA

14C9

CAGGTGCAGCTGGTGGAGTCTGGGGGAGGCGTGGTCCAGCCTGGGAGGTCCCTGAGACTCTCCTGTGCAGCGTC
TGGATTCACCTTCAGTATTTATGGCATGCACTGGGTCCGCCAGGCTCCAGGCAAGGGGCTGGAGTGGGTGACAGT
TATATGGTATGATGGAAGTAATGAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTATTACTGTGCGAGAGAGGA
CTTCGACTCCCACTACGGTATGGACGTCTGGGGCCAAGGGACCACGGTCACCGTCTCCTCA

8B12

CAGGTGCAGCTGGTGGAGTCTGGGGGAGGCGTGGTCCAGCCTGGGAGGTCCCTGAGACTCTCCTGTGCAGCGTC
TGGATTCACCTTCAGTAGCTATGGCATGCACTGGGTCCGCCAGGCTCCAGGCAAGGGGCTGGAGTGGGTGGCAG
TTATATGGTATGATGGAAGTAATGAATACTATGCAGACTCCGTGAAGGGCCGATTCACCATCTCCAGAGACAATTC
CAAGAACACGCTGTATCTACAAATGCACAGCCTGAGAGCCGAGGACACGGCTGTGTATTATTGTGCGAGAGAAGA
ATGGTTCGGGGAGGCGGACTACGGTATGGACGTCTGGGGCCAAGGGACCACGGTCACCGTCTCCTCA

CAGGTGCAGCTGGTGGAGTCTGGGGGAGGCGTGGTCCAGCCAGGGAGGTCCCTGAGACTCTCCTGTGCAGCGTC
TGGATTCACCTTCAGTAGCTATGGCATGCACTGGGTCCGCCAGGCTCCAGGCAAGGGGCTGGAGTGGGTGGCAG
TTATATGGTATGATGGAAGTAATGAATATTATGCAGACTCCGTGAAGGGCCGATTCACCATCTCCAGAGACAATTC
CAAGAACACGCTGTTTCTGCAAATGAACAGCCTGAGAGCCGAGGACACGGCTGTGTATTACTGTGCGAGAGATGA
TTGGTTCGGGGAGGCGGACTACGGTATGGACGTCTGGGGCCAAGGGACCACGGTCACCGTCTCCTCA

16E1

CAGGTGCAGCTGGTGGAGTCTGGGGGAGGCGTGGTCCAGCCTGGGAGGTCCCTGAGACTCTCCTGTGCAGCGTC
TGGATTCACCTTCAGTAACTATGGCATGCACTGGGTCCGCCAGGCTCCAGGCAAGGGGCTGGAGTGGGTGACAGT
TATATGGAATGATGGAAGTAATGAATACTATGCAGACTCCGTGAAGGGCCGATTCACCATCTCCAGAGACAATTCC
AAGAACACGCTGTTTCTGCAAATGAACAGCCTGAGAGCCGAGGACACGGCTGTGTATTACTGTGCGAGAGAAGAT
TGGCTCGGGGAGGCGGACTACGGTATGGACGTCTGGGGCCAAGGGACCACGGTCACCGTCTCCTCA

13A1

CAGGTGCAGCTGGTGGAGTCTGGGGGAGGCGTGGTCCAGCCTGGGAGGTCCCTGAGACTCTCCTGTGCAGCGTC
TGGATTCACCTTCAGTAGCTATGGCATGCACTGGGTCCGCCAGGCTCCAGGCAAGGGGCTGGAGTGGGTGGCAG
TTATATGGTATGATGGAAGTAATAAATACTATGCAGACTCCGTGAAGGGCCGATTCACCATCTCCAGAGACAATTC
CAAGAACACGCTGTATCTGCAAATGAACAGCCTGAGAGCCGAGGACACGGCTGTGTATTACTGTGCGAGAGAAG
AGTGGGAGCTAGAGGACTACGGTATGGACGTCTGGGGCCAAGGGACCACGGTCACCGTCTCCTCA

8F10

CAGGTGCAGTTGGTGGAGTCTGGGGGAGGCGTGGTCCAGCCTGGGAGGTCCCTGAGACTCTCCTGTGCAGCGTC
TGGATTCACCTTCAGTAGTTATGGCATGTACTGGGTCCGCCAGGCTCCAGGCAAGGGGCTGGAGTGGGTGGCAGT
TATATGGTATGATGGAAGTAATAAATACTATGTAGACTCCGTGAAGGGCCGATTCACCATCTCCAGAGACAATTCC
AAGAACACGCTGTATCTGCAAATGAACAGCCTGAGAGCCGAGGACACGGCTGTGTATTACTGTGCGAGAGGAGC
AGTGGCTGGTACGGGACGGGACTACTACTACTACGGTATGGACGTCTGGGGCCAAGGGACCACGGTCACCGTCT
CCTCA

CAGGTGCAGTTGGTGGAGTCTGGGGGAGGCGTGGTCCAGCCTGGGAGGTCCCTGAGACTCTCCTGTGCAGCGTC
TGGATTCACGTTCAGTAGTTATGGCATGTACTGGGTCCGCCAGGCTCCAGGCAAGGGGCTGGAGTGGGTGGCAG
TTATATGGTATGATGGAAGTAATAAATACCATGGAGACTCCGTGAAGGGCCGATTCACCATCTCCAGAGACAATTC
CAAGAATACGCTGTATCTGCAAATGAACAGCCTGAGAGCCGAGGACACGGCTGTGTATTACTGTGCGAAAGGAGC
AGTGGCTGGTACGGGACGGGACTACTACTACTACGGTATGGACGTCTGGGGCCAAGGGACCACGGTCACCGTCT
CCTCA

9B12

CAGGTGCAGCTGGTGGAGTCTGGGGGAGGCGTGGTCCAGCCTGGGAGGTCCCAGAGACTCTCCTGTGCAGCGTC
TGGATTCACCTTTAGTAGTTATGGCATGTACTGGGTCCGCCAGGCTCCAGGCAAGGGGCTGGAGTGGGTGGCAGT
TATATGGTATGATGGAAGTAATAAAAACTATGCAGACTCCGTGAAGGGCCGATTCACCATCTCCAGAGACAATTCC
AAGAATACGTTGTATCTGCAAATGAACAGCCTGAGAGCCGAGGACACGGCTGTGTATCACTGTGCGAAAGGAACA
GTGGCTGGTACGGGACGGGACTACTACTACTACGGTATGGACGTCTGGGGCCAAGGGACCACGGTCACCGTCTCT
TCA

3H5

CAGGTGCAACTGGTGGAGTCTGGGGGAGGCGTGGTCCAGCCTGGGAGGTCCCTGAGACTCTCCTGTGCAGCGTC
TGGATTCACCTTCAGTAGCTTTGGCATGCACTGGGTCCGCCAGGCTCCAGGCAAGGGGCTGGAGTGGGTGGCAGT
TATTTGGTTTGATGGAAGTAATAAATACTATGTAGACTCCGTGAAGGGCCGATTCACCATCTCCAGAGACAATTCC
AAGAATACGCTGTATCTGCAAATGAACAGCCTGAGAGCCGAGGACACGGCTGTGTATTACTGTGCGCGGGACGAT
TTTTGGAGTGATTATCCTTTTGACTACTGGGGCCAGGGAACCCTGGTCACCGTCTCCTCA

18A6

CAGGTGCAACTGGTGGAGTCTGGGGGAGGCGTGGTCCAGCCTGGGAGGTCCCTGAGACTCTCCTGTGCAGCCTCT
GGATTCACCTTCAGGAGCTATGGCATGCACTGGGTCCGCCAGGCTCCAGGCAAGGGGCTGGAGTGGGTGGCAGT
TATATCAGATGATGGAAGTAATAAATACTATGCAGACTCCGTGAAGGGCCGATTCACCATCTCCAGAGACAATTCC
AAGAACACGCTGTATCTGCAAATGAACAGCCTGAGACCTGAGGACACGGCTGTGTATTACTGTGCGAGAGATCTC
TATAGCAGTGCCTGGCCCTTTGACTACTGGGGCCAGGGAACCCTGGTCACCGTCTCCTCA

CAGGTGCAGCTGGTGGAGTCTGGGGGAGGCGTGGTCCAGCCTGGGAGGTCCCTGAGACTCTCCTGTGCAGCGTC
TGGATTCACCTTCAGTAGCTATGACATACACTGGGTCCGCCAGGCTCCAGGCAAGGGGCTGGAGTGGGTGGCAGT
TATATGGAATGATGGAAGTATTAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTATTACTGTGCGAGAGACGG
GGAGCAGTGGCGGGGCTTTGACTACTGGGGCCAGGGAACCCTGGTCACCGTCTCCTCA

10H7

CAGGTGCAGCTGGTGGAGTCTGGGGGAGGCGTGGTCCAGCCTGGGAGGTCCCTGAGACTCTCCTGTGCAGCGTC
TGGATTCACCTTCAGTAGCTATGACATACACTGGGTCCGTCAGGCTCCAGGCAAGGGGCTGGAGTGGGTGGCAGT
TATATGGTATGATGGAAGTATTAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTATTACTGTGCGAGAGATCAG
GAGCAGTGGCTGGCCTTTGACTACTGGGGCCAGGGAACCCTGGTCACCGTCTCCTCA

15A10

CAGGTGCAGTTGGTGGAGTCTGGGGGAGGCGTGGTCCAGCCTGGGAGGTCCCTGAGACTCTCCTGTGCAGCGTC
TGGATTCACCTTCAGTACCTATGGCATGCACTGGGTCCGCCAGGCTCCAGACATGGGGCTGGAGTGGGTGGCAGT
TATATGGTATGATGGAAGTAATAAATACTATGCAGACTCTGTGAAGGGCCGATTCACCATCTCCAGAGACATTTCC
AAGAACACGCTGTATCTGGAAATGAACAGCCTGAGAGCCGAGGACACGGCTGTGTATTACTGTGCGAGAGACAA
CTGGGGATCCGATGCTTTTGATATCTGGGGCCAAGGGACAATGGTCACCGTCTCTTCA

12D2

CAGGTGCAGCTGGTGGAGTCTGGGGGAGGCGTGGTCCAGCCTGGGAGGTCCCTGAGACTCTCCTGTGCAGCGTC
TGGATTCACCTTCAGTACCTATGCCATGCACTGGGTCCGCCAGGCTCCAGGCAAGGGGCTGGAGTGGGTGGCAGT
TATATGGTATGATGGAATTAATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTATTACTGTGCGAGAGGGAG
TTACTATGATAGTAGTGGTTATTACTACGGGGAGGACTTTGACTACTGGGGCCAGGGAACCCTGGTCACCGTCTCC
TCA

CAGGTGCAGCTGGTGGAGTCTGGGGGAGGCGTGGTCCAGCCTGGGAGGTCCCTGAGACTCTCCTGTGCAGCGTC
TGGATTCACCTTCAGTAGCTATGCCATGCACTGGGTCCGCCAGGCTCCAGGCAAGGGGCTGGAGTGGGTGGCAGT
TATCTGGTATGATGGAATTAATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTATTACTGTGCGAGAGGGAG
TTACTATGATAGTAGTGGTTATTACTTCGGGGAGGACTTTGACTACTGGGGCCAGGGAACCCTGGTCACCGTCTCC
TCA

17D3

CAGGTGCAGCTGGTGGAGTCTGGGGGAGGCTTGGTCAAGCCTGGAGGGTCCCTGAGACTCTCCTGTGCAGCCTCT
GGATTCACCTTCAGTGACTACTACATGAGCTGGATCCGCCAGGCTCCAGGGAAGGGGCTGGAGTGGGTTTCATAC
ATTAGTAGTAGTGGTAGTATCATTTTTTACGCAGACTCTGTGAAGGGCCGATTCACCATGTCCAGGGACAACGCCA
AGAACTCACTGTATCTGCAAATGAACAGCCTGAGAGCCGAGGACACGGCCGTGTATTATTGTGTGAGAAGGATTA
GTATAACCCCTTTTGACTACTGGGGCCAGGGAACCCTGGTCACCGTCTCCTCA

15G11

CAGGTCACCTTGAAGGAGTCTGGTCCTGTGCTGGTGAAACCCACAGAGACCCTCACGCTGACCTGCACCGTCTCTG
GGTTCTCACTCAGCAATGCTAGAATGGGTGTGAGCTGGATCCGTCAGCCCCAGGGAAGGCCCTGGAGTGGCTTG
CACACATTTTTTCGAATGACGAAAAATCCTACAGCACATCTCTGAAGAGCAGGCTCACCATCTCCAAGGACACCTCC
AAAAGCCAGGTGGTCCTTACCATGACCAACATGGACCCTGTGGACACAGCCACATATTACTGTGTACGGATACCGA
GATGGCTACAACCCCCCTACTACTACTACGGTATGGACGTCTGGGGCCAAGGGACCACGGTCACCGTCTCCTCA

14D7

CAGGTGCAGCTGCAGGAGTCGGGCCCAGGACTGGTGAAGCCTTCACAGACCCTGTCCCTCACCTGCACTGTCTCT
GGTGGCTCCATCAGCAGTGGTGGTTACTACTGGAACTGGATCCGCCAGCACCCAGGGAAGGGCCTGGAGTGGAT
TGGGTACATCTATTACAGTGGGAACACCCACTACAACCCGTCCCTCAAGAGTCGAGTTACCATATCAGTAGACACG
TCTAAGAACCAGTTCTCCCTGAAGCTGAGCTCTGTGATTGCCGCGGACACGGCCGTGTATTACTGTGCGAGAGACT
GGGGACGTGATGCTTTTGATATCTGGGGCCAAGGGACAATGGTCACCGTCTCTTCA

CAGGTGCAGCTGCAGGAGTCGGGCCCAGGACTGGTGAAGCCTTCACAGACCCTGTCCCTCACCTGCACTGTCTCG
GGTGGCTCCATCAGCAGTGGTGGTTACTACTGGAGCTGGATCCGCCAGCACCCAGGGAAGGGCCTGGAGTGGAT
TGGGTACATCTATTATAGTGGGAGCACCGACTACAACCCGTCCCTCAAGAGTCGAGGTATCATATCAGGAGACAC
GTCTAAGAACCAGTTCTCCCTGAAGCTGAACTCTGTGACTGCCGCGGACACGGCCGTGTATTACTGTGCGAGAGA
GGGGAGGTTCGGGGAGTTAGGCTCCTACTACTTTGACTACTGGGGCCAGGGAACCCTGGTCACCGTCTCCTCA

17D9

CAGGTGCAGCTGCAGGAGTCGGGCCCAGGACTGGTGAAGCCTTCGGAGACCCTGTCCCTCACCTGCACTGTCTCT
GGTGGCTCCGTCAGCAGTGGTGGTTACTACTGGAGCTGGATCCGGCAGCCCCCAGGGAAGGGACTGGAGTGGAT
TGGGAATACCTATTACAGTGGGAGCACCAACTACAAACCCTCCCTCAAGAGTCGAGTCACCATATCAGTAGACACG
TCCAAGAACCAGTTCTCCCTGAAGCTGAGTTCTGTGACCGCTGCGGACACGGCCGTGTATTACTGTGGGAGAGAC
CGGGGTAGAGCAGTGGGTCCCTTTGACTACTGGGGCCAGGGAACCCTGGTCACCGTCTCCTCA

21F8

CAGGTGCAGCTGGTGCAGTCTGGGGCTGAGGTGAAGAAGCCTGGGGCCTCAGTGAAGGTCTCCTGCAAGGCTTC
TGGATACACCTTCACCAATTATGATATCAACTGGGTGCGACAGGCCACTGGACAAGGGCTTGAGTGGATGGGATG
GATGAACCCTAACAGTGGTAACACAGGCTATGCACAGAAGTTCCAGGGCAGAGTCACCATGACCAGGAACACCTC
CATAAGCACAGCCTACATGGAGCTGAGCAGCCTGAGATCTGAGGACACGGCCGTGTATTACTGTGCGAGAAGTA
GGCAGTGGCTGGTACTTGACTACTGGGGCCAGGGAACCCTGGTCACCGTCTCCTCA

22B9

CAGGTGCAGCTGGTGCAGTCTGGGGCTGAGGTGAAGAAGCCTGGGGCCTCAGTGAAGGTCTCCTGCAAGGCTTC
TGGATACACCTTCACCAATTATGATATCAACTGGGTGCGACAGGCCACTGGACAAGGGCTTGAGTGGATGGGATG
GATGAACCCTAACAGTGGTAACACAGGCTATGTACAGAAGTTCCAGGGCAGAGTCACCATGACCAGGAACACCTC
CATAAGCACAGCCTACATGGAGCTGAGCAGCCTGAGATCTGAGGACACGGCCGTGTATTACTGTGCGAGAAGTA
GGCAGTGGCTGGTACTTGACTACTGGGGCCAGGGAACCCTGGTCACCGTCTCCTCA

CAGGTGCAGCTGGTGCAGTCTGGGGCTGAGGTGAAGAAGCCTGGGGCCTCAGTGAAGGTCTCCTGCAAGGCTTC
TGGATACAGGTTCACCAGTTATGATATCAACTGGGTGCGACAGGCCACTGGACAAGGGCTTGAGTGGATGGGAT
GGATGAACCCAAACAGTGGTAACACAGGCTATGCACAGAAGTTCCAGGGCAGAGTCACCATGACCAGGAACACC
TCCATAAGCACAGCCTACATGGAGCTGAGCAGCCTGAGATCTGAGGACACGGCCGTGTATTACTGTGCGAGAAGT
AGGCAGTGGCTGGTACTTGACTACTGGGGCCAGGGAACCCTGGTCACCGTCTCCTCA

14A6

CAGGTGCAGCTGGTGCAGTCTGGGGCTGAGGTGAAGAAGCCTGGGGCCTCAGTGAAGGTCTCCTGCAAGGCTTC
TGGATACACCTTCACCACTTATGATATCAACTGGGTGCGACAGGCCACTGGACAAGGGCTTGAGTGGATGGGATG
GATGAACCCTAACAGTGGTAACACAGGCTATGCACAGAAGTTCCAGGGCAGAGTCACCATGACCAGGAACACCTC
CATAAGCACAGCCTACATGGAGCTGAGCAGCCTAAGATCTGAGGACACGGCCGTGTATTACTGTGCGAGAGGCC
GGCAGTGGCTGGGCTTTGACTACTGGGGCCAGGGAACCCTGGTCACCGTCTCCTCA

11D6

CAGGTGCAGCTGGTGCAGTCTGGGGCTGAGGTGAAGAAGCCTGGGGCCTCAGTGAAGGTCTCCTGCAAGGCTTC
TGGATACACCTTCACCAATTATGATATCAACTGGGTGCGACAGGCCACTGGACAAGGGCTTGAGTGGATGGGATG
GATGAACCCTAATAGTGGTAACACAGGCTATGCACAGAAGTTCCAGGGCAGAGTCACCATGACCAGGAACACCTC
CATAAACACAGCCTACATGGAGCTGAGCAGCCTGAGATCTGAGGACACGGCCGTGTATTACTGTGCGAGAGGCC
GGCAGTGGCTGGGCTTTGACTACTGGGGCCAGGGAACCCTGGTCACCGTCTCCTCA

10A9

GAGGTGCAGCTGGTGCAGTCTGGAGCAGAGGTGAAAAAGCCCGGGGAGTCTCTGAAGATCTCCTGTAAGGGTTC
TGGATACAGCTTTACCAGCCAGTGGATCGGCTGGGTGCGCCAGATGCCCGGGAAAGGCCTGGAGTGGATGGGGA
TCATCTTTCCTGGTGACTCTGATACCAGATACAGCCCGTCCTTCCAAGGCCAGGTCACCATCTCAGCCGACAAGTCC
ATCAGCACCGCCTACCTGCAGTGGAGCAGCCTGAAGGCCTCGGACACCGCCATGTATTACTGTGCGCGACAGGGT
AGAAGTTACCACTACTACGGTATGGACGTCTGGGGCCAAGGGACCACGGTCACCGTCTCCTCA

GAGGTGCAGCTGGTGCAGTCTGGAGCAGAGGTGAAAAAGCCCGGGGAGTCTCTGAAGATCTCCTGTAAGGGTTC
TGGATACGGCTTTACCAACTACTGGATCGGCTGGGTGCGCCAGATGCCCGGAAAAGGCCTGGAGTGGATGGGGA
CCATCTATCCTGGTGACTCTGATACCAGATACAGTCCGTCCTTCCAAGGCCAGGTCACCTTCTCAGCCGACAAGTCC
ATCAGCACCGCCTACCTGCAGTGGAGCAGCCTGAAGGCCTCGGACACCGCCATGTATTACTGTGCGAGACAGGGT
AGAAGTTACTACTACTTCGGTATGGACGTCTGGGGCCAAGGGACCACGGTCACCGTCTCCTCA

14G7

GAGGTGCAGCTGGTGCAGTCTGGAGCAGAGGTGAAAAAGCCCGGGGAGTCTCTGAAGATCTCCTGTAAGGGTTC
TGGATACAGCTTTACCGACTACTGGATCGGCTGGGTGCGCCAGATGCCCGGGAAAGGCCTGGAATGGATGGGGA
TCATCTATCCTTATGACTCTGATACCAGATACAGCCCGTCCTTCCAAGGCCAGGTCACCCTCTCAGCCGACAAGTCC
ATCAGCACCGCCTACCTGCGGTGGAGCAGCCTGAAGGCCTCGGACACCGCCATGTATTACTGTGCGAGACATCGG
GGGGGGAGGTCCTACTACTACGGTATGGACGTCTGGGGCCAAGGGACCACGGTCACCGTCTCCTCA

5H3

GAGGTGCAGCTGGTGCAGTCTGGAGCAGAGGTGAAAAAGCCCGGGGAGTCTCTGAAGATCTCCTGTAAGGGTTC
TGGATACAGCTTTACCAGCTACTGGATCGGCTGGGTGCGCCAGATGCCCGGGAAAGGCCTAGAATGGATGGGGA
TCATCTATCCTGGTGACTCTGATACCACATACAGCCCGTCCTTCCAAGGCCAAGTCACCATCTCAGCCGACAAGTCC
ATCAACACCGCCTACCTGCAGTGGAGCAGCCTGAAGGCCTCGGACACCGCCATGTATTACTGTGCGAGAGAGGGT
TTCGGGGAGTCTATTCACTACGGTTTGGACGTCTGGGGCCAAGGGACCACGGTCACCGTCTCCTCA

2B12

GAGGTGCAGCTGGTGCAGTCTGGAGCAGAGGTGAAAAAGCCCGGGGAGTCTCTGAAGATCTCCTGTAAGGGTTC
TGGATACAATTTTACCAACTACTGGATCGGCTGGGTGCGCCAGATGTCCGGGAAAGGCCTGGAGTGGATGGGAA
TCATCTATCCTGGTGACTCTGAAACCAGATACAGCCCGTCCTTCCAAGGCCAGGTCACCATCTCAGCCGACAAGTC
CATCAGCACCGCCTACCTGCAGTGGAGCAGCCTGAAGGCCTCGGACACCGCCATGTATTACTGTGCGAGACATGG
AGGGGGATGGAGTGGTTGGGGTATGGACGTCTGGGGCCAAGGGACCACGGTCACCGTCTCCTCA

GAGGTGCAGCTGGTGCAGTCTGGAGCAGAGGTGAAAAAGCCCGGGGAGTCTCTGAAGATCTCCTGTAAGGGTTC
TGGATACAGGTTTACCAACTACTGGATCGGCTGGGTGCGCCAGATGCCCGGGAAAGGCCTGGAGTGGATGGGGA
TCATCTATCCTGGTGACTCTGATACCAAATACAGCCCGTCCTTCCAAGGCCAGGTCACCATCTCAGCCGACAAGTCC
ATCAGTACCGCCTACCTGCAGTGGAGCAGCCTGAAGGCCTCGGACACCGCCATGTATTACTGTGCGAGACATGGT
GGATATAGTGGCCGTTCCTACTACTACGGTATGGACGTCTGGGGCCAGGGGACCGCGGTCACCGTCTCCTCA

26C12

GAGGTGCAGCTGGTGCAGTCTGGAGCAGAGGTGAAAAAGCCCGGGGAGTCTCTGAAGATCTCCTGTAAGGGTTC
TGGATACAGGTTTACCAGCTACTGGATCGGCTGGGTGCGCCAGATGCCCGGGAAAGGCCTGGAGTGGATGGGGA
TCATCTTTCCTGGTGACTCTGATACCAGATACAGCCCGTCCTTCCAAGGCCAGGTCACCATCTCAGCCGACAAGTCC
ATCACCACCGCCTACCTGCAGTGGAGCAGCCTGAAGGCCTCGGACACCGCCATCTATTACTGTGCGCGACATGGG
CATGGCAGCTCGTCCGGGCGGACCTACTACTACGGTTTGGACGTCTGGGGCCAAGGGACCACGGTCACCGTCTCC
TCA

2H11

GAGGTGCAGCTGGTGCAATCTGGAGCAGAGGTGAAAAAGCCCGGGGAGTCTCTGAAGATCTCCTGTAAGGGTTC
TGGATACAACTTTACCACCTACTGGATCGGCTGGGTGCGCCAGATGCCCGGGAAAGGCCTGGAGTGGATGGGGA
TCATCTATCCTGGTGACTCTGATACCAGATACAGCCCGTCCTTCCAAGGCCAGGTCACCATTTCAGCCGACAAGTCC
ATCAACACCGCCTACCTGCAGTGGAGCAGCCTGAAGGCCTCGGACACAGCCATTTATTACTGTGCGAGAGACACA
GGATACTTTGACTACTGGGGCCAGGGCACCCTGGTCACCGTCTCCTCA

18H9

CAGGTGCAGTTGGTGGAGTCTGGGGGAGGCGTGGTCCAGCCTGGGAGGTCCCTGAGACTCTCCTGTGCAGCGTC
TGGATTCACCTTCAGTAGCTATGGCATGCACTGGGTCCGCCAGGCTCCAGGCAAGGGCCTGGAGTGGGTGGCAGT
TATCTGGTATGATGGAAGTAATAAATTCTATGTAGACTCCGTGAAGGGCCGATTCACCATCTCCAGAGACAATTCC
AAGAACACGCTGTATCTGCAAATGAACAGCCTGAGAGCCGAGGACACGGCTGTGTATTACTGTGCGAGACCCGG
GTCCGATTACTACTTCTACTACGGTATGGACGTCTGGGGCCAAGGGACCACGGTCACCGTCTCCTCA

SEQUENCE LISTING

<160> NUMBER OF SEQ ID NOS: 308

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 2
<211> LENGTH: 133
<212> TYPE: PRT
<213> ORGANISM: Homo sapiens
<220> FEATURE:
<221> NAME/KEY: MISC_FEATURE
<222> LOCATION: (125)..(125)
<223> OTHER INFORMATION: Wherein X is C, S, V, or A

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Xaa Gln Ser Ile
        115                 120                 125

Ile Ser Thr Leu Thr
    130

<210> SEQ ID NO 3
<211> LENGTH: 227

```
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 226
<212> TYPE: PRT
<213> ORGANISM: Artificial Sequence
<220> FEATURE:
<223> OTHER INFORMATION: Synthetic Polypeptide

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
```

```
                    100                 105                 110
Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

Gly Gly Gly Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 6

Gly Gly Asn Gly Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Tyr Gly Asn Gly Thr
1               5

<210> SEQ ID NO 8
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

```
            20                  25                  30
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
     50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 9
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 9

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Ser Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
     50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 10
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 10

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Arg Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Leu Lys
 50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr
                130

<210> SEQ ID NO 11
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 11

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Ala Arg Met Leu Thr Phe Lys Phe Tyr Met Pro Lys
                 35                  40                  45

Lys Ala Thr Glu Leu Lys His Leu Gln Cys Leu Glu Glu Leu Lys
 50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr
                130

<210> SEQ ID NO 12
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 12

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Glu
                 35                  40                  45

Lys Ala Thr Glu Leu Lys His Leu Gln Cys Leu Glu Glu Leu Lys
 50                  55                  60

Pro Leu Glu Glu Ala Leu Asn Leu Ala Pro Ser Lys Asn Phe His Leu
 65                  70                  75                  80
```

```
Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 13
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Asp Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 14
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 14

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Ala Leu Arg Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
```

```
                100                 105                 110
Thr Ile Val Glu Phe Leu Asn Arg Trp Ile Thr Phe Ala Gln Ser Ile
        115                 120                 125

Ile Ser Thr Leu Thr
        130

<210> SEQ ID NO 15
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 15

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Arg Leu Thr Arg Met Leu Thr Phe Lys Phe Tyr Met Pro Glu
        35                  40                  45

Lys Ala Thr Glu Leu Lys His Leu Gln Cys Leu Glu Glu Glu Leu Lys
50                  55                  60

Pro Leu Glu Asp Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 16
<211> LENGTH: 364
<212> TYPE: PRT
<213> ORGANISM: Artificial Sequence
<220> FEATURE:
<223> OTHER INFORMATION: Synthetic Polypeptide

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Ala Pro Thr Ser Ser Thr Lys Lys
225                 230                 235                 240

Thr Gln Leu Gln Leu Glu His Leu Leu Leu Asp Leu Gln Met Ile Leu
                245                 250                 255

Asn Gly Ile Asn Asn Tyr Lys Asn Pro Lys Leu Thr Arg Met Leu Thr
                260                 265                 270

Phe Lys Phe Tyr Met Pro Lys Lys Ala Thr Glu Leu Lys His Leu Gln
            275                 280                 285

Cys Leu Glu Glu Glu Leu Lys Pro Leu Glu Glu Val Leu Asn Leu Ala
290                 295                 300

Gln Ser Lys Asn Phe His Leu Arg Pro Arg Asp Leu Ile Ser Asn Ile
305                 310                 315                 320

Asn Val Ile Val Leu Glu Leu Lys Gly Ser Glu Thr Thr Phe Met Cys
                325                 330                 335

Glu Tyr Ala Asp Glu Thr Ala Thr Ile Val Glu Phe Leu Asn Arg Trp
            340                 345                 350

Ile Thr Phe Ala Gln Ser Ile Ile Ser Thr Leu Thr
            355                 360

<210> SEQ ID NO 17
<211> LENGTH: 364
<212> TYPE: PRT
<213> ORGANISM: Artificial Sequence
<220> FEATURE:
<223> OTHER INFORMATION: Synthetic Polypeptide

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

-continued

```
Tyr Thr Leu Pro Pro Ser Arg Glu Glu Met Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Gly Gly Gly Ser Ala Pro Thr Ser Ser Thr Lys Lys
225                 230                 235                 240
Thr Gln Leu Gln Leu Glu His Leu Leu Leu Asp Leu Gln Met Ile Leu
                245                 250                 255
Asn Gly Ile Asn Asn Tyr Lys Asn Pro Lys Leu Thr Arg Met Leu Thr
            260                 265                 270
Phe Lys Phe Tyr Met Pro Lys Lys Ala Thr Glu Leu Lys His Leu Gln
        275                 280                 285
Cys Leu Glu Glu Glu Leu Lys Pro Leu Glu Glu Ala Leu Asn Leu Ala
    290                 295                 300
Pro Ser Lys Asn Phe His Leu Arg Pro Arg Asp Leu Ile Ser Asn Ile
305                 310                 315                 320
Asn Lys Ile Val Leu Glu Leu Lys Gly Ser Glu Thr Thr Phe Met Cys
                325                 330                 335
Glu Tyr Ala Asp Glu Thr Ala Thr Ile Val Glu Phe Leu Asn Arg Trp
            340                 345                 350
Ile Thr Phe Ala Gln Ser Ile Ile Ser Thr Leu Thr
        355                 360

<210> SEQ ID NO 18
<211> LENGTH: 364
<212> TYPE: PRT
<213> ORGANISM: Artificial Sequence
<220> FEATURE:
<223> OTHER INFORMATION: Synthetic Polypeptide

<400> SEQUENCE: 18

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Gly Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
```

Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Ala Pro Thr Ser Ser Ser Thr Lys Lys
225                 230                 235                 240

Thr Gln Leu Gln Leu Glu His Leu Leu Leu Asp Leu Gln Met Ile Leu
                245                 250                 255

Asn Gly Ile Asn Asn Tyr Lys Asn Pro Lys Leu Thr Arg Met Leu Thr
            260                 265                 270

Phe Lys Phe Tyr Met Pro Lys Lys Ala Thr Glu Leu Lys His Leu Gln
275                 280                 285

Cys Leu Glu Glu Glu Leu Lys Pro Leu Glu Glu Val Leu Asn Leu Ala
            290                 295                 300

Gln Ser Lys Asn Phe His Leu Arg Pro Arg Asp Leu Ile Ser Asn Ile
305                 310                 315                 320

Asn Lys Ile Val Leu Glu Leu Lys Gly Ser Glu Thr Thr Phe Met Cys
                325                 330                 335

Glu Tyr Ala Asp Glu Thr Ala Thr Ile Val Glu Phe Leu Asn Arg Trp
            340                 345                 350

Ile Thr Phe Ala Gln Ser Ile Ile Ser Thr Leu Thr
            355                 360

<210> SEQ ID NO 19
<211> LENGTH: 364
<212> TYPE: PRT
<213> ORGANISM: Artificial Sequence
<220> FEATURE:
<223> OTHER INFORMATION: Synthetic Polypeptide

<400> SEQUENCE: 19

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

```
Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Ala Pro Thr Ser Ser Ser Thr Lys Lys
225                 230                 235                 240

Thr Gln Leu Gln Leu Glu His Leu Leu Leu Asp Leu Gln Met Ile Leu
                245                 250                 255

Asn Gly Ile Asn Asn Tyr Lys Asn Pro Lys Leu Thr Arg Met Leu Thr
            260                 265                 270

Phe Lys Phe Tyr Met Pro Lys Lys Ala Thr Glu Leu Lys His Leu Gln
            275                 280                 285

Cys Leu Glu Glu Glu Leu Lys Pro Leu Glu Glu Ala Leu Asn Leu Ala
290                 295                 300

Pro Ser Lys Asn Phe His Leu Arg Pro Arg Asp Leu Ile Ser Asp Ile
305                 310                 315                 320

Asn Val Ile Val Leu Glu Leu Lys Gly Ser Glu Thr Thr Phe Met Cys
                325                 330                 335

Glu Tyr Ala Asp Glu Thr Ala Thr Ile Val Glu Phe Leu Asn Arg Trp
            340                 345                 350

Ile Thr Phe Ala Gln Ser Ile Ile Ser Thr Leu Thr
            355                 360

<210> SEQ ID NO 20
<211> LENGTH: 364
<212> TYPE: PRT
<213> ORGANISM: Artificial Sequence
<220> FEATURE:
<223> OTHER INFORMATION: Synthetic Polypeptide

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125
```

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Ala Pro Thr Ser Ser Ser Thr Lys Lys
225                 230                 235                 240

Thr Gln Leu Gln Leu Glu His Leu Leu Leu Asp Leu Gln Met Ile Leu
            245                 250                 255

Asn Gly Ile Asn Asn Tyr Lys Asn Pro Lys Leu Thr Arg Met Leu Thr
            260                 265                 270

Phe Lys Phe Tyr Met Pro Lys Lys Ala Thr Glu Leu Lys His Leu Gln
            275                 280                 285

Cys Leu Glu Glu Glu Leu Lys Pro Leu Glu Glu Val Leu Asn Leu Ala
            290                 295                 300

Gln Ser Lys Asn Phe His Leu Arg Pro Arg Asp Leu Ile Ser Asp Ile
305                 310                 315                 320

Asn Val Ile Val Leu Glu Leu Lys Gly Ser Glu Thr Thr Phe Met Cys
            325                 330                 335

Glu Tyr Ala Asp Glu Thr Ala Thr Ile Val Glu Phe Leu Asn Arg Trp
            340                 345                 350

Ile Thr Phe Ala Gln Ser Ile Ile Ser Thr Leu Thr
            355                 360

<210> SEQ ID NO 21
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 21

His His His His His His
1               5

<210> SEQ ID NO 22
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 22

Thr Gln Lys Ser Leu Ser Leu Ser Pro Gly Lys Gly Gly Gly Gly Ser
1               5                   10                  15

Ala Pro Thr Ser Ser Ser Thr Lys Lys Thr Gln Leu Gln Leu Glu His
            20                  25                  30

Leu Leu Leu Asp Leu Gln Met Ile Leu Asn
        35                  40

<210> SEQ ID NO 23

<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 23

Thr Gln Lys Ser Leu Ser Leu Ser Ser Thr Lys Lys Thr Gln Leu
1               5                   10                  15

Gln Leu Glu His Leu Leu Leu Asp Leu Gln Met Ile Leu Asn
            20                  25                  30

<210> SEQ ID NO 24
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 24

Thr Gln Lys Ser Leu Ser Leu Ser Thr Lys Lys Thr Gln Leu Gln
1               5                   10                  15

Leu Glu His Leu Leu Leu Asp Leu Gln Met Ile Leu Asn
            20                  25

<210> SEQ ID NO 25
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 25

Thr Gln Lys Ser Leu Ser Leu Ser Thr Lys Lys Thr Gln Leu Gln Leu
1               5                   10                  15

Glu His Leu Leu Leu Asp Leu Gln Met Ile Leu Asn
            20                  25

<210> SEQ ID NO 26
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 26

Thr Gln Lys Ser Leu Ser Leu Ser Lys Lys Thr Gln Leu Gln Leu Glu
1               5                   10                  15

His Leu Leu Leu Asp Leu Gln Met Ile Leu Asn
            20                  25

<210> SEQ ID NO 27
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 27

Thr Gln Lys Ser Leu Ser Leu Ser Lys Thr Gln Leu Gln Leu Glu His
1               5                   10                  15

Leu Leu Leu Asp Leu Gln Met Ile Leu Asn
            20                  25

```
<210> SEQ ID NO 28
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 28

Thr Gln Lys Ser Leu Ser Leu Ser Thr Gln Leu Gln Leu Glu His Leu
1               5                   10                  15

Leu Leu Asp Leu Gln Met Ile Leu Asn
            20                  25

<210> SEQ ID NO 29
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 29

Thr Gln Lys Ser Leu Ser Leu Ser Gln Leu Gln Leu Glu His Leu Leu
1               5                   10                  15

Leu Asp Leu Gln Met Ile Leu Asn
            20

<210> SEQ ID NO 30
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 30

Thr Gln Lys Ser Leu Ser Leu Gln Leu Gln Leu Glu His Leu Leu Leu
1               5                   10                  15

Asp Leu Gln Met Ile Leu Asn
            20

<210> SEQ ID NO 31
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 31

Thr Gln Lys Ser Leu Ser Leu Ser Pro Gly Lys Gly Gly Gly Gly Ser
1               5                   10                  15

Ala Pro Thr Ser Ser Ser Thr Lys Lys Thr Gln Leu Gln
            20                  25

<210> SEQ ID NO 32
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 32

Thr Gln Lys Ser Leu Ser Leu Ser Pro Gly Gly Gly Gly Ser Ala
1               5                   10                  15

Pro Thr Ser Ser Ser Thr Lys Lys Thr Gln Leu Gln
            20                  25
```

<210> SEQ ID NO 33
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 33

Thr Gln Lys Ser Leu Ser Leu Ser Pro Gly Ala Ala Pro Thr Ser Ser
1               5                   10                  15

Ser Thr Lys Lys Thr Gln Leu Gln
            20

<210> SEQ ID NO 34
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 34

Thr Gln Lys Ser Leu Ser Leu Ser Pro Gly Ala Ala Pro Ala Ser Ser
1               5                   10                  15

Ser Thr Lys Lys Thr Gln Leu Gln
            20

<210> SEQ ID NO 35
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 35

Thr Gln Lys Ser Leu Ser Leu Ser Pro Gly Gly Gly Gly Gly Ser Ala
1               5                   10                  15

Pro Asn Ser Ser Ser Thr Lys Lys Thr Gln Leu Gln
            20                  25

<210> SEQ ID NO 36
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 36

Thr Gln Lys Ser Leu Ser Leu Ser Pro Gly Gly Gly Gly Gly Ser Ala
1               5                   10                  15

Pro Asn Ser Thr Ser Thr Lys Lys Thr Gln Leu Gln
            20                  25

<210> SEQ ID NO 37
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 37

Thr Gln Lys Ser Leu Ser Leu Ser Pro Gly Gly Gly Asn Gly Thr Ala
1               5                   10                  15

Pro Ala Ser Ser Ser Thr Lys Lys Thr Gln Leu Gln
            20                  25

<210> SEQ ID NO 38
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 38

```
Thr Gln Lys Ser Leu Ser Leu Ser Pro Gly Tyr Gly Asn Gly Thr Ala
1               5                   10                  15

Pro Ala Ser Ser Ser Thr Lys Lys Thr Gln Leu Gln
            20                  25
```

<210> SEQ ID NO 39
<211> LENGTH: 386
<212> TYPE: PRT
<213> ORGANISM: Artificial Sequence
<220> FEATURE:
<223> OTHER INFORMATION: Synthetic polypeptide

<400> SEQUENCE: 39

```
Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Gly Ser Thr Tyr Arg Val Val Ser Val Leu Thr Val Leu His
        100                 105                 110

Gln Asp Trp Leu Asn Gly Lys Glu Tyr Lys Cys Lys Val Ser Asn Lys
    115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
            165                 170                 175

Ser Asp Ile Ala Val Glu Trp Glu Ser Asn Gly Gln Pro Glu Asn Asn
        180                 185                 190

Tyr Lys Thr Thr Pro Pro Val Leu Asp Ser Asp Gly Ser Phe Phe Leu
    195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250                 255

Ser Ser Ser Thr Lys Lys Thr Gln Gly Gln Leu Glu His Leu Leu Leu
        260                 265                 270

Asp Leu Gln Met Ile Leu Asn Gly Ile Asn Asn Tyr Lys Asn Pro Lys
```

```
            275                 280                 285
Leu Thr Arg Met Leu Thr Phe Lys Phe Tyr Met Pro Lys Lys Ala Thr
    290                 295                 300
Glu Leu Lys His Leu Gln Cys Leu Glu Glu Leu Lys Pro Leu Glu
305                 310                 315                 320
Glu Val Leu Asn Leu Ala Gln Ser Lys Asn Phe His Leu Arg Pro Arg
                325                 330                 335
Asp Leu Ile Ser Asn Ile Asn Val Ile Val Leu Glu Leu Lys Gly Ser
                340                 345                 350
Glu Thr Thr Phe Met Cys Glu Tyr Ala Asp Glu Thr Ala Thr Ile Val
                355                 360                 365
Glu Phe Leu Asn Arg Trp Ile Thr Phe Ala Gln Ser Ile Ile Ser Thr
                370                 375                 380
Leu Thr
385

<210> SEQ ID NO 40
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 40

Met Asp Met Arg Val Pro Ala Gln Leu Leu Gly Leu Leu Leu Leu Trp
1               5                   10                  15
Leu Arg Gly Ala Arg Cys Asp Lys Thr His Thr Cys Pro Pro Cys Pro
                20                  25                  30
Ala Pro Glu Leu Leu Gly Gly Pro Ser Val Phe Leu Phe Pro Pro Lys
            35                  40                  45
Pro Lys Asp Thr Leu Met Ile Ser Arg Thr Pro Glu Val Thr Cys Val
    50                  55                  60
Val Val Asp Val Ser His Glu Asp Pro Glu Val Lys Phe Asn Trp Tyr
65                  70                  75                  80
Val Asp Gly Val Glu Val His Asn Ala Lys Thr Lys Pro Arg Glu Glu
                85                  90                  95
Gln Tyr Gly Ser Thr Tyr Arg Val Val Ser Val Leu Thr Val Leu His
            100                 105                 110
Gln Asp Trp Leu Asn Gly Lys Glu Tyr Lys Cys Lys Val Ser Asn Lys
        115                 120                 125
Ala Leu Pro Ala Pro Ile Glu Lys Thr Ile Ser Lys Ala Lys Gly Gln
    130                 135                 140
Pro Arg Glu Pro Gln Val Tyr Thr Leu Pro Pro Ser Arg Glu Glu Met
145                 150                 155                 160
Thr Lys Asn Gln Val Ser Leu Thr Cys Leu Val Lys Gly Phe Tyr Pro
                165                 170                 175
Ser Asp Ile Ala Val Glu Trp Glu Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Tyr Ser Lys Leu Thr Val Asp Lys Ser Arg Trp Gln Gln Gly Asn Val
    210                 215                 220
Phe Ser Cys Ser Val Met His Glu Ala Leu His Asn His Tyr Thr Gln
225                 230                 235                 240
Lys Ser Leu Ser Leu Ser Pro Gly Gly Gly Gly Gly Ser Ala Pro Thr
```

```
            245                 250                 255
Ser Ser Ser Thr Lys Thr Gln Lys Gln Leu Glu His Leu Leu Leu
        260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
    370                 375                 380

Leu Thr
385

<210> SEQ ID NO 41
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 41

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
```

```
            210                 215                 220
Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250                 255

Ser Ser Ser Thr Lys Lys Thr Gln Gln Gln Leu Glu His Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
370                 375                 380

Leu Thr
385

<210> SEQ ID NO 42
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 42

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
```

```
                180             185                 190
Tyr Lys Thr Thr Pro Val Leu Asp Ser Asp Gly Ser Phe Phe Leu
            195                 200             205

Tyr Ser Lys Leu Thr Val Asp Lys Ser Arg Trp Gln Gln Gly Asn Val
        210                 215             220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250             255

Ser Ser Ser Thr Lys Lys Thr Gln Ser Gln Leu Glu His Leu Leu Leu
            260                 265             270

Asp Leu Gln Met Ile Leu Asn Gly Ile Asn Asn Tyr Lys Asn Pro Lys
            275                 280             285

Leu Thr Arg Met Leu Thr Phe Lys Phe Tyr Met Pro Lys Lys Ala Thr
            290                 295             300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345             350

Glu Thr Thr Phe Met Cys Glu Tyr Ala Asp Glu Thr Ala Thr Ile Val
            355                 360             365

Glu Phe Leu Asn Arg Trp Ile Thr Phe Ala Gln Ser Ile Ile Ser Thr
            370                 375             380

Leu Thr
385

<210> SEQ ID NO 43
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 43

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
```

```
            145                 150                 155                 160
        Thr Lys Asn Gln Val Ser Leu Thr Cys Leu Val Lys Gly Phe Tyr Pro
                        165                 170                 175

Ser Asp Ile Ala Val Glu Trp Glu Ser Asn Gly Gln Pro Glu Asn Asn
                        180                 185                 190

Tyr Lys Thr Thr Pro Pro Val Leu Asp Ser Asp Gly Ser Phe Phe Leu
                        195                 200                 205

Tyr Ser Lys Leu Thr Val Asp Lys Ser Arg Trp Gln Gln Gly Asn Val
        210                 215                 220

Phe Ser Cys Ser Val Met His Glu Ala Leu His Asn His Tyr Thr Gln
        225                 230                 235                 240

Lys Ser Leu Ser Leu Ser Pro Gly Gly Gly Gly Ser Ala Pro Thr
                        245                 250                 255

Ser Ser Ser Thr Lys Lys Thr Gln Leu Gly Leu Glu His Leu Leu
                        260                 265                 270

Asp Leu Gln Met Ile Leu Asn Gly Ile Asn Asn Tyr Lys Asn Pro Lys
                        275                 280                 285

Leu Thr Arg Met Leu Thr Phe Lys Phe Tyr Met Pro Lys Lys Ala Thr
        290                 295                 300

Glu Leu Lys His Leu Gln Cys Leu Glu Glu Glu Leu Lys Pro Leu Glu
        305                 310                 315                 320

Glu Val Leu Asn Leu Ala Gln Ser Lys Asn Phe His Leu Arg Pro Arg
                        325                 330                 335

Asp Leu Ile Ser Asn Ile Asn Val Ile Val Leu Glu Leu Lys Gly Ser
                        340                 345                 350

Glu Thr Thr Phe Met Cys Glu Tyr Ala Asp Glu Thr Ala Thr Ile Val
                        355                 360                 365

Glu Phe Leu Asn Arg Trp Ile Thr Phe Ala Gln Ser Ile Ile Ser Thr
                        370                 375                 380

Leu Thr
        385

<210> SEQ ID NO 44
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 44

Met Asp Met Arg Val Pro Ala Gln Leu Leu Gly Leu Leu Leu Leu Trp
        1               5                   10                  15

Leu Arg Gly Ala Arg Cys Asp Lys Thr His Thr Cys Pro Pro Cys Pro
                        20                  25                  30

Ala Pro Glu Leu Leu Gly Gly Pro Ser Val Phe Leu Phe Pro Pro Lys
                        35                  40                  45

Pro Lys Asp Thr Leu Met Ile Ser Arg Thr Pro Glu Val Thr Cys Val
                        50                  55                  60

Val Val Asp Val Ser His Glu Asp Pro Glu Val Lys Phe Asn Trp Tyr
        65                  70                  75                  80

Val Asp Gly Val Glu Val His Asn Ala Lys Thr Lys Pro Arg Glu Glu
                        85                  90                  95

Gln Tyr Gly Ser Thr Tyr Arg Val Val Ser Val Leu Thr Val Leu His
                        100                 105                 110

Gln Asp Trp Leu Asn Gly Lys Glu Tyr Lys Cys Lys Val Ser Asn Lys
```

```
            115                 120                 125
Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Ala His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 45
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 45

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
```

85                  90                  95
Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Gly His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 46
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 46

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val

```
            50                  55                  60
Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
            210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Ser His Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
            290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
            370                 375                 380

Leu Thr
385

<210> SEQ ID NO 47
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 47

Met Asp Met Arg Val Pro Ala Gln Leu Leu Gly Leu Leu Leu Leu Trp
 1               5                  10                  15

Leu Arg Gly Ala Arg Cys Asp Lys Thr His Thr Cys Pro Pro Cys Pro
```

20                  25                  30
Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
            210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu Ala Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
            290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
            370                 375                 380

Leu Thr
385

<210> SEQ ID NO 48
<211> LENGTH: 386
<212> TYPE: PRT
<213> ORGANISM: Artificial Sequence
<220> FEATURE:
<223> OTHER INFORMATION: synthetic polypeptide

```
<400> SEQUENCE: 48

Met Asp Met Arg Val Pro Ala Gln Leu Leu Gly Leu Leu Leu Trp
1               5                   10                  15

Leu Arg Gly Ala Arg Cys Asp Lys Thr His Thr Cys Pro Pro Cys
            20                  25                  30

Pro Ala Pro Glu Leu Leu Gly Gly Pro Ser Val Phe Leu Phe Pro
                35                  40                  45

Pro Lys Pro Lys Asp Thr Leu Met Ile Ser Arg Thr Pro Glu Val
            50                  55                  60

Thr Cys Val Val Val Asp Val Ser His Glu Asp Pro Glu Val Lys
65                  70                  75

Phe Asn Trp Tyr Val Asp Gly Val Glu Val His Asn Ala Lys Thr
                80                  85                  90

Lys Pro Arg Glu Glu Gln Tyr Gly Ser Thr Tyr Arg Val Val Ser
                95                  100                 105

Val Leu Thr Val Leu His Gln Asp Trp Leu Asn Gly Lys Glu Tyr
                    110                 115                 120

Lys Cys Lys Val Ser Asn Lys Ala Leu Pro Ala Pro Ile Glu Lys
                125                 130                 135

Thr Ile Ser Lys Ala Lys Gly Gln Pro Arg Glu Pro Gln Val Tyr
                140                 145                 150

Thr Leu Pro Pro Ser Arg Glu Glu Met Thr Lys Asn Gln Val Ser
                155                 160

Leu Thr Cys Leu Val Lys Gly Phe Tyr Pro Ser Asp Ile Ala Val
            165                 170                 175

Glu Trp Glu Ser Asn Gly Gln Pro Glu Asn Asn Tyr Lys Thr Thr
                180                 185                 190

Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser
                210                 215                 220

Cys Ser Val Met His Glu Ala Leu His Asn His Tyr Thr Gln Lys
225                 230                 235                 240

Ser Leu Ser Leu Ser Pro Gly Gly Gly Gly Ser Ala Pro Thr Ser
            245                 250                 255

Ser Ser Thr Lys Lys Thr Gln Leu Gln Leu Glu Asp Leu Leu Leu
            260                 265                 270

Asp Leu Gln Met Ile Leu Asn Gly Ile Asn Asn Tyr Lys Asn Pro
            275                 280                 285

Lys Leu Thr Arg Met Leu Thr Phe Lys Phe Tyr Met Pro Lys Lys
                290                 295                 300

Ala Thr Glu Leu Lys His Leu Gln Cys Leu Glu Glu Glu Leu Lys
305                 310                 315                 320

Pro Leu Glu Glu Val Leu Asn Leu Ala Gln Ser Lys Asn Phe His
                    325                 330

Leu Arg Pro Arg Asp Leu Ile Ser Asn Ile Asn Val Ile Val Leu
            335                 340                 345

Glu Leu Lys Gly Ser Glu Thr Thr Phe Met Cys Glu Tyr Ala Asp
                350                 355                 360

Glu Thr Ala Thr Ile Val Glu Phe Leu Asn Arg Trp Ile Thr Phe
                365                 370                 375

Ala Gln Ser Ile Ile Ser Thr Leu Thr
                380                 385

<210> SEQ ID NO 49
```

<211> LENGTH: 386
<212> TYPE: PRT
<213> ORGANISM: Artificial Sequence
<220> FEATURE:
<223> OTHER INFORMATION: synthetic polypeptide

<400> SEQUENCE: 49

```
Met Asp Met Arg Val Pro Ala Gln Leu Leu Gly Leu Leu Leu Leu Trp
1               5                   10                  15
Leu Arg Gly Ala Arg Cys Asp Lys Thr His Thr Cys Pro Pro Cys Pro
            20                  25                  30
Ala Pro Glu Leu Leu Gly Gly Pro Ser Val Phe Leu Phe Pro Pro Lys
        35                  40                  45
Pro Lys Asp Thr Leu Met Ile Ser Arg Thr Pro Glu Val Thr Cys Val
    50                  55                  60
Val Val Asp Val Ser His Glu Asp Pro Glu Val Lys Phe Asn Trp Tyr
65                  70                  75                  80
Val Asp Gly Val Glu Val His Asn Ala Lys Thr Lys Pro Arg Glu Glu
                85                  90                  95
Gln Tyr Gly Ser Thr Tyr Arg Val Val Ser Val Leu Thr Val Leu His
            100                 105                 110
Gln Asp Trp Leu Asn Gly Lys Glu Tyr Lys Cys Lys Val Ser Asn Lys
        115                 120                 125
Ala Leu Pro Ala Pro Ile Glu Lys Thr Ile Ser Lys Ala Lys Gly Gln
    130                 135                 140
Pro Arg Glu Pro Gln Val Tyr Thr Leu Pro Pro Ser Arg Glu Glu Met
145                 150                 155                 160
Thr Lys Asn Gln Val Ser Leu Thr Cys Leu Val Lys Gly Phe Tyr Pro
                165                 170                 175
Ser Asp Ile Ala Val Glu Trp Glu Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Tyr Ser Lys Leu Thr Val Asp Lys Ser Arg Trp Gln Gln Gly Asn Val
    210                 215                 220
Phe Ser Cys Ser Val Met His Glu Ala Leu His Asn His Tyr Thr Gln
225                 230                 235                 240
Lys Ser Leu Ser Leu Ser Pro Gly Gly Gly Gly Ser Ala Pro Thr
                245                 250                 255
Ser Ser Ser Thr Lys Lys Thr Gln Leu Gln Leu Glu Gly Leu Leu Leu
            260                 265                 270
Asp Leu Gln Met Ile Leu Asn Gly Ile Asn Asn Tyr Lys Asn Pro Lys
        275                 280                 285
Leu Thr Arg Met Leu Thr Phe Lys Phe Tyr Met Pro Lys Lys Ala Thr
    290                 295                 300
Glu Leu Lys His Leu Gln Cys Leu Glu Glu Glu Leu Lys Pro Leu Glu
305                 310                 315                 320
Glu Val Leu Asn Leu Ala Gln Ser Lys Asn Phe His Leu Arg Pro Arg
                325                 330                 335
Asp Leu Ile Ser Asn Ile Asn Val Ile Val Leu Glu Leu Lys Gly Ser
            340                 345                 350
Glu Thr Thr Phe Met Cys Glu Tyr Ala Asp Glu Thr Ala Thr Ile Val
        355                 360                 365
Glu Phe Leu Asn Arg Trp Ile Thr Phe Ala Gln Ser Ile Ile Ser Thr
    370                 375                 380
```

Leu Thr
385

<210> SEQ ID NO 50
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 50

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu Lys Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

```
Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
370                 375                 380

Leu Thr
385

<210> SEQ ID NO 51
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 51

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu Met Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320
```

```
Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
370                 375                 380

Leu Thr
385

<210> SEQ ID NO 52
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 52

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu Asn Leu Leu Leu
            260                 265                 270

Asp Leu Gln Met Ile Leu Asn Gly Ile Asn Asn Tyr Lys Asn Pro Lys
        275                 280                 285
```

```
Leu Thr Arg Met Leu Thr Phe Lys Phe Tyr Met Pro Lys Lys Ala Thr
            290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
        370                 375                 380

Leu Thr
385

<210> SEQ ID NO 53
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 53

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255
```

```
Ser Ser Ser Thr Lys Lys Thr Gln Leu Gln Leu Glu Arg Leu Leu Leu
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
            290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
            370                 375                 380

Leu Thr
385

<210> SEQ ID NO 54
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 54

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
            165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
            210                 215                 220
```

```
Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250                 255

Ser Ser Ser Thr Lys Lys Thr Gln Leu Gln Leu Glu Ser Leu Leu Leu
        260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
370                 375                 380

Leu Thr
385

<210> SEQ ID NO 55
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 55

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190
```

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu Thr Leu Leu Leu
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
            290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
            370                 375                 380

Leu Thr
385

<210> SEQ ID NO 56
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 56

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Glu Glu Met
145                 150                 155                 160

```
Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu Val Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
            325                 330                 335

Asp Leu Ile Ser Asn Ile Asn Val Ile Val Leu Glu Leu Lys Gly Ser
        340                 345                 350

Glu Thr Thr Phe Met Cys Glu Tyr Ala Asp Glu Thr Ala Thr Ile Val
    355                 360                 365

Glu Phe Leu Asn Arg Trp Ile Thr Phe Ala Gln Ser Ile Ile Ser Thr
370                 375                 380

Leu Thr
385

<210> SEQ ID NO 57
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 57

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Gly Ser Thr Tyr Arg Val Val Ser Val Leu Thr Val Leu His
        100                 105                 110

Gln Asp Trp Leu Asn Gly Lys Glu Tyr Lys Cys Lys Val Ser Asn Lys
    115                 120                 125
```

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu Tyr Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 58
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 58

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Ala
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
370                 375                 380

Leu Thr
385

<210> SEQ ID NO 59
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 59

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Asp
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
            370                 375                 380

Leu Thr
385

<210> SEQ ID NO 60
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 60

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Glu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
370                 375                 380

Leu Thr
385

<210> SEQ ID NO 61
<211> LENGTH: 386
<212> TYPE: PRT
<213> ORGANISM: Artificial Sequence
<220> FEATURE:
<223> OTHER INFORMATION: synthetic polypeptides

<400> SEQUENCE: 61

```
Met Asp Met Arg Val Pro Ala Gln Leu Leu Gly Leu Leu Leu Trp
1               5                   10                  15

Leu Arg Gly Ala Arg Cys Asp Lys Thr His Thr Cys Pro Cys Pro
                20                  25                  30

Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Gly
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
    370                 375                 380

Leu Thr
385

<210> SEQ ID NO 62
<211> LENGTH: 386
```

```
<212> TYPE: PRT
<213> ORGANISM: Artificial Sequence
<220> FEATURE:
<223> OTHER INFORMATION: synthetic polypeptide

<400> SEQUENCE: 62
```

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Gly Ser Thr Tyr Arg Val Val Ser Val Leu Thr Val Leu His
        100                 105                 110

Gln Asp Trp Leu Asn Gly Lys Glu Tyr Lys Cys Lys Val Ser Asn Lys
    115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
            165                 170                 175

Ser Asp Ile Ala Val Glu Trp Glu Ser Asn Gly Gln Pro Glu Asn Asn
        180                 185                 190

Tyr Lys Thr Thr Pro Pro Val Leu Asp Ser Asp Gly Ser Phe Phe Leu
    195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250                 255

Ser Ser Ser Thr Lys Lys Thr Gln Leu Gln Leu Glu His Leu Leu Asn
        260                 265                 270

Asp Leu Gln Met Ile Leu Asn Gly Ile Asn Asn Tyr Lys Asn Pro Lys
    275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
            325                 330                 335

Asp Leu Ile Ser Asn Ile Asn Val Ile Val Leu Glu Leu Lys Gly Ser
        340                 345                 350

Glu Thr Thr Phe Met Cys Glu Tyr Ala Asp Glu Thr Ala Thr Ile Val
    355                 360                 365

Glu Phe Leu Asn Arg Trp Ile Thr Phe Ala Gln Ser Ile Ile Ser Thr
370                 375                 380

Leu Thr
385

<210> SEQ ID NO 63
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 63

Met Asp Met Arg Val Pro Ala Gln Leu Leu Gly Leu Leu Leu Trp
1               5                   10                  15

Leu Arg Gly Ala Arg Cys Asp Lys Thr His Thr Cys Pro Pro Cys
                20                  25                  30

Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Arg
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

```
Glu Thr Thr Phe Met Cys Glu Tyr Ala Asp Glu Thr Thr Ile Val
        355                 360                 365

Glu Phe Leu Asn Arg Trp Ile Thr Phe Ala Gln Ser Ile Ile Ser Thr
370                 375                 380

Leu Thr
385

<210> SEQ ID NO 64
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 64

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Ser
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320
```

```
Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
370                 375                 380

Leu Thr
385

<210> SEQ ID NO 65
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 65

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Thr
            260                 265                 270

Asp Leu Gln Met Ile Leu Asn Gly Ile Asn Asn Tyr Lys Asn Pro Lys
        275                 280                 285
```

```
Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
370                 375                 380

Leu Thr
385

<210> SEQ ID NO 66
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 66

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255
```

```
Ser Ser Ser Thr Lys Lys Thr Gln Leu Gln Leu Glu His Leu Leu Val
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 67
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 67

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220
```

```
Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250                 255

Ser Ser Ser Thr Lys Lys Thr Gln Leu Gln Leu Glu His Leu Leu Leu
        260                 265                 270

Ala Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
370                 375                 380

Leu Thr
385

<210> SEQ ID NO 68
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 68

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190
```

Tyr Lys Thr Thr Pro Pro Val Leu Asp Ser Asp Gly Ser Phe Phe Leu
         195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Glu Leu Gln Met Ile Leu Asn Gly Ile Asn Asn Tyr Lys Asn Pro Lys
                275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
                370                 375                 380

Leu Thr
385

<210> SEQ ID NO 69
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 69

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
                130                 135                 140

Pro Arg Glu Pro Gln Val Tyr Thr Leu Pro Pro Ser Arg Glu Glu Met
145                 150                 155                 160

```
Thr Lys Asn Gln Val Ser Leu Thr Cys Leu Val Lys Gly Phe Tyr Pro
                165                 170                 175
Ser Asp Ile Ala Val Glu Trp Glu Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Tyr Ser Lys Leu Thr Val Asp Lys Ser Arg Trp Gln Gln Gly Asn Val
    210                 215                 220
Phe Ser Cys Ser Val Met His Glu Ala Leu His Asn His Tyr Thr Gln
225                 230                 235                 240
Lys Ser Leu Ser Leu Ser Pro Gly Gly Gly Gly Ser Ala Pro Thr
                245                 250                 255
Ser Ser Ser Thr Lys Lys Thr Gln Leu Gln Leu Glu His Leu Leu Leu
            260                 265                 270
Phe Leu Gln Met Ile Leu Asn Gly Ile Asn Asn Tyr Lys Asn Pro Lys
        275                 280                 285
Leu Thr Arg Met Leu Thr Phe Lys Phe Tyr Met Pro Lys Lys Ala Thr
    290                 295                 300
Glu Leu Lys His Leu Gln Cys Leu Glu Glu Glu Leu Lys Pro Leu Glu
305                 310                 315                 320
Glu Val Leu Asn Leu Ala Gln Ser Lys Asn Phe His Leu Arg Pro Arg
                325                 330                 335
Asp Leu Ile Ser Asn Ile Asn Val Ile Val Leu Glu Leu Lys Gly Ser
            340                 345                 350
Glu Thr Thr Phe Met Cys Glu Tyr Ala Asp Glu Thr Ala Thr Ile Val
        355                 360                 365
Glu Phe Leu Asn Arg Trp Ile Thr Phe Ala Gln Ser Ile Ile Ser Thr
    370                 375                 380
Leu Thr
385

<210> SEQ ID NO 70
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 70

Met Asp Met Arg Val Pro Ala Gln Leu Leu Gly Leu Leu Leu Leu Trp
1               5                   10                  15
Leu Arg Gly Ala Arg Cys Asp Lys Thr His Thr Cys Pro Pro Cys Pro
            20                  25                  30
Ala Pro Glu Leu Leu Gly Gly Pro Ser Val Phe Leu Phe Pro Pro Lys
        35                  40                  45
Pro Lys Asp Thr Leu Met Ile Ser Arg Thr Pro Glu Val Thr Cys Val
    50                  55                  60
Val Val Asp Val Ser His Glu Asp Pro Glu Val Lys Phe Asn Trp Tyr
65                  70                  75                  80
Val Asp Gly Val Glu Val His Asn Ala Lys Thr Lys Pro Arg Glu Glu
                85                  90                  95
Gln Tyr Gly Ser Thr Tyr Arg Val Val Ser Val Leu Thr Val Leu His
            100                 105                 110
Gln Asp Trp Leu Asn Gly Lys Glu Tyr Lys Cys Lys Val Ser Asn Lys
        115                 120                 125
```

```
Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu
            260                 265                 270

Gly Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 71
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 71

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95
```

```
Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Trp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
370                 375                 380

Leu Thr
385

<210> SEQ ID NO 72
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 72

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60
```

```
Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Arg Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
        340                 345                 350

Glu Thr Thr Phe Met Cys Glu Tyr Ala Asp Glu Thr Ala Thr Ile Val
    355                 360                 365

Glu Phe Leu Asn Arg Trp Ile Thr Phe Ala Gln Ser Ile Ile Ser Thr
370                 375                 380

Leu Thr
385

<210> SEQ ID NO 73
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 73

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30
```

Ala Pro Glu Leu Leu Gly Gly Pro Ser Val Phe Leu Phe Pro Pro Lys
35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Ala Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
370                 375                 380

Leu Thr
385

<210> SEQ ID NO 74
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 74

```
Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Gly Ser Thr Tyr Arg Val Val Ser Val Leu Thr Val Leu His
        100                 105                 110

Gln Asp Trp Leu Asn Gly Lys Glu Tyr Lys Cys Lys Val Ser Asn Lys
    115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
            165                 170                 175

Ser Asp Ile Ala Val Glu Trp Glu Ser Asn Gly Gln Pro Glu Asn Asn
        180                 185                 190

Tyr Lys Thr Thr Pro Pro Val Leu Asp Ser Asp Gly Ser Phe Phe Leu
    195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250                 255

Ser Ser Ser Thr Lys Lys Thr Gln Leu Gln Leu Glu His Leu Leu Leu
        260                 265                 270

Asp Leu Gln Met Ile Leu Asn Gly Ile Asn Asn Tyr Lys Asn Pro Lys
    275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Gly Pro Arg
            325                 330                 335

Asp Leu Ile Ser Asn Ile Asn Val Ile Val Leu Glu Leu Lys Gly Ser
        340                 345                 350

Glu Thr Thr Phe Met Cys Glu Tyr Ala Asp Glu Thr Ala Thr Ile Val
    355                 360                 365

Glu Phe Leu Asn Arg Trp Ile Thr Phe Ala Gln Ser Ile Ile Ser Thr
370                 375                 380

Leu Thr
385

<210> SEQ ID NO 75
<211> LENGTH: 386
<212> TYPE: PRT
```

<213> ORGANISM: Artificial Sequence
<220> FEATURE:
<223> OTHER INFORMATION: synthetic polypeptide

<400> SEQUENCE: 75

```
Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Ser Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
```

```
<210> SEQ ID NO 76
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 76
```

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Thr Pro Arg
                325                 330                 335

Asp Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val

-continued

```
                355                 360                 365
Glu Phe Leu Asn Arg Trp Ile Thr Phe Ala Gln Ser Ile Ile Ser Thr
370                 375                 380

Leu Thr
385

<210> SEQ ID NO 77
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 77

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
```

```
                  325                 330                 335
Ala Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
        370                 375                 380

Leu Thr
385

<210> SEQ ID NO 78
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 78

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
```

```
                  290                 295                 300
Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Glu Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
                370                 375                 380

Leu Thr
385

<210> SEQ ID NO 79
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 79

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
                195                 200                 205

Tyr Ser Lys Leu Thr Val Asp Lys Ser Arg Trp Gln Gln Gly Asn Val
                210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
```

```
                   260                 265                 270
Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
        290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Gly Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 80
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 80

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
```

```
                   225                 230                 235                 240
Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
                275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Ile Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
                370                 375                 380

Leu Thr
385

<210> SEQ ID NO 81
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 81

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
                130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
```

```
              195                 200                 205
Tyr Ser Lys Leu Thr Val Asp Lys Ser Arg Trp Gln Gln Gly Asn Val
    210                 215                 220
Phe Ser Cys Ser Val Met His Glu Ala Leu His Asn His Tyr Thr Gln
225                 230                 235                 240
Lys Ser Leu Ser Leu Ser Pro Gly Gly Gly Gly Ser Ala Pro Thr
                245                 250                 255
Ser Ser Ser Thr Lys Lys Thr Gln Leu Gln Leu Glu His Leu Leu Leu
            260                 265                 270
Asp Leu Gln Met Ile Leu Asn Gly Ile Asn Asn Tyr Lys Asn Pro Lys
                275                 280                 285
Leu Thr Arg Met Leu Thr Phe Lys Phe Tyr Met Pro Lys Lys Ala Thr
            290                 295                 300
Glu Leu Lys His Leu Gln Cys Leu Glu Glu Leu Lys Pro Leu Glu
305                 310                 315                 320
Glu Val Leu Asn Leu Ala Gln Ser Lys Asn Phe His Leu Arg Pro Arg
                325                 330                 335
Met Leu Ile Ser Asn Ile Asn Val Ile Val Leu Glu Leu Lys Gly Ser
            340                 345                 350
Glu Thr Thr Phe Met Cys Glu Tyr Ala Asp Glu Thr Ala Thr Ile Val
                355                 360                 365
Glu Phe Leu Asn Arg Trp Ile Thr Phe Ala Gln Ser Ile Ile Ser Thr
370                 375                 380
Leu Thr
385

<210> SEQ ID NO 82
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 82

Met Asp Met Arg Val Pro Ala Gln Leu Leu Gly Leu Leu Leu Leu Trp
1               5                   10                  15
Leu Arg Gly Ala Arg Cys Asp Lys Thr His Thr Cys Pro Pro Cys Pro
            20                  25                  30
Ala Pro Glu Leu Leu Gly Gly Pro Ser Val Phe Leu Phe Pro Pro Lys
        35                  40                  45
Pro Lys Asp Thr Leu Met Ile Ser Arg Thr Pro Glu Val Thr Cys Val
    50                  55                  60
Val Val Asp Val Ser His Glu Asp Pro Glu Val Lys Phe Asn Trp Tyr
65                  70                  75                  80
Val Asp Gly Val Glu Val His Asn Ala Lys Thr Lys Pro Arg Glu Glu
                85                  90                  95
Gln Tyr Gly Ser Thr Tyr Arg Val Val Ser Val Leu Thr Val Leu His
            100                 105                 110
Gln Asp Trp Leu Asn Gly Lys Glu Tyr Lys Cys Lys Val Ser Asn Lys
        115                 120                 125
Ala Leu Pro Ala Pro Ile Glu Lys Thr Ile Ser Lys Ala Lys Gly Gln
    130                 135                 140
Pro Arg Glu Pro Gln Val Tyr Thr Leu Pro Pro Ser Arg Glu Glu Met
145                 150                 155                 160
Thr Lys Asn Gln Val Ser Leu Thr Cys Leu Val Lys Gly Phe Tyr Pro
```

```
                165                 170                 175
Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
            210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
                275                 280                 285

Leu Thr Arg Met Leu Thr Phe Lys Phe Tyr Met Pro Lys Lys Ala Thr
                290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Gln Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
                370                 375                 380

Leu Thr
385

<210> SEQ ID NO 83
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 83

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
```

```
                    130                 135                 140
Pro Arg Glu Pro Gln Val Tyr Thr Leu Pro Pro Ser Arg Glu Met
145                 150                 155                 160

Thr Lys Asn Gln Val Ser Leu Thr Cys Leu Val Lys Gly Phe Tyr Pro
                    165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
        210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                    245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
        290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                    325                 330                 335

Arg Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
        370                 375                 380

Leu Thr
385

<210> SEQ ID NO 84
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 84

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
```

```
                  100                 105                 110
Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
        290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Ser Leu Ile Ser Asn Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 85
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 85

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
```

```
                65                  70                  75                  80
Val Asp Gly Val Glu Val His Asn Ala Lys Thr Lys Pro Arg Glu Glu
                    85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
                195                 200                 205

Tyr Ser Lys Leu Thr Val Asp Lys Ser Arg Trp Gln Gln Gly Asn Val
            210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
            290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Thr Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
            370                 375                 380

Leu Thr
385

<210> SEQ ID NO 86
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 86

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
```

```
                    35                  40                  45
Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
                195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
                275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Arg Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
                370                 375                 380

Leu Thr
385

<210> SEQ ID NO 87
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 87

Met Asp Met Arg Val Pro Ala Gln Leu Leu Gly Leu Leu Leu Leu Trp
```

```
1               5                    10                   15
Leu Arg Gly Ala Arg Cys Asp Lys Thr His Thr Cys Pro Pro Cys Pro
            20                  25                  30
Ala Pro Glu Leu Leu Gly Gly Pro Ser Val Phe Leu Phe Pro Pro Lys
            35                  40                  45
Pro Lys Asp Thr Leu Met Ile Ser Arg Thr Pro Glu Val Thr Cys Val
50                      55                  60
Val Val Asp Val Ser His Glu Asp Pro Glu Val Lys Phe Asn Trp Tyr
65                      70                  75                  80
Val Asp Gly Val Glu Val His Asn Ala Lys Thr Lys Pro Arg Glu Glu
                85                  90                  95
Gln Tyr Gly Ser Thr Tyr Arg Val Val Ser Val Leu Thr Val Leu His
                100                 105                 110
Gln Asp Trp Leu Asn Gly Lys Glu Tyr Lys Cys Lys Val Ser Asn Lys
                115                 120                 125
Ala Leu Pro Ala Pro Ile Glu Lys Thr Ile Ser Lys Ala Lys Gly Gln
                130                 135                 140
Pro Arg Glu Pro Gln Val Tyr Thr Leu Pro Pro Ser Arg Glu Glu Met
145                 150                 155                 160
Thr Lys Asn Gln Val Ser Leu Thr Cys Leu Val Lys Gly Phe Tyr Pro
                165                 170                 175
Ser Asp Ile Ala Val Glu Trp Glu Ser Asn Gly Gln Pro Glu Asn Asn
                180                 185                 190
Tyr Lys Thr Thr Pro Pro Val Leu Asp Ser Asp Gly Ser Phe Phe Leu
                195                 200                 205
Tyr Ser Lys Leu Thr Val Asp Lys Ser Arg Trp Gln Gln Gly Asn Val
210                 215                 220
Phe Ser Cys Ser Val Met His Glu Ala Leu His Asn His Tyr Thr Gln
225                 230                 235                 240
Lys Ser Leu Ser Leu Ser Pro Gly Gly Gly Gly Ser Ala Pro Thr
                245                 250                 255
Ser Ser Ser Thr Lys Lys Thr Gln Leu Gln Leu Glu His Leu Leu Leu
                260                 265                 270
Asp Leu Gln Met Ile Leu Asn Gly Ile Asn Asn Tyr Lys Asn Pro Lys
                275                 280                 285
Leu Thr Arg Met Leu Thr Phe Lys Phe Tyr Met Pro Lys Lys Ala Thr
                290                 295                 300
Glu Leu Lys His Leu Gln Cys Leu Glu Glu Glu Leu Lys Pro Leu Glu
305                 310                 315                 320
Glu Val Leu Asn Leu Ala Gln Ser Lys Asn Phe His Leu Arg Pro Arg
                325                 330                 335
Asp Leu Ile Ser Ala Ile Asn Val Ile Val Leu Glu Leu Lys Gly Ser
                340                 345                 350
Glu Thr Thr Phe Met Cys Glu Tyr Ala Asp Glu Thr Ala Thr Ile Val
                355                 360                 365
Glu Phe Leu Asn Arg Trp Ile Thr Phe Ala Gln Ser Ile Ile Ser Thr
                370                 375                 380
Leu Thr
385

<210> SEQ ID NO 88
<211> LENGTH: 386
<212> TYPE: PRT
<213> ORGANISM: Artificial Sequence
```

```
<220> FEATURE:
<223> OTHER INFORMATION: synthetic polypeptide

<400> SEQUENCE: 88

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Glu Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385
```

<210> SEQ ID NO 89
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 89

```
Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Phe Ile Asn Val Ile Val Leu Glu Leu Lys Gly Ser
            340                 345                 350

Glu Thr Thr Phe Met Cys Glu Tyr Ala Asp Glu Thr Ala Thr Ile Val
        355                 360                 365
```

Glu Phe Leu Asn Arg Trp Ile Thr Phe Ala Gln Ser Ile Ile Ser Thr
            370                 375                 380

Leu Thr
385

<210> SEQ ID NO 90
<211> LENGTH: 386
<212> TYPE: PRT
<213> ORGANISM: Artificial Sequence
<220> FEATURE:
<223> OTHER INFORMATION: sythetic polypeptide

<400> SEQUENCE: 90

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Gly Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
370                 375                 380

Leu Thr
385

<210> SEQ ID NO 91
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 91

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
                195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
                275                 280                 285

Leu Thr Arg Met Leu Thr Phe Lys Phe Tyr Met Pro Lys Lys Ala Thr
                290                 295                 300

```
Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
            325                 330                 335

Asp Leu Ile Ser Met Ile Asn Val Ile Val Leu Glu Leu Lys Gly Ser
                340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
370                 375                 380

Leu Thr
385

<210> SEQ ID NO 92
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 92

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270
```

```
Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
            325                 330                 335

Asp Leu Ile Ser Ser Ile Asn Val Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
            370                 375                 380

Leu Thr
385

<210> SEQ ID NO 93
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 93

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240
```

```
Lys Ser Leu Ser Leu Ser Pro Gly Gly Gly Gly Ser Ala Pro Thr
            245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Val Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
            370                 375                 380

Leu Thr
385

<210> SEQ ID NO 94
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 94

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205
```

```
Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
                260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Trp Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Ala Gln Ser Ile Ile Ser Thr
370                 375                 380

Leu Thr
385

<210> SEQ ID NO 95
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 95

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175
```

```
Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
        290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Asp Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
        370                 375                 380

Leu Thr
385

<210> SEQ ID NO 96
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 96

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140
```

```
Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
            165                 170                 175

Ser Asp Ile Ala Val Glu Trp Glu Ser Asn Gly Gln Pro Glu Asn Asn
        180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
        210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
            245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
            290                 295                 300

Glu Leu Lys His Leu Gln Cys Leu Glu Glu Leu Lys Pro Leu Glu
305                 310                 315                 320

Glu Val Leu Asn Leu Ala Gln Ser Lys Asn Phe His Leu Arg Pro Arg
            325                 330                 335

Asp Leu Ile Ser Asn Ile Asn Glu Ile Val Leu Glu Leu Lys Gly Ser
            340                 345                 350

Glu Thr Thr Phe Met Cys Glu Tyr Ala Asp Glu Thr Ala Thr Ile Val
            355                 360                 365

Glu Phe Leu Asn Arg Trp Ile Thr Phe Ala Gln Ser Ile Ile Ser Thr
            370                 375                 380

Leu Thr
385

<210> SEQ ID NO 97
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 97

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110
```

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Gly Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 98
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 98

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Ser Ile Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 99
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 99

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

```
Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Lys Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 100
<211> LENGTH: 386
<212> TYPE: PRT
<213> ORGANISM: Artificial Sequence
<220> FEATURE:
<223> OTHER INFORMATION: synthetic polypeptide

<400> SEQUENCE: 100

Met Asp Met Arg Val Pro Ala Gln Leu Leu Gly Leu Leu Leu Leu Trp
1               5                   10                  15
```

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Gly Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Gly Gly Gly Ser Ala Pro Thr
                245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
        275                 280                 285

Leu Thr Arg Met Leu Thr Phe Lys Phe Tyr Met Pro Lys Lys Ala Thr
    290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Arg Val Leu Glu Leu Lys Gly Ser
            340                 345                 350

Glu Thr Thr Phe Met Cys Glu Tyr Ala Asp Glu Thr Ala Thr Ile Val
        355                 360                 365

Glu Phe Leu Asn Arg Trp Ile Thr Phe Ala Gln Ser Ile Ile Ser Thr
    370                 375                 380

Leu Thr
385

<210> SEQ ID NO 101
<211> LENGTH: 386
<212> TYPE: PRT
<213> ORGANISM: Artificial Sequence
<220> FEATURE:

<223> OTHER INFORMATION: synthetic polypeptide

<400> SEQUENCE: 101

```
Met Asp Met Arg Val Pro Ala Gln Leu Leu Gly Leu Leu Leu Leu Trp
1               5                   10                  15
Leu Arg Gly Ala Arg Cys Asp Lys Thr His Thr Cys Pro Pro Cys Pro
            20                  25                  30
Ala Pro Glu Leu Leu Gly Gly Pro Ser Val Phe Leu Phe Pro Pro Lys
        35                  40                  45
Pro Lys Asp Thr Leu Met Ile Ser Arg Thr Pro Glu Val Thr Cys Val
    50                  55                  60
Val Val Asp Val Ser His Glu Asp Pro Glu Val Lys Phe Asn Trp Tyr
65                  70                  75                  80
Val Asp Gly Val Glu Val His Asn Ala Lys Thr Lys Pro Arg Glu Glu
                85                  90                  95
Gln Tyr Gly Ser Thr Tyr Arg Val Val Ser Val Leu Thr Val Leu His
            100                 105                 110
Gln Asp Trp Leu Asn Gly Lys Glu Tyr Lys Cys Lys Val Ser Asn Lys
        115                 120                 125
Ala Leu Pro Ala Pro Ile Glu Lys Thr Ile Ser Lys Ala Lys Gly Gln
    130                 135                 140
Pro Arg Glu Pro Gln Val Tyr Thr Leu Pro Pro Ser Arg Glu Glu Met
145                 150                 155                 160
Thr Lys Asn Gln Val Ser Leu Thr Cys Leu Val Lys Gly Phe Tyr Pro
                165                 170                 175
Ser Asp Ile Ala Val Glu Trp Glu Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Tyr Ser Lys Leu Thr Val Asp Lys Ser Arg Trp Gln Gln Gly Asn Val
    210                 215                 220
Phe Ser Cys Ser Val Met His Glu Ala Leu His Asn His Tyr Thr Gln
225                 230                 235                 240
Lys Ser Leu Ser Leu Ser Pro Gly Gly Gly Gly Ser Ala Pro Thr
                245                 250                 255
Ser Ser Ser Thr Lys Lys Thr Gln Leu Gln Leu Glu His Leu Leu Leu
            260                 265                 270
Asp Leu Gln Met Ile Leu Asn Gly Ile Asn Asn Tyr Lys Asn Pro Lys
        275                 280                 285
Leu Thr Arg Met Leu Thr Phe Lys Phe Tyr Met Pro Lys Lys Ala Thr
    290                 295                 300
Glu Leu Lys His Leu Gln Cys Leu Glu Glu Glu Leu Lys Pro Leu Glu
305                 310                 315                 320
Glu Val Leu Asn Leu Ala Gln Ser Lys Asn Phe His Leu Arg Pro Arg
                325                 330                 335
Asp Leu Ile Ser Asn Ile Asn Val Ile Val Leu Glu Leu Lys Gly Ser
            340                 345                 350
Glu Thr Thr Phe Met Cys Glu Tyr Ala Asp Glu Thr Ala Thr Ile Val
        355                 360                 365
Glu Phe Leu Asn Arg Trp Ile Thr Phe Ala Gln Ser Ile Ile Ser Thr
    370                 375                 380
Leu Thr
385
```

<210> SEQ ID NO 102
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 102

```
atggacatga gagtgcctgc acagctgctg ggcctgctgc tgctgtggct gagaggcgcc      60
agatgcgaca aaactcacac atgcccaccg tgcccagcac ctgaactcct gggggaccg     120
tcagtcttcc tcttcccccc aaaacccaag gacacccctca tgatctcccg gacccctgag   180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga accacaggtg tacaccctgc ccccatcccg ggaggagatg   480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
gactccgacg gctccttctt cctctatagc aagctcaccg tggacaagag caggtggcag   660
caggggaacg tcttctcatg ctccgtgatg catgaggctc tgcacaacca ctacacgcag   720
aagagcctct ccctgtctcc gggtggaggt ggtggaagcg ctccaacttc ctcctccact   780
aagaagactc aagggcaatt ggagcacttg ttgttggact tgcaaatgat cttgaatggt   840
atcaataatt acaagaatcc aaagttgact cggatgttga cttttaagtt ttacatgcca   900
aagaaggcta ctgagttgaa gcacttgcaa tgtttggagg aggagttgaa gccattggag   960
gaggttttga atttggctca atccaagaat tttcacttgc ggccacggga cttgatctcc  1020
aatatcaatg tgatcgtttt ggagttgaag ggttccgaga ctactttat gtgtgagtac  1080
gctgacgaga ctgctactat cgttgagttt ttgaatcggt ggatcacttt tgctcaatcc  1140
atcatctcca ctttgact                                                1158
```

<210> SEQ ID NO 103
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 103

```
atggacatga gagtgcctgc acagctgctg ggcctgctgc tgctgtggct gagaggcgcc      60
agatgcgaca aaactcacac atgcccaccg tgcccagcac ctgaactcct gggggaccg     120
tcagtcttcc tcttcccccc aaaacccaag gacacccctca tgatctcccg gacccctgag   180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga accacaggtg tacaccctgc ccccatcccg ggaggagatg   480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
```

```
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aaaagcaatt ggagcacttg ttgttggact gcaaatgat cttgaatggt       840 atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
aatatcaatg tgatcgtttt ggagttgaag ggttccgaga ctactttat gtgtgagtac      1080 gctgacgaga ctgctactat cgttgagttt ttgaatcggt ggatcacttt tgctcaatcc     1140
atcatctcca ctttgact                                                   1158
```

<210> SEQ ID NO 104
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 104

```
atggacatga gagtgcctgc acagctgctg ggcctgctgc tgctgtggct gagaggcgcc       60
agatgcgaca aaactcacac atgcccaccg tgcccagcac ctgaactcct gggggggaccg     120 tcagtcttcc tcttccccc aaaacccaag gacaccctca tgatctcccg gacccctgag      180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420 gccaaaggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact    780
aagaagactc aacagcaatt ggagcacttg ttgttggact gcaaatgat cttgaatggt     840 atcaataatt acaagaatcc aaagttgact cggatgttga cttttaagtt ttacatgcca    900
aagaaggcta ctgagttgaa gcacttgcaa tgtttggagg aggagttgaa gccattggag   960
gaggttttga atttggctca atccaagaat tttcacttgc ggccacggga cttgatctcc  1020
aatatcaatg tgatcgtttt ggagttgaag ggttccgaga ctactttat gtgtgagtac    1080 gctgacgaga ctgctactat cgttgagttt ttgaatcggt ggatcacttt tgctcaatcc  1140
atcatctcca ctttgact                                                1158
```

<210> SEQ ID NO 105
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 105

```
atggacatga gagtgcctgc acagctgctg ggcctgctgc tgctgtggct gagaggcgcc     60
agatgcgaca aaactcacac atgcccaccg tgcccagcac ctgaactcct gggggggaccg    120
tcagtcttcc tcttcccccc aaaacccaag acaccctca tgatctcccg gacccctgag     180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aatcgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc    1020
aatatcaatg tgatcgtttt ggagttgaag ggttccgaga ctactttat gtgtgagtac     1080
gctgacgaga ctgctactat cgttgagttt ttgaatcggt ggatcacttt tgctcaatcc    1140
atcatctcca ctttgact                                                  1158
```

<210> SEQ ID NO 106
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 106

```
atggacatga gagtgcctgc acagctgctg ggcctgctgc tgctgtggct gagaggcgcc     60
agatgcgaca aaactcacac atgcccaccg tgcccagcac ctgaactcct gggggggaccg    120
tcagtcttcc tcttcccccc aaaacccaag acaccctca tgatctcccg gacccctgag     180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgggatt ggagcacttg ttgttggact tgcaaatgat cttgaatggt    840
```

```
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
aatatcaatg tgatcgtttt ggagttgaag ggttccgaga ctactttttat gtgtgagtac    1080 gctgacgaga ctgctactat cgttgagttt ttgaatcggt ggatcacttt tgctcaatcc     1140
atcatctcca ctttgact                                                   1158
```

<210> SEQ ID NO 107
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 107

```
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag gacaccctca tgatctcccg gacccctgag      180
gtcacatgcg tggtggtgga cgtgagccac gaagaccctg aggtcaagtt caactggtac      240
gtggacggcg tggaggtgca taatgccaag acaaagccgc gggaggagca gtacggcagc      300
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420
gccaaagggc agccccgaga accacaggtg tacaccctgc ccccatcccg ggaggagatg      480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggcgcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
aatatcaatg tgatcgtttt ggagttgaag ggttccgaga ctactttttat gtgtgagtac    1080 gctgacgaga ctgctactat cgttgagttt ttgaatcggt ggatcacttt tgctcaatcc     1140
atcatctcca ctttgact                                                   1158
```

<210> SEQ ID NO 108
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 108

```
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag gacaccctca tgatctcccg gacccctgag      180
```

| | |
|---|---|
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggggcacttg ttgttggact tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| aatatcaatg tgatcgtttt ggagttgaag ggttccgaga ctacttttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 109
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 109

| | |
|---|---|
| atggacatga gagtgcctgc acagctgctg ggcctgctgc tgctgtggct gagaggcgcc | 60 |
| agatgcgaca aaactcacac atgcccaccg tgcccagcac ctgaactcct ggggggaccg | 120 |
| tcagtcttcc tcttcccccc aaaacccaag gacaccctca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt gtcgcacttg ttgttggact tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| aatatcaatg tgatcgtttt ggagttgaag ggttccgaga ctacttttat gtgtgagtac | 1080 |

```
gctgacgaga ctgctactat cgttgagttt ttgaatcggt ggatcacttt tgctcaatcc    1140
atcatctcca ctttgact                                                  1158

<210> SEQ ID NO 110
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 110
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggaggccttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc    1020
aatatcaatg tgatcgtttt ggagttgaag ggttccgaga ctactttat gtgtgagtac    1080 gctgacgaga ctgctactat cgttgagttt ttgaatcggt ggatcacttt tgctcaatcc    1140
atcatctcca ctttgact                                                  1158

<210> SEQ ID NO 111
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 111
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
```

| | |
|---|---|
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggaggacttg ttgttggact tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| aatatcaatg tgatcgtttt ggagttgaag ggttccgaga ctactttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 112
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 112

| | |
|---|---|
| atggacatga gagtgcctgc acagctgctg ggcctgctgc tgctgtggct gagaggcgcc | 60 |
| agatgcgaca aaactcacac atgcccaccg tgcccagcac ctgaactcct ggggggaccg | 120 |
| tcagtcttcc tcttcccccc aaaacccaag gacaccctca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggagggcttg ttgttggact tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| aatatcaatg tgatcgtttt ggagttgaag ggttccgaga ctactttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 113
<211> LENGTH: 1158

<212> TYPE: DNA
<213> ORGANISM: Artificial Sequence
<220> FEATURE:
<223> OTHER INFORMATION: synthetic polynucleotide

<400> SEQUENCE: 113

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag gacacactca tgatctcccg gacccctgag    180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagaagttg ttgttggact tgcaaatgat cttgaatggt     840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacggga cttgatctcc    1020
aatatcaatg tgatcgtttt ggagttgaag ggttccgaga ctactttat gtgtgagtac    1080
gctgacgaga ctgctactat cgttgagttt ttgaatcggt ggatcacttt tgctcaatcc    1140
atcatctcca ctttgact                                                  1158
```

<210> SEQ ID NO 114
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 114

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag gacacactca tgatctcccg gacccctgag    180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
```

```
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagatgttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                 1158

<210> SEQ ID NO 115
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 115
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc cccatcccg ggaggagatg     480 accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagaacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                 1158

<210> SEQ ID NO 116
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 116
atggacatga gagtgcctgc acagctgctg ggcctgctgc tgctgtggct gagaggcgcc     60
```

```
agatgcgaca aaactcacac atgcccaccg tgcccagcac ctgaactcct gggggaccg      120
tcagtcttcc tcttcccccc aaaacccaag dacaccctca tgatctcccg dacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaagggc agccccgaga accacaggtg tacaccctgc ccccatcccg ggaggagatg     480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcgcttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac    1080
gctgacgaga ctgctactat cgttgagttt ttgaatcggt ggatcacttt tgctcaatcc   1140
atcatctcca ctttgact                                                 1158
```

<210> SEQ ID NO 117
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 117

```
atggacatga gagtgcctgc acagctgctg ggcctgctgc tgctgtggct gagaggcgcc     60
agatgcgaca aaactcacac atgcccaccg tgcccagcac ctgaactcct gggggaccg    120
tcagtcttcc tcttcccccc aaaacccaag dacaccctca tgatctcccg dacccctgag   180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaagggc agccccgaga accacaggtg tacaccctgc ccccatcccg ggaggagatg    480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
gactccgacg gctccttctt cctctatagc aagctcaccg tggacaagag caggtggcag   660
caggggaacg tcttctcatg ctccgtgatg catgaggctc tgcacaacca ctacacgcag   720
aagagcctct ccctgtctcc gggtggaggt ggtggaagcg ctccaacttc ctcctccact   780
aagaagactc aattgcaatt ggagcgcttg ttgttggact tgcaaatgat cttgaatggt   840
atcaataatt acaagaatcc aaagttgact cggatgttga cttttaagtt ttacatgcca   900
```

```
aagaaggcta ctgagttgaa gcacttgcaa tgtttggagg aggagttgaa gccattggag      960
gaggttttga atttggctca atccaagaat tttcacttgc ggccacggga cttgatctcc     1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc    1140
atcatctcca ctttgact                                                   1158
```

<210> SEQ ID NO 118
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 118

```
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420 gccaagggc agccccgaga accacaggtg tacaccctgc ccccatcccg ggaggagatg      480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagaccttg ttgttggact tgcaaatgat cttgaatggt     840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacggga cttgatctcc    1020
aatatcaatg tgatcgtttt ggagttgaag ggttccgaga ctactttat gtgtgagtac    1080 gctgacgaga ctgctactat cgttgagttt ttgaatcggt ggatcacttt tgctcaatcc   1140
atcatctcca ctttgact                                                 1158
```

<210> SEQ ID NO 119
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 119

```
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
```

```
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420 gccaagggc agccccgaga accacaggtg tacaccctgc ccccatcccg ggaggagatg       480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggaggtcttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc      1020
aatatcaatg tgatcgtttt ggagttgaag ggttccgaga ctacttttat gtgtgagtac      1080
gctgacgaga ctgctactat cgttgagttt ttgaatcggt ggatcacttt tgctcaatcc      1140
atcatctcca ctttgact                                                   1158
```

<210> SEQ ID NO 120
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 120

```
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag gacaccctca tgatctcccg gacccctgag      180
gtcacatgcg tggtggtgga cgtgagccac gaagaccctg aggtcaagtt caactggtac      240
gtggacggcg tggaggtgca taatgccaag acaaagccgc gggaggagca gtacggcagc      300
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420 gccaagggc agccccgaga accacaggtg tacaccctgc ccccatcccg ggaggagatg       480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagtacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc      1020
aatatcaatg tgatcgtttt ggagttgaag ggttccgaga ctacttttat gtgtgagtac      1080
gctgacgaga ctgctactat cgttgagttt ttgaatcggt ggatcacttt tgctcaatcc      1140
```

```
atcatctcca ctttgact                                            1158
```

<210> SEQ ID NO 121
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 121

```
atggacatga gagtgcctgc acagctgctg ggcctgctgc tgctgtggct gagaggcgcc    60
agatgcgaca aaactcacac atgcccaccg tgcccagcac ctgaactcct ggggggaccg   120
tcagtcttcc tcttcccccc aaaacccaag gacaccctca tgatctcccg gacccctgag   180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga accacaggtg tacaccctgc ccccatcccg ggaggagatg   480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
gactccgacg gctccttctt cctctatagc aagctcaccg tggacaagag caggtggcag   660
caggggaacg tcttctcatg ctccgtgatg catgaggctc tgcacaacca ctacacgcag   720
aagagcctct ccctgtctcc gggtggaggt ggtggaagcg ctccaacttc ctcctccact   780
aagaagactc aattgcaatt ggagcacttg ttggcggact gcaaatgat  cttgaatggt   840
atcaataatt acaagaatcc aaagttgact cggatgttga cttttaagtt ttacatgcca   900
aagaaggcta ctgagttgaa gcacttgcaa tgtttggagg aggagttgaa gccattggag   960
gaggttttga atttggctca atccaagaat tttcacttgc ggccacggga cttgatctcc  1020
aatatcaatg tgatcgtttt ggagttgaag ggttccgaga ctactttat gtgtgagtac  1080
gctgacgaga ctgctactat cgttgagttt ttgaatcggt ggatcacttt tgctcaatcc  1140
atcatctcca ctttgact                                               1158
```

<210> SEQ ID NO 122
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 122

```
atggacatga gagtgcctgc acagctgctg ggcctgctgc tgctgtggct gagaggcgcc    60
agatgcgaca aaactcacac atgcccaccg tgcccagcac ctgaactcct ggggggaccg   120
tcagtcttcc tcttcccccc aaaacccaag gacaccctca tgatctcccg gacccctgag   180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga accacaggtg tacaccctgc ccccatcccg ggaggagatg   480
accaagaacc aggtcagcct gacctgcctg gtcaaaggct tctatcccag cgacatcgcc   540
```

```
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttggatgact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac    1080 gctgacgaga ctgctactat cgttgagttt ttgaatcggt ggatcacttt tgctcaatcc   1140
atcatctcca ctttgact                                                 1158
```

<210> SEQ ID NO 123
<211> LENGTH: 1158
<212> TYPE: DNA
<213> ORGANISM: Artificial Sequence
<220> FEATURE:
<223> OTHER INFORMATION: sythetic polynucleotide

<400> SEQUENCE: 123

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttggaggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac    1080 gctgacgaga ctgctactat cgttgagttt ttgaatcggt ggatcacttt tgctcaatcc   1140
atcatctcca ctttgact                                                 1158
```

<210> SEQ ID NO 124
<211> LENGTH: 1158
<212> TYPE: DNA
<213> ORGANISM: Artificial Sequence
<220> FEATURE:

<223> OTHER INFORMATION: synthetic polynucleotide

<400> SEQUENCE: 124

| | | | | | |
|---|---|---|---|---|---|
| atggacatga | gagtgcctgc | acagctgctg | ggcctgctgc | tgctgtggct | gagaggcgcc | 60 |
| agatgcgaca | aaactcacac | atgcccaccg | tgcccagcac | ctgaactcct | gggggggaccg | 120 |
| tcagtcttcc | tcttcccccc | aaacccaag | dacaccctca | tgatctcccg | gaccctgag | 180 |
| gtcacatgcg | tggtggtgga | cgtgagccac | gaagaccctg | aggtcaagtt | caactggtac | 240 |
| gtggacggcg | tggaggtgca | taatgccaag | acaaagccgc | gggaggagca | gtacggcagc | 300 |
| acgtaccgtg | tggtcagcgt | cctcaccgtc | ctgcaccagg | actggctgaa | tggcaaggag | 360 |
| tacaagtgca | aggtctccaa | caaagccctc | ccagccccca | tcgagaaaac | catctccaaa | 420 |
| gccaaagggc | agccccgaga | accacaggtg | tacaccctgc | ccccatcccg | ggaggagatg | 480 |
| accaagaacc | aggtcagcct | gacctgcctg | gtcaaaggct | tctatcccag | cgacatcgcc | 540 |
| gtggagtggg | agagcaatgg | gcagccggag | aacaactaca | agaccacgcc | tcccgtgctg | 600 |
| gactccgacg | gctccttctt | cctctatagc | aagctcaccg | tggacaagag | caggtggcag | 660 |
| caggggaacg | tcttctcatg | ctccgtgatg | catgaggctc | tgcacaacca | ctacacgcag | 720 |
| aagagcctct | ccctgtctcc | gggtggaggt | ggtggaagcg | ctccaacttc | ctcctccact | 780 |
| aagaagactc | aattgcaatt | ggagcacttg | ttggggact | tgcaaatgat | cttgaatggt | 840 |
| atcaataatt | acaagaatcc | aaagttgact | cggatgttga | ctttttaagtt | ttacatgcca | 900 |
| aagaaggcta | ctgagttgaa | gcacttgcaa | tgtttggagg | aggagttgaa | gccattggag | 960 |
| gaggttttga | atttggctca | atccaagaat | tttcacttgc | ggccacggga | cttgatctcc | 1020 |
| aatatcaatg | tgatcgtttt | ggagttgaag | ggttccgaga | ctactttttat | gtgtgagtac | 1080 |
| gctgacgaga | ctgctactat | cgttgagttt | ttgaatcggt | ggatcacttt | tgctcaatcc | 1140 |
| atcatctcca | ctttgact | | | | | 1158 |

<210> SEQ ID NO 125
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 125

| | | | | | |
|---|---|---|---|---|---|
| atggacatga | gagtgcctgc | acagctgctg | ggcctgctgc | tgctgtggct | gagaggcgcc | 60 |
| agatgcgaca | aaactcacac | atgcccaccg | tgcccagcac | ctgaactcct | gggggggaccg | 120 |
| tcagtcttcc | tcttcccccc | aaacccaag | gacaccctca | tgatctcccg | gaccctgag | 180 |
| gtcacatgcg | tggtggtgga | cgtgagccac | gaagaccctg | aggtcaagtt | caactggtac | 240 |
| gtggacggcg | tggaggtgca | taatgccaag | acaaagccgc | gggaggagca | gtacggcagc | 300 |
| acgtaccgtg | tggtcagcgt | cctcaccgtc | ctgcaccagg | actggctgaa | tggcaaggag | 360 |
| tacaagtgca | aggtctccaa | caaagccctc | ccagccccca | tcgagaaaac | catctccaaa | 420 |
| gccaaagggc | agccccgaga | accacaggtg | tacaccctgc | ccccatcccg | ggaggagatg | 480 |
| accaagaacc | aggtcagcct | gacctgcctg | gtcaaaggct | tctatcccag | cgacatcgcc | 540 |
| gtggagtggg | agagcaatgg | gcagccggag | aacaactaca | agaccacgcc | tcccgtgctg | 600 |
| gactccgacg | gctccttctt | cctctatagc | aagctcaccg | tggacaagag | caggtggcag | 660 |
| caggggaacg | tcttctcatg | ctccgtgatg | catgaggctc | tgcacaacca | ctacacgcag | 720 |
| aagagcctct | ccctgtctcc | gggtggaggt | ggtggaagcg | ctccaacttc | ctcctccact | 780 |

```
aagaagactc aattgcaatt ggagcacttg ttgaatgact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac    1080
gctgacgaga ctgctactat cgttgagttt ttgaatcggt ggatcacttt tgctcaatcc   1140
atcatctcca ctttgact                                                 1158
```

<210> SEQ ID NO 126
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 126

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc cccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgcgggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac    1080
gctgacgaga ctgctactat cgttgagttt ttgaatcggt ggatcacttt tgctcaatcc   1140
atcatctcca ctttgact                                                 1158
```

<210> SEQ ID NO 127
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 127

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
```

```
tcagtcttcc tcttccccccc aaaacccaag acacccctca tgatctcccg gacccctgag      180
gtcacatgcg tggtggtgga cgtgagccac gaagaccctg aggtcaagtt caactggtac      240
gtggacggcg tggaggtgca taatgccaag acaaagccgc gggaggagca gtacggcagc      300
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420
gccaaagggc agccccgaga accacaggtg tacaccctgc ccccatcccg ggaggagatg      480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagcacttg ttgtcggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
aatatcaatg tgatcgtttt ggagttgaag ggttccgaga ctacttttat gtgtgagtac     1080
gctgacgaga ctgctactat cgttgagttt ttgaatcggt ggatcacttt tgctcaatcc     1140
atcatctcca ctttgact                                                   1158

<210> SEQ ID NO 128
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 128
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag acacccctca tgatctcccg gacccctgag      180
gtcacatgcg tggtggtgga cgtgagccac gaagaccctg aggtcaagtt caactggtac      240
gtggacggcg tggaggtgca taatgccaag acaaagccgc gggaggagca gtacggcagc      300
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420
gccaaagggc agccccgaga accacaggtg tacaccctgc ccccatcccg ggaggagatg      480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagcacttg ttgacggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
```

```
aatatcaatg tgatcgtttt ggagttgaag ggttccgaga ctactttat gtgtgagtac    1080 gctgacgaga ctgctactat cgttgagttt ttgaatcggt ggatcacttt tgctcaatcc    1140
atcatctcca ctttgact                                                  1158
```

<210> SEQ ID NO 129
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 129

```
atggacatga gagtgcctgc acagctgctg ggcctgctgc tgctgtggct gagaggcgcc      60
agatgcgaca aaactcacac atgcccaccg tgcccagcac ctgaactcct gggggggaccg    120 tcagtcttcc tcttccccc aaaacccaag gacaccctca tgatctcccg gacccctgag     180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttggtggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac   1080 gctgacgaga ctgctactat cgttgagttt ttgaatcggt ggatcacttt tgctcaatcc   1140
atcatctcca ctttgact                                                 1158
```

<210> SEQ ID NO 130
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 130

```
atggacatga gagtgcctgc acagctgctg ggcctgctgc tgctgtggct gagaggcgcc      60
agatgcgaca aaactcacac atgcccaccg tgcccagcac ctgaactcct gggggggaccg    120 tcagtcttcc tcttccccc aaaacccaag gacaccctca tgatctcccg gacccctgag     180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
```

| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggagcacttg ttgttggcct tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| aatatcaatg tgatcgtttt ggagttgaag ggttccgaga ctactttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 131
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 131

| atggacatga gagtgcctgc acagctgctg ggcctgctgc tgctgtggct gagaggcgcc | 60 |
| agatgcgaca aaactcacac atgcccaccg tgcccagcac ctgaactcct gggggaccg | 120 |
| tcagtcttcc tcttcccccc aaaacccaag gacaccctca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggagcacttg ttgttggagt tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| aatatcaatg tgatcgtttt ggagttgaag ggttccgaga ctactttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 132
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 132

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagcacttg ttgttgttct gcaaatgat cttgaatggt     840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacggga cttgatctcc    1020
aatatcaatg tgatcgtttt ggagttgaag ggttccgaga ctactttat gtgtgagtac    1080
gctgacgaga ctgctactat cgttgagttt ttgaatcggt ggatcacttt tgctcaatcc    1140
atcatctcca ctttgact                                                 1158
```

<210> SEQ ID NO 133
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 133

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
```

```
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgtttgggct tgcaaatgat cttgaatggt   840
atcaataatt acaagaatcc aaagttgact cggatgttga ctttttaagtt ttacatgcca   900 aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                1158

<210> SEQ ID NO 134
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 134
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgtttgtgg tt gcaaatgat cttgaatggt  840 atcaataatt acaagaatcc aaagttgact cggatgttga ctttttaagtt ttacatgcca   900 aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                1158

<210> SEQ ID NO 135
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 135
```

```
atggacatga gagtgcctgc acagctgctg ggcctgctgc tgctgtggct gagaggcgcc    60
agatgcgaca aaactcacac atgcccaccg tgcccagcac ctgaactcct gggggggaccg   120
tcagtcttcc tcttcccccc aaaacccaag acaccctca tgatctcccg acccctgag    180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga accacaggtg tacaccctgc ccccatcccg ggaggagatg   480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
gactccgacg gctccttctt cctctatagc aagctcaccg tggacaagag caggtggcag   660
caggggaacg tcttctcatg ctccgtgatg catgaggctc tgcacaacca ctacacgcag   720
aagagcctct ccctgtctcc gggtggaggt ggtggaagcg ctccaacttc ctcctccact   780
aagaagactc aattgcaatt ggagcacttg ttgttggact tgcaaaggat cttgaatggt   840
atcaataatt acaagaatcc aaagttgact cggatgttga cttttaagtt ttacatgcca   900
aagaaggcta ctgagttgaa gcacttgcaa tgtttggagg aggagttgaa gccattggag   960
gaggttttga atttggctca atccaagaat tttcacttgc ggccacggga cttgatctcc  1020
aatatcaatg tgatcgtttt ggagttgaag ggttccgaga ctactttat gtgtgagtac  1080
gctgacgaga ctgctactat cgttgagttt ttgaatcggt ggatcacttt tgctcaatcc  1140
atcatctcca ctttgact                                                1158
```

<210> SEQ ID NO 136
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 136

```
atggacatga gagtgcctgc acagctgctg ggcctgctgc tgctgtggct gagaggcgcc    60
agatgcgaca aaactcacac atgcccaccg tgcccagcac ctgaactcct gggggggaccg   120
tcagtcttcc tcttcccccc aaaacccaag acaccctca tgatctcccg acccctgag    180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga accacaggtg tacaccctgc ccccatcccg ggaggagatg   480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
gactccgacg gctccttctt cctctatagc aagctcaccg tggacaagag caggtggcag   660
caggggaacg tcttctcatg ctccgtgatg catgaggctc tgcacaacca ctacacgcag   720
aagagcctct ccctgtctcc gggtggaggt ggtggaagcg ctccaacttc ctcctccact   780
aagaagactc aattgcaatt ggagcacttg ttgttggact tgcaaatgat cttgaatggt   840
```

```
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgg cgccacggga cttgatctcc     1020
aatatcaatg tgatcgtttt ggagttgaag ggttccgaga ctactttat gtgtgagtac      1080 gctgacgaga ctgctactat cgttgagttt ttgaatcggt ggatcacttt tgctcaatcc     1140
atcatctcca ctttgact                                                    1158

<210> SEQ ID NO 137
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 137
atggacatga gagtgcctgc acagctgctg ggcctgctgc tgctgtggct gagaggcgcc       60
agatgcgaca aaactcacac atgcccaccg tgcccagcac ctgaactcct gggggggaccg     120 tcagtcttcc tcttcccccc aaaacccaag gacaccctca tgatctcccg gacccctgag      180
gtcacatgcg tggtggtgga cgtgagccac gaagaccctg aggtcaagtt caactggtac      240
gtggacggcg tggaggtgca taatgccaag acaaagccgc gggaggagca gtacggcagc      300
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420
gccaaagggc agccccgaga accacaggtg tacaccctgc ccccatcccg ggaggagatg      480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgg ggccacggga cttgatctcc     1020
aatatcaatg tgatcgtttt ggagttgaag ggttccgaga ctactttat gtgtgagtac      1080 gctgacgaga ctgctactat cgttgagttt ttgaatcggt ggatcacttt tgctcaatcc     1140
atcatctcca ctttgact                                                    1158

<210> SEQ ID NO 138
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 138
atggacatga gagtgcctgc acagctgctg ggcctgctgc tgctgtggct gagaggcgcc       60
agatgcgaca aaactcacac atgcccaccg tgcccagcac ctgaactcct gggggggaccg     120 tcagtcttcc tcttcccccc aaaacccaag gacaccctca tgatctcccg gacccctgag      180
gtcacatgcg tggtggtgga cgtgagccac gaagaccctg aggtcaagtt caactggtac      240
```

```
gtggacggcg tggaggtgca taatgccaag acaaagccgc gggaggagca gtacggcagc      300
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420 gccaagggc agccccgaga accacaggtg tacaccctgc ccccatcccg ggaggagatg       480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgt cgccacggga cttgatctcc     1020
aatatcaatg tgatcgtttt ggagttgaag ggttccgaga ctacttttat gtgtgagtac     1080
gctgacgaga ctgctactat cgttgagttt ttgaatcggt ggatcacttt tgctcaatcc     1140
atcatctcca cttttgact                                                  1158
```

<210> SEQ ID NO 139
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 139

```
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttccccc aaaacccaag gacaccctca tgatctcccg gacccctgag       180
gtcacatgcg tggtggtgga cgtgagccac gaagaccctg aggtcaagtt caactggtac      240
gtggacggcg tggaggtgca taatgccaag acaaagccgc gggaggagca gtacggcagc      300
acgtaccgtg tggtcagcgt cctcaccgtc ctgcaccagg actggctgaa tggcaaggag      360
tacaagtgca aggtctccaa caaagccctc ccagccccca tcgagaaaac catctccaaa      420 gccaagggc agccccgaga accacaggtg tacaccctgc ccccatcccg ggaggagatg       480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttga cgccacggga cttgatctcc     1020
aatatcaatg tgatcgtttt ggagttgaag ggttccgaga ctacttttat gtgtgagtac     1080
```

```
gctgacgaga ctgctactat cgttgagttt tgaatcggt ggatcacttt tgctcaatcc    1140
atcatctcca ctttgact                                                  1158
```

<210> SEQ ID NO 140
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 140

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact gcaaatgat cttgaatggt    840 atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacgggc cttgatctcc   1020
aatatcaatg tgatcgtttt ggagttgaag ggttccgaga ctactttat gtgtgagtac   1080 gctgacgaga ctgctactat cgttgagttt tgaatcggt ggatcacttt tgctcaatcc   1140
atcatctcca ctttgact                                                 1158
```

<210> SEQ ID NO 141
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 141

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
```

```
accaagaacc aggtcagcct gacctgcctg gtcaaaggct tctatcccag cgacatcgcc      540
gtggagtggg agagcaatgg gcagccgag aacaactaca agaccacgcc tcccgtgctg       600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga gttgatctcc     1020
aatatcaatg tgatcgtttt ggagttgaag ggttccgaga ctactttat gtgtgagtac      1080 gctgacgaga ctgctactat cgttgagttt ttgaatcggt ggatcacttt tgctcaatcc     1140
atcatctcca ctttgact                                                    1158

<210> SEQ ID NO 142
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 142
atggacatga gagtgcctgc acagctgctg ggcctgctgc tgctgtggct gagaggcgcc       60
agatgcgaca aaactcacac atgcccaccg tgcccagcac ctgaactcct gggggaccg      120 tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccgag aacaactaca agaccacgcc tcccgtgctg      600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagcacttg ttgttggact tgcaaatgat cttgaatggt     840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacgggg cttgatctcc    1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc    1140
atcatctcca ctttgact                                                   1158

<210> SEQ ID NO 143
<211> LENGTH: 1158
<212> TYPE: DNA
```

<213> ORGANISM: Artificial Sequence
<220> FEATURE:
<223> OTHER INFORMATION: synthetic polynucleotide

<400> SEQUENCE: 143

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagcacttg ttgttggact gcaaatgat cttgaatggt      840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacggat cttgatctcc    1020
aatatcaatg tgatcgtttt ggagttgaag ggttccgaga ctacttttat gtgtgagtac    1080
gctgacgaga ctgctactat cgttgagttt ttgaatcggt ggatcacttt tgctcaatcc    1140
atcatctcca ctttgact                                                  1158
```

<210> SEQ ID NO 144
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 144

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
```

```
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggat gttgatctcc   1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                 1158

<210> SEQ ID NO 145
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 145
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg acccctgag    180 gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc cccatcccg ggaggagatg     480 accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggca gttgatctcc   1020
aatatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                 1158

<210> SEQ ID NO 146
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 146
atggacatga gagtgcctgc acagctgctg ggcctgctgc tgctgtggct gagaggcgcc     60
```

| | |
|---|---|
| agatgcgaca aaactcacac atgcccaccg tgcccagcac ctgaactcct ggggggaccg | 120 |
| tcagtcttcc tcttcccccc aaaacccaag acacccctca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggagcacttg ttgttggact tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggcg cttgatctcc | 1020 |
| aatatcaatg tgatcgtttt ggagttgaag ggttccgaga ctactttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 147
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 147

| | |
|---|---|
| atggacatga gagtgcctgc acagctgctg ggcctgctgc tgctgtggct gagaggcgcc | 60 |
| agatgcgaca aaactcacac atgcccaccg tgcccagcac ctgaactcct ggggggaccg | 120 |
| tcagtcttcc tcttcccccc aaaacccaag acacccctca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggagcacttg ttgttggact tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 | gaggttttga atttggctca atccaagaat tttcacttgc ggccacggag cttgatctcc   1020 aatatcaatg tgatcgtttt ggagttgaag ggttccgaga ctactttat gtgtgagtac   1080 gctgacgaga ctgctactat cgttgagttt ttgaatcggt ggatcacttt tgctcaatcc   1140 atcatctcca ctttgact                                                  1158

<210> SEQ ID NO 148
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 148
atggacatga gagtgcctgc acagctgctg ggcctgctgc tgctgtggct gagaggcgcc     60
agatgcgaca aaactcacac atgcccaccg tgcccagcac ctgaactcct gggggaccg    120 tcagtcttcc tcttcccccc aaaacccaag gacaccctca tgatctcccg gacccctgag   180
gtcacatgcg tggtggtgga cgtgagccac gaagaccctg aggtcaagtt caactggtac   240
gtggacggcg tggaggtgca taatgccaag acaaagccgc gggaggagca gtacggcagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga ccacaggtg tacaccctgc ccccatcccg ggaggagatg    480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
gactccgacg gctccttctt cctctatagc aagctcaccg tggacaagag caggtggcag   660
caggggaacg tcttctcatg ctccgtgatg catgaggctc tgcacaacca ctacacgcag   720
aagagcctct ccctgtctcc gggtggaggt ggtggaagcg ctccaacttc ctcctccact   780
aagaagactc aattgcaatt ggagcacttg ttgttggact tgcaaatgat cttgaatggt   840
atcaataatt acaagaatcc aaagttgact cggatgttga cttttaagtt ttacatgcca   900
aagaaggcta ctgagttgaa gcacttgcaa tgtttggagg aggagttgaa gccattggag   960
gaggttttga atttggctca atccaagaat tttcacttgc ggccacggac cttgatctcc   1020
aatatcaatg tgatcgtttt ggagttgaag ggttccgaga ctactttat gtgtgagtac   1080 gctgacgaga ctgctactat cgttgagttt ttgaatcggt ggatcacttt tgctcaatcc   1140
atcatctcca ctttgact                                                  1158

<210> SEQ ID NO 149
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 149
atggacatga gagtgcctgc acagctgctg ggcctgctgc tgctgtggct gagaggcgcc     60
agatgcgaca aaactcacac atgcccaccg tgcccagcac ctgaactcct gggggaccg    120 tcagtcttcc tcttcccccc aaaacccaag gacaccctca tgatctcccg gacccctgag   180
gtcacatgcg tggtggtgga cgtgagccac gaagaccctg aggtcaagtt caactggtac   240
gtggacggcg tggaggtgca taatgccaag acaaagccgc gggaggagca gtacggcagc   300

```
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420 gccaagggc agccccgaga accacaggtg tacaccctgc ccccatcccg ggaggagatg     480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
gctatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                  1158
```

<210> SEQ ID NO 150
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 150

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420 gccaaaggc agccccgaga accacaggtg tacaccctgc ccccatcccg ggaggagatg     480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
gctatcaatg tgatcgtttt ggagttgaag ggttccgaga ctactttat gtgtgagtac     1080 gctgacgaga ctgctactat cgttgagttt ttgaatcggt ggatcacttt tgctcaatcc   1140
atcatctcca ctttgact                                                  1158
```

<210> SEQ ID NO 151
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 151

| | | |
|---|---|---|
| atggacatga gagtgcctgc acagctgctg ggcctgctgc tgctgtggct gagaggcgcc | 60 |
| agatgcgaca aaactcacac atgcccaccg tgcccagcac ctgaactcct gggggggaccg | 120 |
| tcagtcttcc tcttcccccc aaaacccaag gacacactca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggagcacttg ttgttggact tgcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| gagatcaatg tgatcgtttt ggagttgaag ggttccgaga ctactttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 152
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 152

| | | |
|---|---|---|
| atggacatga gagtgcctgc acagctgctg ggcctgctgc tgctgtggct gagaggcgcc | 60 |
| agatgcgaca aaactcacac atgcccaccg tgcccagcac ctgaactcct gggggggaccg | 120 |
| tcagtcttcc tcttcccccc aaaacccaag gacacactca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |

```
gtggagtggg agagcaatgg gcagccgag aacaactaca agaccacgcc tcccgtgctg       600
gactccgacg gctccttctt cctctatagc aagctcaccg tggacaagag caggtggcag       660
caggggaacg tcttctcatg ctccgtgatg catgaggctc tgcacaacca ctacacgcag       720
aagagcctct ccctgtctcc gggtggaggt ggtggaagcg ctccaacttc ctcctccact       780
aagaagactc aattgcaatt ggagcacttg ttgttggact tgcaaatgat cttgaatggt       840
atcaataatt acaagaatcc aaagttgact cggatgttga cttttaagtt ttacatgcca       900
aagaaggcta ctgagttgaa gcacttgcaa tgtttggagg aggagttgaa gccattggag       960
gaggttttga atttggctca atccaagaat tttcacttgc ggccacggga cttgatctcc      1020
tttatcaatg tgatcgtttt ggagttgaag ggttccgaga ctacttttat gtgtgagtac      1080
gctgacgaga ctgctactat cgttgagttt ttgaatcggt ggatcacttt tgctcaatcc      1140
atcatctcca ctttgact                                                    1158

<210> SEQ ID NO 153
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 153
atggacatga gagtgcctgc acagctgctg ggcctgctgc tgctgtggct gagaggcgcc        60
agatgcgaca aaactcacac atgcccaccg tgcccagcac ctgaactcct ggggggaccg       120
tcagtcttcc tcttcccccc aaaacccaag gacacccctca tgatctcccg gacccctgag       180
gtcacatgcg tggtggtgga cgtgagccac gaagaccctg aggtcaagtt caactggtac       240
gtggacggcg tggaggtgca taatgccaag acaaagccgc gggaggagca gtacggcagc       300
acgtaccgtg tggtcagcgt cctcaccgtc ctgcaccagg actggctgaa tggcaaggag       360
tacaagtgca aggtctccaa caaagccctc ccagccccca tcgagaaaac catctccaaa       420
gccaaagggc agccccgaga accacaggtg tacaccctgc cccatcccg ggaggagatg       480 accaagaacc aggtcagcct gacctgcctg gtcaaaggct tctatcccag cgacatcgcc       540
gtggagtggg agagcaatgg gcagccggag aacaactaca agaccacgcc tcccgtgctg       600
gactccgacg gctccttctt cctctatagc aagctcaccg tggacaagag caggtggcag       660
caggggaacg tcttctcatg ctccgtgatg catgaggctc tgcacaacca ctacacgcag       720
aagagcctct ccctgtctcc gggtggaggt ggtggaagcg ctccaacttc ctcctccact       780
aagaagactc aattgcaatt ggagcacttg ttgttggact tgcaaatgat cttgaatggt       840
atcaataatt acaagaatcc aaagttgact cggatgttga cttttaagtt ttacatgcca       900
aagaaggcta ctgagttgaa gcacttgcaa tgtttggagg aggagttgaa gccattggag       960
gaggttttga atttggctca atccaagaat tttcacttgc ggccacggga cttgatctcc      1020
ggtatcaatg tgatcgtttt ggagttgaag ggttccgaga ctacttttat gtgtgagtac      1080
gctgacgaga ctgctactat cgttgagttt ttgaatcggt ggatcacttt tgctcaatcc      1140
atcatctcca ctttgact                                                    1158

<210> SEQ ID NO 154
<211> LENGTH: 1158
<212> TYPE: DNA
<213> ORGANISM: Artificial Sequence
<220> FEATURE:
<223> OTHER INFORMATION: synthetic polynucleotide
```

<400> SEQUENCE: 154

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag acacccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagcacttg ttgttggact tgcaaatgat cttgaatggt     840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacggga cttgatctcc    1020
atgatcaatg tgatcgtttt ggagttgaag ggttccgaga ctacttttat gtgtgagtac    1080
gctgacgaga ctgctactat cgttgagttt ttgaatcggt ggatcacttt tgctcaatcc    1140
atcatctcca ctttgact                                                   1158
```

<210> SEQ ID NO 155
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 155

```
atggacatga gagtgcctgc acagctgctg ggcctgctgc tgctgtggct gagaggcgcc      60
agatgcgaca aaactcacac atgcccaccg tgcccagcac ctgaactcct ggggggaccg     120
tcagtcttcc tcttcccccc aaaacccaag acacccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
```

```
aagaagactc aattgcaatt ggagcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
agtatcaatg tgatcgtttt ggagttgaag ggttccgaga ctactttat gtgtgagtac      1080 gctgacgaga ctgctactat cgttgagttt ttgaatcggt ggatcacttt tgctcaatcc     1140
atcatctcca ctttgact                                                   1158

<210> SEQ ID NO 156
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 156
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag gacacccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420 gccaagggc agccccgaga accacaggtg tacaccctgc cccatcccg ggaggagatg       480 accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
gttatcaatg tgatcgtttt ggagttgaag ggttccgaga ctactttat gtgtgagtac      1080 gctgacgaga ctgctactat cgttgagttt ttgaatcggt ggatcacttt tgctcaatcc     1140
atcatctcca ctttgact                                                   1158

<210> SEQ ID NO 157
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 157
atggacatga gagtgcctgc acagctgctg ggcctgctgc tgctgtggct gagaggcgcc       60
agatgcgaca aaactcacac atgcccaccg tgcccagcac ctgaactcct ggggggaccg      120
tcagtcttcc tcttcccccc aaaacccaag gacacccctca tgatctcccg gacccctgag     180
```

-continued

```
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420 gccaagggc agccccgaga ccacaggtg tacaccctgc ccccatcccg ggaggagatg     480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc    1020
tggatcaatg tgatcgtttt ggagttgaag ggttccgaga ctactttat gtgtgagtac    1080 gctgacgaga ctgctactat cgttgagttt ttgaatcggt ggatcacttt tgctcaatcc    1140
atcatctcca ctttgact                                                 1158
```

<210> SEQ ID NO 158
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 158

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttcccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420 gccaagggc agccccgaga ccacaggtg tacaccctgc ccccatcccg ggaggagatg     480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc    1020
```

| | |
|---|---|
| aatatcaatg atatcgtttt ggagttgaag ggttccgaga ctacttttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 159
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 159

| | |
|---|---|
| atggacatga gagtgcctgc acagctgctg ggcctgctgc tgctgtggct gagaggcgcc | 60 |
| agatgcgaca aaactcacac atgcccaccg tgcccagcac ctgaactcct gggggggaccg | 120 |
| tcagtcttcc tcttcccccc aaaacccaag gacaccctca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |
| gccaaagggc agccccgaga accacaggtg tacaccctgc ccccatcccg ggaggagatg | 480 |
| accaagaacc aggtcagcct gacctgcctg gtcaaaggct tctatcccag cgacatcgcc | 540 |
| gtggagtggg agagcaatgg gcagccggag aacaactaca agaccacgcc tcccgtgctg | 600 |
| gactccgacg gctccttctt cctctatagc aagctcaccg tggacaagag caggtggcag | 660 |
| caggggaacg tcttctcatg ctccgtgatg catgaggctc tgcacaacca ctacacgcag | 720 |
| aagagcctct ccctgtctcc gggtggaggt ggtggaagcg ctccaacttc ctcctccact | 780 |
| aagaagactc aattgcaatt ggagcacttg ttgttggact gcaaatgat cttgaatggt | 840 |
| atcaataatt acaagaatcc aaagttgact cggatgttga cttttaagtt ttacatgcca | 900 |
| aagaaggcta ctgagttgaa gcacttgcaa tgtttggagg aggagttgaa gccattggag | 960 |
| gaggttttga atttggctca atccaagaat tttcacttgc ggccacggga cttgatctcc | 1020 |
| aatatcaatg agatcgtttt ggagttgaag ggttccgaga ctacttttat gtgtgagtac | 1080 |
| gctgacgaga ctgctactat cgttgagttt ttgaatcggt ggatcacttt tgctcaatcc | 1140 |
| atcatctcca ctttgact | 1158 |

<210> SEQ ID NO 160
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 160

| | |
|---|---|
| atggacatga gagtgcctgc acagctgctg ggcctgctgc tgctgtggct gagaggcgcc | 60 |
| agatgcgaca aaactcacac atgcccaccg tgcccagcac ctgaactcct gggggggaccg | 120 |
| tcagtcttcc tcttcccccc aaaacccaag gacaccctca tgatctcccg gacccctgag | 180 |
| gtcacatgcg tggtggtgga cgtgagccac gaagaccctg aggtcaagtt caactggtac | 240 |
| gtggacggcg tggaggtgca taatgccaag acaaagccgc gggaggagca gtacggcagc | 300 |
| acgtaccgtg tggtcagcgt cctcaccgtc ctgcaccagg actggctgaa tggcaaggag | 360 |
| tacaagtgca aggtctccaa caaagccctc ccagccccca tcgagaaaac catctccaaa | 420 |

```
gccaaagggc agccccgaga accacaggtg tacaccctgc ccccatcccg ggaggagatg      480
accaagaacc aggtcagcct gacctgcctg gtcaaaggct tctatcccag cgacatcgcc      540
gtggagtggg agagcaatgg gcagccggag aacaactaca agaccacgcc tcccgtgctg      600
gactccgacg gctccttctt cctctatagc aagctcaccg tggacaagag caggtggcag      660
caggggaacg tcttctcatg ctccgtgatg catgaggctc tgcacaacca ctacacgcag      720
aagagcctct ccctgtctcc gggtggaggt ggtggaagcg ctccaacttc ctcctccact      780
aagaagactc aattgcaatt ggagcacttg ttgttggact tgcaaatgat cttgaatggt      840
atcaataatt acaagaatcc aaagttgact cggatgttga cttttaagtt ttacatgcca      900
aagaaggcta ctgagttgaa gcacttgcaa tgtttggagg aggagttgaa gccattggag      960
gaggttttga atttggctca atccaagaat tttcacttgc ggccacggga cttgatctcc     1020
aatatcaatg ggatcgtttt ggagttgaag ggttccgaga ctactttat gtgtgagtac      1080 gctgacgaga ctgctactat cgttgagttt ttgaatcggt ggatcacttt tgctcaatcc     1140
atcatctcca ctttgact                                                  1158
```

<210> SEQ ID NO 161
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 161

```
atggacatga gagtgcctgc acagctgctg ggcctgctgc tgctgtggct gagaggcgcc       60
agatgcgaca aaactcacac atgcccaccg tgcccagcac ctgaactcct gggggggaccg     120 tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagcacttg ttgttggact tgcaaatgat cttgaatggt     840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacggga cttgatctcc    1020
aatatcaatt cgatcgtttt ggagttgaag ggttccgaga ctactttat gtgtgagtac     1080 gctgacgaga ctgctactat cgttgagttt ttgaatcggt ggatcacttt tgctcaatcc    1140
atcatctcca ctttgact                                                 1158
```

<210> SEQ ID NO 162

```
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 162
atggacatga gagtgcctgc acagctgctg ggcctgctgc tgctgtggct gagaggcgcc      60
agatgcgaca aaactcacac atgcccaccg tgcccagcac ctgaactcct gggggggaccg     120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
caggggaacg tcttctcatg ctccgtgatg catgaggctc tgcacaacca ctacacgcag     720
aagagcctct ccctgtctcc gggtggaggt ggtggaagcg ctccaacttc ctcctccact     780
aagaagactc aattgcaatt ggagcacttg ttgttggact tgcaaatgat cttgaatggt     840
atcaataatt acaagaatcc aaagttgact cggatgttga cttttaagtt ttacatgcca     900
aagaaggcta ctgagttgaa gcacttgcaa tgtttggagg aggagttgaa gccattggag     960
gaggttttga atttggctca atccaagaat tttcacttgc ggccacggga cttgatctcc    1020
aatatcaatg tgaaggtttt ggagttgaag ggttccgaga ctactttat gtgtgagtac    1080
gctgacgaga ctgctactat cgttgagttt ttgaatcggt ggatcacttt tgctcaatcc    1140
atcatctcca ctttgact                                                  1158

<210> SEQ ID NO 163
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 163
atggacatga gagtgcctgc acagctgctg ggcctgctgc tgctgtggct gagaggcgcc      60
agatgcgaca aaactcacac atgcccaccg tgcccagcac ctgaactcct gggggggaccg     120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacggcagc     300
acgtaccgtg tggtcagcgt cctcaccgtc ctgcaccagg actggctgaa tggcaaggag     360
tacaagtgca aggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctatagc aagctcaccg tggacaagag caggtggcag     660
```

```
cagggqaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgagagtttt ggagttgaag ggttccgaga ctactttat gtgtgagtac    1080 gctgacgaga ctgctactat cgttgagttt ttgaatcggt ggatcacttt tgctcaatcc   1140
atcatctcca ctttgact                                                 1158
```

<210> SEQ ID NO 164
<211> LENGTH: 1158
<212> TYPE: DNA
<213> ORGANISM: Artificial Sequence
<220> FEATURE:
<223> OTHER INFORMATION: synthetic polynucleotide

<400> SEQUENCE: 164

```
atggacatga gagtgcctgc acagctgctg ggcctgctgc tgctgtggct gagaggcgcc     60
agatgcgaca aaactcacac atgcccaccg tgcccagcac ctgaactcct ggggggaccg    120
tcagtcttcc tcttccccc aaaacccaag gacaccctca tgatctcccg gacccctgag    180
gtcacatgcg tggtggtgga cgtgagccac gaagaccctg aggtcaagtt caactggtac    240
gtggacggcg tggaggtgca taatgccaag acaaagccgc gggaggagca gtacggcagc    300
acgtaccgtg tggtcagcgt cctcaccgtc ctgcaccagg actggctgaa tggcaaggag    360
tacaagtgca aggtctccaa caaagccctc ccagccccca tcgagaaaac catctccaaa    420
gccaaagggc agccccgaga accacaggtg tacaccctgc ccccatcccg ggaggagatg    480
accaagaacc aggtcagcct gacctgcctg gtcaaaggct tctatcccag cgacatcgcc    540
gtggagtggg agagcaatgg gcagccggag aacaactaca agaccacgcc tcccgtgctg    600
gactccgacg gctccttctt cctctatagc aagctcaccg tggacaagag caggtggcag    660
caggggaacg tcttctcatg ctccgtgatg catgaggctc tgcacaacca ctacacgcag    720
aagagcctct ccctgtctcc gggtggaggt ggtggaagcg ctccaacttc ctcctccact    780
aagaagactc aattgcaatt ggagcacttg ttgttggact tgcaaatgat cttgaatggt    840
atcaataatt acaagaatcc aaagttgact cggatgttga cttttaagtt ttacatgcca    900
aagaaggcta ctgagttgaa gcacttgcaa tgtttggagg aggagttgaa gccattggag    960
gaggttttga atttggctca atccaagaat tttcacttgc ggccacggga cttgatctcc   1020
aatatcaatg tgatcgtttt ggggttgaag ggttccgaga ctactttat gtgtgagtac    1080 gctgacgaga ctgctactat cgttgagttt ttgaatcggt ggatcacttt tgctcaatcc   1140
atcatctcca ctttgact                                                 1158
```

<210> SEQ ID NO 165
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 165

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Glu Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Thr Gly Ser Asp Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
            100                 105                 110

Lys Arg

<210> SEQ ID NO 166
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 166

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Val Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Gly
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg
            100                 105

<210> SEQ ID NO 167
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 167

Asp Ile Val Leu Thr Gln Thr Pro Leu Ser Ser Pro Val Thr Leu Gly
1               5                   10                  15

Gln Pro Ala Ser Ile Ser Cys Arg Ser Ser His Ser Leu Ile His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Thr Gly Ser Gly Ser Gly Thr Asp Phe Thr Leu Lys Ile
65                  70                  75                  80
```

Ser Arg Val Glu Ala Gly Asp Val Gly Val Tyr Tyr Cys Met Gln Thr
            85                  90                  95

Thr Gln Phe Pro Thr Phe Gly Gln Gly Thr Lys Val Glu Ile Lys Arg
            100                 105                 110

<210> SEQ ID NO 168
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 168

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Asn Leu Val Gln Ser
            20                  25                  30

Asp Gly Asn Thr Tyr Leu Ser Trp Leu His Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Thr
            85                  90                  95

Thr Gln Phe Pro Thr Phe Gly Gln Gly Thr Lys Val Glu Ile Lys Arg
            100                 105                 110

<210> SEQ ID NO 169
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 169

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ile Leu Val Asn Ser
            20                  25                  30

Asp Gly Asn Thr Tyr Leu Ser Trp Leu His Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
            85                  90                  95

Thr Gln Phe Pro Thr Phe Gly Gln Gly Thr Lys Val Glu Ile Lys Arg
            100                 105                 110

<210> SEQ ID NO 170
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 170

Asp Ile Val Met Thr Gln Thr Pro Leu Ser Ser Pro Val Thr Leu Gly

```
1               5                   10                  15
Gln Pro Ala Ser Ile Ser Cys Arg Ser Ser Gln Ser Leu Val Arg Ser
                20                  25                  30

Asp Gly Asn Thr Tyr Leu Ser Trp Leu His Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Phe Pro Thr Phe Gly Gln Gly Thr Lys Val Glu Ile Lys Arg
            100                 105                 110

<210> SEQ ID NO 171
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 171

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
                20                  25                  30

Asp Gly His Thr Tyr Leu Ser Trp Leu Gln Gln Arg Pro Gly Gln Pro
            35                  40                  45

Pro Arg Leu Leu Leu Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Phe Pro Thr Phe Gly Gly Gly Thr Lys Val Glu Ile Lys Arg
            100                 105                 110

<210> SEQ ID NO 172
<211> LENGTH: 113
<212> TYPE: PRT
<213> ORGANISM: Artificial Sequence
<220> FEATURE:
<223> OTHER INFORMATION: synthetic polypeptide

<400> SEQUENCE: 172

Asp Ile Ala Met Ser Gln Ser Pro Leu Ser Leu Pro Val Thr Pro Gly
1               5                   10                  15

Glu Pro Ala Ser Met Ser Cys Arg Ser Ser Gln Ser Leu Leu His Ser
                20                  25                  30

Asn Gly Phe Asn Tyr Leu Asp Trp Tyr Leu Gln Lys Pro Gly Gln Ser
            35                  40                  45

Pro Gln Val Leu Ile His Leu Gly Ser Asp Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95
```

```
Leu Gln Thr Pro Leu Thr Phe Gly Gly Gly Thr Lys Val Glu Ile Lys
            100                 105                 110
Arg
```

<210> SEQ ID NO 173
<211> LENGTH: 113
<212> TYPE: PRT
<213> ORGANISM: Artificial Sequence
<220> FEATURE:
<223> OTHER INFORMATION: synthetic polypeptide

<400> SEQUENCE: 173

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Phe Asn Tyr Leu Asp Trp Phe Leu Gln Lys Pro Gly Gln Ser
         35                  40                  45

Pro Gln Pro Leu Ile Tyr Leu Gly Ser Asp Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
Arg
```

<210> SEQ ID NO 174
<211> LENGTH: 113
<212> TYPE: PRT
<213> ORGANISM: Artificial Sequence
<220> FEATURE:
<223> OTHER INFORMATION: synthetic polypeptide

<400> SEQUENCE: 174

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Phe Asn Tyr Leu Asp Trp Tyr Leu Gln Lys Pro Gly Gln Ser
         35                  40                  45

Pro Gln Leu Leu Ile Tyr Leu Gly Ser Asp Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
Arg
```

<210> SEQ ID NO 175
<211> LENGTH: 112
<212> TYPE: PRT
<213> ORGANISM: Artificial Sequence
<220> FEATURE:
<223> OTHER INFORMATION: synthetic polypeptide -continued

<400> SEQUENCE: 175

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Asn Ile
            20                  25                  30

Asp Gly Ser Thr His Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Phe Pro Thr Phe Gly Gln Gly Thr Arg Leu Glu Ile Lys Arg
            100                 105                 110

<210> SEQ ID NO 176
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 176

Glu Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Gln Ser
            20                  25                  30

Asp Gly Ile Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Phe Pro Thr Phe Gly Gln Gly Thr Lys Val Glu Ile Lys Arg
            100                 105                 110

<210> SEQ ID NO 177
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 177

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Asn Ser
            20                  25                  30

Asp Gly Asn Thr Tyr Leu Asn Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

```
Ser Arg Val Glu Ala Glu Asp Val Gly Val Tyr Tyr Cys Met Gln Ala
                85                  90                  95

Thr Gln Phe Pro Thr Phe Gly Gln Gly Thr Lys Val Glu Ile Lys Arg
            100                 105                 110
```

<210> SEQ ID NO 178
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 178

```
Asp Ile Val Met Thr Gln Thr Pro Leu Ser Ser Pro Val Thr Leu Gly
1               5                   10                  15

Gln Pro Ala Ser Ile Ser Cys Arg Ser Ser His Asn Leu Val Arg Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Gly Ala Glu Asp Val Gly Val Tyr Tyr Cys Met Gln Ala
                85                  90                  95

Thr Gln Phe Pro Thr Phe Gly Gln Gly Thr Arg Leu Glu Ile Lys Arg
            100                 105                 110
```

<210> SEQ ID NO 179
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 179

```
Asn Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Gln Thr
            20                  25                  30

Asp Gly Asn Thr Tyr Leu Ser Trp Leu Gln Gln Arg Pro Gly Gln Pro
        35                  40                  45

Pro Arg Pro Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Thr Gln Phe Pro Thr Phe Gly Gln Gly Thr Arg Leu Glu Ile Lys Arg
            100                 105                 110
```

<210> SEQ ID NO 180
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 180

```
Asp Ile Val Met Thr Gln Thr Pro Leu Ser Ser Pro Val Thr Leu Gly
```

```
                1               5                  10                 15
            Gln Pro Ala Ser Ile Ser Cys Arg Ser Ser His Asn Leu Ile His Ser
                            20                  25                  30

Asp Gly Asn Thr Tyr Leu Ser Trp Leu His Gln Arg Pro Gly Gln Pro
                        35                  40                  45

Pro Arg Leu Leu Ile Tyr Lys Ile Ser Asn Arg Phe Ser Gly Val Pro
                    50                  55                  60

Asp Arg Phe Ser Gly Ser Gly Ala Gly Thr Asp Phe Thr Leu Lys Ile
             65                  70                  75                  80

Ser Arg Val Glu Ala Glu Asp Val Gly Val Tyr Tyr Cys Met Gln Thr
                            85                  90                  95

Ser Gln Phe Pro Thr Phe Gly Gly Gly Thr Lys Val Glu Ile Lys Arg
                        100                 105                 110

<210> SEQ ID NO 181
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 181

Asp Ile Val Met Thr Gln Thr Pro Leu Ser Ser Pro Val Thr Leu Gly
 1               5                  10                  15

Gln Pro Ala Ser Ile Ser Cys Arg Ser Ser His Asn Leu Leu His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Glu Ile Ser Asn Arg Phe Ser Gly Val Pro
        50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Val
                85                  90                  95

Thr Gln Phe Pro Thr Phe Gly Gly Gly Thr Lys Val Glu Ile Lys Arg
            100                 105                 110

<210> SEQ ID NO 182
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 182

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95
```

Leu Thr Phe Gly Gly Gly Thr Lys Val Glu Ile Lys Arg
            100                 105

<210> SEQ ID NO 183
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 183

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile His Gly Pro Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Ser
                85                  90                  95

Ile Thr Phe Gly Gln Gly Thr Arg Leu Glu Ile Lys Arg
            100                 105

<210> SEQ ID NO 184
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Tyr Ile Pro Arg
                85                  90                  95

Thr Phe Gly Gln Gly Thr Lys Val Glu Ile Lys Arg
            100                 105

<210> SEQ ID NO 185
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 185

Ser Tyr Glu Leu Thr Gln Pro Pro Ser Val Ser Val Ser Pro Gly Gln
1               5                   10                  15

Thr Ala Arg Ile Ala Cys Ser Gly Asp Ala Leu Pro Arg Lys Phe Ala

```
                20                  25                  30
Tyr Trp Tyr Gln Gln Lys Ser Gly Gln Ala Pro Val Leu Val Ile Ser
             35                  40                  45

Glu Asp Ser Arg Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Phe Ser Thr Asp Ser Ser Ala Asn His
                 85                  90                  95

Arg Val Phe Gly Gly Gly Thr Lys Leu Thr Val Leu Gly
            100                 105
```

<210> SEQ ID NO 186
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 186

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Gly Ser Leu Gln Pro
 65                  70                  75                  80

Glu Asp Phe Thr Thr Tyr Tyr Cys Leu Gln His Asn Ser Tyr Pro Leu
                 85                  90                  95

Thr Phe Gly Gly Gly Thr Lys Val Glu Ile Lys Arg
            100                 105
```

<210> SEQ ID NO 187
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 187

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asp Asp
             20                  25                  30

Leu Gly Trp Tyr Gln Gln Lys Pro Gly Lys Ala Pro Lys Arg Leu Ile
             35                  40                  45

Tyr Ile Ala Thr Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Ile Ser Tyr Pro Trp
                 85                  90                  95

Thr Phe Gly Gln Gly Thr Lys Val Glu Ile Lys Arg
            100                 105
```

<210> SEQ ID NO 188
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asp Asp
            20                  25                  30

Leu Gly Trp Tyr Gln Gln Lys Pro Gly Lys Ala Pro Lys Arg Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Ile Ser Tyr Pro Trp
                85                  90                  95

Thr Phe Gly Gln Gly Thr Lys Val Glu Ile Lys Arg
            100                 105

<210> SEQ ID NO 189
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asp Asp
            20                  25                  30

Leu Gly Trp Tyr Gln Gln Lys Pro Gly Lys Ala Pro Lys Arg Leu Ile
        35                  40                  45

Tyr Val Val Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys Arg
            100                 105

<210> SEQ ID NO 190
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Gln Arg Leu Ile

```
                35                  40                  45
Tyr Ser Ala Ser Ser Leu Pro Ser Gly Val Pro Ser Arg Phe Ser Gly
             50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                 85                  90                  95

Ser Phe Gly Gln Gly Thr Lys Leu Glu Ile Arg Arg
            100                 105
```

```
<210> SEQ ID NO 191
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 191

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Glu His Asp
             20                  25                  30

Leu Gly Trp Tyr Gln Gln Lys Pro Gly Lys Ala Pro Lys Arg Leu Ile
         35                  40                  45

Tyr Ala Ala Ser Thr Leu Pro Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Phe Pro Arg
                 85                  90                  95

Ser Phe Gly Gln Gly Thr Gln Leu Glu Ile Lys Arg
            100                 105
```

```
<210> SEQ ID NO 192
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 192

Asp Ile Val Met Thr Gln Thr Pro Leu Ser Leu Pro Val Thr Pro Gly
 1               5                  10                  15

Glu Pro Ala Ser Ile Ser Cys Arg Ser Thr Gln Ser Leu Leu Asp Gly
             20                  25                  30

Asp Asp Gly Asn Thr Leu Leu Asp Trp Tyr Leu Gln Lys Pro Gly Gln
         35                  40                  45

Ser Pro Gln Leu Leu Ile Tyr Thr Leu Ser Tyr Arg Ala Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Leu Glu Phe Pro Leu Thr Phe Gly Gly Gly Thr Lys Val Glu Ile
            100                 105                 110

Lys Arg
```

```
<210> SEQ ID NO 193
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 193

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Glu Gly Asn Thr Phe Leu Asp Trp Tyr Leu Gln Lys Pro Gly Gln
        35                  40                  45

Pro Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
            100                 105                 110

Lys Arg

<210> SEQ ID NO 194
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Glu Thr Asp Phe Thr Phe Thr Ile Ser Ser Leu Gln Pro
65                  70                  75                  80

Glu Asp Ile Ala Thr Tyr Tyr Cys Gln Gln Tyr Glu Asn Leu Pro Phe
                85                  90                  95

Thr Phe Gly Pro Gly Thr Lys Val Asp Ile Lys Arg
            100                 105

<210> SEQ ID NO 195
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 195

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30
```

```
Tyr Trp Tyr Gln Gln Lys Pro Gly Gln Ala Pro Met Leu Val Ile Tyr
            35                  40                  45

Lys Asp Ser Glu Arg Pro Ser Gly Ile Pro Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Val Val Phe Gly Gly Gly Thr Lys Leu Thr Val Leu Gly
             100                 105

<210> SEQ ID NO 196
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 196

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Tyr Ala
             20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Gly Asn His
                 85                  90                  95

Tyr Val Phe Gly Thr Gly Thr Lys Val Thr Val Leu Gly
             100                 105

<210> SEQ ID NO 197
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 197

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Phe Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Phe Phe Thr Ile Ser Asn Leu Gln Pro
 65                  70                  75                  80

Glu Asp Ile Ala Thr Tyr Phe Cys Gln Gln Asp Asp Asn Leu Pro Phe
                 85                  90                  95

Thr Phe Gly Pro Gly Thr Lys Val Asp Ile Lys Arg
             100                 105

<210> SEQ ID NO 198
```

```
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Phe Tyr Cys Gln Gln Tyr Asp Asn Leu Pro Phe
                85                  90                  95

Thr Phe Gly Pro Gly Thr Lys Val Asp Ile Lys Arg
            100                 105

<210> SEQ ID NO 199
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 199

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Lys Phe Ala
            20                  25                  30

Tyr Trp Tyr Gln Gln Lys Ser Gly Gln Ala Pro Val Leu Val Ile Tyr
        35                  40                  45

Glu Asp Arg Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Arg Ser Gly Asp His
                85                  90                  95

Val Val Phe Gly Gly Gly Thr Lys Leu Thr Val Leu Gly
            100                 105

<210> SEQ ID NO 200
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 200

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Val Trp Tyr Gln Gln Lys Pro Gly Lys Pro Pro Lys Leu Leu Ile
        35                  40                  45
```

Tyr Ala Ala Ser Ser Leu Gln Asn Gly Val Pro Ser Arg Phe Ser Gly
            50                  55                  60

Ser Gly Ser Gly Thr Asp Phe Thr Leu Thr Ile Ser Ser Leu Gln Thr
 65                  70                  75                  80

Glu Asp Phe Ala Thr Tyr Tyr Cys Gln Gln Ala Leu Ser Phe Pro Trp
                 85                  90                  95

Thr Phe Gly Pro Gly Thr Lys Val Glu Val Lys Arg
            100                 105

<210> SEQ ID NO 201
<211> LENGTH: 342
<212> TYPE: DNA
<213> ORGANISM: Artificial Sequence
<220> FEATURE:
<223> OTHER INFORMATION: nucleic acid

<400> SEQUENCE: 201
gatattgtga tgacccagac tccactctcc ttgcccgtca cccctggaga gccggcctcc      60
atctcctgca ggtctagtca gagcctctta gatagtgatg agggaaacac ctatttggac     120
tggtacctgc agaagccagg gcagtctcca cagctcctga tctatacgct ttcctatcgg     180
gcctctggag tcccagacag gttcagtggc actgggtcag acactgattt cacactgaaa     240
atcagcaggg tggaggctga ggatgttgga gtttattact gcatgcaacg tatagagttt     300
cctctcactt tcggcggagg gaccaaggtg gagatcaaac ga                        342

<210> SEQ ID NO 202
<211> LENGTH: 327
<212> TYPE: DNA
<213> ORGANISM: Artificial Sequence
<220> FEATURE:
<223> OTHER INFORMATION: nucleic acid

<400> SEQUENCE: 202
gaaattgtat tgacgcagtc tccaggcacc ctgtctttgt ctccagggga aagagccacc      60
ctctcctgca gggccagtca gagttttagc agcagctact tagtctggta ccagcagaaa     120
cctggccagg ctcccaggct cctcatctat ggtgcatcca gcagggccac tggcatccca     180
gacaggttcg gtggcagtgg gtctgggaca gacttcactc tcaccatcag cagactggag     240
cctgaagatt ttgcagtgta ttactgtcag cagtatggta gctcacctct cactttcggc     300
ggagggacca aggtggagat caaacga                                         327

<210> SEQ ID NO 203
<211> LENGTH: 336
<212> TYPE: DNA
<213> ORGANISM: Artificial Sequence
<220> FEATURE:
<223> OTHER INFORMATION: nucleic acid

<400> SEQUENCE: 203
gatattgtgc tgacccagac tccactctcc tcacctgtca cccttggaca gccggcctcc      60
atctcctgca ggtctagtca tcacctcata cacagtgatg gaaacaccta cttgagttgg     120
cttcagcaga ggccaggcca gcctccaaga ctcctaattt ataagatttc taaccggttc     180
tctggggtcc cagacagatt cactggcagt gggacaggga cagatttcac actgaaaatc     240
agcagggtgg aagctgggga tgtcggggtt tattactgca tgcaaactac acaatttccg     300
acgttcggcc aagggaccaa ggtggaaatc aaacga                               336

```
<210> SEQ ID NO 204
<211> LENGTH: 336
<212> TYPE: DNA
<213> ORGANISM: Artificial Sequence
<220> FEATURE:
<223> OTHER INFORMATION: nucleic acid

<400> SEQUENCE: 204
gatattgtga tgacccagac tccactctcc tcacctgtca cccttggaca gccggcctcc      60
atctcctgca ggtccagtca aaacctcgtt caaagtgatg aaacaccta cttgagttgg     120 cttcaccaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tatttctgca tgcaaactac acaatttccg     300
acgttcggcc aagggaccaa ggtggaaatc aaacga                               336

<210> SEQ ID NO 205
<211> LENGTH: 336
<212> TYPE: DNA
<213> ORGANISM: Artificial Sequence
<220> FEATURE:
<223> OTHER INFORMATION: nucleic acid

<400> SEQUENCE: 205
gatattgtga tgacccagac tccactctcc tcacctgtca cccttggaca gccggcctcc      60
atttcctgca ggtctagtca atcctcgta aacagtgatg aaacaccta cttgagttgg      120 cttcaccaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaaactac acaatttccg     300
acgttcggcc aagggaccaa ggtggaaatc aaacga                               336

<210> SEQ ID NO 206
<211> LENGTH: 336
<212> TYPE: DNA
<213> ORGANISM: Artificial Sequence
<220> FEATURE:
<223> OTHER INFORMATION: nucleic acid

<400> SEQUENCE: 206
gatattgtga tgacccagac tccactctcc tcacctgtca cccttggaca gccggcctcc      60
atctcctgca ggtctagtca aagcctcgta cgcagtgatg aaacaccta cttgagttgg      120 cttcaccaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaaactac acaatttccg     300
acgttcggcc aagggaccaa ggtggaaatc aaacga                               336

<210> SEQ ID NO 207
<211> LENGTH: 336
<212> TYPE: DNA
<213> ORGANISM: Artificial Sequence
<220> FEATURE:
<223> OTHER INFORMATION: nucleic acid

<400> SEQUENCE: 207
gatattgtga tgacccagac tccactctcc tcacctgtca cccttggaca gccggcctcc      60
atctcctgca ggtctagtca cagcctcgta cacagtgatg gacacaccta cttgagttgg     120
```

```
cttcagcaga ggccaggcca gcctccaaga ctcctacttt ataagatttc taaccggttc    180
tctggggtcc cagacagatt cagtggcagt ggggcaggga cagatttcac actgaaaatc    240
agcagggtgg aagctgagga tgtcggggtt tattactgca tgcaaactac acaatttccc    300
actttcggcg gagggaccaa ggtggagatc aaacga                              336
```

```
<210> SEQ ID NO 208
<211> LENGTH: 339
<212> TYPE: DNA
<213> ORGANISM: Artificial Sequence
<220> FEATURE:
<223> OTHER INFORMATION: nucleic acid

<400> SEQUENCE: 208
gatattgcga tgagtcagtc tccactctcc ctgcccgtca cccctggaga gccggcctcc     60
atgtcatgca ggtctagtca gagcctcctg catagtaatg gattcaacta tttggattgg    120
tacctgcaga agccagggca gtctccacag gtcctgatcc atttgggttc tgatcgggcc    180
tccggggtcc ctgacaggtt cagtggcagt ggatcaggca cagatttac  attgaaaatc    240 agcagagtgg aggctgagga tgttggaatt tattactgca tgcaagctct acaaactcct    300
ctcactttcg gcggagggac caaggtggag atcaaacga                           339
```

```
<210> SEQ ID NO 209
<211> LENGTH: 339
<212> TYPE: DNA
<213> ORGANISM: Artificial Sequence
<220> FEATURE:
<223> OTHER INFORMATION: nucleic acid

<400> SEQUENCE: 209
gatattgtga tgactcagtc tccactctcc ctgcccgtca cccctggaga gccggcctcc     60
atctcctgca ggtctagtca gagcctccta catagtaatg gattcaacta tttggattgg    120
ttcctgcaga agccaggaca gtctccacag ccc ctgatct atttgggttc tgatcgggcc   180
tccggggtcc ctgacaggtt cagtggcagt ggatcaggca cagatttac  actgaaaatc    240 agcagagtgg aggctgagga tgttgggggtt tattactgca tgcaagctct acaaactccg   300
ctcactttcg gcggagggac caaggtggag atcaaacga                           339
```

```
<210> SEQ ID NO 210
<211> LENGTH: 339
<212> TYPE: DNA
<213> ORGANISM: Artificial Sequence
<220> FEATURE:
<223> OTHER INFORMATION: nucleic acid

<400> SEQUENCE: 210
gatattgtga tgactcagtc tccactctcc ctgcccgtca cccctggaga gccggcctcc     60
atctcctgca ggtctagtca gagcctcctg catagtaatg gattcaacta tttggattgg    120
tacctgcaga agccagggca gtctccacag ctcctgatct atttgggttc tgatcgggcc    180
tccggggtcc ctgacaggtt cagtggcagt ggatcaggca cagatttac  actgaaaatc    240 agcagagtgg aggctgagga tgttgggggtt tattactgca tgcaagctct acaaactccg   300
ctcactttcg gcggagggac caaggtggag atcaaacga                           339
```

```
<210> SEQ ID NO 211
<211> LENGTH: 336
<212> TYPE: DNA
<213> ORGANISM: Artificial Sequence
```

```
<220> FEATURE:
<223> OTHER INFORMATION: nucleic acid

<400> SEQUENCE: 211
gatattgtga tgacccagac tccactctcc tcacctgtca cccttggaca gccggcctcc      60
atatcctgca ggtccagtca aagcctcgta acattgatg gaagtaccca cttgagttgg     120
cttcagcaga ggccaggcca gcctccaaga ctcctaattt ataagatttc taaccggttc    180
tctggggtcc cagacagatt cagtggcagt ggggcaggga cagatttcac actgaagatc    240
agcagggtgg aagctgagga tgtcggggtt tattactgca tgcaaactac acaattcccc    300
accttcggcc aagggacacg actggagatt aaacga                              336

<210> SEQ ID NO 212
<211> LENGTH: 336
<212> TYPE: DNA
<213> ORGANISM: Artificial Sequence
<220> FEATURE:
<223> OTHER INFORMATION: nucleic acid

<400> SEQUENCE: 212
gaaattgtga tgacccagac tccactctcc tcacctgtca cccttggaca gccggcctcc      60
atttcctgca ggtctagtca aagcctcgtt cagagtgatg gaatcaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaaactac acaatttccg    300
acgttcggcc aagggaccaa ggtggaaatc aaacga                              336

<210> SEQ ID NO 213
<211> LENGTH: 336
<212> TYPE: DNA
<213> ORGANISM: Artificial Sequence
<220> FEATURE:
<223> OTHER INFORMATION: nucleic acid

<400> SEQUENCE: 213
gatattgtga tgacccagac tccactctcc tcacctgtca cccttggaca gccggcctcc      60
atctcctgca ggtctagtca aagcctcgta acagtgatg gaaacaccta cttgaattgg     120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaatttccg    300
acgttcggcc aagggaccaa ggtggaaatc aaacga                              336

<210> SEQ ID NO 214
<211> LENGTH: 336
<212> TYPE: DNA
<213> ORGANISM: Artificial Sequence
<220> FEATURE:
<223> OTHER INFORMATION: nucleic acid

<400> SEQUENCE: 214
gatattgtga tgacccagac tccactctcc tcacctgtca cccttggaca gccggcctcc      60
atctcctgca ggtccagtca caacctcgta cgcagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
```

```
agcagggtgg gagctgagga tgtcgggggtt tattactgca tgcaagctac acaatttccc    300
accttcggcc aagggacgcg actggagatt aaacga                              336
```

<210> SEQ ID NO 215
<211> LENGTH: 336
<212> TYPE: DNA
<213> ORGANISM: Artificial Sequence
<220> FEATURE:
<223> OTHER INFORMATION: nucleic acid

<400> SEQUENCE: 215

```
aatattgtga tgacccagac tccactctcc tcacctgtca cccttggaca gccggcctcc    60
atctcctgca ggtctagtca aagcctcgta caaactgatg gaaacacata tttgagttgg   120
cttcagcaga ggccaggcca gcctccaaga cccctaattt ataagatttc taaccggttt   180
tctggggtcc cagacagatt cagtggcagt ggggcaggga cagatttcac actgaaaatc   240
agcagggtgg aagctgagga tgtcgggggtt tattactgca tgcaagtaac acaatttccc   300
accttcggcc aagggacacg actggagatt aaacga                              336
```

<210> SEQ ID NO 216
<211> LENGTH: 336
<212> TYPE: DNA
<213> ORGANISM: Artificial Sequence
<220> FEATURE:
<223> OTHER INFORMATION: nucleic acid

<400> SEQUENCE: 216

```
gatattgtga tgacccagac tccactctcc tcacctgtca cccttggaca gccggcctcc    60
atctcctgta ggtctagtca taacctcata cacagtgatg gaaacaccta cttgagttgg   120
cttcaccaga ggccaggcca gcctccaaga ctcctaattt ataagatttc taaccggttc   180
tctggggtcc cggacagatt cagtggcagt ggggcaggga cagatttcac actgaaaatc   240
agcagggtgg aagctgagga tgtcgggggtt tattactgca tgcaaacttc acagtttccc   300
actttcggcg gagggaccaa ggtggagatc aaacga                              336
```

<210> SEQ ID NO 217
<211> LENGTH: 336
<212> TYPE: DNA
<213> ORGANISM: Artificial Sequence
<220> FEATURE:
<223> OTHER INFORMATION: nucleic acid

<400> SEQUENCE: 217

```
gatattgtga tgacccagac tccactctcc tcacctgtca cccttggaca gccggcctcc    60
atctcctgca ggtctagtca taacctccta cacagtgatg gaaacaccta cttgagttgg   120
cttcagcaga ggccaggcca gcctccaaga ctcctaattt atgagatttc taaccggttc   180
tctggggtcc cagacagatt cagtggcagt ggggcaggga cagatttcac actgaaaatc   240
agcagggtgg aagctgagga tgtcgggggtt tattactgca tgcaagttac acaatttccc   300
actttcggcg gcgggaccaa ggtggagatc aaacga                              336
```

<210> SEQ ID NO 218
<211> LENGTH: 327
<212> TYPE: DNA
<213> ORGANISM: Artificial Sequence
<220> FEATURE:
<223> OTHER INFORMATION: nucleic acid

<400> SEQUENCE: 218

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgct cactttcggc   300
ggagggacca aggtggagat caaacga                                        327
```

<210> SEQ ID NO 219
<211> LENGTH: 327
<212> TYPE: DNA
<213> ORGANISM: Artificial Sequence
<220> FEATURE:
<223> OTHER INFORMATION: nucleic acid

<400> SEQUENCE: 219

```
gaaattgtgt tgacgcagtc tccaggcacc ctgtctttgt ctccagggga aagagccacc    60
ctctcctgta gggccagtca gagtgttagc agcaggtact tagcctggta ccagcagaaa   120
cctggccagg ctcccaggct cctcatccat ggtccattca gcagggccac tggcatccca   180
gacaggttca gtggcagtgg gtctgggaca gatttcactc tcaccatcag cagactggag   240
cctgaagatt ttgcagtgta ttactgtcag cagtatggta attcatcgat caccttcggc   300
caagggacac gactggagat taaacga                                        327
```

<210> SEQ ID NO 220
<211> LENGTH: 324
<212> TYPE: DNA
<213> ORGANISM: Artificial Sequence
<220> FEATURE:
<223> OTHER INFORMATION: nucleic acid

<400> SEQUENCE: 220

```
gacatccaga tgacccagtc tccatcctcc ctgtctgcat ctgtaggaga cagagtcacc    60
atcacttgcc gggcaagtca gaccattagc agttatttaa attggtatca gcagaaacca   120
gggaaagccc ctaaggtcct gatctatgct gcatccagtt tccaaagtgg ggtcccatca   180
aggttcagtg gcagtggatc tgggacagat ttcactctca ccatcagcag tctgcaacct   240
gaagattttg caacttacta ctgtcaacag agtcactata tccctcggac gttcggccaa   300
gggaccaagg tggaaatcaa acga                                           324
```

<210> SEQ ID NO 221
<211> LENGTH: 327
<212> TYPE: DNA
<213> ORGANISM: Artificial Sequence
<220> FEATURE:
<223> OTHER INFORMATION: nucleic acid

<400> SEQUENCE: 221

```
tcctatgagc tgacacagcc accctcggtg tcagtgtccc caggacaaac ggccaggatc    60
gcctgctctg gagatgcatt gccaagaaaa tttgcttatt ggtaccagca gaagtcaggc   120
caggcccctg tgctggtcat ctctgaggac agcagacgac cctccgggat ccctgagaga   180
ttctctggct ccagctcagg gacaatggcc accttgacta tcagtggggc caggtggag    240 gatgaagctg actactactg tttctcaaca gacagcagtg ctaatcatag ggtattcggc   300
ggagggacca agctgaccgt cctaggt                                        327
```

<210> SEQ ID NO 222
<211> LENGTH: 324
<212> TYPE: DNA
<213> ORGANISM: Artificial Sequence
<220> FEATURE:
<223> OTHER INFORMATION: nucleic acid

<400> SEQUENCE: 222

```
gacatccaga tgacccagtc tccatcctcc ctgtctgcat ctgtaggaga cagagtcacc    60
atcacttgcc gggcaagtca ggacattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcggcag cctgcagcct   240
gaagatttta caacttatta ctgtctacag cataatagtt acccgctcac tttcggcgga   300
gggaccaagg tggagatcaa acga                                          324
```

<210> SEQ ID NO 223
<211> LENGTH: 324
<212> TYPE: DNA
<213> ORGANISM: Artificial Sequence
<220> FEATURE:
<223> OTHER INFORMATION: nucleic acid

<400> SEQUENCE: 223

```
gacatccaga tgacccagtc tccatcctcc ctgtctgcat ctgtaggaga cagagtcacc    60
atcacttgcc gggcaagtca gggcattaga gatgatttag gctggtatca gcagaaacca   120
gggaaagccc ctaagcgcct gatctatatt gcaaccagtt tgcaaagtgg ggtcccatca   180
aggttcagcg gcagtggatc tgggacagaa ttcactctca caatcagcag cctgcagcct   240
gaagattttg caacttatta ctgtctacag catattagtt acccgtggac gttcggccaa   300
gggaccaagg tggaaatcaa acga                                          324
```

<210> SEQ ID NO 224
<211> LENGTH: 324
<212> TYPE: DNA
<213> ORGANISM: Artificial Sequence
<220> FEATURE:
<223> OTHER INFORMATION: nucleic acid

<400> SEQUENCE: 224

```
gacatccaga tgacccagtc tccatcctcc ctgtctgcat ctgtaggaga cagagtcacc    60
atcacttgcc gggcaagtca ggacatcaga gatgatttag gctggtatca gcagaaacca   120
gggaaagccc ctaagcgcct gatctatgtt gcatccagtt tgcaaagtgg ggtcccatca   180
aggttcagcg gcagtggatc tgggacagaa ttcactctca caatcagcag cctgcagcct   240
gaagattttg caacttatta ctgtctacag catattagtt acccgtggac gttcggccaa   300
gggaccaagg tggaaatcaa acga                                          324
```

<210> SEQ ID NO 225
<211> LENGTH: 324
<212> TYPE: DNA
<213> ORGANISM: Artificial Sequence
<220> FEATURE:
<223> OTHER INFORMATION: nucleic acid

<400> SEQUENCE: 225

```
gacatccaga tgacccagtc tccatcctcc ctgtctgcat ctgtaggaga cagagtcacc    60
atcacttgcc gggcaagtca ggacattaga gatgatttag gctggtatca gcagaaacca   120
```

```
gggaaagccc ctaagcgcct gatctatgtt gtatccagtt tgcaaagtgg ggtcccatca    180
aggttcagcg gcagtggatc tgggacagag ttcactctca caatcagcag cctgcagcct    240
gaagattttg caacttatta ctgtctacag cataatggtt acccgtggac gttcggccaa    300
gggaccaagg tggaaatcaa acga                                           324

<210> SEQ ID NO 226
<211> LENGTH: 324
<212> TYPE: DNA
<213> ORGANISM: Artificial Sequence
<220> FEATURE:
<223> OTHER INFORMATION: nucleic acid

<400> SEQUENCE: 226
gacatccaga tgacccagtc tccatcctcc ctgtctgcat ctgtaggaga cagagtcacc     60
atcacttgcc gggcaagtca gggcattgga gatgatttag gctggtatca gcagaagcca    120
ggaaaagccc ctcagcgcct gatctattct gcatccagtt tgccaagtgg ggtcccatca    180
aggttcagcg gcagtggatc tgggacagaa ttcactctca caatcagcag cctgcagcct    240
gaagattttg caacttatta ctgtctacag cataatagtt accctcgcag ttttggccag    300
gggaccaagc tggagatcag acga                                           324

<210> SEQ ID NO 227
<211> LENGTH: 324
<212> TYPE: DNA
<213> ORGANISM: Artificial Sequence
<220> FEATURE:
<223> OTHER INFORMATION: nucleic acid

<400> SEQUENCE: 227
gacatccaga tgacccagtc tccatcctcc ctgtctgcat ctgtaggaga cagagtcacc     60
atcacttgcc gggcaagtca ggacattgaa catgatttag gctggtatca gcagaaacca    120
gggaaagccc ctaagcgcct gatctatgct gcatccactt tgccaagtgg ggtcccatca    180
aggttcagcg gcagtggatc tgggacagaa ttcactctca caatcagcag cctgcagcct    240
gaagattttg caacttatta ctgtctacag cataatagtt ccctcgcag ttttggccag    300 gggacccagc tggagatcaa acga                                           324

<210> SEQ ID NO 228
<211> LENGTH: 342
<212> TYPE: DNA
<213> ORGANISM: Artificial Sequence
<220> FEATURE:
<223> OTHER INFORMATION: nucleic acid

<400> SEQUENCE: 228
gatattgtga tgacccagac tccactctcc ctgcccgtca cccctggaga gccggcctcc     60
atctcctgca ggtctactca gagcctcttg gatggtgatg atggaaacac cttttggac    120 tggtacctgc agaagccagg gcagtctcca cagctcctga tctatacgct ttcctatcgg    180
gcctctggag tcccagacag gttcagtggc agtgggtcag gcactgattt cacactgaaa    240
atcagcaggg tggaggctga ggatgttgga gtttattact gcatgcaacg tttagagttt    300
cctctcactt tcggcggagg gaccaaggtg gagatcaaac ga                       342

<210> SEQ ID NO 229
<211> LENGTH: 342
<212> TYPE: DNA
```

```
<213> ORGANISM: Artificial Sequence
<220> FEATURE:
<223> OTHER INFORMATION: nucleic acid

<400> SEQUENCE: 229
gacattgtga tgacccagac tccactctcc ttgcccgtca cccctggaga gccggcctcc      60
atctcctgca ggtctagtca gagcctcttg gatagtgatg aaggaaacac cttttttggat    120 tggtacctgc agaagccagg gcagcctcca cagctcctga tctatacgct ttcctatcgg    180
gcctctggag tcccagacag gttcagtggc agtgggtcag gcactgattt cacactgaaa    240
atcagcaggg tggaggctga ggatgttgga gtttattact gcatgcaacg tatagagttt    300
cctctcactt tcggcggagg gaccaaggtg gagatcaaac ga                       342

<210> SEQ ID NO 230
<211> LENGTH: 324
<212> TYPE: DNA
<213> ORGANISM: Artificial Sequence
<220> FEATURE:
<223> OTHER INFORMATION: nucleic acid

<400> SEQUENCE: 230
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg gaagtggatc tgagacagat tttactttca ccatcagcag cctgcagcct    240
gaagatattg caacatatta ctgtcaacag tatgaaaatc tcccattcac tttcggccct    300
gggaccaaag tggatatcaa acga                                           324

<210> SEQ ID NO 231
<211> LENGTH: 327
<212> TYPE: DNA
<213> ORGANISM: Artificial Sequence
<220> FEATURE:
<223> OTHER INFORMATION: nucleic acid

<400> SEQUENCE: 231
tcctatgagc tgacacagcc accctcggtg tcagtgtccc caggacagac ggccaggatc     60
acctgctctg gagatgcatt gccaaggcaa tatgcttatt ggtaccagca gaagccaggc    120
caggccccta tgctggtgat atataaagac agtgagaggc cctcagggat ccctgagcga    180
ttctctggct ccagctcagg gacaacagtc acgttgacca tcagtggagt ccaggcagaa    240
gacgaggctg actattactg tcaatcagca gacagcagtg gtacttatgt ggtattcggc    300
ggagggacca agctgaccgt cctaggt                                        327

<210> SEQ ID NO 232
<211> LENGTH: 327
<212> TYPE: DNA
<213> ORGANISM: Artificial Sequence
<220> FEATURE:
<223> OTHER INFORMATION: nucleic acid

<400> SEQUENCE: 232
tcctatgagc tgacacagcc accctcggtg tcagtgtccc caggacaaac ggccaggatc     60
acctgctctg gagatgcatt gccaagaaaa tatgcttatt ggtaccagca gaagtcaggc    120
caggcccctg tgctggtcat ctatgaggac agcaaacgac cctccgggat ccctgagaga    180
ttctctggct ccagctcagg gacaatggcc accttgacta tcagtggggc ccaggtggag    240
```

```
gacgaagctg actactactg ttactcaaca gacagcagtg gtaatcatta tgtcttcgga    300
actgggacca aggtcaccgt cctaggt                                        327
```

<210> SEQ ID NO 233
<211> LENGTH: 324
<212> TYPE: DNA
<213> ORGANISM: Artificial Sequence
<220> FEATURE:
<223> OTHER INFORMATION: nucleic acid

<400> SEQUENCE: 233

```
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagttcct gatctacgat gcatccaatt tggaaacagg ggtcccatca    180
aggttcagtg gaagtggatc tgggacagat tttttttttca ccatcagcaa cctgcagcct   240
gaagatattg caacatattt ctgtcaacag gatgataatc tcccattcac tttcggccct    300
gggaccaaag tggatatcaa acga                                           324
```

<210> SEQ ID NO 234
<211> LENGTH: 324
<212> TYPE: DNA
<213> ORGANISM: Artificial Sequence
<220> FEATURE:
<223> OTHER INFORMATION: nucleic acid

<400> SEQUENCE: 234

```
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaaactcct gatctacgat gcatccaatt tggaaacagg ggtcccatca    180
aggttcagtg gaagtggatc tgggacagat tttactttca ccatcagcag cctgcagcct    240
gaagatattg caacattta ctgtcaacag tatgataatc tcccattcac tttcggccct     300
gggaccaaag tggatatcaa acga                                           324
```

<210> SEQ ID NO 235
<211> LENGTH: 327
<212> TYPE: DNA
<213> ORGANISM: Artificial Sequence
<220> FEATURE:
<223> OTHER INFORMATION: nucleic acid

<400> SEQUENCE: 235

```
tcctatgagc tgacacagcc accctcggtg tcagtgtccc aggacaaaac ggccaggatc     60
acctgctctg gagatgcatt gccaagaaaa tttgcttatt ggtaccagca gaagtcaggc    120
caggcccctg tgctggtcat ctatgaggac aggaaacgac cctccgggat ccctgagaga    180
ttctctggct ccagctcagg gacaatggcc accttgacta tcagtggggc ccaggtggag    240
gatgaagctg actactactg ttactcaaca gaccgcagtg gtgatcatgt ggtattcggc    300
ggagggacca agctgaccgt cctaggt                                        327
```

<210> SEQ ID NO 236
<211> LENGTH: 324
<212> TYPE: DNA
<213> ORGANISM: Artificial Sequence
<220> FEATURE:
<223> OTHER INFORMATION: nucleic acid

<400> SEQUENCE: 236

```
gacatccaga tgacccagtc tccatcttcc gtgtctgcat ctgtaggaga cagagtcacc    60
atcacttgtc gggcgagtca gggtattagc aactggttag tctggtatca gcagaaacca   120
gggaaacccc ctaaactcct gatctatgct gcatccagtt tgcaaaatgg ggtcccatca   180
agattcagcg gcagtggatc tgggacagat tcactctca ccatcagcag cctgcagact    240
gaagattttg caacttacta ttgtcaacag gctctcagtt tcccgtggac gttcggccca   300
gggaccaagg tggaagtcaa acga                                          324
```

<210> SEQ ID NO 237
<211> LENGTH: 121
<212> TYPE: PRT
<213> ORGANISM: Artificial Sequence
<220> FEATURE:
<223> OTHER INFORMATION: synthetic polypeptide

<400> SEQUENCE: 237

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile His Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Thr Arg Gln Gly Arg Ser Phe Tyr Tyr Tyr Gly Met Asp Val Trp Gly
            100                 105                 110

Gln Gly Thr Thr Val Thr Val Ser Ser
        115                 120
```

<210> SEQ ID NO 238
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 238

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Ala Ala Tyr
65                  70                  75                  80

Leu Gln Trp Ser Ser Leu Lys Ala Ser Asp Thr Ala Met Tyr Tyr Cys
                85                  90                  95

Ala Arg Gln Gln Val Ala Gly Met Leu Asp Tyr Trp Gly Gln Gly Thr
            100                 105                 110
```

Leu Val Thr Val Ser Ser
        115

<210> SEQ ID NO 239
<211> LENGTH: 120
<212> TYPE: PRT
<213> ORGANISM: Artificial Sequence
<220> FEATURE:
<223> OTHER INFORMATION: synthetic polypeptide

<400> SEQUENCE: 239

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Phe Asp Ser His Tyr Gly Met Asp Val Trp Gly Gln
            100                 105                 110

Gly Thr Thr Val Thr Val Ser Ser
        115                 120

<210> SEQ ID NO 240
<211> LENGTH: 122
<212> TYPE: PRT
<213> ORGANISM: Artificial Sequence
<220> FEATURE:
<223> OTHER INFORMATION: synthetic polypeptide

<400> SEQUENCE: 240

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Arg Glu Glu Trp Phe Gly Glu Ala Asp Tyr Gly Met Asp Val Trp
            100                 105                 110

Gly Gln Gly Thr Thr Val Thr Val Ser Ser
        115                 120

<210> SEQ ID NO 241
<211> LENGTH: 122
<212> TYPE: PRT
<213> ORGANISM: Artificial Sequence
<220> FEATURE:
<223> OTHER INFORMATION: synthetic polypeptide

```
<400> SEQUENCE: 241

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Asp Trp Phe Gly Glu Ala Asp Tyr Gly Met Asp Val Trp
            100                 105                 110

Gly Gln Gly Thr Thr Val Thr Val Ser Ser
        115                 120

<210> SEQ ID NO 242
<211> LENGTH: 122
<212> TYPE: PRT
<213> ORGANISM: Artificial Sequence
<220> FEATURE:
<223> OTHER INFORMATION: synthetic polypeptide

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Thr Val Ile Trp Asn Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Asp Trp Leu Gly Glu Ala Asp Tyr Gly Met Asp Val Trp
            100                 105                 110

Gly Gln Gly Thr Thr Val Thr Val Ser Ser
        115                 120

<210> SEQ ID NO 243
<211> LENGTH: 121
<212> TYPE: PRT
<213> ORGANISM: Artificial Sequence
<220> FEATURE:
<223> OTHER INFORMATION: synthetic polypeptide

<400> SEQUENCE: 243

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Trp Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Glu Trp Glu Leu Glu Asp Tyr Gly Met Asp Val Trp Gly
                100                 105                 110
Gln Gly Thr Thr Val Thr Val Ser Ser
                115                 120
```

<210> SEQ ID NO 244
<211> LENGTH: 126
<212> TYPE: PRT
<213> ORGANISM: Artificial Sequence
<220> FEATURE:
<223> OTHER INFORMATION: synthetic polypeptide

<400> SEQUENCE: 244

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
                 20                  25                  30
Gly Met Tyr Trp Val Arg Gln Ala Pro Gly Lys Gly Leu Glu Trp Val
                 35                  40                  45
Ala Val Ile Trp Tyr Asp Gly Ser Asn Lys Tyr Tyr Val Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Ala Val Ala Gly Thr Gly Arg Asp Tyr Tyr Tyr Tyr Gly
                100                 105                 110
Met Asp Val Trp Gly Gln Gly Thr Thr Val Thr Val Ser Ser
                115                 120                 125
```

<210> SEQ ID NO 245
<211> LENGTH: 126
<212> TYPE: PRT
<213> ORGANISM: Artificial Sequence
<220> FEATURE:
<223> OTHER INFORMATION: synthetic polypeptide

<400> SEQUENCE: 245

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
                 20                  25                  30
Gly Met Tyr Trp Val Arg Gln Ala Pro Gly Lys Gly Leu Glu Trp Val
                 35                  40                  45
Ala Val Ile Trp Tyr Asp Gly Ser Asn Lys Tyr His Gly Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Gly Ala Val Ala Gly Thr Gly Arg Asp Tyr Tyr Tyr Tyr Gly
                100                 105                 110
```

```
Met Asp Val Trp Gly Gln Gly Thr Thr Val Thr Val Ser Ser
        115                 120                 125

<210> SEQ ID NO 246
<211> LENGTH: 126
<212> TYPE: PRT
<213> ORGANISM: Artificial Sequence
<220> FEATURE:
<223> OTHER INFORMATION: synthetic polypeptide

<400> SEQUENCE: 246

Gln Val Gln Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Lys Gly Thr Val Ala Gly Thr Gly Arg Asp Tyr Tyr Tyr Tyr Gly
            100                 105                 110

Met Asp Val Trp Gly Gln Gly Thr Thr Val Thr Val Ser Ser
        115                 120                 125

<210> SEQ ID NO 247
<211> LENGTH: 120
<212> TYPE: PRT
<213> ORGANISM: Artificial Sequence
<220> FEATURE:
<223> OTHER INFORMATION: synthetic polypeptide

<400> SEQUENCE: 247

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Phe Trp Ser Asp Tyr Pro Phe Asp Tyr Trp Gly Gln
            100                 105                 110

Gly Thr Leu Val Thr Val Ser Ser
        115                 120

<210> SEQ ID NO 248
<211> LENGTH: 120
<212> TYPE: PRT
<213> ORGANISM: Artificial Sequence
<220> FEATURE:
<223> OTHER INFORMATION: synthetic polypeptide
```

<400> SEQUENCE: 248

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Ser Asp Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Arg Asp Leu Tyr Ser Ser Ala Trp Pro Phe Asp Tyr Trp Gly Gln
            100                 105                 110

Gly Thr Leu Val Thr Val Ser Ser
        115                 120

<210> SEQ ID NO 249
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 249

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Val Ile Trp Asn Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Glu Gln Trp Arg Gly Phe Asp Tyr Trp Gly Gln Gly
            100                 105                 110

Thr Leu Val Thr Val Ser Ser
        115

<210> SEQ ID NO 250
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 250

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Val Ile Trp Tyr Asp Gly Ser Ile Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Glu Gln Trp Leu Ala Phe Asp Tyr Trp Gly Gln Gly
                100                 105                 110

Thr Leu Val Thr Val Ser Ser
            115

<210> SEQ ID NO 251
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 251

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
             20                  25                  30

Gly Met His Trp Val Arg Gln Ala Pro Asp Met Gly Leu Glu Trp Val
         35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Ile Ser Lys Asn Thr Leu Tyr
 65                  70                  75                  80

Leu Glu Met Asn Ser Leu Arg Ala Glu Asp Thr Ala Val Tyr Tyr Cys
                 85                  90                  95

Ala Arg Asp Asn Trp Gly Ser Asp Ala Phe Asp Ile Trp Gly Gln Gly
                100                 105                 110

Thr Met Val Thr Val Ser Ser
            115

<210> SEQ ID NO 252
<211> LENGTH: 126
<212> TYPE: PRT
<213> ORGANISM: Artificial Sequence
<220> FEATURE:
<223> OTHER INFORMATION: synthetic polypeptide

<400> SEQUENCE: 252

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
             20                  25                  30

Ala Met His Trp Val Arg Gln Ala Pro Gly Lys Gly Leu Glu Trp Val
         35                  40                  45

Ala Val Ile Trp Tyr Asp Gly Ile Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Tyr Tyr Asp Ser Ser Gly Tyr Tyr Tyr Gly Glu Asp

```
                100                 105                 110
Phe Asp Tyr Trp Gly Gln Gly Thr Leu Val Thr Val Ser Ser
            115                 120                 125

<210> SEQ ID NO 253
<211> LENGTH: 126
<212> TYPE: PRT
<213> ORGANISM: Artificial Sequence
<220> FEATURE:
<223> OTHER INFORMATION: synthetic polypeptide

<400> SEQUENCE: 253

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Trp Tyr Asp Gly Ile Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Ser Ser Gly Tyr Tyr Phe Gly Glu Asp
            100                 105                 110

Phe Asp Tyr Trp Gly Gln Gly Thr Leu Val Thr Val Ser Ser
        115                 120                 125

<210> SEQ ID NO 254
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 254

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Ile Ile Phe Tyr Ala Asp Ser Val
        50                  55                  60

Lys Gly Arg Phe Thr Met Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Arg Ile Ser Ile Thr Pro Phe Asp Tyr Trp Gly Gln Gly Thr
            100                 105                 110

Leu Val Thr Val Ser Ser
        115

<210> SEQ ID NO 255
<211> LENGTH: 126
<212> TYPE: PRT
<213> ORGANISM: Artificial Sequence
<220> FEATURE:
```

<223> OTHER INFORMATION: synthetic polypeptide

<400> SEQUENCE: 255

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Ile Pro Arg Trp Leu Gln Pro Tyr Tyr Tyr Tyr Gly
            100                 105                 110

Met Asp Val Trp Gly Gln Gly Thr Thr Val Thr Val Ser Ser
        115                 120                 125

<210> SEQ ID NO 256
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 256

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Asn Trp Ile Arg Gln His Pro Gly Lys Gly Leu Glu
        35                  40                  45

Trp Ile Gly Tyr Ile Tyr Tyr Ser Gly Asn Thr His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Ile Ala Ala Asp Thr Ala Val Tyr Tyr
                85                  90                  95

Cys Ala Arg Asp Trp Gly Arg Asp Ala Phe Asp Ile Trp Gly Gln Gly
            100                 105                 110

Thr Met Val Thr Val Ser Ser
        115

<210> SEQ ID NO 257
<211> LENGTH: 124
<212> TYPE: PRT
<213> ORGANISM: Artificial Sequence
<220> FEATURE:
<223> OTHER INFORMATION: synthetic polypeptide

<400> SEQUENCE: 257

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu

```
                35                  40                  45
Trp Ile Gly Tyr Ile Tyr Tyr Ser Gly Ser Thr Asp Tyr Asn Pro Ser
            50                  55                  60
Leu Lys Ser Arg Gly Ile Ile Ser Gly Asp Thr Ser Lys Asn Gln Phe
65                  70                  75                  80
Ser Leu Lys Leu Asn Ser Val Thr Ala Ala Asp Thr Ala Val Tyr Tyr
                85                  90                  95
Cys Ala Arg Glu Gly Arg Phe Gly Glu Leu Gly Ser Tyr Tyr Phe Asp
                100                 105                 110
Tyr Trp Gly Gln Gly Thr Leu Val Thr Val Ser Ser
            115                 120
```

<210> SEQ ID NO 258
<211> LENGTH: 121
<212> TYPE: PRT
<213> ORGANISM: Artificial Sequence
<220> FEATURE:
<223> OTHER INFORMATION: synthetic polypeptide

<400> SEQUENCE: 258

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser Ser Gly
                20                  25                  30
Gly Tyr Tyr Trp Ser Trp Ile Arg Gln Pro Pro Gly Lys Gly Leu Glu
            35                  40                  45
Trp Ile Gly Asn Thr Tyr Tyr Ser Gly Ser Thr Asn Tyr Lys Pro Ser
            50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Gly Arg Asp Arg Gly Arg Ala Val Gly Pro Phe Asp Tyr Trp Gly
                100                 105                 110
Gln Gly Thr Leu Val Thr Val Ser Ser
            115                 120
```

<210> SEQ ID NO 259
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 259

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Asp Ile Asn Trp Val Arg Gln Ala Thr Gly Gln Gly Leu Glu Trp Met
            35                  40                  45
Gly Trp Met Asn Pro Asn Ser Gly Asn Thr Gly Tyr Ala Gln Lys Phe
            50                  55                  60
Gln Gly Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
```

Ala Arg Ser Arg Gln Trp Leu Val Leu Asp Tyr Trp Gly Gln Gly Thr
            100                 105                 110

Leu Val Thr Val Ser Ser
        115

<210> SEQ ID NO 260
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 260

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Val Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gln Trp Leu Val Leu Asp Tyr Trp Gly Gln Gly Thr
            100                 105                 110

Leu Val Thr Val Ser Ser
        115

<210> SEQ ID NO 261
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 261

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gln Trp Leu Val Leu Asp Tyr Trp Gly Gln Gly Thr
            100                 105                 110

Leu Val Thr Val Ser Ser
        115

<210> SEQ ID NO 262
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 262

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Trp Leu Gly Phe Asp Tyr Trp Gly Gln Gly Thr
            100                 105                 110

Leu Val Thr Val Ser Ser
        115

<210> SEQ ID NO 263
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 263

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Trp Leu Gly Phe Asp Tyr Trp Gly Gln Gly Thr
            100                 105                 110

Leu Val Thr Val Ser Ser
        115

<210> SEQ ID NO 264
<211> LENGTH: 121
<212> TYPE: PRT
<213> ORGANISM: Artificial Sequence
<220> FEATURE:
<223> OTHER INFORMATION: synthetic polypeptide

<400> SEQUENCE: 264

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Gln
            20                  25                  30

```
Trp Ile Gly Trp Val Arg Gln Met Pro Gly Lys Gly Leu Glu Trp Met
            35                  40                  45

Gly Ile Ile Phe Pro Gly Asp Ser Asp Thr Arg Tyr Ser Pro Ser Phe
 50                      55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Gly Arg Ser Tyr His Tyr Tyr Gly Met Asp Val Trp Gly
                100                 105                 110

Gln Gly Thr Thr Val Thr Val Ser Ser
            115                 120
```

<210> SEQ ID NO 265
<211> LENGTH: 121
<212> TYPE: PRT
<213> ORGANISM: Artificial Sequence
<220> FEATURE:
<223> OTHER INFORMATION: synthetic polypeptide

<400> SEQUENCE: 265

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Gly Phe Thr Asn Tyr
            20                  25                  30

Trp Ile Gly Trp Val Arg Gln Met Pro Gly Lys Gly Leu Glu Trp Met
            35                  40                  45

Gly Thr Ile Tyr Pro Gly Asp Ser Asp Thr Arg Tyr Ser Pro Ser Phe
 50                      55                  60

Gln Gly Gln Val Thr Phe Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Gly Arg Ser Tyr Tyr Tyr Phe Gly Met Asp Val Trp Gly
                100                 105                 110

Gln Gly Thr Thr Val Thr Val Ser Ser
            115                 120
```

<210> SEQ ID NO 266
<211> LENGTH: 122
<212> TYPE: PRT
<213> ORGANISM: Artificial Sequence
<220> FEATURE:
<223> OTHER INFORMATION: synthetic polypeptide

<400> SEQUENCE: 266

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Trp Ile Gly Trp Val Arg Gln Met Pro Gly Lys Gly Leu Glu Trp Met
            35                  40                  45

Gly Ile Ile Tyr Pro Tyr Asp Ser Asp Thr Arg Tyr Ser Pro Ser Phe
 50                      55                  60

Gln Gly Gln Val Thr Leu Ser Ala Asp Lys Ser Ile Ser Thr Ala Tyr
 65                  70                  75                  80

Leu Arg Trp Ser Ser Leu Lys Ala Ser Asp Thr Ala Met Tyr Tyr Cys
                 85                  90                  95
```

Ala Arg His Arg Gly Gly Arg Ser Tyr Tyr Tyr Gly Met Asp Val Trp
            100                 105                 110

Gly Gln Gly Thr Thr Val Thr Val Ser Ser
            115                 120

<210> SEQ ID NO 267
<211> LENGTH: 122
<212> TYPE: PRT
<213> ORGANISM: Artificial Sequence
<220> FEATURE:
<223> OTHER INFORMATION: synthetic polypeptide

<400> SEQUENCE: 267

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Thr Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Phe Gly Glu Ser Ile His Tyr Gly Leu Asp Val Trp
            100                 105                 110

Gly Gln Gly Thr Thr Val Thr Val Ser Ser
            115                 120

<210> SEQ ID NO 268
<211> LENGTH: 121
<212> TYPE: PRT
<213> ORGANISM: Artificial Sequence
<220> FEATURE:
<223> OTHER INFORMATION: synthetic polypeptide

<400> SEQUENCE: 268

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Asn Tyr
            20                  25                  30

Trp Ile Gly Trp Val Arg Gln Met Ser Gly Lys Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Gly Gly Trp Ser Gly Trp Gly Met Asp Val Trp Gly
            100                 105                 110

Gln Gly Thr Thr Val Thr Val Ser Ser
            115                 120

<210> SEQ ID NO 269
<211> LENGTH: 124
<212> TYPE: PRT

```
<213> ORGANISM: Artificial Sequence
<220> FEATURE:
<223> OTHER INFORMATION: synthetic polypeptide

<400> SEQUENCE: 269

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Lys Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Gly Tyr Ser Gly Arg Ser Tyr Tyr Tyr Gly Met Asp
            100                 105                 110

Val Trp Gly Gln Gly Thr Ala Val Thr Val Ser Ser
        115                 120

<210> SEQ ID NO 270
<211> LENGTH: 126
<212> TYPE: PRT
<213> ORGANISM: Artificial Sequence
<220> FEATURE:
<223> OTHER INFORMATION: synthetic polypeptide

<400> SEQUENCE: 270

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile Phe Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Ile Tyr Tyr Cys
                85                  90                  95

Ala Arg His Gly His Gly Ser Ser Ser Gly Arg Thr Tyr Tyr Tyr Gly
            100                 105                 110

Leu Asp Val Trp Gly Gln Gly Thr Thr Val Thr Val Ser Ser
        115                 120                 125

<210> SEQ ID NO 271
<211> LENGTH: 116
<212> TYPE: PRT
<213> ORGANISM: Artificial Sequence
<220> FEATURE:
<223> OTHER INFORMATION: synthetic polypeptide

<400> SEQUENCE: 271

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Thr Tyr
            20                  25                  30
```

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp Thr Gly Tyr Phe Asp Tyr Trp Gly Gln Gly Thr Leu Val
            100                 105                 110

Thr Val Ser Ser
        115

<210> SEQ ID NO 272
<211> LENGTH: 122
<212> TYPE: PRT
<213> ORGANISM: Artificial Sequence
<220> FEATURE:
<223> OTHER INFORMATION: synthetic polypeptide

<400> SEQUENCE: 272

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Asp Tyr Tyr Phe Tyr Tyr Gly Met Asp Val Trp
            100                 105                 110

Gly Gln Gly Thr Thr Val Thr Val Ser Ser
        115                 120

<210> SEQ ID NO 273
<211> LENGTH: 363
<212> TYPE: DNA
<213> ORGANISM: Artificial Sequence
<220> FEATURE:
<223> OTHER INFORMATION: nucleic acid

<400> SEQUENCE: 273
gaggtgcagt tggtgcagtc tggagcagag gtgaaaaagc ccggggagtc tctgaagatc     60
tcctgtaagg gttctggata caggtttacc agctactgga tcggctgggt gcgccagatg    120
cccgggaaag gcctggagtg gatggggatc atccatcctg gtgactctga taccagatac    180
agcccgtcct tccaaggcca ggtcaccatc tcagccgaca gtccatcag caccgcctac    240 ctgcagtgga gcagcctgaa ggcctcggac actgccatat attactgtac gagacagggt    300
agaagcttct actactacgg tatggacgtc tggggccaag gaccacggt caccgtctcc    360 tca                                                                  363

<210> SEQ ID NO 274

```
<211> LENGTH: 354
<212> TYPE: DNA
<213> ORGANISM: Artificial Sequence
<220> FEATURE:
<223> OTHER INFORMATION: nucleic acid

<400> SEQUENCE: 274
gaggtgcagc tggtgcagtc tggagcagag gtgaaaaagc cggggagtc tctgaagatc      60 tcctgtaagg gttctggata caggtttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag cgccgcctac    240 ctgcagtgga gcagcctgaa ggcctcggac accgccatgt attactgtgc gagacaacaa    300
gtggctggta tgttggacta ctggggccag ggaaccctgg tcaccgtctc ctca         354

<210> SEQ ID NO 275
<211> LENGTH: 360
<212> TYPE: DNA
<213> ORGANISM: Artificial Sequence
<220> FEATURE:
<223> OTHER INFORMATION: nucleic acid

<400> SEQUENCE: 275
caggtgcagc tggtggagtc tgggggaggc gtggtccagc ctgggaggtc cctgagactc      60
tcctgtgcag cgtctggatt caccttcagt atttatggca tgcactgggt ccgccaggct    120
ccaggcaagg ggctggagtg ggtgacagtt atatggtatg atggaagtaa tgaatactat    180
gcagactccg tgaagggccg attcaccatc tccagagaca attccaagaa cacgctgtat    240
ctgcaaatga acagcctgag agccgaggac acggctgtgt attactgtgc gagagaggac    300
ttcgactccc actacggtat ggacgtctgg ggccaaggga ccacggtcac cgtctcctca    360

<210> SEQ ID NO 276
<211> LENGTH: 366
<212> TYPE: DNA
<213> ORGANISM: Artificial Sequence
<220> FEATURE:
<223> OTHER INFORMATION: nucleic acid

<400> SEQUENCE: 276
caggtgcagc tggtggagtc tgggggaggc gtggtccagc ctgggaggtc cctgagactc      60
tcctgtgcag cgtctggatt caccttcagt agctatggca tgcactgggt ccgccaggct    120
ccaggcaagg ggctggagtg ggtggcagtt atatggtatg atggaagtaa tgaatactat    180
gcagactccg tgaagggccg attcaccatc tccagagaca attccaagaa cacgctgtat    240
ctacaaatgc acagcctgag agccgaggac acggctgtgt attattgtgc gagagaagaa    300
tggttcgggg aggcggacta cggtatggac gtctggggcc aagggaccac ggtcaccgtc    360
tcctca                                                                366

<210> SEQ ID NO 277
<211> LENGTH: 366
<212> TYPE: DNA
<213> ORGANISM: Artificial Sequence
<220> FEATURE:
<223> OTHER INFORMATION: nucleic acid

<400> SEQUENCE: 277
caggtgcagc tggtggagtc tgggggaggc gtggtccagc agggaggtc cctgagactc      60 tcctgtgcag cgtctggatt caccttcagt agctatggca tgcactgggt ccgccaggct    120
```

```
ccaggcaagg ggctggagtg ggtggcagtt atatggtatg atggaagtaa tgaatattat    180
gcagactccg tgaagggccg attcaccatc tccagagaca attccaagaa cacgctgttt    240
ctgcaaatga acagcctgag agccgaggac acggctgtgt attactgtgc gagagatgat    300
tggttcgggg aggcggacta cggtatggac gtctggggcc aagggaccac ggtcaccgtc    360
tcctca                                                               366

<210> SEQ ID NO 278
<211> LENGTH: 366
<212> TYPE: DNA
<213> ORGANISM: Artificial Sequence
<220> FEATURE:
<223> OTHER INFORMATION: nucleic acid

<400> SEQUENCE: 278
caggtgcagc tggtggagtc tgggggaggc gtggtccagc ctgggaggtc cctgagactc     60
tcctgtgcag cgtctggatt caccttcagt aactatggca tgcactgggt ccgccaggct    120
ccaggcaagg ggctggagtg ggtgacagtt atatggaatg atggaagtaa tgaatactat    180
gcagactccg tgaagggccg attcaccatc tccagagaca attccaagaa cacgctgttt    240
ctgcaaatga acagcctgag agccgaggac acggctgtgt attactgtgc gagagaagat    300
tggctcgggg aggcggacta cggtatggac gtctggggcc aagggaccac ggtcaccgtc    360
tcctca                                                               366

<210> SEQ ID NO 279
<211> LENGTH: 363
<212> TYPE: DNA
<213> ORGANISM: Artificial Sequence
<220> FEATURE:
<223> OTHER INFORMATION: nucleic acid

<400> SEQUENCE: 279
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagaagag    300
tgggagctag aggactacgg tatggacgtc tggggccaag gaccacggt caccgtctcc    360 tca                                                                  363

<210> SEQ ID NO 280
<211> LENGTH: 378
<212> TYPE: DNA
<213> ORGANISM: Artificial Sequence
<220> FEATURE:
<223> OTHER INFORMATION: nucleic acid

<400> SEQUENCE: 280
caggtgcagt tggtggagtc tgggggaggc gtggtccagc ctgggaggtc cctgagactc     60
tcctgtgcag cgtctggatt caccttcagt agttatggca tgtactgggt ccgccaggct    120
ccaggcaagg ggctggagtg ggtggcagtt atatggtatg atggaagtaa taaatactat    180
gtagactccg tgaagggccg attcaccatc tccagagaca attccaagaa cacgctgtat    240
ctgcaaatga acagcctgag agccgaggac acggctgtgt attactgtgc gagaggagca    300
```

```
gtggctggta cgggacggga ctactactac tacggtatgg acgtctgggg ccaagggacc    360
acggtcaccg tctcctca                                                  378
```

<210> SEQ ID NO 281
<211> LENGTH: 378
<212> TYPE: DNA
<213> ORGANISM: Artificial Sequence
<220> FEATURE:
<223> OTHER INFORMATION: nucleic acid

<400> SEQUENCE: 281

```
caggtgcagt tggtggagtc tgggggaggc gtggtccagc ctgggaggtc cctgagactc    60
tcctgtgcag cgtctggatt cacgttcagt agttatggca tgtactgggt ccgccaggct    120
ccaggcaagg ggctggagtg ggtggcagtt atatggtatg atggaagtaa taaataccat    180
ggagactccg tgaagggccg attcaccatc tccagagaca attccaagaa tacgctgtat    240
ctgcaaatga acagcctgag agccgaggac acggctgtgt attactgtgc gaaaggagca    300
gtggctggta cgggacggga ctactactac tacggtatgg acgtctgggg ccaagggacc    360
acggtcaccg tctcctca                                                  378
```

<210> SEQ ID NO 282
<211> LENGTH: 378
<212> TYPE: DNA
<213> ORGANISM: Artificial Sequence
<220> FEATURE:
<223> OTHER INFORMATION: nucleic acid

<400> SEQUENCE: 282

```
caggtgcagc tggtggagtc tgggggaggc gtggtccagc ctgggaggtc ccagagactc    60
tcctgtgcag cgtctggatt cacctttagt agttatggca tgtactgggt ccgccaggct    120
ccaggcaagg ggctggagtg ggtggcagtt atatggtatg atggaagtaa taaaaactat    180
gcagactccg tgaagggccg attcaccatc tccagagaca attccaagaa tacgttgtat    240
ctgcaaatga acagcctgag agccgaggac acggctgtgt atcactgtgc gaaaggaaca    300
gtggctggta cgggacggga ctactactac tacggtatgg acgtctgggg ccaagggacc    360
acggtcaccg tctcttca                                                  378
```

<210> SEQ ID NO 283
<211> LENGTH: 360
<212> TYPE: DNA
<213> ORGANISM: Artificial Sequence
<220> FEATURE:
<223> OTHER INFORMATION: nucleic acid

<400> SEQUENCE: 283

```
caggtgcaac tggtggagtc tgggggaggc gtggtccagc ctgggaggtc cctgagactc    60
tcctgtgcag cgtctggatt caccttcagt agctttggca tgcactgggt ccgccaggct    120
ccaggcaagg ggctggagtg ggtggcagtt atttggtttg atggaagtaa taaatactat    180
gtagactccg tgaagggccg attcaccatc tccagagaca attccaagaa tacgctgtat    240
ctgcaaatga acagcctgag agccgaggac acggctgtgt attactgtgc gcggacgat     300 tttggagtg attatccttt tgactactgg ggccagggaa ccctggtcac cgtctcctca     360
```

<210> SEQ ID NO 284
<211> LENGTH: 360
<212> TYPE: DNA
<213> ORGANISM: Artificial Sequence

```
<220> FEATURE:
<223> OTHER INFORMATION: nucleic acid

<400> SEQUENCE: 284
caggtgcaac tggtggagtc tggggaggc gtggtccagc ctgggaggtc cctgagactc       60
tcctgtgcag cctctggatt caccttcagg agctatggca tgcactgggt ccgccaggct     120
ccaggcaagg ggctggagtg ggtggcagtt atatcagatg atggaagtaa taaatactat    180
gcagactccg tgaagggccg attcaccatc tccagagaca attccaagaa cacgctgtat    240
ctgcaaatga acagcctgag acctgaggac acggctgtgt attactgtgc gagagatctc    300
tatagcagtg cctggccctt tgactactgg ggccagggaa ccctggtcac cgtctcctca    360

<210> SEQ ID NO 285
<211> LENGTH: 357
<212> TYPE: DNA
<213> ORGANISM: Artificial Sequence
<220> FEATURE:
<223> OTHER INFORMATION: nucleic acid

<400> SEQUENCE: 285
caggtgcagc tggtggagtc tggggaggc gtggtccagc ctgggaggtc cctgagactc       60
tcctgtgcag cgtctggatt caccttcagt agctatgaca tacactgggt ccgccaggct     120
ccaggcaagg ggctggagtg ggtggcagtt atatggaatg atggaagtat taaatactat    180
gcagactccg tgaagggccg attcaccatc tccagagaca attccaagaa cacgctgtat    240
ctgcaaatga acagcctgag agccgaggac acggctgtgt attactgtgc gagagacggg    300
gagcagtggc ggggctttga ctactgggc cagggaaccc tggtcaccgt ctcctca       357

<210> SEQ ID NO 286
<211> LENGTH: 357
<212> TYPE: DNA
<213> ORGANISM: Artificial Sequence
<220> FEATURE:
<223> OTHER INFORMATION: nucleic acid

<400> SEQUENCE: 286
caggtgcagc tggtggagtc tggggaggc gtggtccagc ctgggaggtc cctgagactc       60
tcctgtgcag cgtctggatt caccttcagt agctatgaca tacactgggt ccgtcaggct     120
ccaggcaagg ggctggagtg ggtggcagtt atatggtatg atggaagtat taaatactat    180
gcagactccg tgaagggccg attcaccatc tccagagaca attccaagaa cacgctgtat    240
ctgcaaatga acagcctgag agccgaggac acggctgtgt attactgtgc gagagatcag    300
gagcagtggc tggcctttga ctactgggc cagggaaccc tggtcaccgt ctcctca       357

<210> SEQ ID NO 287
<211> LENGTH: 357
<212> TYPE: DNA
<213> ORGANISM: Artificial Sequence
<220> FEATURE:
<223> OTHER INFORMATION: nucleic acid

<400> SEQUENCE: 287
caggtgcagt tggtggagtc tggggaggc gtggtccagc ctgggaggtc cctgagactc       60
tcctgtgcag cgtctggatt caccttcagt acctatggca tgcactgggt ccgccaggct     120
ccagacatgg ggctggagtg ggtggcagtt atatggtatg atggaagtaa taaatactat    180
gcagactctg tgaagggccg attcaccatc tccagagaca tttccaagaa cacgctgtat    240
```

```
ctggaaatga acagcctgag agccgaggac acggctgtgt attactgtgc gagagacaac      300 tgggatccg atgctttga tatctggggc caagggacaa tggtcaccgt ctcttca           357
```

<210> SEQ ID NO 288
<211> LENGTH: 378
<212> TYPE: DNA
<213> ORGANISM: Artificial Sequence
<220> FEATURE:
<223> OTHER INFORMATION: nucleic acid

<400> SEQUENCE: 288

```
caggtgcagc tggtggagtc tgggggaggc gtggtccagc ctgggaggtc cctgagactc       60
tcctgtgcag cgtctggatt caccttcagt acctatgcca tgcactgggt ccgccaggct      120
ccaggcaagg ggctggagtg ggtggcagtt atatggtatg atggaattaa taaatactat      180
gcagactccg tgaagggccg attcaccatc tccagagaca attccaagaa cacgctgtat      240
ctgcaaatga acagcctgag agccgaggac acggctgtgt attactgtgc gagagggagt      300
tactatgata gtagtggtta ttactacggg gaggactttg actactgggg ccagggaacc      360
ctggtcaccg tctcctca                                                    378
```

<210> SEQ ID NO 289
<211> LENGTH: 378
<212> TYPE: DNA
<213> ORGANISM: Artificial Sequence
<220> FEATURE:
<223> OTHER INFORMATION: nucleic acid

<400> SEQUENCE: 289

```
caggtgcagc tggtggagtc tgggggaggc gtggtccagc ctgggaggtc cctgagactc       60
tcctgtgcag cgtctggatt caccttcagt agctatgcca tgcactgggt ccgccaggct      120
ccaggcaagg ggctggagtg ggtggcagtt atctggtatg atggaattaa taaatactat      180
gcagactccg tgaagggccg attcaccatc tccagagaca attccaagaa cacgctgtat      240
ctgcaaatga acagcctgag agccgaggac acggctgtgt attactgtgc gagagggagt      300
tactatgata gtagtggtta ttacttcggg gaggactttg actactgggg ccagggaacc      360
ctggtcaccg tctcctca                                                    378
```

<210> SEQ ID NO 290
<211> LENGTH: 354
<212> TYPE: DNA
<213> ORGANISM: Artificial Sequence
<220> FEATURE:
<223> OTHER INFORMATION: nucleic acid

<400> SEQUENCE: 290

```
caggtgcagc tggtggagtc tgggggaggc ttggtcaagc ctggagggtc cctgagactc       60
tcctgtgcag cctctggatt caccttcagt gactactaca tgagctggat ccgccaggct      120
ccagggaagg ggctggagtg ggtttcatac attagtagta gtggtagtat catttttac       180 gcagactctg tgaagggccg attcaccatg tccagggaca acgccaagaa ctcactgtat      240
ctgcaaatga acagcctgag agccgaggac acggccgtgt attattgtgt gagaaggatt      300
agtataaccc cttttgacta ctggggccag ggaaccctgg tcaccgtctc ctca            354
```

<210> SEQ ID NO 291
<211> LENGTH: 378
<212> TYPE: DNA
<213> ORGANISM: Artificial Sequence
<220> FEATURE:
<223> OTHER INFORMATION: nucleic acid

<400> SEQUENCE: 291

```
caggtcacct tgaaggagtc tggtcctgtg ctggtgaaac ccacagagac cctcacgctg    60
acctgcaccg tctctgggtt ctcactcagc aatgctagaa tgggtgtgag ctggatccgt   120
cagcccccag ggaaggccct ggagtggctt gcacacattt tttcgaatga cgaaaaatcc   180
tacagcacat ctctgaagag caggctcacc atctccaagg acacctccaa aagccaggtg   240
gtccttacca tgaccaacat ggaccctgtg acacagcca catattactg tgtacggata    300
ccgagatggc tacaaccccc ctactactac tacggtatgg acgtctgggg ccaagggacc   360
acggtcaccg tctcctca                                                  378
```

<210> SEQ ID NO 292
<211> LENGTH: 357
<212> TYPE: DNA
<213> ORGANISM: Artificial Sequence
<220> FEATURE:
<223> OTHER INFORMATION: nucleic acid

<400> SEQUENCE: 292

```
caggtgcagc tgcaggagtc gggcccagga ctggtgaagc cttcacagac cctgtccctc    60
acctgcactg tctctggtgg ctccatcagc agtggtggtt actactggaa ctggatccgc   120
cagcacccag ggaagggcct ggagtggatt gggtacatct attacagtgg gaacacccac   180
tacaacccgt ccctcaagag tcgagttacc atatcagtag acacgtctaa gaaccagttc   240
tccctgaagc tgagctctgt gattgccgcg gacacggccg tgtattactg tgcgagagac   300
tggggacgtg atgcttttga tatctggggc caagggacaa tggtcaccgt ctcttca      357
```

<210> SEQ ID NO 293
<211> LENGTH: 372
<212> TYPE: DNA
<213> ORGANISM: Artificial Sequence
<220> FEATURE:
<223> OTHER INFORMATION: nucleic acid

<400> SEQUENCE: 293

```
caggtgcagc tgcaggagtc gggcccagga ctggtgaagc cttcacagac cctgtccctc    60
acctgcactg tctcgggtgg ctccatcagc agtggtggtt actactggag ctggatccgc   120
cagcacccag ggaagggcct ggagtggatt gggtacatct attatagtgg gagcaccgac   180
tacaacccgt ccctcaagag tcgaggtatc atatcaggag acacgtctaa gaaccagttc   240
tccctgaagc tgaactctgt gactgccgcg gacacggccg tgtattactg tgcgagagag   300
gggaggttcg gggagttagg ctcctactac tttgactact ggggccaggg aaccctggtc   360
accgtctcct ca                                                       372
```

<210> SEQ ID NO 294
<211> LENGTH: 363
<212> TYPE: DNA
<213> ORGANISM: Artificial Sequence
<220> FEATURE:
<223> OTHER INFORMATION: nucleic acid

<400> SEQUENCE: 294

```
caggtgcagc tgcaggagtc gggcccagga ctggtgaagc cttcggagac cctgtccctc    60
acctgcactg tctctggtgg ctccgtcagc agtggtggtt actactggag ctggatccgg   120
```

```
cagcccccag ggaagggact ggagtggatt gggaatacct attacagtgg gagcaccaac    180
tacaaaccct ccctcaagag tcgagtcacc atatcagtag acacgtccaa gaaccagttc    240
tccctgaagc tgagttctgt gaccgctgcg gacacggccg tgtattactg tgggagagac    300
cggggtagag cagtgggtcc ctttgactac tggggccagg gaaccctggt caccgtctcc    360
tca                                                                  363
```

<210> SEQ ID NO 295
<211> LENGTH: 354
<212> TYPE: DNA
<213> ORGANISM: Artificial Sequence
<220> FEATURE:
<223> OTHER INFORMATION: nucleic acid

<400> SEQUENCE: 295

```
caggtgcagc tggtgcagtc tggggctgag gtgaagaagc ctggggcctc agtgaaggtc     60
tcctgcaagg cttctggata caccttcacc aattatgata tcaactgggt gcgacaggcc    120
actggacaag gcttgagtg gatgggatgg atgaaccta acagtggtaa cacaggctat    180
gcacagaagt tccagggcag agtcaccatg accaggaaca cctccataag cacagcctac    240
atggagctga gcagcctgag atctgaggac acggccgtgt attactgtgc gagaagtagg    300
cagtggctgg tacttgacta ctggggccag ggaaccctgg tcaccgtctc ctca          354
```

<210> SEQ ID NO 296
<211> LENGTH: 354
<212> TYPE: DNA
<213> ORGANISM: Artificial Sequence
<220> FEATURE:
<223> OTHER INFORMATION: nucleic acid

<400> SEQUENCE: 296

```
caggtgcagc tggtgcagtc tggggctgag gtgaagaagc ctggggcctc agtgaaggtc     60
tcctgcaagg cttctggata caccttcacc aattatgata tcaactgggt gcgacaggcc    120
actggacaag gcttgagtg gatgggatgg atgaaccta acagtggtaa cacaggctat    180
gtacagaagt tccagggcag agtcaccatg accaggaaca cctccataag cacagcctac    240
atggagctga gcagcctgag atctgaggac acggccgtgt attactgtgc gagaagtagg    300
cagtggctgg tacttgacta ctggggccag ggaaccctgg tcaccgtctc ctca          354
```

<210> SEQ ID NO 297
<211> LENGTH: 354
<212> TYPE: DNA
<213> ORGANISM: Artificial Sequence
<220> FEATURE:
<223> OTHER INFORMATION: nucleic acid

<400> SEQUENCE: 297

```
caggtgcagc tggtgcagtc tggggctgag gtgaagaagc ctggggcctc agtgaaggtc     60
tcctgcaagg cttctggata caggttcacc agttatgata tcaactgggt gcgacaggcc    120
actggacaag gcttgagtg gatgggatgg atgaacccaa acagtggtaa cacaggctat    180
gcacagaagt tccagggcag agtcaccatg accaggaaca cctccataag cacagcctac    240
atggagctga gcagcctgag atctgaggac acggccgtgt attactgtgc gagaagtagg    300
cagtggctgg tacttgacta ctggggccag ggaaccctgg tcaccgtctc ctca          354
```

<210> SEQ ID NO 298
<211> LENGTH: 354

```
<212> TYPE: DNA
<213> ORGANISM: Artificial Sequence
<220> FEATURE:
<223> OTHER INFORMATION: nucleic acid

<400> SEQUENCE: 298
caggtgcagc tggtgcagtc tggggctgag gtgaagaagc ctggggcctc agtgaaggtc      60
tcctgcaagg cttctggata caccttcacc acttatgata tcaactgggt gcgacaggcc     120
actggacaag ggcttgagtg gatgggatgg atgaaccta acagtggtaa cacaggctat      180
gcacagaagt tccagggcag agtcaccatg accaggaaca cctccataag cacagcctac     240
atggagctga gcagcctaag atctgaggac acggccgtgt attactgtgc gagaggccgg     300
cagtggctgg gctttgacta ctggggccag ggaaccctgg tcaccgtctc ctca          354

<210> SEQ ID NO 299
<211> LENGTH: 354
<212> TYPE: DNA
<213> ORGANISM: Artificial Sequence
<220> FEATURE:
<223> OTHER INFORMATION: nucleic acid

<400> SEQUENCE: 299
caggtgcagc tggtgcagtc tggggctgag gtgaagaagc ctggggcctc agtgaaggtc      60
tcctgcaagg cttctggata caccttcacc aattatgata tcaactgggt gcgacaggcc     120
actggacaag ggcttgagtg gatgggatgg atgaaccta atagtggtaa cacaggctat      180
gcacagaagt tccagggcag agtcaccatg accaggaaca cctccataaa cacagcctac     240
atggagctga gcagcctgag atctgaggac acggccgtgt attactgtgc gagaggccgg     300
cagtggctgg gctttgacta ctggggccag ggaaccctgg tcaccgtctc ctca          354

<210> SEQ ID NO 300
<211> LENGTH: 363
<212> TYPE: DNA
<213> ORGANISM: Artificial Sequence
<220> FEATURE:
<223> OTHER INFORMATION: nucleic acid

<400> SEQUENCE: 300
gaggtgcagc tggtgcagtc tggagcagag gtgaaaaagc ccggggagtc tctgaagatc      60
tcctgtaagg gttctggata cagctttacc agccagtgga tcggctgggt gcgccagatg     120
cccgggaaag gcctggagtg gatgggggatc atctttcctg gtgactctga taccagatac     180
agcccgtcct tccaaggcca ggtcaccatc tcagccgaca gtccatcag cacccgcctac     240 ctgcagtgga gcagcctgaa ggcctcggac accgccatgt attactgtgc gcgacagggt     300
agaagttacc actactacgg tatggacgtc tggggccaag gaccacggt caccgtctcc     360 tca                                                                 363

<210> SEQ ID NO 301
<211> LENGTH: 363
<212> TYPE: DNA
<213> ORGANISM: Artificial Sequence
<220> FEATURE:
<223> OTHER INFORMATION: nucleic acid

<400> SEQUENCE: 301
gaggtgcagc tggtgcagtc tggagcagag gtgaaaaagc ccggggagtc tctgaagatc      60
tcctgtaagg gttctggata cggctttacc aactactgga tcggctgggt gcgccagatg     120
```

```
cccggaaaag gcctggagtg gatggggacc atctatcctg gtgactctga taccagatac    180
agtccgtcct tccaaggcca ggtcaccttc tcagccgaca agtccatcag caccgcctac    240
ctgcagtgga gcagcctgaa ggcctcggac accgccatgt attactgtgc gagacagggt    300
agaagttact actacttcgg tatggacgtc tggggccaag gaccacggt caccgtctcc    360 tca                                                                  363
```

```
<210> SEQ ID NO 302
<211> LENGTH: 366
<212> TYPE: DNA
<213> ORGANISM: Artificial Sequence
<220> FEATURE:
<223> OTHER INFORMATION: nucleic acid

<400> SEQUENCE: 302
gaggtgcagc tggtgcagtc tggagcagag gtgaaaaagc ccggggagtc tctgaagatc     60
tcctgtaagg gttctggata cagctttacc gactactgga tcggctgggt gcgccagatg    120
cccggaaaag gcctggaatg gatggggatc atctatcctt atgactctga taccagatac    180
agcccgtcct tccaaggcca ggtcaccctc tcagccgaca agtccatcag caccgcctac    240
ctgcggtgga gcagcctgaa ggcctcggac accgccatgt attactgtgc gagacatcgg    300 gggggaggt cctactacta cggtatggac gtctggggcc aagggaccac ggtcaccgtc    360
tcctca                                                               366
```

```
<210> SEQ ID NO 303
<211> LENGTH: 366
<212> TYPE: DNA
<213> ORGANISM: Artificial Sequence
<220> FEATURE:
<223> OTHER INFORMATION: nucleic acid

<400> SEQUENCE: 303
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccggaaaag gcctagaatg gatggggatc atctatcctg gtgactctga taccacatac    180
agcccgtcct tccaaggcca agtcaccatc tcagccgaca agtccatcaa caccgcctac    240
ctgcagtgga gcagcctgaa ggcctcggac accgccatgt attactgtgc gagagagggt    300
ttcggggagt ctattcacta cggtttggac gtctggggcc aagggaccac ggtcaccgtc    360
tcctca                                                               366
```

```
<210> SEQ ID NO 304
<211> LENGTH: 363
<212> TYPE: DNA
<213> ORGANISM: Artificial Sequence
<220> FEATURE:
<223> OTHER INFORMATION: nucleic acid

<400> SEQUENCE: 304
gaggtgcagc tggtgcagtc tggagcagag gtgaaaaagc ccggggagtc tctgaagatc     60
tcctgtaagg gttctggata caattttacc aactactgga tcggctgggt gcgccagatg    120
tccggaaaag gcctggagtg gatgggaatc atctatcctg gtgactctga aaccagatac    180
agcccgtcct tccaaggcca ggtcaccatc tcagccgaca agtccatcag caccgcctac    240
ctgcagtgga gcagcctgaa ggcctcggac accgccatgt attactgtgc gagacatgga    300
gggggatgga gtggttgggg tatggacgtc tggggccaag gaccacggt caccgtctcc    360
```

```
tca                                                             363

<210> SEQ ID NO 305
<211> LENGTH: 372
<212> TYPE: DNA
<213> ORGANISM: Artificial Sequence
<220> FEATURE:
<223> OTHER INFORMATION: nucleic acid

<400> SEQUENCE: 305
gaggtgcagc tggtgcagtc tggagcagag gtgaaaaagc ccggggagtc tctgaagatc    60
tcctgtaagg gttctggata caggtttacc aactactgga tcggctgggt gcgccagatg   120
cccgggaaag gcctggagtg gatggggatc atctatcctg gtgactctga taccaaatac   180
agcccgtcct tccaaggcca ggtcaccatc tcagccgaca gtccatcag taccgcctac    240 ctgcagtgga gcagcctgaa ggcctcggac accgccatgt attactgtgc gagacatggt   300
ggatatagtg gccgttccta ctactacggt atggacgtct ggggccaggg gaccgcggtc   360
accgtctcct ca                                                       372

<210> SEQ ID NO 306
<211> LENGTH: 378
<212> TYPE: DNA
<213> ORGANISM: Artificial Sequence
<220> FEATURE:
<223> OTHER INFORMATION: nucleic acid

<400> SEQUENCE: 306
gaggtgcagc tggtgcagtc tggagcagag gtgaaaaagc ccggggagtc tctgaagatc    60
tcctgtaagg gttctggata caggtttacc agctactgga tcggctgggt gcgccagatg   120
cccgggaaag gcctggagtg gatggggatc atctttcctg gtgactctga taccagatac   180
agcccgtcct tccaaggcca ggtcaccatc tcagccgaca gtccatcac caccgcctac   240 ctgcagtgga gcagcctgaa ggcctcggac accgccatct attactgtgc gcgacatggg   300
catggcagct cgtccgggcg gacctactac tacggtttgg acgtctgggg ccaagggacc   360
acggtcaccg tctcctca                                                 378

<210> SEQ ID NO 307
<211> LENGTH: 348
<212> TYPE: DNA
<213> ORGANISM: Artificial Sequence
<220> FEATURE:
<223> OTHER INFORMATION: nucleic acid

<400> SEQUENCE: 307
gaggtgcagc tggtgcaatc tggagcagag gtgaaaaagc ccggggagtc tctgaagatc    60
tcctgtaagg gttctggata caactttacc acctactgga tcggctgggt gcgccagatg   120
cccgggaaag gcctggagtg gatggggatc atctatcctg gtgactctga taccagatac   180
agcccgtcct tccaaggcca ggtcaccatt tcagccgaca gtccatcaa caccgcctac    240 ctgcagtgga gcagcctgaa ggcctcggac acagccattt attactgtgc gagagacaca   300
ggatactttg actactgggg ccagggcacc ctggtcaccg tctcctca                348

<210> SEQ ID NO 308
<211> LENGTH: 366
<212> TYPE: DNA
<213> ORGANISM: Artificial Sequence
<220> FEATURE:
```

<223> OTHER INFORMATION: nucleic acid

<400> SEQUENCE: 308

```
caggtgcagt tggtggagtc tgggggaggc gtggtccagc ctgggaggtc cctgagactc    60
tcctgtgcag cgtctggatt caccttcagt agctatggca tgcactgggt ccgccaggct   120
ccaggcaagg gcctggagtg ggtggcagtt atctggtatg atggaagtaa taaattctat   180
gtagactccg tgaagggccg attcaccatc tccagagaca attccaagaa cacgctgtat   240
ctgcaaatga acagcctgag agccgaggac acggctgtgt attactgtgc gagacccggg   300
tccgattact acttctacta cggtatggac gtctggggcc aagggaccac ggtcaccgtc   360
tcctca                                                              366
```

US 10,851,144 B2

INTERLEUKIN-2 MUTEINS FOR THE EXPANSION OF T-REGULATORY CELLS

CROSS-REFERENCE TO RELATED APPLICATIONS

This application is a National Stage application under 35 U.S.C. § 371 of International Application No. PCT/US2016/030843, having an international filing date of May 4, 2016, which claims the benefit of U.S. Provisional Patent Application No. 62/146,136, filed Apr. 10, 2015, all of which are incorporated herein by reference in their entirety for all purposes.

BACKGROUND

IL-2 binds three transmembrane receptor subunits: IL-2Rβ and IL-2Rγ which together activate intracellular signaling events upon IL-2 binding, and CD25 (IL-2Rα) which serves to stabilize the interaction between IL-2 and IL-2Rβγ. The signals delivered by IL-2Rγ include those of the PI3-kinase, Ras-MAP-kinase, and STAT5 pathways.

T cells require expression of CD25 to respond to the low concentrations of IL-2 that typically exist in tissues. T cells that express CD25 include both FOXP3+ regulatory T cells (Treg cells), which are essential for suppressing autoimmune inflammation, and FOXP3− T cells that have been activated to express CD25. FOXP3− CD25+T effector cells (Teff) may be either CD4+ or CD8+ cells, both of which may contribute to inflammation, autoimmunity, organ graft rejection, or graft-versus-host disease. IL-2-stimulated STAT5 signaling is crucial for normal T-reg cell growth and survival and for high FOXP3 expression.

In co-owned WO 2010/085495, we describe the use of IL-2 muteins to preferentially expand or stimulate Treg cells. When administered to a subject, the effect on Treg cells is useful for treating inflammatory and autoimmune diseases. Although the IL-2 muteins described therein are useful for expanding Treg over Teff cells in vivo, it was desirable to create IL-2 muteins that had optimal attributes for a human therapeutic.

SUMMARY

Described herein are IL-2 muteins, anti-IL-2 antibodies, and anti-IL-2 antibody/IL-2 complexes that are amenable to high-yield manufacturability and have pharmacological activity. In the effort to produce such molecules for use as human therapeutics, a number of unexpected and unpredictable observations occurred. The compositions and methods described herein resulted from that effort.

The IL-2 muteins described herein have a relatively low likelihood of creating an immune response against the IL-2 mutein and/or endogenous IL-2 and provide Treg preferential expansion and activation. Moreover, in certain embodiments, the IL-2 mutein is fused to a molecule, e.g. an antibody Fc, that increases the serum half-life when administered to a subject. IL-2 muteins have a short serum half-life (3 to 5 hrs for sub-cutaneous injection). Exemplary IL-2 mutein Fc fusions described herein have a half-life in humans of at least 1 day, at least 3 days, at least 5 days, at least 10 days, at least 15 days, at least 20 days, or at least 25 days. This effect on the pharmacokinetics of the IL-2 muteins allows for decreased or less frequent dosing of the IL-2 mutein therapeutic.

Moreover, when creating a pharmaceutical large molecule, consideration must be made for the ability to produce the large molecule in large quantities, while minimizing aggregation and maximizing the stability of the molecule. The IL-2 mutein Fc-fusion molecules demonstrate such attributes.

Additionally, in certain embodiments, the IL-2 mutein Fc-fusion protein contains an IgG1 Fc region. When it is desirable to abolish the effector functions of IgG1 (e.g., ADCC activity), it was found that mutation of the asparagine at position 297 to glycine (N297G; EU numbering scheme) provided greatly improved purification efficiency and biophysical properties over other mutations that lead to an aglycosylation IgG1 Fc. In preferred embodiments, cysteines are engineered into the Fc to allow disulfide bonds, which increased stability of the aglycosylated Fc-containing molecule. The usefulness of the aglycosylated Fc goes beyond the IL-2 mutein Fc-fusion context. Thus, provided herein are Fc-containing molecules, Fc-fusions and antibodies, comprising a N297G substitution and optionally substitution of one or more additional residues to cysteine.

In one aspect, the present invention provides a human interleukin-2 (IL-2) mutein comprising an amino acid sequence that is at least 90% identical to the amino acid sequence set forth in SEQ ID NO:1, wherein said IL-2 mutein has at least one mutation selected from L12G, L12K, L12Q, L12S, Q13G, E15A, E15G, E15S, H16A, H16D, H16G, H16K, H16M, H16N, H16R, H16S, H16T, H16V, H16Y, L19A, L19D, L19E, L19G, L19N, L19R, L19S, L19T, L19V, D20A, D20E, D20F, D20G, D20T, D20W, M23R, R81A, R81G, R81S, R81T, D84A, D84E, D84G, D84I, D84M, D84Q, D84R, D84S, D84T, S87R, N88A, N88D, N88E, N88F, N88G, N88M, N88R, N88S, N88V, N88W, V91D, V91E, V91G, V91S, I92K, I92R, and E95G and preferentially stimulates T regulatory cells relative to other T cells or NK cells, both in in vitro assays and in humanized mice (NSG mice reconstituted with CD34+ hematopoietic stem cells). In one embodiment, said mutein is at least 95% identical to the amino acid sequence set forth in SEQ ID NO:1. In another embodiment, said mutein is at least 97% identical to the amino acid sequence set forth in SEQ ID NO:1. In another embodiment, the amino acid sequence of said mutein differs from the amino acid sequence set forth in SEQ ID NO:1 only at C125A and at one position selected from L12G, L12K, L12Q, L12S, Q13G, E15A, E15G, E15S, H16A, H16D, H16G, H16K, H16M, H16N, H16R, H16S, H16T, H16V, H16Y, L19A, L19D, L19E, L19G, L19N, L19R, L19S, L19T, L19V, D20A, D20E, D20F, D20G, D20T, D20W, M23R, R81A, R81G, R81S, R81T, D84A, D84E, D84G, D84I, D84M, D84Q, D84R, D84S, D84T, S87R, N88A, N88D, N88E, N88F, N88G, N88M, N88R, N88S, N88V, N88W, V91D, V91E, V91G, V91S, I92K, I92R, and E95G. In another embodiment, the amino acid sequence of said mutein differs from the amino acid sequence set forth in SEQ ID NO:1 only at C125A and at one position selected from D20E, D20G, D20W, D84A, D84S, H16D, H16G, H16K, H16R, H16T, H16V, I92K, I92R, L12K, L19D, L19N, L19T, N88D, N88R, N88S, V91D, V91G, V91K, and V91S.

In another aspect, the present invention provides an Fc-fusion protein comprising an Fc and the human IL-2 mutein as described above. In one embodiment, the Fc is a human IgG1 Fc. In another embodiment, the human IgG1 Fc comprises one or more mutations altering effector function of said Fc. In another embodiment, the human IgG1 comprises a substitution at N297. In another embodiment, the substitution at N297 is N297G. In another embodiment, the Fc-fusion protein comprises a substitution or deletion of the C-terminal lysine of said human IgG Fc. In another embodiment, the C-terminal lysine of said human IgG Fc is deleted. In another embodiment, a linker connects the Fc and human IL-2 mutein portions of said protein. In another embodiment, the linker is GGGGS (SEQ ID NO: 5), GGNGT, or (SEQ ID NO: 6), and YGNGT (SEQ ID NO: 7). In another embodiment, the linker is GGGGS (SEQ ID NO: 5). In another embodiment, the IL-2 mutein further comprises an amino acid addition, substitution, or deletion altering glycosylation of said Fc-fusion protein when expressed in mammalian cells. In another embodiment, the IL-2 mutein comprises a T3 substitution. In another embodiment, the IL-2 mutein comprises a T3N or T3A substitution. In another embodiment, the IL-2 mutein comprises a T3N substitution. In another embodiment, the IL-2 mutein further comprises an S5 mutation. In another embodiment, the IL-2 mutein further comprises an S5T mutation. In another embodiment, said Fc-fusion protein comprises an Fc dimer. In another embodiment, said Fc-fusion protein comprises two IL-2 muteins. In another embodiment, said Fc-fusion protein comprises a single IL-2 mutein.

In another aspect, the present invention provides an isolated nucleic acid encoding a human IL-2 mutein as described above.

In another aspect, the present invention provides an isolated nucleic acid encoding an Fc portion of an antibody and a human IL-2 mutein as described above. In one embodiment, said Fc portion of an antibody and the human IL-2 mutein are encoded within a single open-reading frame. In another embodiment, the Fc is a human IgG1 Fc. In another embodiment, the human IgG1 Fc comprises one or more mutations altering effector function of said Fc. In another embodiment, the human IgG1 comprises a substitution at N297. In another embodiment, the substitution at N297 is N297G. In another embodiment, the nucleic acid encodes a substitution or deletion of the C-terminal lysine of said human IgG Fc. In another embodiment, the C-terminal lysine of said human IgG Fc is deleted. In another embodiment, the nucleic acid further encodes a linker connecting the Fc portion of an antibody and the human IL-2 mutein. In another embodiment, the linker is GGGGS (SEQ ID NO: 5), GGNGT, or (SEQ ID NO: 6), and YGNGT (SEQ ID NO: 7). In another embodiment, the linker is GGGGS (SEQ ID NO: 5). In another embodiment, the IL-2 mutein further comprises an amino acid addition, substitution, or deletion altering glycosylation of a protein comprising said IL-2 mutein when expressed in mammalian cells. In another embodiment, the IL-2 mutein comprises a T3 substitution. In another embodiment, the IL-2 mutein comprises a T3N or T3A substitution. In another embodiment, the IL-2 mutein comprises a T3N substitution. In another embodiment, the IL-2 mutein further comprises an S5 mutation. In another embodiment, the IL-2 mutein further comprises an S5T mutation.

In another aspect, the present invention provides an expression vector comprising an isolated nucleic acid described above operably linked to a promoter.

In another aspect, the present invention provides a host cell comprising an isolated nucleic acid described above. In one embodiment, the isolated nucleic acid is operably linked to a promoter. In another embodiment, said host cell is a prokaryotic cell. In another embodiment, the host cell is *E. coli*.

In another embodiment, said host cell is a eukaryotic cell. In another embodiment, the host cell is a mammalian cell. In another embodiment, the host cell is a Chinese hamster ovary (CHO) cell line.

In another aspect, the present invention provides a method of making a human IL-2 mutein, comprising culturing a host cell as described above under conditions in which said promoter is expressed and harvesting the human IL-2 mutein from said culture.

In another aspect, the present invention provides a method of making a Fc-fusion protein, comprising culturing a host cell as described above under conditions in which said promoter is expressed and harvesting the Fc-fusion protein from said culture.

In another aspect, the present invention provides a method of increasing the ratio of regulatory T cells (Tregs) to non-regulatory T cells within a population of T cells, comprising contacting the population of T cells with an effective amount of a human IL-2 mutein as described above. In one embodiment, the ratio of CD3+FoxP3+ cells to CD3+FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to non-regulatory T cells within a population of T cells, comprising contacting the population of T cells with an effective amount of an Fc-fusion protein as described above. In one embodiment, the ratio of CD3+FoxP3+ cells to CD3+FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to non-regulatory T cells within peripheral blood of a subject, comprising administering an effective amount of a human IL-2 mutein as described above. In one embodiment, the ratio of CD3+FoxP3+ cells to CD3+FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to non-regulatory T cells within the peripheral blood of a subject, comprising administering an effective amount of an Fc-fusion protein as described above. In one embodiment, the ratio of CD3+FoxP3+ cells to CD3+FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to natural killer (NK) cells within the peripheral blood of a subject, comprising administering an effective amount of a human IL-2 mutein as described above. In one embodiment, the ratio of CD3+FoxP3+ cells to CD3−CD19− lymphocytes expressing CD56 and/or CD16 increases. In another embodiment, the ratio of CD3+FoxP3+ cells to CD3−CD19− lymphocytes expressing CD56 and/or CD16 increases at least 50%.

In another aspect, the present invention provides a method of increasing the ratio of regulatory T cells (Tregs) to natural killer (NK) cells within the peripheral blood of a subject, comprising administering an effective amount of an Fc-fusion protein as described above. In one embodiment, the ratio of CD3+FoxP3+ cells to CD3−CD19− lymphocytes expressing CD56 and/or CD16 increases. In another embodiment, the ratio of CD3+FoxP3+ cells to CD3−CD19− lymphocytes expressing CD56 and/or CD16 increases at least 50%.

In another aspect, the present invention provides a method of treating a subject with an inflammatory or autoimmune disease, said method comprising administering to said subject a therapeutically effective amount of an IL-2 mutein as described above or a therapeutically effective amount of an Fc-fusion protein as described above. In one embodiment, administration causes reduction of at least one symptom of the disease. In another embodiment, the ratio of regulatory T cells (Tregs) to non-regulatory T cells within the peripheral blood of a subject increases after the administration. In another embodiment, the ratio of regulatory T cells (Tregs) to non-regulatory T cells within the peripheral blood of a subject remains essentially the same after the administration. In another embodiment, the inflammatory or autoimmune disease is lupus, graft-versus-host disease, hepatitis C-induced vasculitis, type I diabetes, type II diabetes, multiple sclerosis, rheumatoid arthritis, alopecia areata, atherosclerosis, psoriasis, organ transplant rejection, Sjögren's Syndrome, Behcet's disease, spontaneous loss of pregnancy, atopic diseases, asthma, or inflammatory bowel diseases.

In another aspect, the present invention provides a polypeptide comprising an Fc region of a human IgG1 antibody wherein said Fc region comprises an N297G mutation and said Fc region of a human IgG1 comprises at least 90% identity to the amino acid sequence set forth in SEQ ID NO:3. In one embodiment, said Fc region of a human IgG1 comprises at least 95% identity to the amino acid sequence set forth in SEQ ID NO:3. In another embodiment, said Fc region of a human IgG1 comprises the amino acid sequence set forth in SEQ ID NO:3. In another embodiment, said Fc region of a human IgG1 further comprises one or more mutations to stabilize the polypeptide. In another embodiment, one or more amino acids set forth in SEQ ID NO:3 are substituted with cysteine. In another embodiment, V259, A287, R292, V302, L306, V323, or I332 of the amino acid sequence set forth in SEQ ID NO:3 is substituted with cysteine. In another embodiment, said Fc region comprises an A287C and L306C substitution within the amino acid sequence set forth in SEQ ID NO:3. In another embodiment, said Fc region comprises an V259C and L306C substitution within the amino acid sequence set forth in SEQ ID NO:3. In another embodiment, said Fc region comprises an R292C and V302C substitution within the amino acid sequence set forth in SEQ ID NO:3. In another embodiment, said Fc region comprises an V323C and I332C substitution within the amino acid sequence set forth in SEQ ID NO:3.

In another aspect, the present invention provides an antibody comprising an Fc region as described above.

In another aspect, the present invention provides an Fc-fusion protein comprising an Fc region as described above.

In another aspect, the present invention provides a polypeptide comprising a linker, wherein the linker is GGNGT (SEQ ID NO: 6) or YGNGT (SEQ ID NO: 7). In one embodiment, the linker comprises N-glycosylation. In another embodiment, the linker is inserted into or replaces a loop in the polypeptide structure.

In another aspect, the present invention provides a method of making an aglycosylated IgG1 Fc-containing molecule, said method comprising:
 a) expressing a nucleic acid encoding a polypeptide as described above in a mammalian cell culture; and
 b) harvesting the aglycosylated IgG1 Fc-containing molecule from said culture.

In another aspect, the present invention provides a method of making an IgG1 Fc-containing molecule aglycosylated when expressed in mammalian cells, said method comprising the step of mutating a codon for N297 in the Fc region to a glycine codon.

In another aspect, the present invention provides an Fc-fusion protein wherein the amino acid sequence of said Fc-fusion protein is at least 90% identical to the amino acid sequence of a human IL-2 mutein fusion protein illustrated in FIG. 24. In one embodiment, the amino acid sequence of said Fc-fusion protein is at least 95% identical to the amino acid sequence of a human IL-2 mutein fusion protein illustrated in FIG. 24. In another embodiment, the amino acid sequence of said Fc-fusion protein is at least 97% identical to the amino acid sequence of a human IL-2 mutein fusion protein illustrated in FIG. 24. In another embodiment, the amino acid sequence of said Fc-fusion protein is at least 99% identical to the amino acid sequence of a human IL-2 mutein fusion protein illustrated in FIG. 24. In another embodiment, the amino acid sequence of said Fc-fusion protein is identical to the amino acid sequence of a human IL-2 mutein fusion protein illustrated in FIG. 24.

In another aspect, the present invention provides a nucleic acid encoding the Fc-fusion as described above.

In another aspect, the present invention provides a cell comprising the nucleic acid as described above.

In another aspect, the present invention provides a method of making an Fc-fusion protein comprising incubating the cell as described above under conditions allowing it to express said Fc-fusion protein.

In another aspect, the present invention provides a method of treating an inflammatory or auto-immune condition in a subject comprising administering an effective amount of the Fc-fusion protein as described above to said subject. In one embodiment, said inflammatory or auto-immune condition is lupus, graft-versus-host disease, hepatitis C-induced vasculitis, type I diabetes, type II diabetes, multiple sclerosis, rheumatoid arthritis, alopecia areata, atherosclerosis, psoriasis, organ transplant rejection, Sjögren's Syndrome, Behcet's disease, spontaneous loss of pregnancy, atopic diseases, asthma, or inflammatory bowel diseases.

In another aspect, the present invention provides a method of monitoring the response of a subject to treatment with the human interleukin-2 (IL-2) mutein as described above, the Fc-fusion protein as described above, or the Fc-fusion protein as described above, comprising detecting a change in said subject, said change being: an increase in body temperature, an increase in CRP in said subject's peripheral blood, a decrease in platelets in said subject's peripheral blood, a decrease in neutrophils in said subject's peripheral blood, or a decrease in albumin in said subject's peripheral blood, wherein said treatment is terminated, suspended, reduced in dosing frequency, or reduced in dosing amount after said change is detected. In one embodiment, said change comprises: an increase in body temperature of at least 0.5° C., an increase in CRP in said subject's peripheral blood of at least 0.2 mg/mL, a decrease in platelets in said subject's peripheral blood of at least 0.8-fold, a decrease in neutrophils in said subject's peripheral blood of at least 0.8-fold, or a decrease in albumin in said subject's peripheral blood of at least 0.4-fold.

In another aspect, the present invention provides an isolated anti-human IL-2 antibody, wherein said antibody: comprises a heavy chain variable domain that is at least 90% identical to the heavy variable domain of a reference antibody, and a light chain variable domain that is at least 90% identical to the light chain variable domain of said reference antibody, wherein said reference antibody is 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 221D10, 14A6, 11D6, 10A9, 16E3, 14G7, 5H3, 2B12, 26H7, 26C12, 2H11, or 18H9, and wherein the heavy chain variable domain and light chain variable domain of said reference antibody is as illustrated in FIG. 28 and FIG. 26, respectively; or comprises a heavy chain variable domain that comprises CDR1, CDR2, and CDR3 of the heavy chain variable domain of a reference antibody, and a light chain variable domain that comprises CDR1, CDR2, and CDR3 of the light chain variable domain of said reference antibody, and wherein said heavy chain CDRs and said light chain CDRs are as illustrated in FIG. 28 and FIG. 26, respectively; or cross-competes for binding to wild-type human IL-2 cytokine with a reference antibody, wherein said reference antibody is 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 221D10, 14A6, 11D6, 10A9, 16E3, 14G7, 5H3, 2B12, 26H7, 26C12, 2H11, or 18H9. In one embodiment, said antibody comprises a heavy chain variable domain amino acid sequence that is at least 90% identical to the heavy chain variable domain amino acid sequence of a reference antibody, and a light chain variable domain amino acid sequence that is at least 90% identical to the light chain variable domain amino acid sequence of said reference antibody, wherein said reference antibody is 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 221D10, 14A6, 11D6, 10A9, 16E3, 14G7, 5H3, 2B12, 26H7, 26C12, 2H11, or 18H9, and wherein the heavy chain variable domain amino acid sequence and light chain variable domain amino acid sequence of said reference antibody is as illustrated in FIG. 28 and FIG. 26, respectively. In another embodiment, said antibody comprises a heavy chain variable domain amino acid sequence that is at least 95% identical to the heavy variable domain amino acid sequence of a reference antibody, and a light chain variable domain amino acid sequence that is at least 95% identical to the light chain variable domain amino acid sequence of said reference antibody, wherein said reference antibody is 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 221D10, 14A6, 11D6, 10A9, 16E3, 14G7, 5H3, 2B12, 26H7, 26C12, 2H11, or 18H9, and wherein the heavy chain variable domain amino acid sequence and light chain variable domain amino acid sequence of said reference antibody is as illustrated in FIG. 28 and FIG. 26, respectively. In another embodiment, said antibody comprises a heavy chain variable domain amino acid sequence that is at least 97% identical to the heavy variable domain amino acid sequence of a reference antibody, and a light chain variable domain amino acid sequence that is at least 97% identical to the light chain variable domain amino acid sequence of said reference antibody, wherein said reference antibody is 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 221D10, 14A6, 11D6, 10A9, 16E3, 14G7, 5H3, 2B12, 26H7, 26C12, 2H11, or 18H9, and wherein the heavy chain variable domain amino acid sequence and light chain variable domain amino acid sequence of said reference antibody is as illustrated in FIG. 28 and FIG. 26, respectively. In another embodiment, said antibody comprises a heavy chain variable domain amino acid sequence that is at least 99% identical to the heavy variable domain amino acid sequence of a reference antibody, and a light chain variable domain amino acid sequence that is at least 99% identical to the light chain variable domain amino acid sequence of said reference antibody, wherein said reference antibody is 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 221D10, 14A6, 11D6, 10A9, 16E3, 14G7, 5H3, 2B12, 26H7, 26C12, 2H11, or 18H9, and wherein the heavy chain variable domain amino acid sequence and light chain variable domain amino acid sequence of said reference antibody is as illustrated in FIG. 28 and FIG. 26, respectively. In another embodiment, said antibody comprises a heavy chain variable domain amino acid sequence of a reference antibody, and a light chain variable domain amino acid sequence of said reference antibody, wherein said reference antibody is 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 221D10, 14A6, 11D6, 10A9, 16E3, 14G7, 5H3, 2B12, 26H7, 26C12, 2H11, or 18H9, and wherein the heavy chain variable domain amino acid sequence and light chain variable domain amino acid sequence of said reference antibody is as illustrated in FIG. 28 and FIG. 26, respectively. In another embodiment, said isolated antibody is: a human antibody; a humanized antibody; a chimeric antibody; a monoclonal antibody; a polyclonal antibody; a recombinant antibody; an antigen-binding antibody fragment; a single chain antibody; a diabody; a triabody; a tetrabody; a Fab fragment; a F(ab')2 fragment; a domain antibody; an IgD antibody; an IgE antibody; an IgM antibody; an IgG1 antibody; an IgG2 antibody; an IgG3 antibody; an IgG4 antibody; or an IgG4 antibody having at least one mutation in a hinge region that alleviates a tendency to form intra-H chain disulfide bond. In another embodiment, said isolated antibody comprises a human IgG1 Fc. In another embodiment, said human IgG1 Fc has one or more mutations altering effector function of said Fc. In another embodiment, said human IgG1 Fc comprises a substitution at N297. In another embodiment, said substitution at N297 is N297G. In another embodiment, the antibody comprises a substitution or deletion of the C-terminal lysine of said human IgG Fc. In another embodiment, the C-terminal lysine of said human IgG Fc is deleted. In another embodiment, said isolated antibody comprises a human IgG1 Fc. In another embodiment, said human IgG1 Fc has one or more mutations altering effector function of said Fc. In another embodiment, said human IgG1 Fc comprises a substitution at N297. In another embodiment, said substitution at N297 is N297G. In another embodiment, the antibody comprises a substitution or deletion of the C-terminal lysine of said human IgG Fc. In another embodiment, the C-terminal lysine of said human IgG Fc is deleted.

In another aspect, the present invention provides an isolated complex comprising an isolated anti-human IL-2 antibody as described above bound to a human IL-2 cytokine.

In another aspect, the present invention provides an isolated nucleic acid encoding the light chain, the heavy chain, or both the light chain and the heavy chain of the isolated anti-human IL-2 antibody as described above.

In another aspect, the present invention provides an expression vector comprising the isolated nucleic acid as described above operably linked to a promoter.

In another aspect, the present invention provides a host cell comprising the isolated nucleic acid as described above. In one embodiment, the isolated nucleic acid is operably linked to a promoter. In another embodiment, said host cell is a prokaryotic cell. In another embodiment, the host cell is *E. coli*. In another embodiment, said host cell is a eukaryotic cell. In another embodiment, the host cell is a mammalian cell. In another embodiment, the host cell is a Chinese hamster ovary (CHO) cell line.

In another aspect, the present invention provides a method of making an anti-human IL-2 antibody, comprising culturing a host cell as described above under conditions in which said promoter is expressed and harvesting the human IL-2 mutein from said culture.

In another aspect, the present invention provides a method of treating an inflammatory or auto-immune condition in a subject comprising administering an effective amount of the anti-human IL-2 antibody or isolated complex comprising an isolated anti-human IL-2 antibody as described above to said subject. In one embodiment, said inflammatory or auto-immune condition is lupus, graft-versus-host disease, hepatitis C-induced vasculitis, type I diabetes, type II diabetes, multiple sclerosis, rheumatoid arthritis, alopecia areata, atherosclerosis, psoriasis, organ transplant rejection, Sjögren's Syndrome, Behcet's disease, spontaneous loss of pregnancy, atopic diseases, asthma, or inflammatory bowel diseases.

BRIEF DESCRIPTION OF THE FIGURES

FIG. 2A and FIG. 2B IL-2 muteins with the indicated mutations and fused to the C-terminus of one side of an Fc-heterodimer were tested for their ability to stimulate STAT5 phosphorylation in T cells. These muteins also contained three mutations conferring high affinity for CD25 (V69A, N71R, Q74P). Their activity was compared to three forms of IL-2 without Fc fusion (open symbols): WT IL-2, HaWT (high affinity for CD25) (N29S, Y31H, K35R, T37A, K48E, V69A, N71R, Q74P), and HaD (high affinity for CD25 and reduced signaling activity) (N29S, Y31H, K35R, T37A, K48E, V69A, N71R, Q74P, N88D). Phospho-STAT5 responses are shown for gated FOXP3+CD4+ and FOXP3−CD4+ T cells.

FIG. 9A Fc.V91K and Fc.N88D persist on the surface of activated T cells through association with CD25.

FIG. 14 Discovery Studio predicted $\Delta\Delta G_{binding}$ (kcal/mol) of IL-2:IL-2Rβ interaction for various IL-2 muteins. Positive value of $\Delta\Delta G_{binding}$ indicates a weaker binding of the mutein compared to the wild-type IL-2. $\Delta\Delta G_{binding}$ values for N88 and D20 mutants are likely to be under-predicted. The muteins shown in boxes were selected.

FIG. 15 Schrödinger predicted $\Delta\Delta G_{binding}$ (kcal/mol) of IL-2:IL-2Rβ interaction for various IL-2 mutants. Positive value of $\Delta\Delta G_{binding}$ indicates a weaker binding of the mutant compared to the WT. The muteins shown in boxes were selected.

FIG. 16A and FIG. 16B Primary human PBMCs were pre-activated with 100 ng/ml OKT3 for two days. Cells were then rested for three days after three washes to remove OKT3 antibody. The bioactivities of Fc.IL-2 mutein fusion proteins were tested by stimulating these rested pre-activated PBMCs with titrations (1 nM, 100 pM, 33 pM, 11 pM) of IL-2 muteins at 37° C. for 10 min followed by a standard PHOSFLOW™ (BD, Franklin Lakes, N.J.) assay to detect phospho-STAT5 levels. The bioactivity of Fc.IL-2 muteins is presented as phospho-STAT5 mean fluorescence intensity (MFI) in gated CD4+ T cells. The muteins were assayed as supernatants of transfected 293-6E cells and the concentrations of Fc.IL-2 fusion proteins were determined by Protein A binding (OCTET Q SYSTEM®, Pall forteBIO Co., Menlo Park, Calif.). The "pTT5" sample represents the supernatant fraction from cells transfected with an empty DNA expression vector. A) Phospho-STAT5 responses to titrated Fc.IL-2 mutein fusion proteins, in T cells from one donor. B) Ranked pSTAT5 responses to 33 pM Fc.IL-2 muteins for two donors.

Figure 17:
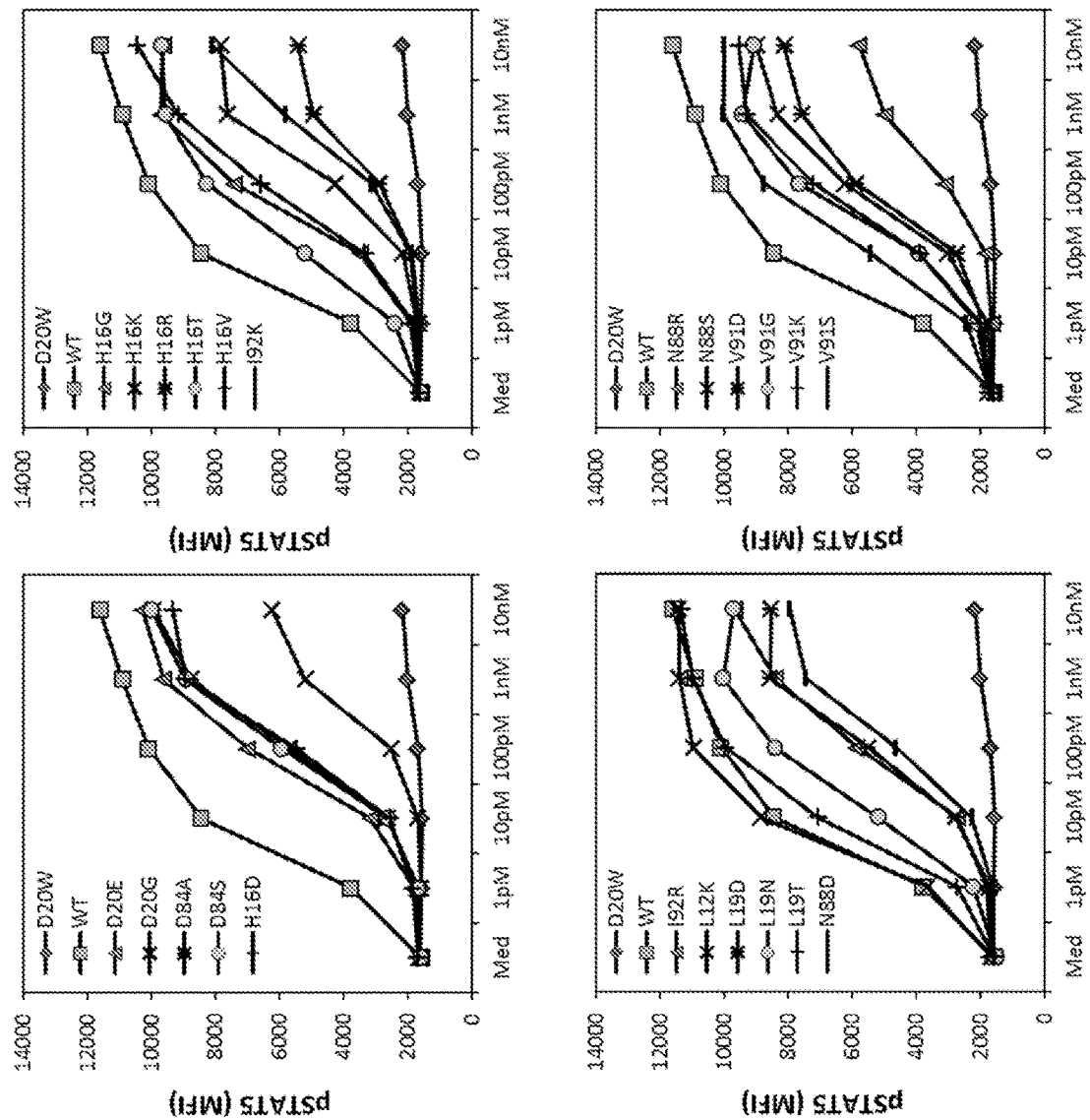

FIG. 17 Primary human PBMCs were pre-activated with 100 ng/ml OKT3 for two days. Cells were then rested for three days after three washes to remove OKT3 antibody. The bioactivity of IL-2 muteins was tested by stimulating these rested pre-activated PBMCs with titrations of IL-2 muteins at 37° C. for 10 min followed by a standard PHOSFLOW™ (BD, Franklin Lakes, N.J.) assay to detect phospho-STAT5 levels. The bioactivity of IL-2 muteins is presented as phospho-STAT5 mean fluorescence intensity (MFI) in gated CD25highCD4$^+$ T cells. Fc.IL-2(D20W, C125A) did not activate pSTAT5, and this molecule and Fc.IL-2(WT, C125A) are shown in each plot as a positive and negative control. Consistent results were obtained for two different PBMC donors.

FIG. 18 Total PBMCs were activated at 3 million/ml with 100 ng OKT3. On day two, cells were washed three times and rested in fresh media for five days. Cells were then labeled with CFSE and further cultured in a twenty-four well plate at 0.5 million/well in IL-2 containing media for seven days before FACS analysis. The proliferation of T cell subsets is presented as CFSE dilution (median CFSE fluorescence) for FOXP3$^-$CD4$^+$ cells (A), FOXP3$^-$CD8$^+$ cells (B), and HELIOS$^+$FOXP3$^+$CD4$^+$ (C). The capacity for muteins to upregulate FOXP3 in HELIOS$^+$FOXP3$^+$CD4$^+$ cells is also shown (D).

FIG. 19 MACS sorted CD16$^+$ NK cells were cultured with titrations of the indicated Fc.IL-2 muteins for three days at 0.1 million/well in ninety-six well plates. 0.5 µCi 3H-thymidine was added to each well during the final eighteen hours of incubation.

Figure 20A:
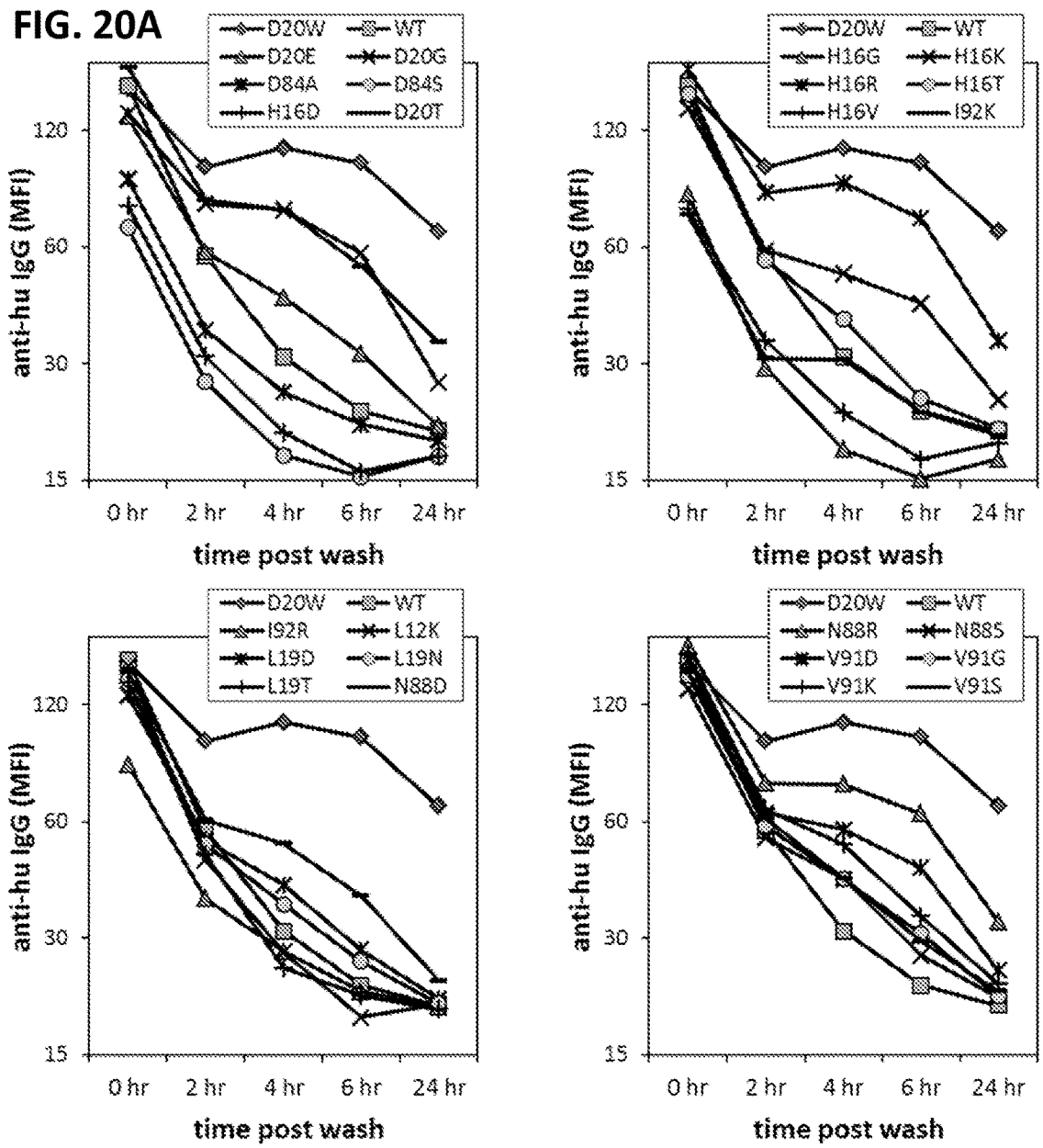
Figure 20B:
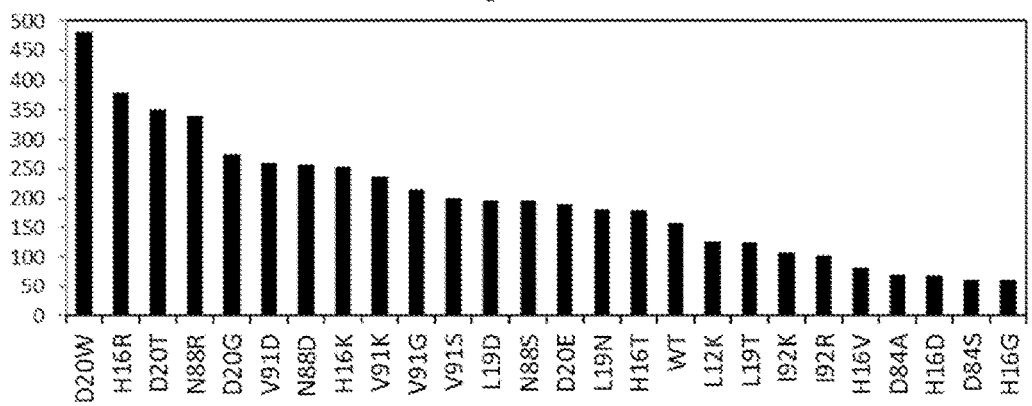

FIG. 20 Primary human PBMCs were pre-stimulated for two days with 100 ng/ml OKT3. Cells were harvested, washed four times and rested overnight in medium. Cells were then pulsed with 400 pM Fc.IL-2 for 30 min at 37° C. After pulse, cells were either harvested for T0 after one wash, or washed an additional three times in 12 ml of warm medium and cultured for the indicated times. To detect cell-associated Fc.IL-2, cells were stained with anti-human IgG-FITC (Jackson Immunoresearch, West Grove, Pa.) and anti-CD25-APC (A). To rank the muteins for cell surface retention, the sum of the hu IgG MFI values for 4, 6, and 24 hr timepoints was averaged for two PBMC donors (B).

FIG. 21 pSTAT5 signal retention after pulse-wash, as in FIG. 20, except cells were pulsed with 100 pM Fc.IL-2.

Figure 22:
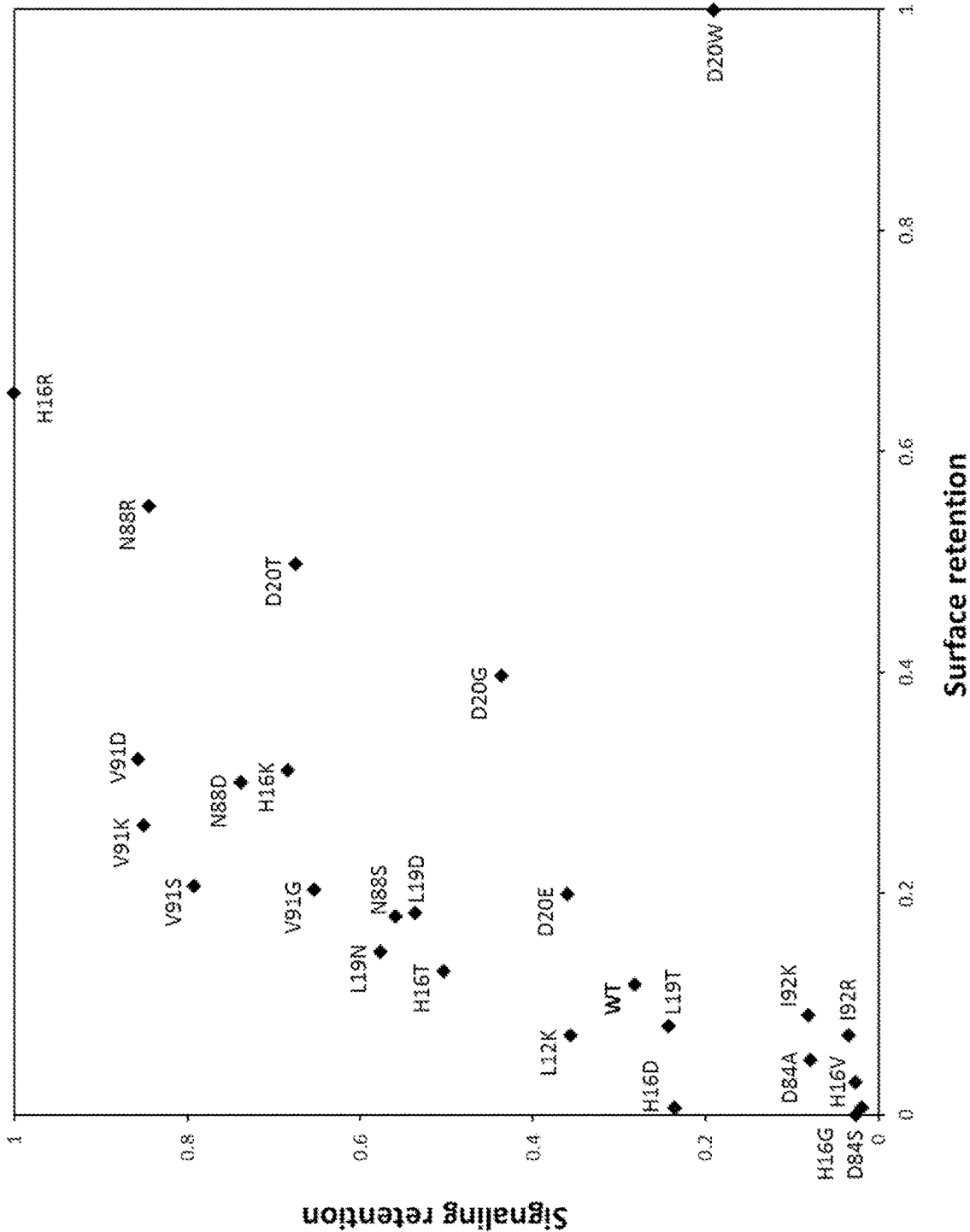

FIG. 22 Correlation of cell surface retention and IL-2R signaling retention. The scaled surface retention and pSTAT5 signal retention values were calculated by adding the hu-IgG MFI (surface) or the pSTAT5 MFI (signaling) values for the 6 and 24 hr time points, scaling the values from 0 to 1, and averaging the scaled values for two donors.

Figure 23A:
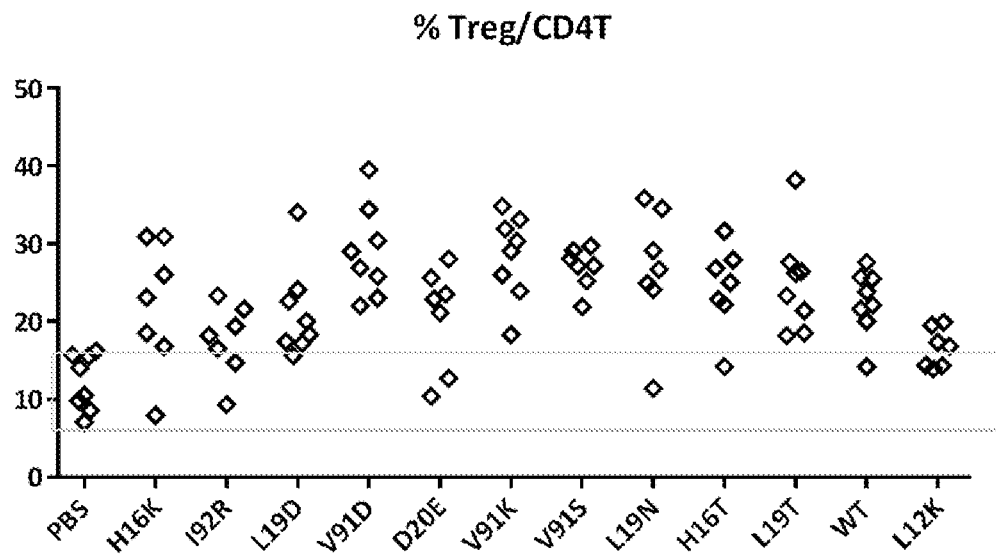
Figure 23B:
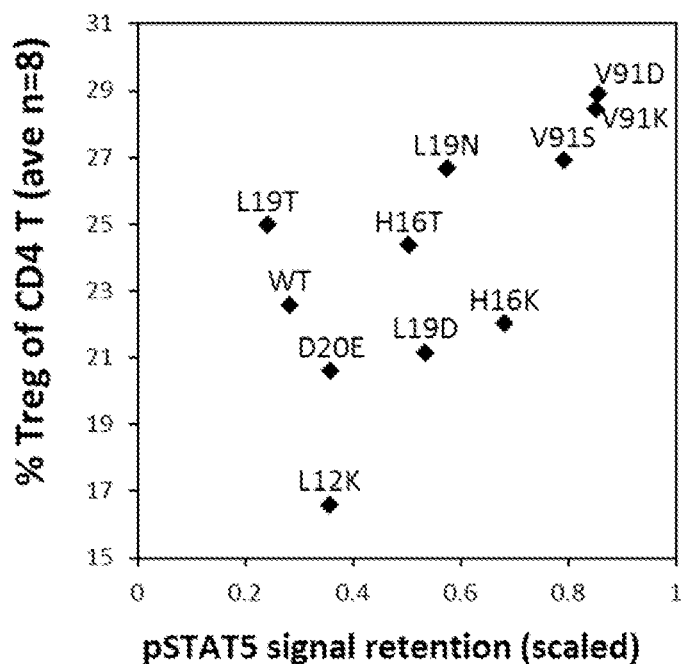

FIG. 23A and FIG. 23B Percent Treg of CD4 T cells in blood of humanized mice (NSG mice reconstituted with CD34$^+$ hematopoietic stem cells) on day four after subcutaneous dose of 1 µg Fc.IL-2 mutein at day zero. (B) Correlation of Treg enrichment with pSTAT5 signal retention. The scaled pSTAT5 signal retention values were calculated by adding the pSTAT5 MFI for the 6 and 24 hr timepoints, scaling the values from 0 to 1, and averaging the scaled values for two donors.

FIG. 24 (A)-(P) Amino acid sequences of the human IL-2 mutein fusion proteins created and tested according to Examples 13 and 14. Bold text=leader sequence; italics=Fc domain (comprising the N297G and delK mutations); underlined text=linker sequence; plain text=IL-2 (comprising C125A and the indicated mutations). Together, the Fc domain, linker sequence, and IL-2 comprise the mature form of the protein.

FIG. 25 (A)-(LL) Nucleic acid sequences of the human IL-2 mutein fusion proteins created and tested according to Examples 13 and 14.

Figure 26:
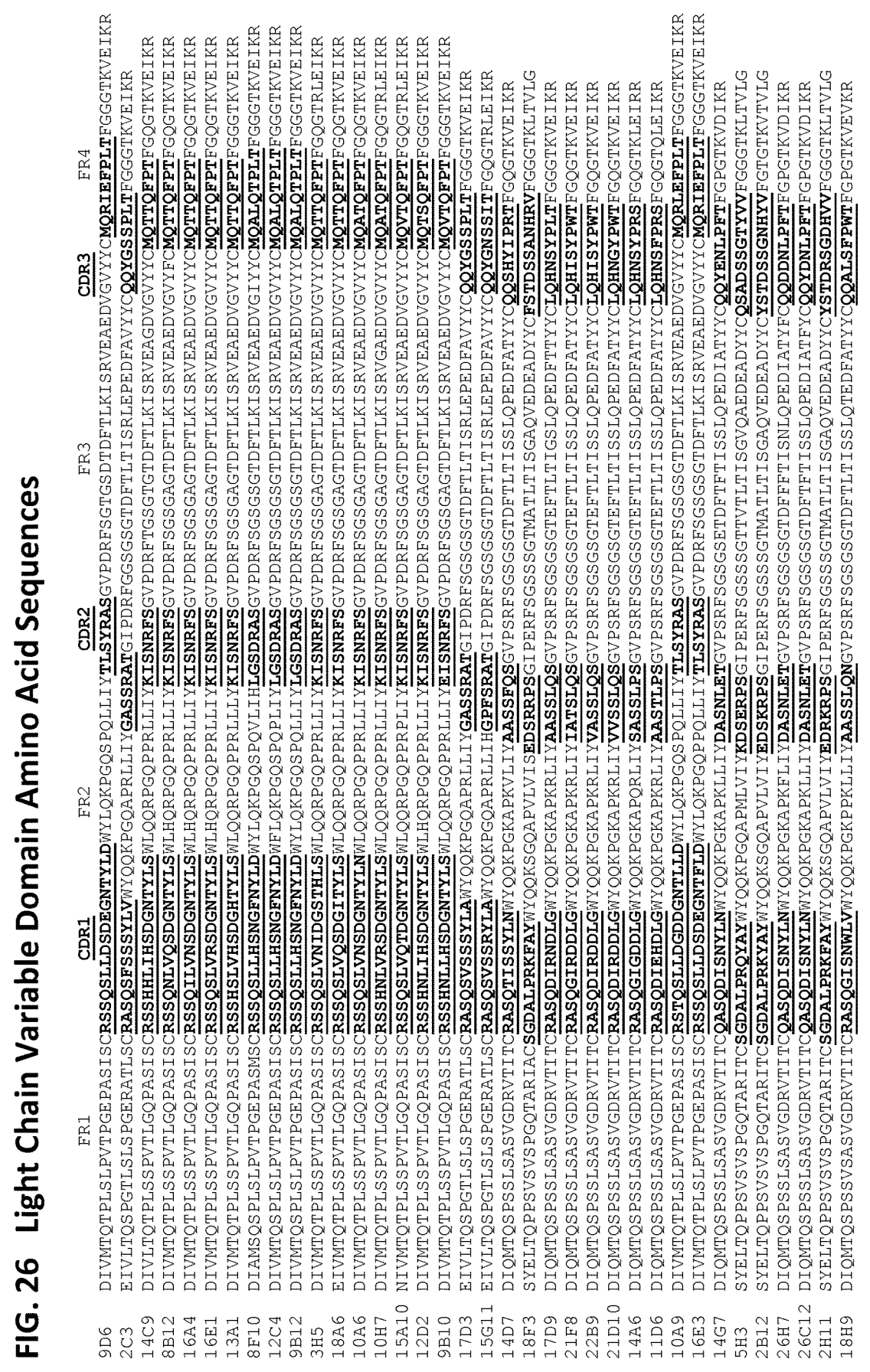

FIG. 26 Amino acid sequences of the light chain variable domains of the antibodies isolated and tested according to Example 15. CDRs 1, 2, and 3 (defined according to Kabat) are indicated in bold and underlined; framework regions 1, 2, 3, and 4 are in plain text.

FIG. 27(A)-(I) Nucleic acid sequences of the light chain variable domains of the antibodies isolated and tested according to Example 15.

FIG. 28 Amino acid sequences of the heavy chain variable domains of the antibodies isolated and tested according to Example 15. CDRs 1, 2, and 3 (defined according to Kabat) are indicated in bold and underlined; framework regions 1, 2, 3, and 4 are in plain text.

FIG. 29(A)-(I) Nucleic acid sequences of the heavy chain variable domains of the antibodies isolated and tested according to Example 15.

Figure 30:
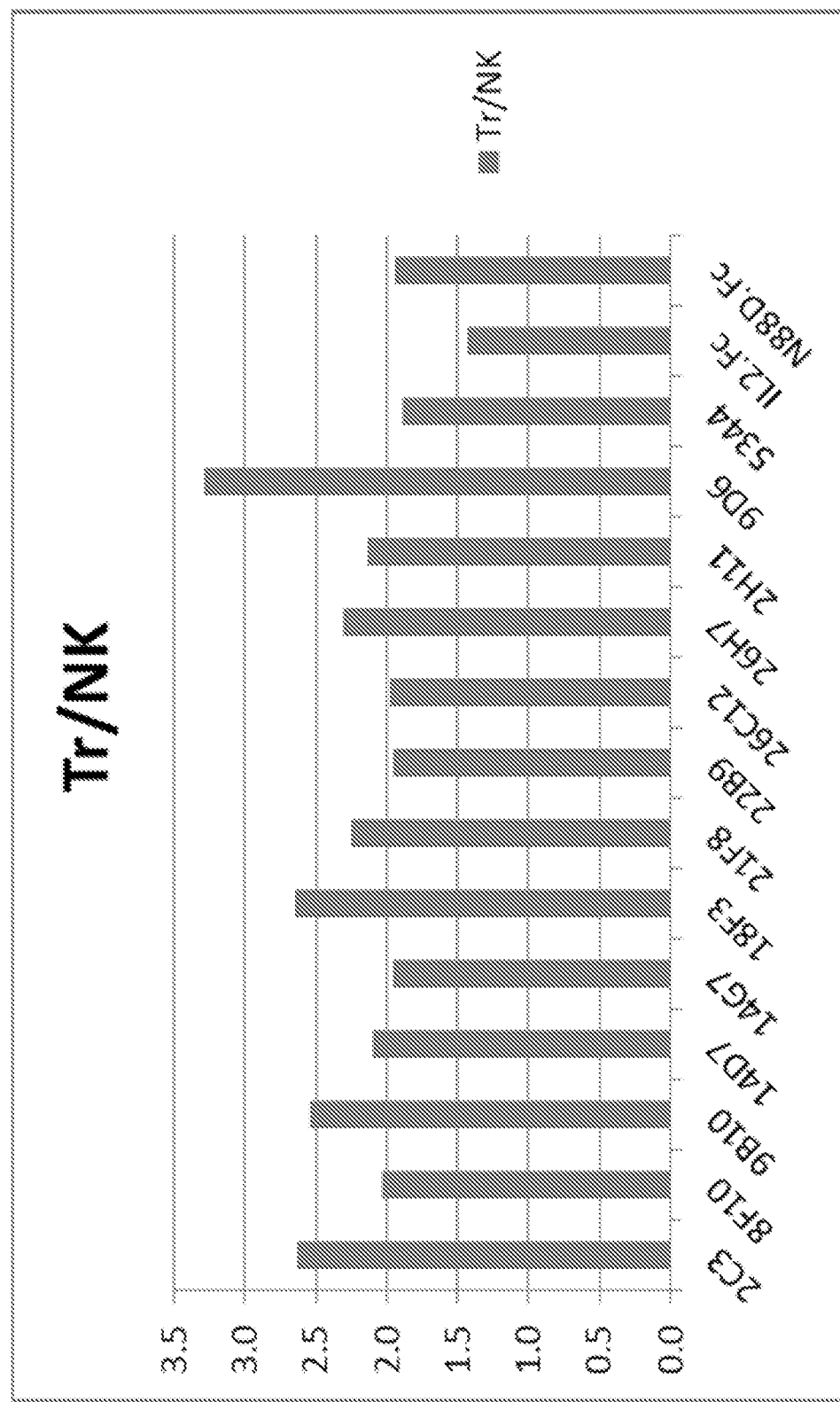

FIG. 30 Ratio of activation of Treg cells expansion to NK cell expansion in NSG SCID/Hu mice treated with a single injection of 8 µg of anti-IL-2 antibody complexed with 1.5 µg wild-type human IL-2) as described in Example 15.

DETAILED DESCRIPTION OF PREFERRED EMBODIMENTS

The section headings used herein are for organizational purposes only and are not to be construed as limiting the subject matter described. All references cited within the body of this specification are expressly incorporated by reference in their entirety.

Standard techniques may be used for recombinant DNA, oligonucleotide synthesis, tissue culture and transformation, protein purification, etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manuel*, 3$^{rd}$ ed., Cold Spring Harbor Laboratory Press, cold Spring Harbor, N.Y., which is incorporated herein by reference for any purpose. Unless specific definitions are provided, the nomenclature used in connection with, and the laboratory procedures and techniques of, analytic chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

IL-2

The IL-2 muteins described herein are variants of wild-type human IL-2. As used herein, "wild-type human IL-2," "wild-type IL-2," or "WT IL-2" shall mean the polypeptide having the following amino acid sequence:

APTSSSTKKTQLQLEHLLLDLQMILNGINNYKN-PKLTRMLTFKFYMPKKATELKHLQCLEEELKPLEEV-LNLAQSKNFHLR PRDLISNINVIVLELKGSETTFMC-EYADETATIVEFLNRWITFXQSIISTLT

Wherein X is C, S, V, or A (SEQ ID NO:2).

Variants may contain one or more substitutions, deletions, or insertions within the wild-type IL-2 amino acid sequence. Residues are designated herein by the one letter amino acid code followed by the IL-2 amino acid position, e.g., K35 is the lysine residue at position 35 of SEQ ID NO: 2. Substitutions are designated herein by the one letter amino acid code followed by the IL-2 amino acid position followed by the substituting one letter amino acid code, e.g., K35A is a substitution of the lysine residue at position 35 of SEQ ID NO:2 with an alanine residue.

IL-2 Muteins and Anti-IL-2 Antibodies

Provided herein are human IL-2 muteins and anti-IL-2 antibodies that preferentially stimulate T regulatory (Treg) cells. As used herein "preferentially stimulates T regulatory cells" means the mutein or antibody promotes the proliferation, survival, activation and/or function of CD3+FoxP3+ T cells over CD3+FoxP3− T cells. Methods of measuring the ability to preferentially stimulate Tregs can be measured by flow cytometry of peripheral blood leukocytes, in which there is an observed increase in the percentage of FOXP3+ CD4+ T cells among total CD4+ T cells, an increase in percentage of FOXP3+CD8+ T cells among total CD8+ T cells, an increase in percentage of FOXP3+ T cells relative to NK cells, and/or a greater increase in the expression level of CD25 on the surface of FOXP3+ T cells relative to the increase of CD25 expression on other T cells. Preferential growth of Treg cells can also be detected as increased representation of demethylated FOXP3 promoter DNA (i.e. the Treg-specific demethylated region, or TSDR) relative to demethylated CD3 genes in DNA extracted from whole blood, as detected by sequencing of polymerase chain reaction (PCR) products from bisulfite-treated genomic DNA (J. Sehouli, et al. 2011. Epigenetics 6:2, 236-246).

IL-2 muteins or anti-IL-2 antibodies that preferentially stimulate Treg cells increase the ratio of CD3+FoxP3+ T cells over CD3+FoxP3− T cells in a subject or a peripheral blood sample at least 30%, at least 40%, at least 50%, at least 60%, at least 70%, at least 80%, at least 90%, at least 100%, at least 150%, at least 200%, at least 300%, at least 400%, at least 500%, at least 600%, at least 700%, at least 800%, at least 900%, or at least 1000%.

Examples of IL-2 muteins include, but are not limited to, IL-2 muteins comprising H16T, H16K, H16R, L19N, L19D, D20E, D20G, D20T, N88D, N88R, N88S, V91D, V91G, V91K, and/or V91S substitution(s) in the amino acid sequence set forth in SEQ ID NO:2. Exemplary IL-2 muteins are set forth in FIG. 24. IL-2 muteins of the present invention optionally comprise a C125A substitution. Although it may be advantageous to reduce the number of further mutations to the wild-type IL-2 sequence, the invention includes IL-2 muteins also including truncations and/or additional insertions, deletions, and/or substitutions in addition to the H16T, H16K, H16R, L19N, L19D, D20E, D20G, D20T, N88D, N88R, N88S, V91D, V91G, V91K, and/or V91S substitution, provided that said muteins maintain the activity of preferentially simulating Tregs. Thus, embodiments include IL-2 muteins that preferentially stimulate Treg cells and comprise an amino acid sequence having a H16T, H16K, H16R, L19N, L19D, D20E, D20G, D20T, N88D, N88R, N88S, V91D, V91G, V91K, and/or V91S substitution and that is at least 90%, at least 91%, at least 92%, at least 93%, at least 94%, at least 95%, at least 96%, at least 97%, at least 98%, or at least 99% identical to the amino acid sequence set forth in SEQ ID NO:2. In particularly preferred embodiments, such IL-2 muteins comprise an amino acid sequence that is at least 90%, at least 91%, at least 92%, at least 93%, at least 94%, at least 95%, at least 96%, at least 97%, at least 98%, or at least 99% identical to the amino acid sequence set forth in SEQ ID NO:2.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

While the site or region for introducing an amino acid sequence variation may be predetermined, the mutation per se need not be predetermined. For example, in order to optimize the performance of a mutation at a given site, random mutagenesis may be conducted at the target codon or region and the expressed IL-2 mutein screened for the optimal combination of desired activity. Techniques for making substitution mutations at predetermined sites in DNA having a known sequence are well known, for example, M13 primer mutagenesis and PCR mutagenesis. Screening of the mutants may be done using assays described herein, for example.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 1.

TABLE 1

| Original Residue | Exemplary Substitutions |
| --- | --- |
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr, Trp |
| Ser | Thr |
| Thr | Ser |
| Trp | Tyr, Phe |
| Tyr | Trp, Phe |
| Val | Ile, Leu |

Substantial changes in function or immunological identity are made by selecting substitutions that are less conservative than those shown in TABLE 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the IL-2 mutein as needed. Alternatively, the variant may be designed such that the biological activity of the IL-2 mutein is altered. For example, glycosylation sites may be altered or removed as discussed herein.

In another embodiment, the present invention provides an antibody comprising the heavy and light chain variable domains of one of the antibodies designated herein as 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 21D10, 14A6, 11D6, 10A9, 16E3, 14G7, 5H3, 2B12, 26H7, 26C12, 2H11, and 18H9.

In another embodiment, the present invention provides an anti-IL-2 antibody comprising a light chain variable domain comprising a sequence of amino acids that differs from the sequence of the light chain variable domain of 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 21D10, 14A6, 11D6, 10A9, 16E3, 14G7, 5H3, 2B12, 26H7, 26C12, 2H11, or 18H9, only at 15, 14, 13, 12, 11, 10, 9, 8, 7, 6, 5, 4, 3, 2, or 1 residue(s), wherein each such sequence difference is independently either a deletion, insertion, or substitution of one amino acid residue. In another embodiment, the light chain variable domain comprises a sequence of amino acids that is at least 70%, 75%, 80%, 85%, 90%, 95%, 97%, or 99% identical to the sequence of the light chain variable domain of 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 21D10, 14A6, 11D6, 10A9, 16E3, 14G7, 5H3, 2B12, 26H7, 26C12, 2H11, or 18H9. In another embodiment, the light chain variable domain comprises a sequence of amino acids that is encoded by a polynucleotide that hybridizes under moderately stringent conditions to the complement of a nucleotide sequence of FIG. 27.

In another embodiment, the present invention provides an anti-IL-2 antibody comprising a heavy chain variable domain comprising a sequence of amino acids that differs from the sequence of the heavy chain variable domain of 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 21D10, 14A6, 11D6, 10A9, 16E3, 14G7, 5H3, 2B12, 26H7, 26C12, 2H11, or 18H9, only at 15, 14, 13, 12, 11, 10, 9, 8, 7, 6, 5, 4, 3, 2, or 1 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of the heavy chain variable domain of 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 21D10, 14A6, 11D6, 10A9, 16E3, 14G7, 5H3, 2B12, 26H7, 26C12, 2H11, or 18H9. In another embodiment, the heavy chain variable domain comprises a sequence of amino acids that is encoded by a polynucleotide that hybridizes under moderately stringent conditions to the complement of a nucleotide sequence of FIG. 29.

In another embodiment, the present invention provides anti-IL-2 antibodies that comprise all three light chain CDR sequences and all three heavy chain CDR sequences of antibody 9D6, 2C3, 14C9, 8B12, 16A4, 16E1, 13A1, 8F10, 12C4, 9B12, 3H5, 18A6, 10A6, 10H7, 15A10, 12D2, 9B10, 17D3, 15G11, 14D7, 18F3, 17D9, 21F8, 22B9, 21D10, 14A6, 11D6, 10A9, 16E3, 14G7, 5H3, 2B12, 26H7, 26C12, 2H11, or 18H9.

In another embodiment, the present invention provides anti-IL-2 antibodies that cross-inhibit for binding to IL-2 as described in Example 15.

IL-2 Muteins and Anti-IL-2 Antibodies Having Extended Serum Half-Life

Because the IL-2 muteins provided herein preferentially expand Tregs over, for example Teff or NK cells, it is expected that the safety profile when administered to a patient will differ from that of wild-type IL-2 or PROLEUKIN® (aldesleukin; Novartis, Basel, Switzerland). Side-effects associated with wild-type IL-2 or PROLEUKIN® include flu-like symptoms, chills/rigor, arthralgia, fever, rash, pruritus, injection site reactions, hypotension, diarrhea, nausea, anxiety, confusion, and depression. The IL-2 muteins provided herein may be altered to include or fused to molecules that extend the serum half-life of the mutein without increasing the risk that such half-life extension would increase the likelihood or the intensity of a side-effect or adverse event in a patient. Subcutaneous dosing of such an extended serum half-life mutein may allow for prolonged target coverage with lower systemic maximal exposure ($C_{max}$). Extended serum half-life may allow a lower or less frequent dosing regimen of the mutein.

The serum half-life of the IL-2 muteins provided herein may be extended by essentially any method known in the art. Such methods include altering the sequence of the IL-2 mutein to include a peptide that binds to the neonatal Fcγ receptor or bind to a protein having extended serum half-life, e.g., IgG or human serum albumin. In other embodiments, the IL-2 mutein is fused to a polypeptide that confers extended half-life on the fusion molecule. Such polypeptides include an IgG Fc or other polypeptides that bind to the neonatal Fcγ receptor, human serum albumin, or polypeptides that bind to a protein having extended serum half-life. In preferred embodiments, the IL-2 mutein is fused to an IgG Fc molecule.

The IL-2 mutein may be fused to the N-terminus or the C-terminus of the IgG Fc region. As shown in the Examples, fusion to the C-terminus of the IgG Fc region maintains the IL-2 mutein activity to a greater extent than when fused to the N-terminus of the IgG Fc.

One embodiment of the present invention is directed to a dimer comprising two Fc-fusion polypeptides created by fusing an IL-2 mutein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain bonds form between the Fc moieties to yield the dimer.

The term "Fc polypeptide" or "Fc region" as used herein includes native and mutein forms of polypeptides derived from the Fc region of an antibody and can be part of either the IL-2 mutein fusion proteins or the anti-IL-2 antibodies of the invention. Truncated forms of such polypeptides containing the hinge region that promotes dimerization also are included. In certain embodiments, the Fc region comprises an antibody CH2 and CH3 domain. Along with extended serum half-life, fusion proteins comprising Fc moieties (and oligomers formed therefrom) offer the advantage of facile purification by affinity chromatography over Protein A or Protein G columns. Preferred Fc regions are derived from human IgG, which includes IgG1, IgG2, IgG3, and IgG4. Herein, specific residues within the Fc are identified by position. All Fc positions are based on the EU numbering scheme.

One of the functions of the Fc portion of an antibody is to communicate to the immune system when the antibody binds its target. This is considered "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fc with proteins of the complement system, e.g., C1q.

The IgG subclasses vary in their ability to mediate effector functions. For example, IgG1 is much superior to IgG2 and IgG4 at mediating ADCC and CDC. Thus, in embodiments wherein effector function is undesirable, an IgG2 Fc would be preferred. IgG2 Fc-containing molecules, however, are known to be more difficult to manufacture and have less attractive biophysical properties, such as a shorter half-life, as compared to IgG1 Fc-containing molecules.

The effector function of an antibody can be increased, or decreased, by introducing one or more mutations into the Fc. Embodiments of the invention include IL-2 mutein Fc fusion proteins having an Fc engineered to increase effector function (U.S. Pat. No. 7,317,091 and Strohl, *Curr. Opin. Biotech.*, 20:685-691, 2009; both incorporated herein by reference in its entirety). Exemplary IgG1 Fc molecules having increased effector function include those having the following substitutions:

S239D/I332E
S239D/A330S/I332E
S239D/A330L/I332E
S298A/D333A/K334A
P247I/A339D
P247I/A339Q
D280H/K290S
D280H/K290S/S298D
D280H/K290S/S298V
F243L/R292P/Y300L
F243L/R292P/Y300L/P396L
F243L/R292P/Y300L/V305I/P396L
G236A/S239D/I332E
K326A/E333A
K326W/E333S
K290E/S298G/T299A
K290N/S298G/T299A
K290E/S298G/T299A/K326E
K290N/S298G/T299A/K326E

Another method of increasing effector function of IgG Fc-containing proteins is by reducing the fucosylation of the Fc. Removal of the core fucose from the biantennary complex-type oligosachharides attached to the Fc greatly increased ADCC effector function without altering antigen binding or CDC effector function. Several ways are known for reducing or abolishing fucosylation of Fc-containing molecules, e.g., antibodies. These include recombinant expression in certain mammalian cell lines including a FUT8 knockout cell line, variant CHO line Lec13, rat hybridoma cell line YB2/0, a cell line comprising a small interfering RNA specifically against the FUT8 gene, and a cell line coexpressing β-1,4-N-acetylglucosaminyltransferase III and Golgi α-mannosidase II. Alternatively, the Fc-containing molecule may be expressed in a non-mammalian cell such as a plant cell, yeast, or prokaryotic cell, e.g., *E. coli.*

In certain embodiments, the IL-2 mutein Fc-fusion proteins or anti-IL-2 antibodies of the invention comprise an Fc engineered to decrease effector function. Exemplary Fc molecules having decreased effector function include those having the following substitutions:

N297A or N297Q (IgG1)
L234A/L235A (IgG1)

V234A/G237A (IgG2)
L235A/G237A/E318A (IgG4)
H268Q/V309L/A330S/A331S (IgG2)
C220S/C226S/C229S/P238S (IgG1)
C226S/C229S/E233P/L234V/L235A (IgG1)
L234F/L235E/P331S (IgG1)
S267E/L328F (IgG1)

It is known that human IgG1 has a glycosylation site at N297 (EU numbering system) and glycosylation contributes to the effector function of IgG1 antibodies. An exemplary IgG1 sequence is provided in SEQ ID NO:3:

```
Asp Lys Thr His Thr Cys Pro Pro Cys Pro Ala Pro Glu Leu Leu Gly
1               5                  10                 15
Gly Pro Ser Val Phe Leu Phe Pro Pro Lys Pro Lys Asp Thr Leu Met
            20                  25                 30
Ile Ser Arg Thr Pro Glu Val Thr Cys Val Val Val Asp Val Ser His
            35                  40                 45
Glu Asp Pro Glu Val Lys Phe Asn Trp Tyr Val Asp Gly Val Glu Val
    50                  55                 60
His Asn Ala Lys Thr Lys Pro Arg Glu Glu Gln Tyr Asn Ser Thr Tyr
65                  70                  75                 80
Arg Val Val Ser Val Leu Thr Val Leu His Gln Asp Trp Leu Asn Gly
                85                  90                 95
Lys Glu Tyr Lys Cys Lys Val Ser Asn Lys Ala Leu Pro Ala Pro Ile
                100                 105                110
Glu Lys Thr Ile Ser Lys Ala Lys Gly Gln Pro Arg Glu Pro Gln Val
            115                 120                125
Tyr Thr Leu Pro Pro Ser Arg Glu Glu Met Thr Lys Asn Gln Val Ser
    130                 135                 140
Leu Thr Cys Leu Val Lys Gly Phe Tyr Pro Ser Asp Ile Ala Val Glu
145                 150                 155                160
Trp Glu Ser Asn Gly Gln Pro Glu Asn Asn Tyr Lys Thr Thr Pro Pro
                165                 170                175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
        210                 215                 220
Pro Gly Lys
225
```

Groups have mutated N297 in an effort to make aglycosylated antibodies. The mutations have focuses on substituting N297 with amino acids that resemble asparagine in physiochemical nature such as glutamine (N297Q) or with alanine (N297A) which mimics asparagines without polar groups.

As used herein, "aglycosylated antibody" or "aglycosylated fc" refers to the glycosylation status of the residue at position 297 of the Fc. An antibody or other molecule may contain glycosylation at one or more other locations but may still be considered an aglycosylated antibody or aglcosylated Fc-fusion protein.

In the effort to make an effector functionless IgG1 Fc, it was discovered that mutation of amino acid N297 of human IgG1 to glycine, i.e., N297G, provides far superior purification efficiency and biophysical properties over other amino acid substitutions at that residue. See Example 8.

Thus, in preferred embodiments, the IL-2 mutein Fc-fusion protein comprises a human IgG1 Fc having a N297G substitution. The Fc comprising the N297G substitution is useful in any context wherein a molecule comprises a human IgG1 Fc, and is not limited to use in the context of an IL-2 mutein Fc-fusion. In certain embodiments, an antibody comprises the Fc having a N297G substitution.

An Fc comprising a human IgG1 Fc having the N297G mutation may also comprise further insertions, deletions, and substitutions. In certain embodiments the human IgG1 Fc comprises the N297G substitution and is at least 90% identical, at least 91% identical, at least 92% identical, at least 93% identical, at least 94% identical, at least 95% identical, at least 96% identical, at least 97% identical, at least 98% identical, or at least 99% identical to the amino acid sequence set forth in SEQ ID NO:3. In a particularly preferred embodiment, the C-terminal lysine residue is substituted or deleted. The amino acid sequence of human IgG1 comprising the N297G substitution and deletion of the C-terminal lysine is set forth in SEQ ID NO:4.

A glycosylated IgG1 Fc-containing molecules were shown to be less stable than glycosylated IgG1 Fc-containing molecules. The Fc region may be further engineered to increase the stability of the aglycosylated molecule. In some embodiments, one or more amino acids are substituted to cysteine so to form di-sulfide bonds in the dimeric state. Residues V259, A287, R292, V302, L306, V323, or I332 of the amino acid sequence set forth in SEQ ID NO:3 may be substituted with cysteine. In preferred embodiments, specific pairs of residues are substitution such that they preferentially form a di-sulfide bond with each other, thus limiting or preventing di-sulfide bond scrambling. Preferred pairs include, but are not limited to, A287C and L306C, V259C and L306C, R292C and V302C, and V323C and I332C.

Provided herein are Fc-containing molecules wherein one or more of residues V259, A287, R292, V302, L306, V323, or I332 are substituted with cysteine, examples of which include those comprising A287C and L306C, V259C and L306C, R292C and V302C, or V323C and I332C substitutions.

Additional mutations that may be made to the IgG1 Fc include those facilitate heterodimer formation amongst Fc-containing polypeptides. In some embodiments, Fc region is engineering to create "knobs" and "holes" which facilitate heterodimer formation of two different Fc-containing polypeptide chains when co-expressed in a cell. U.S. Pat. No. 7,695,963. In other embodiments, the Fc region is altered to use electrostatic steering to encourage heterodimer formation while discouraging homodimer formation of two different Fc-containing polypeptide when co-expressed in a cell. WO 09/089,004, which is incorporated herein by reference in its entirety. Preferred heterodimeric Fc include those wherein one chain of the Fc comprises D399K and E356K substitutions and the other chain of the Fc comprises K409D and K392D substitutions. In other embodiments, one chain of the Fc comprises D399K, E356K, and E357K substitutions and the other chain of the Fc comprises K409D, K392D, and K370D substitutions.

In certain embodiments, it may be advantageous for the IL-2 mutein Fc-fusion protein to be monomeric, i.e., contain only a single IL-2 mutein molecule. Similarly, a bi-, tri-, or tetra-specific antibody that can specifically bind one or more additional targets may be desired. In such embodiments, the Fc-region of the fusion protein or antibody may contain one or more mutations that facilitate heterodimer formation. The fusion protein or antibody is co-expressed with an Fc-region having reciprocal mutations to those in the IL-2 mutein Fc-fusion polypeptide but lacking an IL-2 mutein or anti-IL-2 heavy chain variable domain. When the heterodimer of the two Fc-containing polypeptides forms, the resulting protein comprises only a single IL-2 mutein or anti-IL-2 binding domain.

Another method of creating a monomeric IL-2 mutein Fc-fusion protein is fusing the IL-2 mutein to a monomeric Fc, i.e., an Fc region that does not dimerize. Stable monomeric Fcs comprise mutations that discourage dimerization and that stabilize the molecule in the monomeric form. Preferred monomeric Fcs are disclosed in WO 2011/063348, which is incorporated herein by reference in its entirety. In certain embodiments, IL-2 mutein Fc fusion proteins comprise an Fc comprising negatively charged amino acids at positions 392 and 409 along with a threonine substitution at Y349, L351, L368, V397, L398, F405, or Y407.

In certain embodiments, the IL-2 mutein Fc-fusion protein comprises a linker between the Fc and the IL-2 mutein. Many different linker polypeptides are known in the art and may be used in the context of an IL-2 mutein Fc-fusion protein. In preferred embodiments, the IL-2 mutein Fc-fusion protein comprises one or more copies of a peptide consisting of GGGGS (SEQ ID NO:5), GGNGT (SEQ ID NO: 6), or YGNGT (SEQ ID NO: 7) between the Fc and the IL-2 mutein. In some embodiments, the polypeptide region between the Fc region and the IL-2 mutein region comprises a single copy of GGGGS (SEQ ID NO: 5), GGNGT (SEQ ID NO: 6), or YGNGT (SEQ ID NO: 7). As shown herein, the linkers GGNGT (SEQ ID NO: 6) or YGNGT (SEQ ID NO: 7) are glycosylated when expressed in the appropriate cells and such glycosylation may help stabilize the protein in solution and/or when administered in vivo. Thus, in certain embodiments, an IL-2 mutein fusion protein comprises a glycosylated linker between the Fc region and the IL-2 mutein region.

It is contemplated that the glycosylated linker may be useful when placed in the context of a polypeptide. Provided herein are polypeptides comprising GGNGT (SEQ ID NO: 6) or YGNGT (SEQ ID NO: 7) inserted into the amino acid sequence of the polypeptide or replacing one or more amino acids within the amino acid sequence of the polypeptide. In preferred embodiments, GGNGT (SEQ ID NO: 6) or YGNGT (SEQ ID NO: 7) is inserted into a loop of the polypeptides tertiary structure. In other embodiments, one or more amino acids of a loop are replaced with GGNGT (SEQ ID NO: 6) or YGNGT (SEQ ID NO: 7).

The C-terminal portion of the Fc and/or the amino terminal portion of the IL-2 mutein may contain one or more mutations that alter the glycosylation profile of the IL-2 mutein Fc-fusion protein when expressed in mammalian cells. In certain embodiments, the IL-2 mutein further comprises a T3 substitution, e.g., T3N or T3A. The IL-2 mutein may further comprise an S5 substitution, such as S5T Covalent modifications of IL-2 mutein and IL-2 mutein Fc-fusion proteins and anti-IL-2 antibodies are included within the scope of this invention, and are generally, but not always, done post-translationally. For example, several types of covalent modifications are introduced into the molecule by reacting certain of its amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the IL-2 mutein, IL-2 mutein Fc-fusion, or anti-IL-2 antibody included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the IL-2 mutein, IL-2 mutein Fc-fusion, or anti-IL-2 antibody may be conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the IL-2 mutein, IL-2 mutein Fc-fusion, or anti-IL-2 antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the IL-2 mutein, IL-2 mutein Fc-fusion, or anti-IL-2 antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem*., pp. 259-306.

Removal of carbohydrate moieties present on the starting IL-2 mutein, IL-2 mutein Fc-fusion, or anti-IL-2 antibody may be accomplished chemically or enzymatically. Chemical deglycosylation requires exposure of the protein to the compound trifluoromethanesulfonic acid, or an equivalent compound.

This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys*. 259:52 and by Edge et al., 1981, *Anal. Biochem*. 118:131. Enzymatic cleavage of carbohydrate moieties on polypeptides can be achieved by the use of a variety of endo- and exo-glycosidases as described by Thotakura et al., 1987, *Meth. Enzymol*. 138:350. Glycosylation at potential glycosylation sites may be prevented by the use of the compound tunicamycin as described by Duskin et al., 1982, *J. Biol. Chem*. 257:3105. Tunicamycin blocks the formation of protein-N-glycoside linkages.

Another type of covalent modification of the IL-2 mutein, IL-2 mutein Fc-fusion, or anti-IL-2 antibody comprises linking the protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, amino acid substitutions may be made in various positions within the IL-2 mutein, IL-2 mutein Fc-fusion, or anti-IL-2 antibody to facilitate the addition of polymers such as PEG. Thus, embodiments of the invention include PEGylated IL-2 mutein, IL-2 mutein Fc-fusion, or anti-IL-2 antibody. Such PEGylated proteins may have increased half-life and/or reduced immunogenicity over their non-PEGylated forms.

Polynucleotides Encoding IL-2 Muteins and IL-2 Mutein Fc-Fusion Proteins

Encompassed within the invention are nucleic acids encoding IL-2 muteins, IL-2 mutein Fc-fusions, or anti-IL-2 antibodies. Aspects of the invention include polynucleotide variants (e.g., due to degeneracy) that encode the amino acid sequences described herein.

Nucleotide sequences corresponding to the amino acid sequences described herein, to be used as probes or primers for the isolation of nucleic acids or as query sequences for database searches, can be obtained by "back-translation" from the amino acid sequences. The well-known polymerase chain reaction (PCR) procedure can be employed to isolate and amplify a DNA sequence encoding IL-2 muteins and IL-2 mutein Fc-fusion protein. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The IL-2 muteins according to the invention are ordinarily prepared by site specific mutagenesis of nucleotides in the DNA encoding the IL-2 mutein or IL-2 mutein Fc-fusion protein, using cassette or PCR mutagenesis or other techniques well known in the art, to produce DNA encoding the variant, and thereafter expressing the recombinant DNA in cell culture as outlined herein. However, IL-2 muteins and IL-2 mutein Fc-fusion may be prepared by in vitro synthesis using established techniques. The variants typically exhibit the same qualitative biological activity as the naturally occurring analogue, e.g., Treg expansion, although variants can also be selected which have modified characteristics as will be more fully outlined below.

As will be appreciated by those in the art, due to the degeneracy of the genetic code, each IL-2 mutein, IL-2 mutein Fc-fusion, and anti-IL-2 antibody of the present invention is encoded by an extremely large number of nucleic acids, each of which is within the scope of the invention and can be made using standard techniques. Thus, having identified a particular amino acid sequence, those skilled in the art could make any number of different nucleic acids, by simply modifying the sequence of one or more codons in a way that does not change the amino acid sequence of the encoded protein.

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the IL-2 mutein, IL-2 mutein Fc-fusion, or anti-IL-2 antibody-encoding sequence; the oligonucleotide sequence encodes polyHis (such as hexaHis (SEQ ID NO: 21)), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of it from the host cell. Affinity purification can be accomplished, for example, by column chromatography using antibodies against the tag as an affinity matrix. Optionally, the tag can subsequently be removed by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thyrnidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and, consequently, of a gene that encodes a desired polypeptide, such as an IL-2 mutein, IL-2 mutein Fc-fusion, or the heavy and/or light chain of an anti-IL-2 antibody. As a result, increased quantities of the polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the IL-2 mutein, IL-2 mutein Fc-fusion, or the heavy and/or light chain of an anti-IL-2 antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the IL-2 mutein, IL-2 mutein Fc-fusion, or heavy and/or light chain of an anti-IL-2 antibody. The choice of signal peptide or leader depends on the type of host cells in which the protein is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846. In one embodiment, IL-2 mutein Fc-fusions of the invention comprise a leader sequence as illustrated in FIG. 24.

The vector may contain one or more elements that facilitate expression when the vector is integrated into the host cell genome. Examples include an EASE element (Aldrich et al. 2003 *Biotechnol Prog.* 19:1433-38) and a matrix attachment region (MAR). MARs mediate structural organization of the chromatin and may insulate the integrated vector from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding an IL-2 mutein, IL-2 mutein Fc-fusion, or the heavy and/or light chain of anti-IL-2 antibody has been inserted into the proper site of the vector, the completed vector may be inserted into a suitable host cell for amplification and/or polypeptide expression. The transformation of an expression vector into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an IL-2 mutein, IL-2 mutein Fc-fusion, or the heavy and/or light chain of an anti-IL-2 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention. In general, host cells are transformed with a recombinant expression vector that comprises DNA encoding a desired IL-2 mutein, IL-2 mutein Fc-fusion, or anti-IL-2 antibody. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., 1998, *Cytotechnology* 28: 31), HeLa cells, BHK (ATCC CRL 10) cell lines, and the CVI/EBNA cell line derived from the African green monkey kidney cell line CVI (ATCC CCL 70) as described by McMahan et al., 1991, *EMBO J.* 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays.

Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces strains, Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods.

The polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, *Bio/Technology* 6:47 (1988). Cell-free translation systems could also be employed to produce polypeptides using RNAs derived from nucleic acid constructs disclosed herein. Appropriate cloning and expression vectors for use with bacterial, fungal, yeast, and mammalian cellular hosts are described by Pouwels et al. (*Cloning Vectors: A Laboratory Manual, Elsevier*, New York, 1985). A host cell that comprises an isolated nucleic acid of the invention, preferably operably linked to at least one expression control sequence, is a "recombinant host cell".

In certain aspects, the invention includes an isolated nucleic acid encoding a human IL-2 mutein that preferentially stimulates T regulatory cells and comprises a D20E, D20G, D20W, D84A, D84S, H16D, H16G, H16K, H16R, H16T, H16V, I92K, I92R, L12K, L19D, L19N, L19T, N88D, N88R, N88S, V91D, V91G, V91K, and/or V91S substitution and an amino acid sequence at least 90%, at least 91%, at least 92%, at least 93%, at least 94%, at least 95%, at least 96%, at least 97%, at least 98%, at least 99%, or 100% identical to the amino acid sequence set forth in SEQ ID NO:1.

Also included are isolated nucleic acids encoding any of the exemplary IL-2 mutein Fc-fusion proteins described herein. In preferred embodiments, the Fc portion of an antibody and the human IL-2 mutein are encoded within a single open-reading frame, optionally with a linker encoded between the Fc region and the IL-2 mutein.

In another aspect, provided herein are expression vectors comprising the above IL-2 mutein- or IL-2 mutein Fc-fusion protein-encoding nucleic acids operably linked to a promoter.

In another aspect, provided herein are host cells comprising the isolated nucleic acids encoding the above IL-2 muteins, IL-2 mutein Fc-fusion proteins, or anti-IL-2 antibodies. The host cell may be a prokaryotic cell, such as *E. coli*, or may be a eukaryotic cell, such as a mammalian cell. In certain embodiments, the host cell is a Chinese hamster ovary (CHO) cell line.

In another aspect, provided herein are methods of making a human IL-2 mutein. The methods comprising culturing a host cell under conditions in which a promoter operably linked to a human IL-2 mutein is expressed. Subsequently, the human IL-2 mutein is harvested from said culture. The IL-2 mutein may be harvested from the culture media and/or host cell lysates.

In another aspect, provided herein are methods of making a human IL-2 mutein Fc-fusion protein. The methods comprising culturing a host cell under conditions in which a promoter operably linked to a human IL-2 mutein Fc-fusion protein is expressed. Subsequently, the human IL-2 mutein Fc-fusion protein is harvested from said culture. The human IL-2 mutein Fc-fusion protein may be harvested from the culture media and/or host cell lysates.

In another aspect, provided herein are methods of making an anti-IL-2 antibody. The methods comprising culturing a host cell under conditions in which promoters operably linked to the heavy and light chains of an anti-IL-2 antibody are expressed. Subsequently, the anti-IL-2 antibody is harvested from said culture. The anti-IL-2 antibody may be harvested from the culture media and/or host cell lysates.

Pharmaceutical Compositions

In some embodiments, the invention provides a pharmaceutical composition comprising a therapeutically effective amount of an IL-2 mutein or anti-IL-2 antibody together with a pharmaceutically effective diluents, carrier, solubilizer, emulsifier, preservative, and/or adjuvant. In certain embodiments, the IL-2 mutein is within the context of an IL-2 mutein Fc-fusion protein. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of an IL-2 mutein containing therapeutic molecule, e.g, an IL-2 mutein Fc-fusion, are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, 11-2 mutein or anti-IL-2 antibody compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the IL-2 mutein or anti-IL-2 antibody product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired IL-2 mutein or anti-IL-2 antibody composition in a pharmaceutically acceptable vehicle. A particularly suitable vehicle for parenteral injection is sterile distilled water in which the mutein or anti-IL-2 antibody composition is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the IL-2 mutein or anti-IL-2 antibody composition.

Additional pharmaceutical compositions will be evident to those skilled in the art, including formulations involving IL-2 mutein or anti-IL-2 antibody compositions in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering IL-2 mutein or anti-IL-2 antibody formulations, which can be used as pharmaceutical compositions, as described in international patent application WO 06138181A2 (PCT/US2006/022599), which is incorporated by reference in its entirety herein.

As discussed above, certain embodiments provide IL-2 mutein or anti-IL-2 antibody compositions, particularly pharmaceutical 11-2 mutein Fc-fusion proteins, that comprise, in addition to the IL-2 mutein or anti-IL-2 antibody composition, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in IL-2 mutein or anti-IL-2 antibody formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of IL-2 mutein and/or anti-IL-2 antibody formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of IL-2 mutein or anti-IL-2 antibody formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of IL-2 mutein or anti-IL-2 antibody formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol.

In one embodiment, an IL-2 mutein or Fc-fusion of an IL-2 mutein, such as, for example, Fc.IL-2(H16T), Fc.IL-2(H16K), Fc.IL-2(H16R), Fc.IL-2(L19N), Fc.IL-2(L19D), Fc.IL-2(D20E), Fc.IL-2(D20G), Fc.IL-2(D20T), Fc.IL-2(N88D), Fc.IL-2(N88R), Fc.IL-2(N88S), Fc.IL-2(V91D), Fc.IL-2(V91G), Fc.IL-2(V91K), or Fc.IL-2(V91S), is formulated to 10 mg/mL in 10 mM L-Glutamic Acid, 3.0% (w/v) L-Proline, at pH 5.2. In another embodiment, an IL-2 mutein or Fc-fusion of an IL-2 mutein, such as, for example, Fc.IL-2(H16T), Fc.IL-2(H16K), Fc.IL-2(H16R), Fc.IL-2(L19N), Fc.IL-2(L19D), Fc.IL-2(D20E), Fc.IL-2(D20G), Fc.IL-2(D20T), Fc.IL-2(N88D), Fc.IL-2(N88R), Fc.IL-2(N88S), Fc.IL-2(V91D), Fc.IL-2(V91G), Fc.IL-2(V91K), or Fc.IL-2(V91S), is formulated in 10 mM KPi, 161 mM L-arginine, at pH 7.6.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

In another aspect, the present invention provides IL-2 muteins, anti-IL-2 antibodies, or Fc-fusions of IL-2 muteins, in lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

IL-2 mutein or anti-IL-2 antibody formulations generally will be designed for specific routes and methods of administration, for specific administration dosages and frequencies of administration, for specific treatments of specific diseases, with ranges of bio-availability and persistence, among other things. Formulations thus may be designed in accordance with the invention for delivery by any suitable route, including but not limited to orally, aurally, opthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an IL-2 mutein- or anti-IL-2 antibody-containing pharmaceutical composition to be employed will depend, for example, upon the therapeutic context and objectives. One skilled in the art will appreciate that the appropriate dosage levels for treatment will vary depending, in part, upon the molecule delivered, the indication for which the IL-2 mutein or anti-IL-2 antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 μg/kg to up to about 1 mg/kg or more, depending on the factors mentioned above. In specific embodiments, the dosage may range from 0.5 μg/kg up to about 100 μg/kg, optionally from 2.5 μg/kg up to about 50 μg/kg.

A therapeutic effective amount of an IL-2 mutein or anti-IL-2 antibody preferably results in a decrease in severity of disease symptoms, in an increase in frequency or duration of disease symptom-free periods, or in a prevention of impairment or disability due to the disease affliction.

Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163, all incorporated by reference herein.

In one embodiment, a pharmaceutical composition is provided comprising

Methods of Treating Autoimmune or Inflammatory Disorders

In certain embodiments, an IL-2 mutein or anti-IL-2 antibody of the invention is used to treat an autoimmune or inflammatory disorder. In preferred embodiments, an IL-2 mutein Fc-fusion protein is used.

Disorders that are particularly amenable to treatment with IL-2 mutein or anti-IL-2 antibody disclosed herein include, but are not limited to, inflammation, autoimmune disease, atopic diseases, paraneoplastic autoimmune diseases, cartilage inflammation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, vasculitis, myolitis, polymyolitis, dermatomyolitis, polyarteritis nodossa, Wegener's granulomatosis, arteritis, ploymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophogitis, eosinophilic bronchitis, Guillain-Barre disease, Type I diabetes mellitus, thyroiditis (e.g., Graves' disease), Addison's disease, Raynaud's phenomenon, autoimmune hepatitis, GVHD, transplantation rejection, kidney damage, hepatitis C-induced vasculitis, spontaneous loss of pregnancy, and the like.

In preferred embodiments, the autoimmune or inflammatory disorder is lupus, graft-versus-host disease, hepatitis C-induced vasculitis, Type I diabetes, multiple sclerosis, spontaneous loss of pregnancy, atopic diseases, and inflammatory bowel diseases.

In another embodiment, a patient having or at risk for developing an autoimmune or inflammatory disorder is treated with an IL-2 mutein or anti-IL-2 antibody (for example, an IL-2 mutein disclosed herein, such as an IL-2 mutein Fc-fusion as disclosed herein, or another IL-2 mutein known in the art or wild-type IL-2, optionally as part of an Fc-fusion molecule of the type described herein) and the patient's response to the treatment is monitored. The patient's response that is monitored can be any detectable or measurable response of the patient to the treatment, or any combination of such responses. For example, the response can be a change in a physiological state of the patient, such as body temperature or fever, appetence, sweating, headache, nausea, fatigue, hunger, thirst, mental acuity, or the like. Alternatively, the response can be a change in the amount of a cell type or gene product (for example, a protein, peptide, or nucleic acid), for example, in a sample of peripheral blood taken from the patient. In one embodiment, the patient's treatment regimen is altered if the patient has a detectable or measurable response to the treatment, or if such response crosses a particular threshold. The alteration can be a reduction or increase in the frequency in dosing, or a reduction or increase in the amount of the IL-2 mutein or anti-IL-2 antibody administered per dose, or a "holiday" from dosing (i.e., a temporary cessation of treatment, either for a specified period of time, or until a treating physician determines that treatment should continue, or until a monitored response of the patient indicates that treatment should or can resume), or the termination of treatment. In one embodiment, the response is a change in the patient's temperature or CRP levels. For example, the response can be an increase in the patient's body temperature, or an increase of the CRP levels in a sample of peripheral blood, or both. In one particular embodiment, the patient's treatment is reduced, suspended, or terminated if the patient's body temperature increases during the course of treatment by at least 0.1°, 0.2°, 0.3°, 0.4°, 0.5°, 0.7°, 1°, 1.5°, 2°, or 2.5° C. In another particular embodiment, the patient's treatment is reduced, suspended, or terminated if the concentration of CRP in a sample of the patient's peripheral blood increases during the course of treatment by at least 0.1, 0.2, 0.3, 0.4, 0.5, 0.7, 1, 1.5, or 2 mg/mL. Other patient reactions that can be monitored and used in deciding whether to modify, reduce, suspend, or terminate treatment include the development or worsening of capillary leak syndrome (hypotension and cardiovascular instability), impaired neutrophil function (for example, resulting in or detected the development or worsening of an infection), thrombocytopenia, thrombotic angiopathy, injection site reactions, vasculitis (such as Hepatitis C virus vasculitis), or inflammatory symptoms or diseases. Further patient reactions that can be monitored and used in deciding whether to modify, reduce, increase, suspend, or terminate treatment include an increase in the number of NK cells, Treg cells, FOXP3$^-$ CD4 T cells, FOXP3$^+$ CD4 T cells, FOXP3– CD8 T cells, or eosinophils. Increases of these cell types can be detected, for example, as an increase in the number of such cells per unit of peripheral blood (for example, expressed as an increase in cells per milliliter of blood) or as an increase in the percentage of such cell type compared to another type of cell or cells in the blood sample. Another patient reaction that can be monitored is an increase in the amount of cell surface-bound IL-2 mutein or anti-IL-2 antibody on CD25$^+$ cells in a sample of the patient's peripheral blood.

Methods of Expanding Treg Cells

The IL-2 mutein, anti-IL-2 antibody, or IL-2 mutein Fc-fusion protein may be used to expand Treg cells within a subject or sample. Provided herein are methods of increasing the ratio of Tregs to non-regulatory T cells. The method comprises contacting a population of T cells with an effective amount of a human IL-2 mutein, anti-IL-2 antibody or IL-2 mutein Fc-fusion. The ratio may be measured by determining the ratio of CD3+FOXP3+ cells to CD3+ FOXP3– cells within the population of T cells. The typical Treg frequency in human blood is 5-10% of total CD4+ CD3+ T cells, however, in the diseases listed above this percentage may be lower or higher. In preferred embodiments, the percentage of Treg increases at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000%. Maximal fold increases in Treg may vary for particular diseases; however, a maximal Treg frequency that might be obtained through IL-2 mutein treatment is 50% or 60% of total CD4+CD3+ T cells. In certain embodiments, the IL-2 mutein, anti-IL-2 antibody, or IL-2 mutein Fc-fusion protein is administered to a subject and the ratio of regulatory T cells (Tregs) to non-regulatory T cells within peripheral blood of a subject increases.

Because the IL-2 mutein, anti-IL-2 antibody, and IL-2 mutein Fc-fusion proteins preferentially expand Tregs over other cell types, they also are useful for increasing the ratio of regulatory T cells (Tregs) to natural killer (NK) cells within the peripheral blood of a subject. The ratio may be measured by determining the ratio of CD3+FOXP3+ cells to CD16+ and/or CD56+ lymphocytes that are CD19− and CD3−.

It is contemplated that the IL-2 mutein, anti-IL-2 antibody, or IL-2 mutein Fc-fusion protein may have a therapeutic effect on a disease or disorder within a patient without significantly expanding the ratio of Tregs to non-regulatory T cells or NK cells within the peripheral blood of the patient. The therapeutic effect may be due to localized activity of the IL-2 mutein, anti-IL-2 antibody, or IL-2 mutein Fc-fusion protein at the site of inflammation or autoimmunity.

EXAMPLES

The following examples, both actual and prophetic, are provided for the purpose of illustrating specific embodiments or features of the present invention and are not intended to limit its scope.

Example 1—Reducing Number of Mutations that Confer High Affinity for CD25

IL-2 muteins with elevated affinity for CD25 and reduced signaling strength through IL-2Rγ preferentially promote Treg growth and function. To reduce the potential immunogenicity, the minimum number of mutations required to achieve high affinity for CD25 was sought. The crystal structure of IL-2 in complex with its three receptors (PDB code—2B5I) shows V69A and Q74P are located in the helical structure that interacts with CD25. This may explain why V69A and Q74P were frequently isolated in two independent IL-2 mutagenesis screens for high CD25 binding affinity (Rao et al. 2005; Thanos et al. 2006). This Example explores which of the other mutations in IL-2 mutein "2-4" identified in the screen of Rao et al. are most important to increase the affinity above that observed with V69A and Q74P alone. The following proteins were screened by flow cytometry for binding to CD25 on the surface of activated T cells. All constructs also included a C-terminal FLAG and poly-His tag for purification and detection. The specific mutations are provided in parenthesis.

```
HaMut1D (V69A, Q74P, N88D, C125A)
                                       (SEQ ID NO: 8)
APTSSSTKKTQLQLEHLLLDLQMILNGINNYKNPKLTRMLTFKFYMPKKA
TELKHLQCLEEELKPLEEALNLAPSKNFHLRPRDLISDINVIVLELKGSE
TTFMCEYADETATIVEFLNRWITFAQSIISTLT

HaMut2D (N30S, V69A, Q74P, N88D, C125A)
                                       (SEQ ID NO: 9)
APTSSSTKKTQLQLEHLLLDLQMILNGINSYKNPKLTRMLTFKFYMPKKA
TELKHLQCLEEELKPLEEALNLAPSKNFHLRPRDLISDINVIVLELKGSE
TTFMCEYADETATIVEFLNRWITFAQSIISTLT

HaMut3D (K35R, V69A, Q74P, N88D, C125A)
                                       (SEQ ID NO: 10)
APTSSSTKKTQLQLEHLLLDLQMILNGINNYKNPRLTRMLTFKFYMPKKA
TELKHLQCLEEELKPLEEALNLAPSKNFHLRPRDLISDINVIVLELKGSE
TTFMCEYADETATIVEFLNRWITFAQSIISTLT

HaMut4D (T37A, V69A, Q74P, N88D, C125A)
                                       (SEQ ID NO: 11)
APTSSSTKKTQLQLEHLLLDLQMILNGINNYKNPKLARMLTFKFYMPKKA
TELKHLQCLEEELKPLEEALNLAPSKNFHLRPRDLISDINVIVLELKGSE
TTFMCEYADETATIVEFLNRWITFAQSIISTLT

HaMut5D (K48E, V69A, Q74P, N88D, C125A)
                                       (SEQ ID NO: 12)
APTSSSTKKTQLQLEHLLLDLQMILNGINNYKNPKLTRMLTFKFYMPEKA
TELKHLQCLEEELKPLEEALNLAPSKNFHLRPRDLISDINVIVLELKGSE
TTFMCEYADETATIVEFLNRWITFAQSIISTLT

HaMut6D (E68D, V69A, Q74P, N88D ,C125A)
                                       (SEQ ID NO: 13)
APTSSSTKKTQLQLEHLLLDLQMILNGINNYKNPKLTRMLTFKFYMPKKA
TELKHLQCLEEELKPLEDALNLAPSKNFHLRPRDLISDINVIVLELKGSE
TTFMCEYADETATIVEFLNRWITFAQSIISTLT

HaMut7D (N71R, V69A, Q74P, N88D, C125A)
                                       (SEQ ID NO: 14)
APTSSSTKKTQLQLEHLLLDLQMILNGINNYKNPKLTRMLTFKFYMPKKA
TELKHLQCLEEELKPLEEALRLAPSKNFHLRPRDLISDINVIVLELKGSE
TTFMCEYADETATIVEFLNRWITFAQSIISTLT

HaMut8D (K35R, K48E, E68D, N88D, C125A)
                                       (SEQ ID NO: 15)
APTSSSTKKTQLQLEHLLLDLQMILNGINNYKNPRLTRMLTFKFYMPEKA
TELKHLQCLEEELKPLEDVLNLAQSKNFHLRPRDLISDINVIVLELKGSE
TTFMCEYADETATIVEFLNRWITFAQSIISTLT
```

HaMut7D bound CD25 with nearly the same affinity as the original isolate "2-4" (~200 pM), indicating that mutation N71R was capable of greatly increasing the affinity above that observed with V69A, Q74P alone (HaMut1D, ~2 nM). The other constructs possessed affinities similar to or slightly higher than HaMut1D, with the exception of HaMut8D whose affinity was only slightly higher than that of WT IL-2.

Example 2—IL-2 Muteins Fused to IgG1-Fc Domains for Improved Half-Life

To reduce the dosing frequency required to achieve Treg enrichment with an IL-2 mutein, various fusions between IL-2 and IgG1-Fc domains were evaluated. The Fc domains contained point mutations to abolish effector functions mediated by IgG1, such as target cell lysis. The Fc effector function mutations utilized were either A327Q, Ala Ala (L234A+L235A) or N297G. Because the Treg-selective IL-2 muteins have partial reduction in IL-2 potency, it was important to fuse IL-2 to Fc in such a way that did not significantly impact IL-2R signaling. Thus, IL-2 muteins were tested for IL-2R activation with and without Fc fusion.

To determine if IL-2 dimerization by Fc fusion would increase IL-2R signaling strength due to increased avidity for IL-2R, a weaker IL-2 mutein (haD5) (US20110274650) was fused to the amino terminus of Fc, separated by a GGGGS (SEQ ID NO: 5) linker sequence. This mutein possessed 3 mutations impacting IL-2R signaling (E15Q, H16N, N88D), 8 mutations to confer high affinity for CD25 (N29S, Y31H, K35R, T37A, K48E, V69A, N71R, Q74P) (Rao et al. 2005), and C125S to prevent cysteine mispairing and aggregation. Fusion to Fc in this manner completely abrogated the biological activity of haD5, while its high-affinity binding to cell surface CD25 was enhanced, likely due to increased avidity from dimerization.

IL-2 muteins were also fused to either the N- or C-terminus of an Fc heterodimer, such that only one chain of the Fc dimer bore the IL-2 domain. Heterodimeric pairing between two asymmetric Fc chains was promoted by electrostatic interactions between introduced lysines on one Fc chain and introduced aspartic acids on the other Fc chain. IL-2 mutein haD6 was fused to the N-terminus of one Fc chain or the other, in the event that one configuration was preferred, resulting in two protein constructs termed haD6.FcDD and haD6.FcKK. Mutein haMut7D was also fused to the C-terminus of the Fc heterodimer with one or two GGGGS (SEQ ID NO: 5) linkers (FcKK(G4S) haMut7D, FcKK(G4S)2haMut7D). Fusion of the IL-2 mutein haD6 to the N-terminus of the Fc heterodimer resulted in a partial loss of activity relative to free haD6 in both pSTAT5 and T cell proliferation experiments. In contrast, fusion of haMut7D to the C-terminus of the Fc heterodimer with either one or two GGGGS (SEQ ID NO: 5) linkers did not alter the potency of haMut7D.

Fusion of an IL-2 mutein to the C-terminus of an Fc homodimer was also investigated. Total PBMC were activated in T75 tissue culture flasks at 300 million cells per 100 ml with 100 ng/ml anti-CD3 (OKT3). On day 3 of culture, cells were washed 3 times and rested in fresh media for 3 days. Cells were then stimulated with IL-2 variants at 10× dose titration ranging from 1 pM to 10 nM at a final volume of 50 μl. The level of STAT5 phosphorylation was measured using BD phosflow buffer kit. Briefly, 1 ml of BD lyse/fix phosflow buffer was added to stop stimulation. Cells were fixed for 20 min at 37° C. and permeabilized with 1×BD phosflow perm buffer on ice before stained for CD4, CD25, FOXP3 and pSTAT5.

Figure 1:
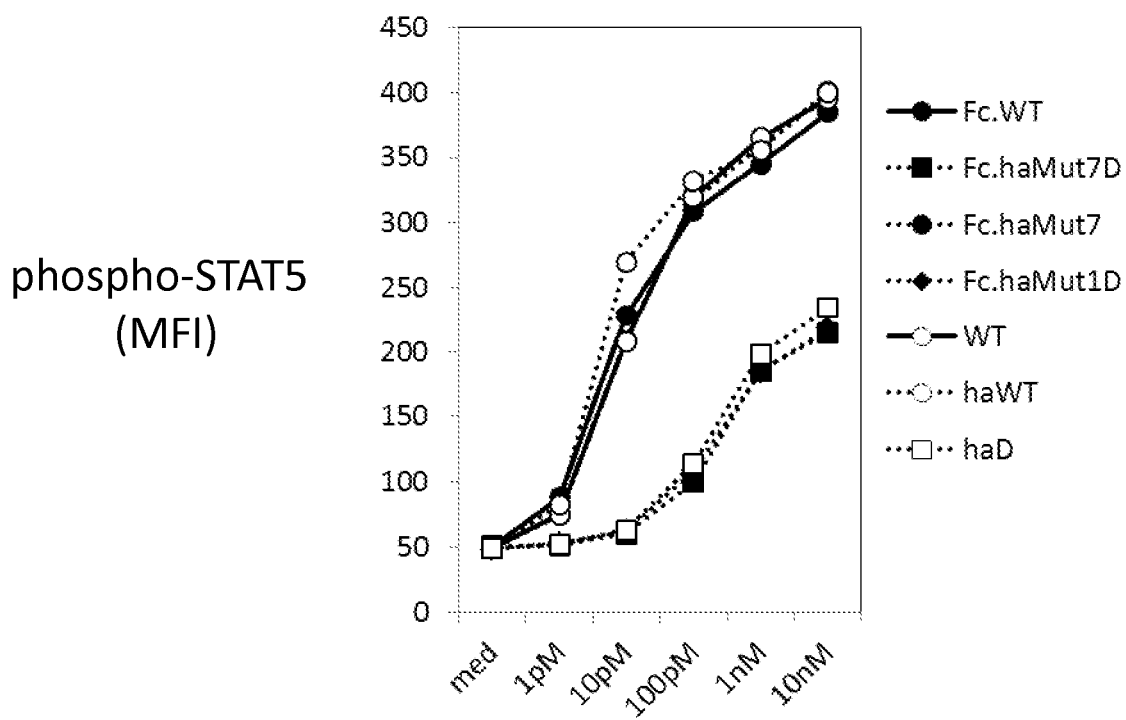
FIG. 1 In a short term stimulation assay, homodimerization by fusion to the C-terminus of IgG-Fc does not alter the activity of IL-2 muteins with reduced potency and with high affinity for CD25.

As can be seen in FIG. 1, the bioactivity of muteins haMut1D and haMut7D was not altered by fusion to the C-terminus of an Fc homodimer. Thus, fusion between the N-terminus of IL-2 and C-terminus of Fc did not compromise the agonist activity of the IL-2 muteins, even in the context of an Fc.IL-2 homodimer. In these constructs, the C125A mutation was used in place of C125S for improved manufacturing.

Example 3—Tuning IL-2 Mutein Potency to Achieve Preferential Treg Growth

The initial panel of IL-2 muteins contained N88D alone or with 1 or 2 additional mutations impacting IL-2R signaling. A second panel of muteins was designed, all with single point mutations, with the goal of identifying muteins with either similar or slightly more potent agonism than those of the N88D series. A panel of 24 signaling mutations was identified based on predicted IL-2Rβ-interacting amino acids (crystal structure, PDB code—2B5I). Particular substitutions were selected based on predicted decrease in the binding free energy between the mutein and IL-2Rβ. The binding free energy was calculated using EGAD computational algorithm (Handel's Laboratory, University of California at San Diego, USA). The binding free energy of a mutant is defined as $\Delta\Delta G_{mut} = \mu\, (\Delta G_{mut} - \Delta G_{wt})$. Where, $\mu$ (=0.1, in general) is the scaling factor used to normalize the predicted changes in binding affinity to have a slope of 1 when comparing with the experimental energies (Pokala and Handel 2005). The free energy of dissociation (AG) was defined as the energy difference between the complex ($\Delta G_{bound}$) and free states ($\Delta G_{free}$). The dissociation energy ΔGmut was calculated for each substitution.

A panel of IL-2 muteins with the following substitutions (H16E, H16Q L19K, D20R, D20K, D20H, D20Y, M23H, D84K, D84H, S87Y, N88D, N88K, N88I, N88H, N88Y, V91N, V91K, V91H, V91R, I92H, E95K, E95R, or E95I) was expressed as C-terminal fusions to the Fc heterodimer. These constructs also contained the haMut7 mutations for high CD25 binding affinity (V69A, N71R, Q74P) and C125A for efficient folding.

The panel was screened for potency in the T cell STAT5 phosphorylation assay of Example 2, and H16E, D84K, V91N, V91K, and V91R were found to possess activity less than wild type IL-2 and more than N88D (FIG. 2).

H16E, D84K, V91N, V91K, and V91R possessed activity less than wild type IL-2 and more than N88D.

Selected muteins were also tested in T cell and NK growth assays.

For the T-cell assay, total PBMCs were activated at 3 million/ml with 100 ng OKT3. On day 2, cells were washed 3 times and rested in fresh media for 5 days. Cells were then labeled with CFSE and further cultured in a 24 well plate at 0.5 million/well in IL-2 containing media for 7 days before FACS analysis. The proliferation of T cell subsets is presented in FIG. 3 as CFSE dilution (median CFSE fluorescence).

For the NK-cell assay, MACS sorted CD16+ NK cells were cultured in IL-2 containing media for 3 days at 0.1 million/well in 96 well plates. 0.5 μCi $^3$H-thymidine was added to each well during the final 18 hours of incubation. The results are shown in FIG. 4.

Figure 3:
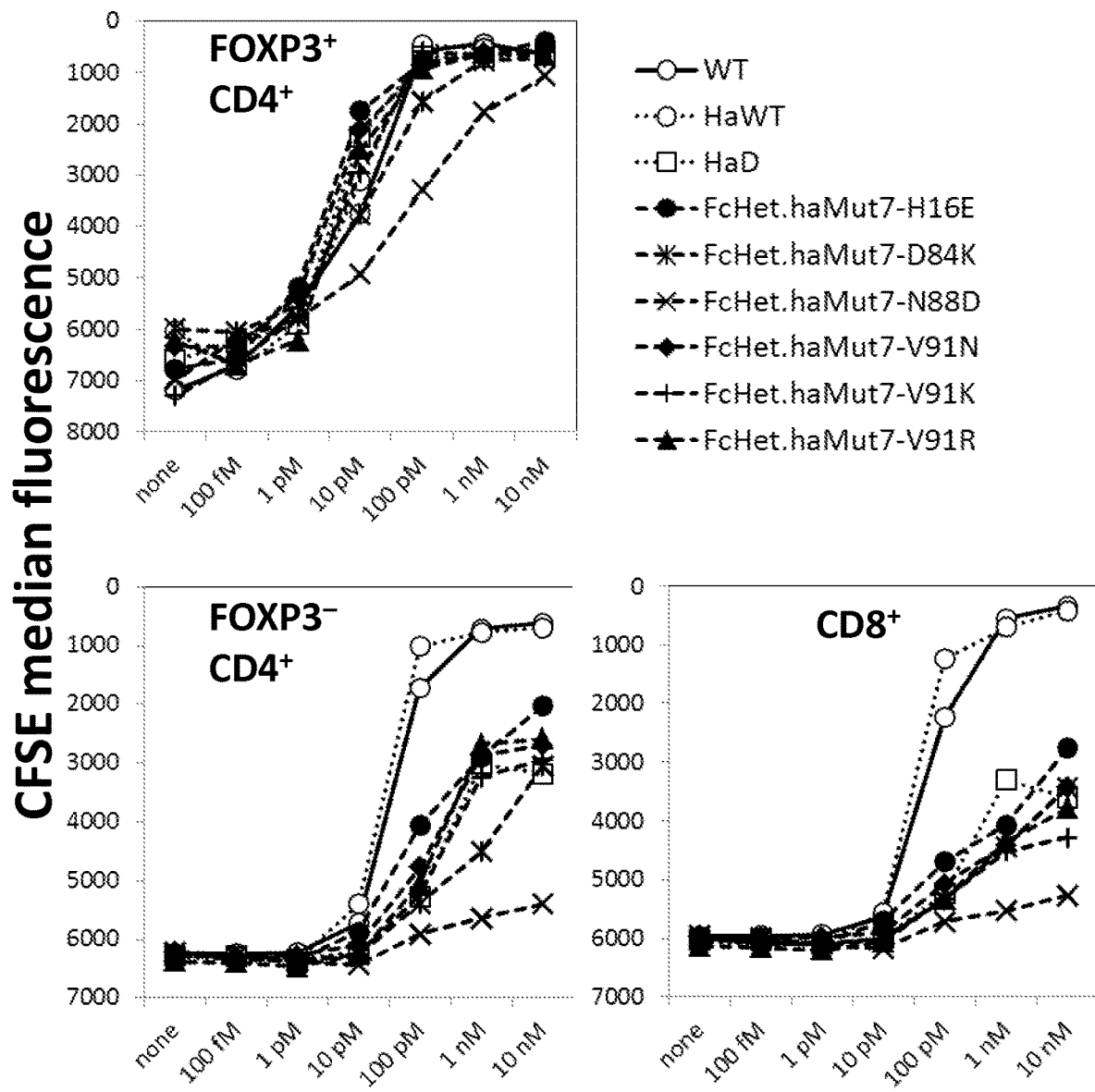
FIG. 3 Proliferation of T cell subsets in response to titrations of IL-2 muteins fused to Fc-heterodimer. Activity of fusion proteins was compared to three forms of IL-2 without Fc fusion (open symbols): WT IL-2, HaWT (high affinity for CD25) (N29S, Y31H, K35R, T37A, K48E, V69A, N71R, Q74P), and HaD (high affinity for CD25 and reduced signaling activity) (N29S, Y31H, K35R, T37A, K48E, V69A, N71R, Q74P, N88D)
Figure 4:
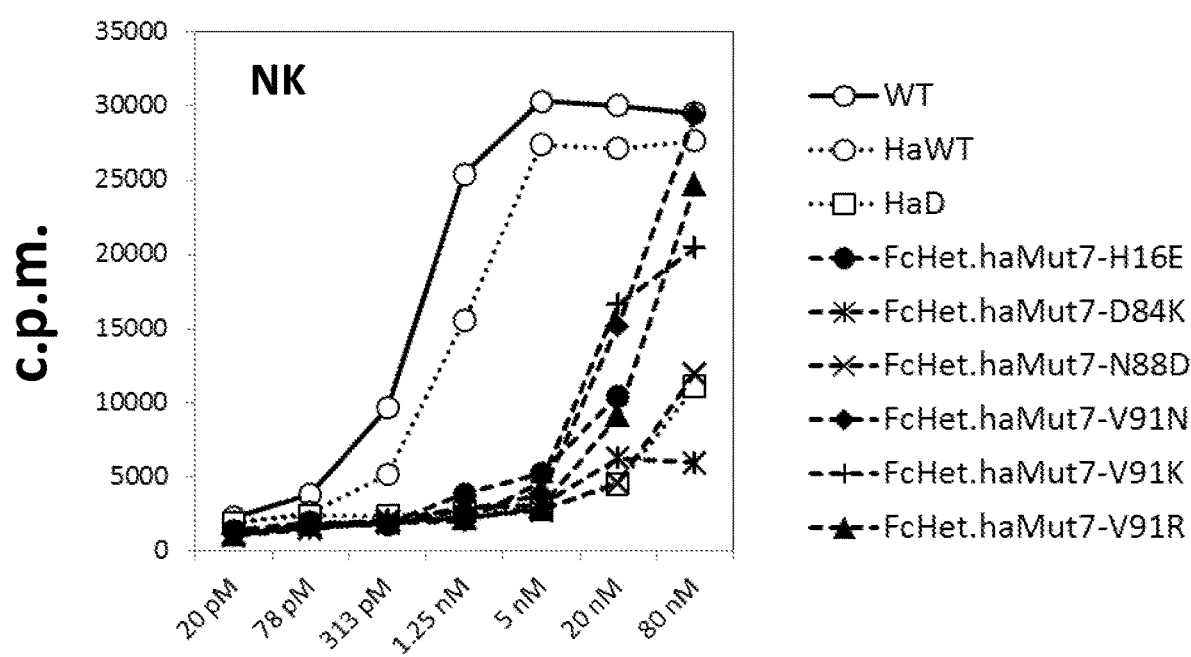
FIG. 4 Proliferation of NK cells in response to titrations of IL-2 muteins fused to Fc-heterodimer. Activity of fusion proteins was compared to three forms of IL-2 without Fc fusion (open symbols): WT IL-2, HaWT (high affinity for CD25) (N29S, Y31H, K35R, T37A, K48E, V69A, N71R, Q74P), and HaD (high affinity for CD25 and reduced signaling activity) (N29S, Y31H, K35R, T37A, K48E, V69A, N71R, Q74P, N88D)

Mutants H16E, D84K, V91N, V91K, and V91R mutants were capable of stimulating Treg growth similar to WT IL-2 but were approximately 10× less potent on other T cells (FIG. 3), and approximately 100× less potent on NK cells (FIG. 4).

A separate panel of Fc.IL-2 fusion proteins was designed in which the distance between the Fc heterodimer and the mutein haMut7 (V69A, N71R, Q74P, C125A) was reduced by a series of individual amino acid truncations.

| | | |
|---|---|---|
| Fc.haMut7 | Fc...<u>TQKSLSLSPGKGGGGS</u>APTSSSTKKTQLQLEHLLLDLQMILN...haMut7 | (SEQ ID NO: 22) |
| Trunc1 | Fc...<u>TQKSLSLS</u>SSTKKTQLQLEHLLLDLQMILN...haMut7 | (SEQ ID NO: 23) |
| Trunc2 | Fc...<u>TQKSLSLS</u>-STKKTQLQLEHLLLDLQMILN...haMut7 | (SEQ ID NO: 24) |
| Trunc3 | Fc...<u>TQKSLSLS</u>--TKKTQLQLEHLLLDLQMILN...haMut7 | (SEQ ID NO: 25) |
| Trunc4 | Fc...<u>TQKSLSLS</u>---KKTQLQLEHLLLDLQMILN...haMut7 | (SEQ ID NO: 26) |
| Trunc5 | Fc...<u>TQKSLSLS</u>----KTQLQLEHLLLDLQMILN...haMut7 | (SEQ ID NO: 27) |
| Trunc6 | Fc...<u>TQKSLSLS</u>-----TQLQLEHLLLDLQMILN...haMut7 | (SEQ ID NO: 28) |
| Trunc7 | Fc...<u>TQKSLSLS</u>------QLQLEHLLLDLQMILN...haMut7 | (SEQ ID NO: 29) |
| Trunc8 | Fc...<u>TQKSLSL</u>-------QLQLEHLLLDLQMILN...haMut7 | (SEQ ID NO: 30) |

Trunc1-Trunc4 possessed potency equal to the full length parent construct Fc.haMut7 as measured by STAT5 phosphorylation and by T cell and NK cell proliferation as described for FIGS. 2, 3, and 4. Trunc5 and Trunc6 stimulated weaker responses yet stronger than those stimulated by the N88D mutation (haD and haMut7D) and very similar to those stimulated by V91K. Trunc7 was weaker than N88D muteins, and Trunc8 had very little activity. When tested on NK cells, however, Trunc5 and Trunc6 were stronger agonists than V91K, indicating that Treg selectivity was more readily achieved with signaling mutations rather than steric hindrance by a proximal Fc domain.

Example 4—High CD25 Affinity Mutations in the Context of an Fc Homodimer

Figure 5:
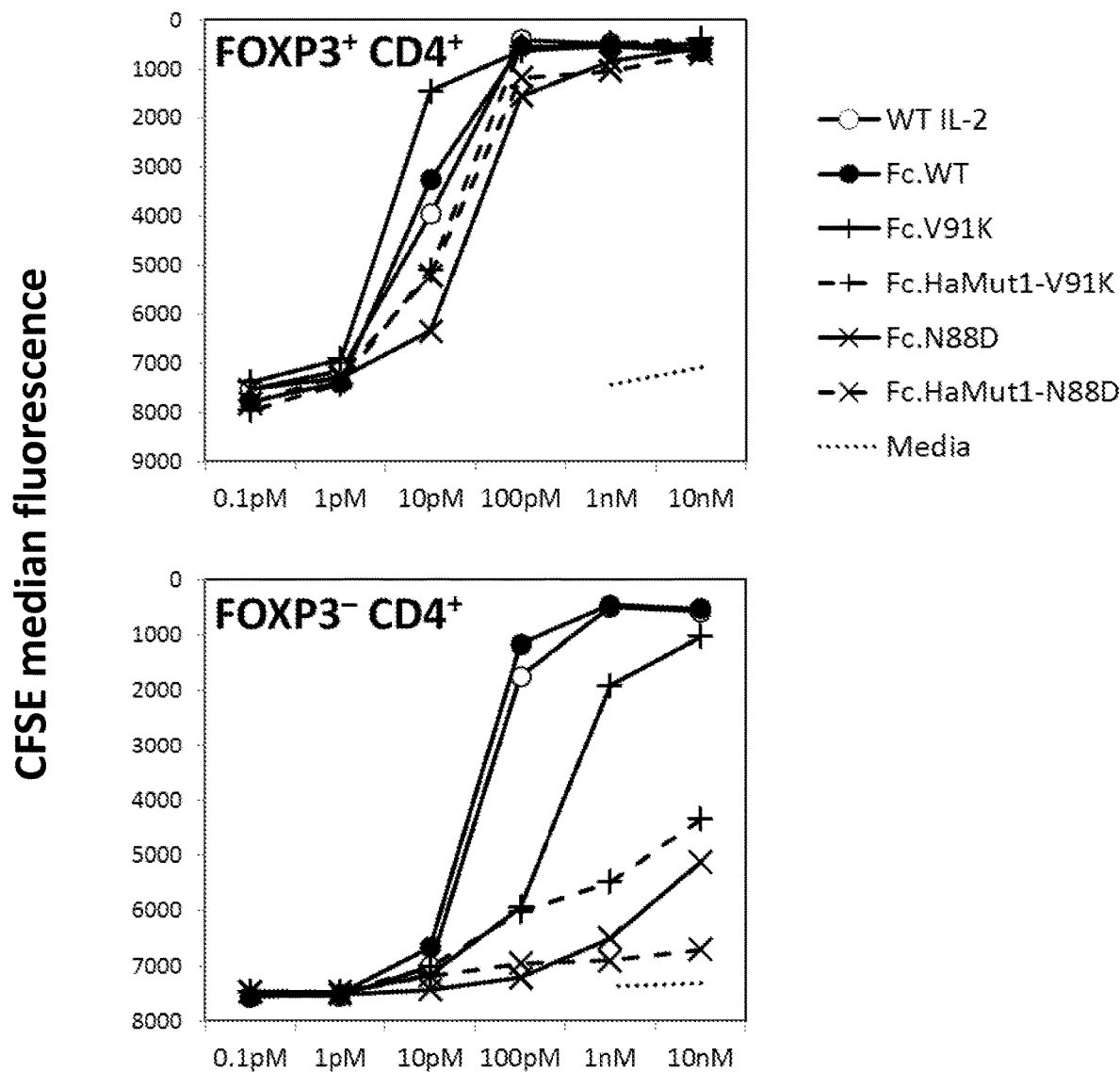
FIG. 5 Proliferation of T cell subsets in response to titrations of IL-2 muteins fused to Fc-homodimer N297G. Activity of Fc.muteins was compared to WT IL-2 (open circles) and Fc.WT (closed circles). Mutations that confer high affinity for CD25 (HaMut1) were V69A and Q74P.
Figure 6:
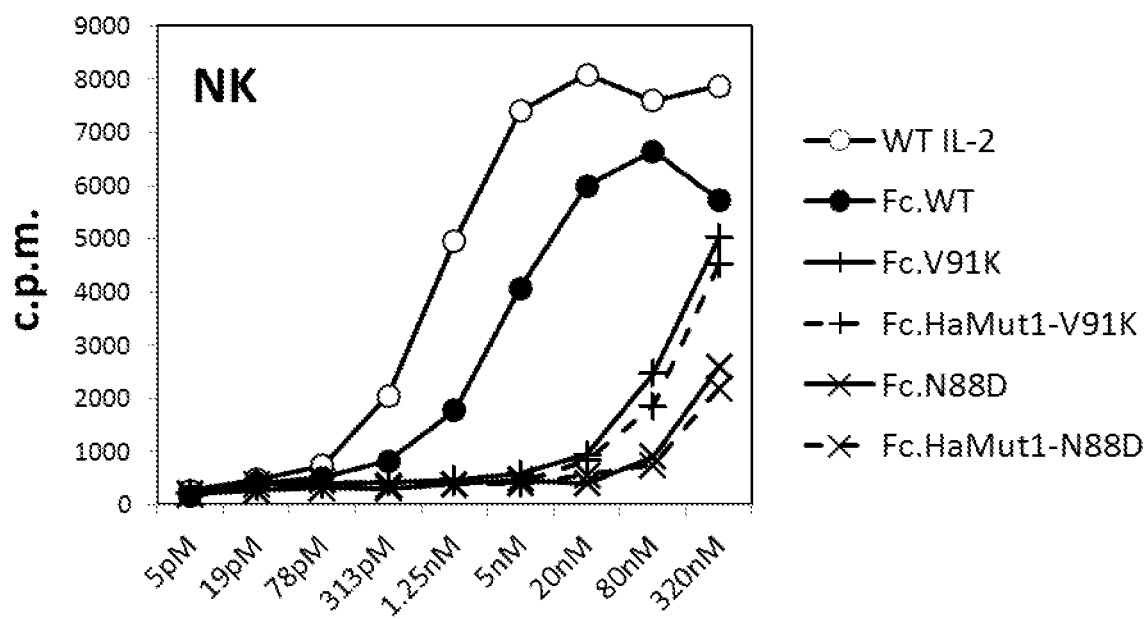
FIG. 6 Proliferation of NK cells in response to titrations of IL-2 muteins fused to Fc-homodimer N297G. Activity of Fc.muteins was compared to WT IL-2 (open circles) and Fc.WT (closed circles).

The mutations that conferred high CD25 binding affinity were considered advantageous because they increased tropism for CD25-high T cells, and because they promoted long term CD25::IL-2mutein association and prolonged signaling. However, reducing mutation number may reduce immunogenicity potential. The N88D or the V91K muteins, with and without the haMut1 high affinity mutations V69A and Q74P, were expressed as fusions to the C-terminus of an Fc homodimer and compared for bioactivity. In pSTAT5 stimulation assays, the homodimerization had no effect on signal strength relative to monomeric mutein. The reversion of the high affinity mutations V69A and Q74P also did not affect pSTAT5 signaling. In T cell growth assays, the high affinity mutations reduced activity on conventional CD4 T cells and CD8 T cells but not on regulatory T cells (FIG. 5). The high affinity mutations also did not alter proliferative responses in NK cells (FIG. 6).

Figure 7A:
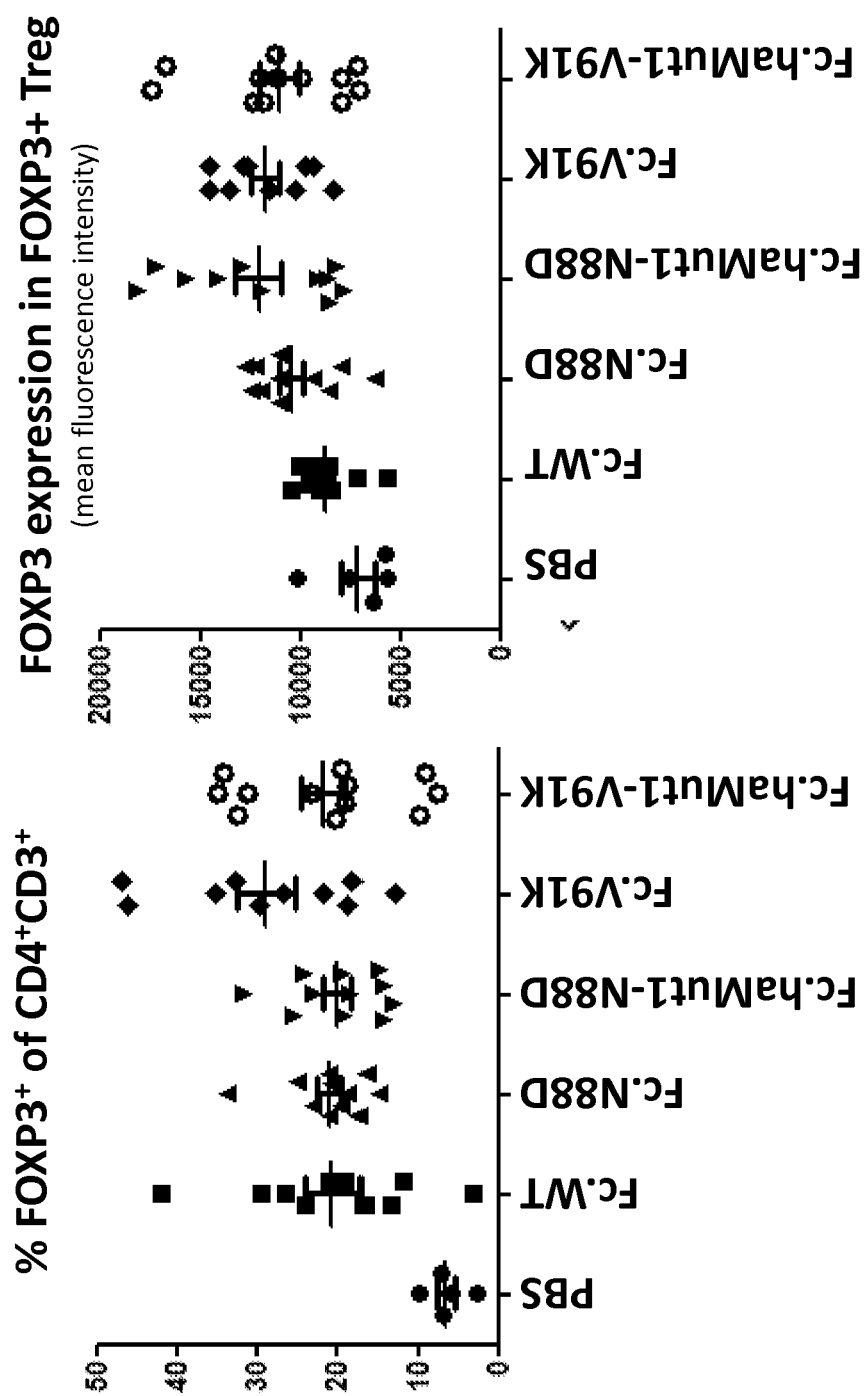
FIG. 7A and FIG. 7B Fc.IL-2 muteins without mutations that confer high affinity for CD25 promote Treg expansion and FOXP3 upregulation in humanized mice.
Figure 7B:
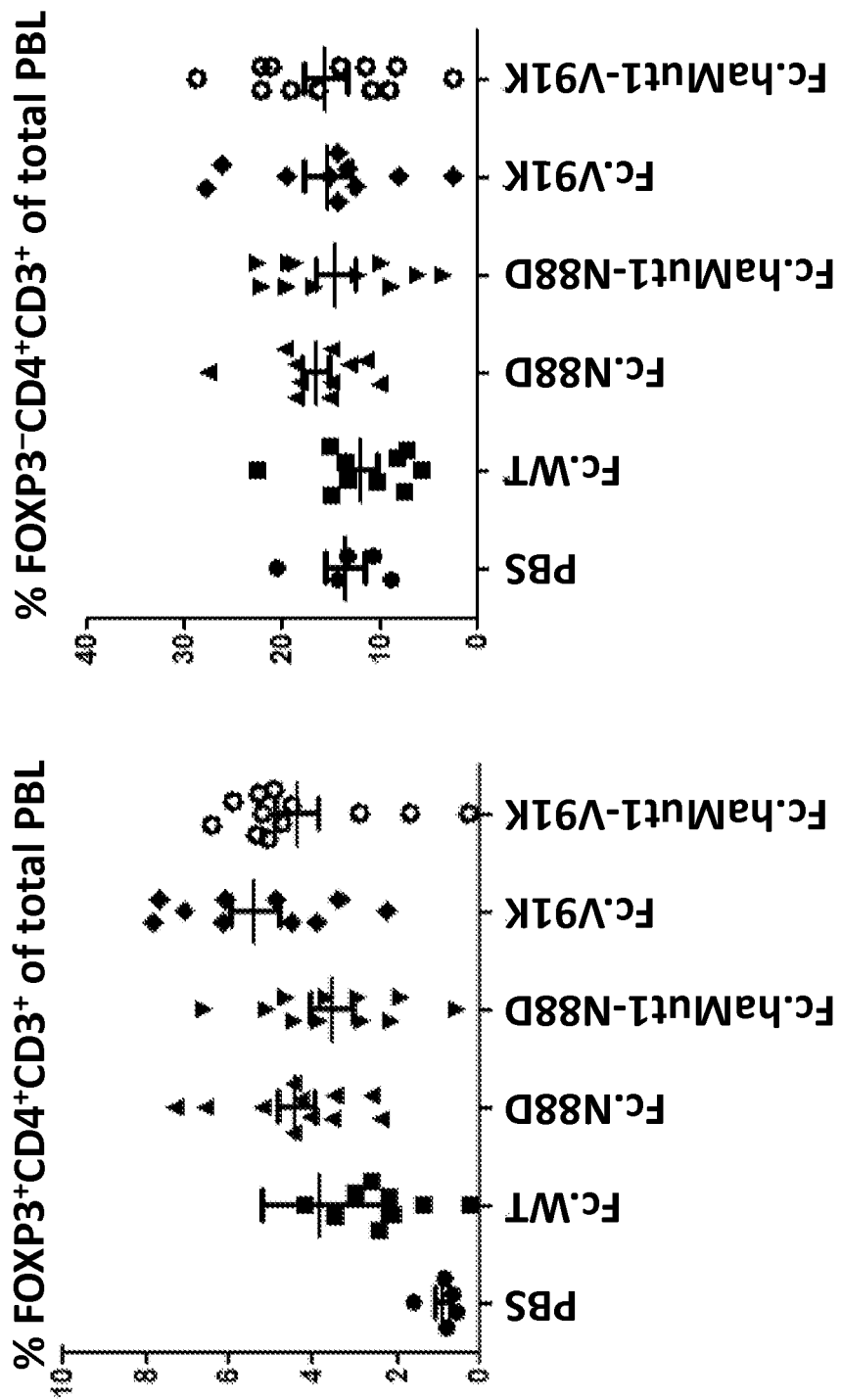

To determine if the high affinity mutations impacted T cell responses in vivo, humanized mice (NOD.SCID.Il2rg-null mice reconstituted with human CD34+ hematopoietic stem cells) were dosed with the Fc.IL-2 mutein fusion proteins and monitored Treg expansion. Seven week old NOD.SCID.Il2rg-null (NSG) mice (Jackson Labs, Bar Harbor, Me.) were irradiated (180 rad) and reconstituted with 94,000 human fetal liver CD34$^+$ hematopoietic stem cells. At 21 weeks, mice were distributed into 6 groups based on equal distribution of percent chimerism (determined by flow cytometry of PBL) and were given 1 μg sub-cutaneous injections of the indicated Fc.mutein fusion proteins or PBS on day 0 and day 7. On day 11, T cell subset frequencies in blood were determined by flow cytometry. At the low dose of 1 μg per animal, the high affinity mutations did not improve Treg expansion beyond that observed with the N88D or V91K mutations alone (FIG. 7).

Treg expansion was selective in that FOXP3$^-$CD4$^+$ T cells did not increase in abundance relative to total peripheral blood leukocytes (PBL) which includes a mixture of human B and T cells, and mouse myeloid cells. Furthermore, at higher doses, the high affinity mutations promoted an increase in CD25$^+$FOXP3$^-$ T cells, thus reducing Treg selectivity. Thus, in the context of the Fc homodimer, the high affinity mutations were not considered necessary for promoting preferential Treg growth.

```
Fc.WT IgG1Fc(N297G_delK)::G4S::huIL-2(C125A)
                                                               (SEQ ID NO: 16)
DKTHTCPPCPAPELLGGPSVFLFPPKPKDTLMISRTPEVTCVVVDVSHEDPEVKFNWYVDGVEVHNAKTKPREEQYGSTY

RVVSVLTVLHQDWLNGKEYKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLSLSPG

GGGGS

APTSSSTKKTQLQLEHLLLDLQMILNGINNYKNPKLTRMLTFKFYMPKKATELKHLQCLEEELKPLEEVLNLAQSKNFHLRPRDLI

SNINVIVLELKGSETTFMCEYADETATIVEFLNRWITFAQSIISTLT

Fc.haMut1V91K IgG1Fc(N297G_delK)::G4S::huIL-2(V69A, Q74P, V91K, C125A)
                                                               (SEQ ID NO: 17)
DKTHTCPPCPAPELLGGPSVFLFPPKPKDTLMISRTPEVTCVVVDVSHEDPEVKFNWYVDGVEVHNAKTKPREEQYGSTY

RVVSVLTVLHQDWLNGKEYKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLSLSPG

GGGGS

APTSSSTKKTQLQLEHLLLDLQMILNGINNYKNPKLTRMLTFKFYMPKKATELKHLQCLEEELKPLEEALNLAPSKNFHLRPRDLI

SNINKIVLELKGSETTFMCEYADETATIVEFLNRWITFAQSIISTLT

Fc.V91K (or Fc.IL-2(V91K)) IgG1Fc(N297G_delK)::G4S::huIL-2(V91K, C125A)
                                                               (SEQ ID NO: 18)
DKTHTCPPCPAPELLGGPSVFLFPPKPKDTLMISRTPEVTCVVVDVSHEDPEVKFNWYVDGVEVHNAKTKPREEQYGSTY

RVVSVLTVLHQDWLNGKEYKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLSLSPG

GGGGS

APTSSSTKKTQLQLEHLLLDLQMILNGINNYKNPKLTRMLTFKFYMPKKATELKHLQCLEEELKPLEEVLNLAQSKNFHLRPRDLI

SNINKIVLELKGSETTFMCEYADETATIVEFLNRWITFAQSIISTLT

Fc.haMut1N88D IgG1Fc(N297G_delK)::G4S::huIL-2(V69A, Q74P, N88D, C125A)
```

-continued (SEQ ID NO: 19)
DKTHTCPPCPAPELLGGPSVFLFPPKPKDTLMISRTPEVTCVVVDVSHEDPEVKFNWYVDGVEVHNAKTKPREEQYGSTY

RVVSVLTVLHQDWLNGKEYKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLSLSPG

GGGGS

APTSSSTKKTQLQLEHLLLDLQMILNGINNYKNPKLTRMLTFKFYMPKKATELKHLQCLEEELKPLEEALNLAPSKNFHLRPRDLI

SDINVIVLELKGSETTFMCEYADETATIVEFLNRWITFAQSIISTLT

Fc.N88D (or Fc.IL-2(N88D))  IgG1Fc(N297G_delK)::G4S::huIL-2(N88D, C125A)
(SEQ ID NO: 20)
DKTHTCPPCPAPELLGGPSVFLFPPKPKDTLMISRTPEVTCVVVDVSHEDPEVKFNWYVDGVEVHNAKTKPREEQYGSTY

RVVSVLTVLHQDWLNGKEYKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLSLSPG

GGGGS

APTSSSTKKTQLQLEHLLLDLQMILNGINNYKNPKLTRMLTFKFYMPKKATELKHLQCLEEELKPLEEVLNLAQSKNFHLRPRDLI

SDINVIVLELKGSETTFMCEYADETATIVEFLNRWITFAQSIISTLT

Example 5—Prolonged Cell Surface CD25 Association of Fc.IL-2 Muteins

Figure 8:
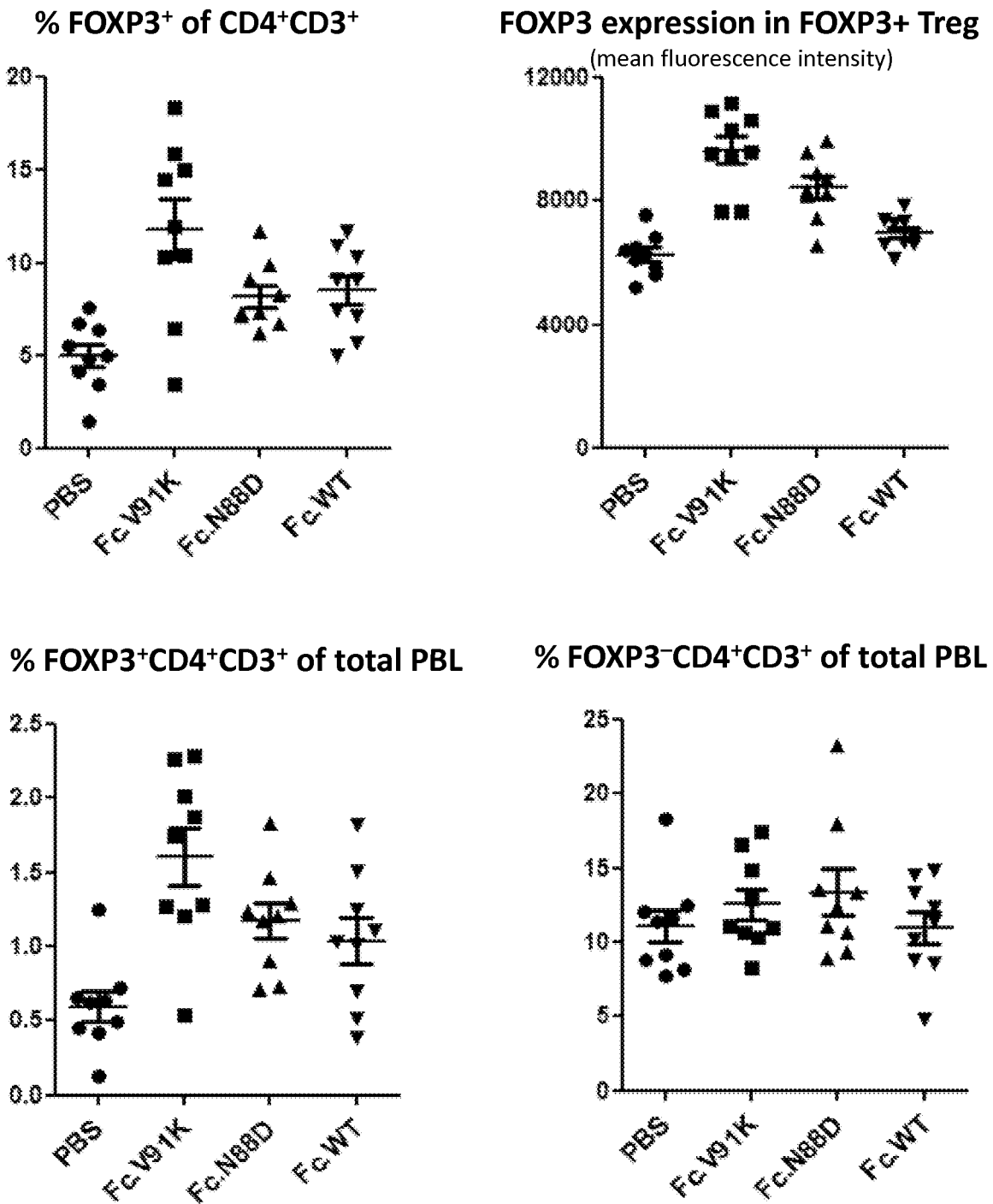
FIG. 8 Low weekly doses (0.5 μg per animal) of Fc.IL-2 muteins promote Treg expansion and FOXP3 upregulation in humanized mice, with better activity observed for Fc.V91K relative to Fc.N88D and Fc.WT.

An unexpected result from the humanized mouse studies was that, despite their reduced signaling capacity, the muteins induced more robust Treg enrichment relative to Fc.WT IL-2. Greater Treg enrichment and FOXP3 upregulation relative to that seen with Fc.WT was observed at a dose of 1 μg/mouse (FIG. 7) and at a lower dose of 0.5 μg/mouse (FIG. 8). This increased potency in vivo may have resulted from reduced consumption by T cells, making more Fc.IL-2 mutein available for prolonged signaling.

In vitro and in vivo PK studies failed, however, to demonstrate significantly increased persistence of Fc.V91K or Fc.N88D relative to Fc.WT in supernatants from activated T cell cultures or serum from dosed mice. Because the Fc fusions bore two IL-2 mutein domains, increased endosomal recycling may result in prolonged cell surface association due to increased avidity for CD25. Indeed, it was found that Fc.V91K and Fc.N88D persisted more efficiently than Fc.WT on the surface of previously activated T cells following a brief exposure the fusion proteins (FIGS. 9A and B).

Primary PBMCs were prestimulated for two days with 100 ng/ml OKT3. Cells were harvested, washed four times and rested for overnight in media. Cells were then pulsed with 400 pM Fc.IL-2 for 30 min at 37° C. After the pulse, cells were either harvested for T0 after one wash, or washed an additional three times in 12 ml of warm media and cultured for four hours. To detect cell-associated Fc.IL-2, cells were stained with anti-human IgG-FITC (Jackson Immunoresearch, West Grove, Pa.) and anti-CD25-APC (FIG. 9A).

Figure 9B:
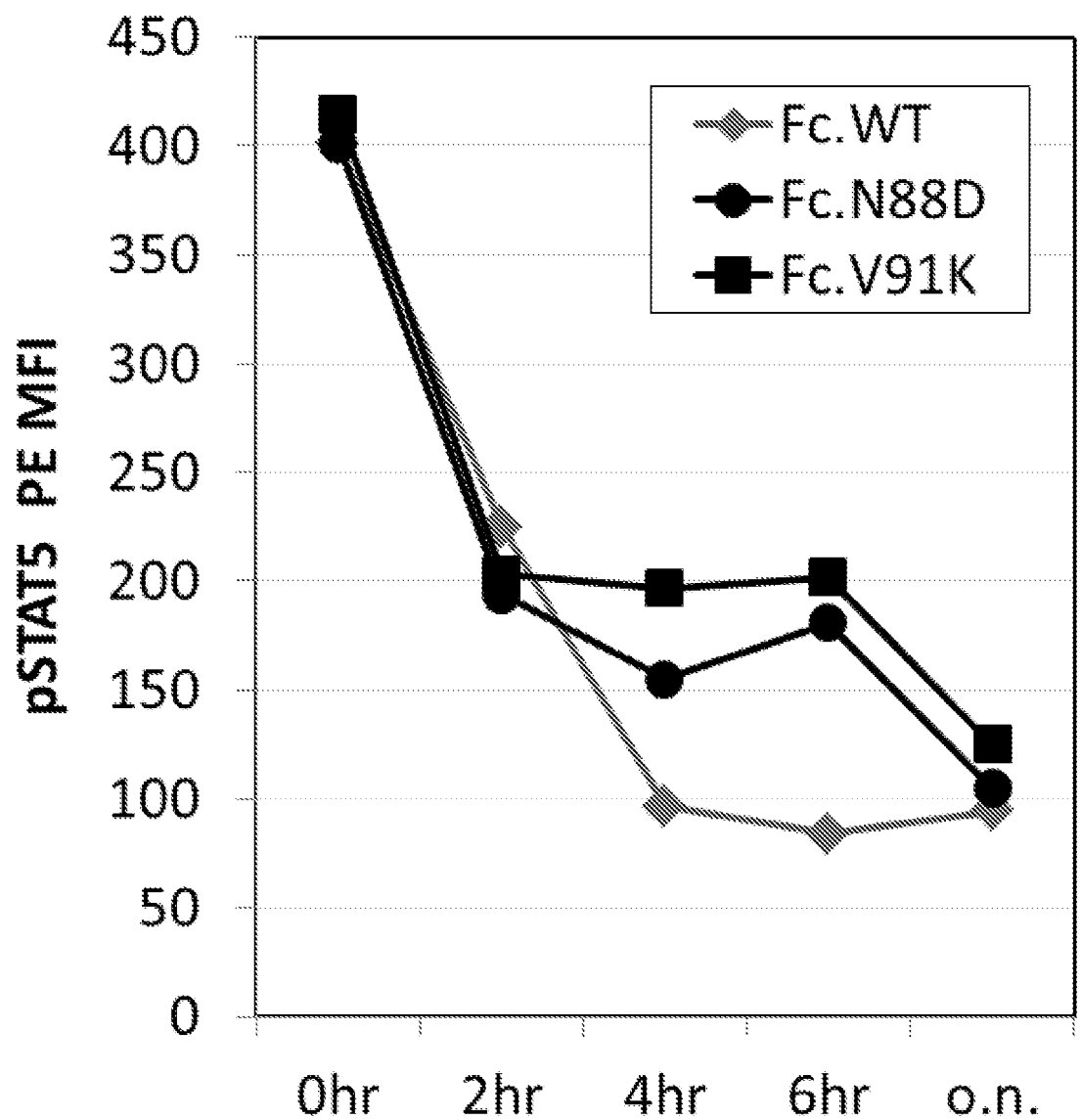
FIG. 9B Persistence of IL-2R signaling with Fc.V91K and Fc.N88D relative to Fc.WT.

The persistence of IL-2R signaling with Fc.V91K and Fc.N88D relative to Fc.WT was observed by intracellular immunodetection of phospho-STAT5 at the same time points. Phospho-STAT5 MFI for FOXP3+CD4+ T cells is shown (FIG. 9B).

Example 6—Fusion Sequence Optimization

In preclinical studies in mice, the Fc.IL-2 muteins showed differential exposure when serum concentrations of the intact molecule were compared that of the human Fc portion only, indicative of circulating human Fc catabolite. To optimize the in vivo stability and pharmacokinetics of the Fc.IL-2 muteins, fusion sequence modifications were characterized for their impact on proteolytic degradation of Fc.IL-2 muteins in systemic circulation and during recycling through the reticuloendothelial system. The following constructs were evaluated for proteolytic degradation in vitro and in vivo.

| | | | |
|---|---|---|---|
| (Ala Ala) | ...TQKSLSLSPGKGGGGSAPTSSSIKKTQLQ...ha7N88D | (SEQ ID NO: 31) |
| (N297G_delK)_G4S | ...TQKSLSLSPG GGGGSAPTSSSIKKTQLQ...ha1V91K | (SEQ ID NO: 32) |
| (N297G_KtoA)_AAPT | ...TQKSLSLSPGA     APTSSSIKKTQLQ...ha1V91K | (SEQ ID NO: 33) |
| (N297G_KtoA)_AAPA | ...TQKSLSLSPGA     APASSSIKKTQLQ...ha1V91K | (SEQ ID NO: 34) |

Stability was measured by quantitative immunoassays comparing concentrations over time of total human Fc to that of intact Fc.IL-2 mutein. Proteolysis of Fc.IL-2 muteins was verified by western blot analysis utilizing anti-IL-2 and anti-human Fc antibodies, followed by immunocapture of catabolites and characterization by mass spectrometry. Characterization by mass spectrometry of catabolites of (Ala_Ala)_G4S from in vitro and in vivo samples identified the C-terminal Lys of the Fc domain as a proteolytic cleavage site. Deletion or mutation of the C-terminal lysine of the Fc domain ((N297G_delK)_G4S and (N297G_KtoA)_AAPT) resulted in prolonged in vitro stability in mouse serum at 37° C. compared to Fc constructs with the C-terminal lysine ((Ala_Ala)_G4S). This prolonged in vitro serum stability translated to greater exposure in mice as measured by the area under the Fc.IL-2 mutein serum concentration versus time curve (AUC). This prolonged stability of Fc.IL-2 muteins lacking the C-terminal Fc lysine was also observed in vitro in serum from cynomolgus monkeys and humans. Mutation of Thr-3 of IL-2 to Ala ((N297G_KtoA)_AAPA) resulted in decreased in vitro stability at 37° C. (compared to (N297G_KtoA)_AAPT) in mouse serum and in separate incubations with recombinant human cathepsin D and L. This decreased in vitro serum stability translated to lower exposure (AUC) in mice in vivo for (N297G_KtoA)_AAPA compared to (N297G_KtoA)_AAPT. Characterization of catabolites of (N297G_KtoA)_AAPA from in vitro and in vivo samples by mass spectrometry identified Lys 8 and Lys 9 of the IL-2 mutein domain as residues susceptible to proteolysis which was not observed for equivalent samples of (N297G_KtoA)_AAPT. Decreased stability at 37° C. of (N297G_KtoA)_AAPA to that of (N297G_KtoA)_AAPT was also observed in vitro in serum from cynomolgus monkeys and humans.

Because of the importance of glycosylation in this region, and to potentially improve upon the manufacturability of the fusion protein, the fusion sequences were altered to promote N-linked rather than O-linked glycosylation, as follows.

```
Original

IgG1Fc(N297G_deIK)::G4S::huIL-2(V91K,C125A)
                                    (SEQ ID NO: 32)
TQKSLSLSPGGGGGSAPTSSSTKKTQLQ

Altered

IgG1Fc(N297G_deIK)::G4S::huIL-2(T3N,V91K,C125A)
                                    (SEQ ID NO: 35)
TQKSLSLSPGGGGGSAPNSSSTKKTQLQ

IgG1Fc(N297G_deIK)::G4S::huIL-2(T3N,S5T,V91K,C125A)
                                    (SEQ ID NO: 36)
TQKSLSLSPGGGGGSAPNSTSTKKTQLQ

IgG1Fc(N297G_deIK)::GGNGT::huIL-2(T3A,V91K,C125A)
                                    (SEQ ID NO: 37)
TQKSLSLSPGGNGTAPASSSTKKTQLQ

IgG1Fc(N297G_deIK)::YGNGT::huIL-2(T3A,V91K,C125A)
                                    (SEQ ID NO: 38)
TQKSLSLSPGYGNGTAPASSSTKKTQLQ
```

Example 7—Cynomolgus Monkey PK/PD Determination

Standard IL-2 immune stimulating therapies require drug free holidays (no exposure) between dosing cycles to avoid undesirable side effects. In contrast, Treg expansion or stimulation therapies may require prolonged exposure with sustained trough drug levels (serum $C_{min}$) sufficient for Treg stimulation but with maximal exposures (serum $C_{max}$) below drug levels that lead to immune activation. This example demonstrates dosing strategies of half-life extended muteins in cynomolgus monkeys for extended target coverage (serum $C_{min}$) while maintaining maximal exposures (serum $C_{max}$) below drug levels contemplated to be necessary for proinflammatory immune activation.

Cynomolgus monkeys are dosed with Fc.V91K (IgG1Fc (N297G_delK)::G4S::huIL-2(V91K, C125A) in four groups (A-D), with three groups (A-C) dosed subcutaneously and one group (D) dosed intravenously. For each group, four biologically naïve male cynomolgus monkeys are dosed per the dosing strategy outlined below. Subcutaneous dosing of half-life extended muteins may allow for greater lymphatic absorption resulting in lower maximal exposure (serum $C_{max}$) and/or a more robust pharmacological response (Treg expansion). Dosing strategy for group A consists of three consecutive 10 microgram per kilogram doses on Day 0, 2, and 4 for cycle 1 and 10 microgram per kilogram on Day 14, allowing prolonged target coverage similar to a higher initial dose of 50 microgram per kilogram while maintaining a lower maximal exposure ($C_{max}$). The dosing strategy for group B is 50 microgram per kilogram dosed on Day 0 and 14 for comparison to Group A. The dosing strategy for group C is 50 microgram per kilogram dosed on Day 0 and 28. Allowing the determination of whether trough coverage is required for sustaining Treg enrichment or whether a drug free holiday is beneficial between dosing cycles. The dosing strategy for the intravenous dosing arm group D is 50 microgram per kilogram dosed on Day 0, allowing a comparison of maximal exposures ($C_{max}$) and Treg enrichment differences to that of subcutaneous dosing.

Pharmacokinetics (quantitative immunoassay for intact molecule and total human Fc), anti-drug antibodies, shed soluble CD25, and serum cytokines (IL-1β, TNF-α, IFN-γ, IL-10, IL-5, IL-4, and IL-13) are measured at the following time points for each dose group specified:

Group A: pre-dose (first cycle; dose 1), 48 (pre-dose first cycle; dose 2), 96 (pre-dose first cycle; dose 3), 100, 104, 120, 168, 216, 264, 336 (pre-dose second cycle), 340, 344, 360, 408, 456, 504, 576, 672, 744, 840, and 1008 hours.

Group B: pre-dose (first cycle), 4, 8, 24, 72, 120, 168, 240, 336 (pre-dose second cycle), 340, 344, 360, 408, 456, 504, 576, 672, 744, 840, and 1008 hours.

Group C: pre-dose (first cycle), 4, 8, 24, 72, 120, 168, 240, 336, 408, 504, 672 (pre-dose second cycle), 676, 680, 696, 744, 792, 840, 912, 1008, 1080, and 1176 hours.

Group D: pre-dose (first cycle), 0.25, 1, 4, 8, 24, 72, 120, 168, 240, 336, 408, 504, and 672 hours.

Pharmacodynamics (immunopheotyping and enumeration of peripheral blood Tregs, non-regulatory CD4 and CD8 T cells, and NK cells) is measured at the following time points for each dose group specified:

Group A: pre-dose (first cycle; dose 1), 96 (pre-dose first cycle; dose 3), 168, 336 (pre-dose second cycle), 456, and 576 hours.

Group B: pre-dose (first cycle), 120, 240, 336 (pre-dose second cycle), 456, and 576 hours.

Group C: pre-dose (first cycle), 120, 240, 672 (pre-dose second cycle), 792, and 912 hours.

Group D: pre-dose (first cycle), 120 and 240 hours.

Hematology and clinical chemistry are assessed for all animals and dose groups pre-dose and at 24 hours post initial dose per dose group. The following parameters are evaluated.

Hematology:
  leukocyte count (total and absolute differential)
  erythrocyte count
  hemoglobin
  hematocrit
  mean corpuscular hemoglobin, mean corpuscular volume, mean corpuscular hemoglobin concentration (calculated)
  absolute reticulocytes
  platelet count
  blood cell morphology
  red cell distribution width
  mean platelet volume
Clinical Chemistry:
  alkaline phosphatase
  total bilirubin (with direct bilirubin if total bilirubin exceeds 1 mg/dL)

aspartate aminotransferase
alanine aminotransferase
gamma glutamyl transferase
urea nitrogen
creatinine
total protein
albumin
globulin and A/G (albumin/globulin) ratio (calculated)
glucose
total cholesterol
triglycerides
electrolytes (sodium, potassium, chloride)
calcium
phosphorus Example 8—Aglycosylated IgG1 Fc Naturally occurring IgG antibodies posses a glycosylation site in the constant domain 2 of the heavy chain (CH2). For example, human IgG1 antibodies have a glycosylation site located at the position Asn297 (EU numbering). To date, the strategies for making aglycosylated antibodies involve replacing the Asn residue with an amino acid that resembles Asn in terms of physico-chemical properties (e.g., Gln) or with Ala residue which mimics the Asn side chain without the polar groups. This Example demonstrates the benefits of replacing Asn with Glycine (N297G). N297G Fc are aglcosylated molecules with better biophysical properties and manufacturability attributes (e.g., recovery during purification).

Examination of multiple known crystal structures of Fc fragments and IgG antibodies revealed considerable conformational flexibility around the glycosylated loop segment, particularly at the position Asn297 that is glycosylated. In many of the known crystal structures, Asn297 adapted positive backbone dihedral angles. Gly has high propensity to adapt positive backbone dihedral angle due to the lack of side chain atoms. Therefore, based on this conformation and structure reason, Gly may be a better replacement for Asn than N297Q or N297A.

Mutating Asn297 with Gly leads to aglcosylated molecules with much improved recovery (or efficiency) in the purification process and biophysical properties. For example, the percentage of recovery (final yield) from the protein A pool was 82.6% for the N297G mutation, compared to 45.6% for N297Q and 39.6% for N297A. SPHP column analysis revealed the lower percentage of recovery for the N297Q and N297A mutants was due to a tailing peak, which indicates high molecular weight aggregation and/or misfolded species. This result was re-confirmed at a larger, 2 L scale run.

In the biopharmaceutical industry, molecules with potential need for large-scale production, e.g, potential to be sold as a drug, are assessed for a number of attributes to mitigate the risk that the molecule is not amenable to large-scale production and purification. In the manufacturability assessments, N297G revealed robustness to pH changes. N297G had no aggregation issue; whereas N297Q and N297A had 20% and 10% increase in aggregation, respectively. Although N297G had better manufacturability attributes, it was similar to N297Q and N297A in all the functional assays in which it was tested. For example, in ADCC assays, N297G lacked cytotoxicity similarly to N297Q and N297A.

Example 9—Stabilized Aglyosylated IgG1 Fc

This Example describes a method of improving stability of IgG antibody scaffolds by introducing engineered disulfide bond(s). Naturally occurring IgG antibodies are stable molecules. However, for some therapeutic applications, it may be necessary to make mutations or create aglycosylated molecules. For example, aglycosylated IgG molecules may be used in therapeutic indications where there is a need to avoid ADCC and binding to Fcgamma receptors. However, the aglycosylated IgG1 has much lower melting temperature (CH2 domain melting temperature decreases by about 10° C.; 70° C. to 60° C.) than the glycosylated IgG1. The observed lower melting temperature negatively impacts various biophysical properties of the aglycosylated IgG1. For example, aglycosylated IgG1 has increased level of aggregation at low pH compared to glycosylated IgG1.

In order to engineer disulfide bonds, a structure based method involving distance calculation between the C-alpha atoms was initially used to identify 54 residue pairs in the Fc region for mutation to Cys. These 54 sites were further narrowed down to 4 residue pairs (V259C-L306C, R292C-V302C, A287C-L306C, and V323C-I332C). The criteria used included (i) positions within the CH2 domain, (ii) away from loops, turns and carbohydrates, (iii) away from Fcgamma receptor and FcRn interaction sites, (iv) solvent accessibility (preferred buried positions), etc.

The paired cysteine substitutions were created in the context of the aglycosylated N297G Fc. Non-reduced peptide mapping analysis revealed that three of the four engineered sites formed disulfide bond as expected and designed in that context. The V259C-L306C mutation did not form disulfide bonds correctly and led to mis-pairing with the native disulfide already present in the CH2 domain. The other three designs, R292C-V302C, A287C-L306C, and V323C-I332C, formed disulfide bond correctly as predicted and designed. Adding the disulfide bond to the N297G mutation led to about 15° C. improvement in thermal stability over the N297G mutation alone. Of the R292C-V302C, A287C-L306C, and V323C-I332C disulfide variants, R292C-V302C and A287C-L306C had good pharmacokinetics when administered to rats ($t_{1/2}$ of eleven days and nine days, respectively). This is in contrast to the pharmacokinetics profile observed in rats for the previously published CH2 domain disulfide bond (Gong et al., *J. Biol. Chem.* 2009 284: 14203-14210), which had a $t_{1/2}$ of five days.

Engineering a disulfide bond in the CH2 domain improves the stability of the aglycosylated molecule on par with glycosylated IgG1 molecules (10° to 15° C. improvement in the melting temperature as determined by Differential Scanning Calorimetry). The engineered sites described herein do not lead to disulfide scrambling and the disulfides are formed as predicted in approximately 100% of the population. More importantly, unlike the published disulfide bond site in the CH2 domain, the disulfide bonds described herein do not impact the rat PK.

Example 10

The effects of the V91K and N88D mutations on responses in T and NK cells from cynomolgus monkeys and humans were compared in vitro. In the presence of CD25 ($CD4^+CD25^+$ gated T cells in whole blood pSTAT5 responses), the effect of the V91K mutation on cynomolgus IL-2R signaling was negligible compared to its reduced activity on human IL-2R. However, in the absence of CD25 (both $CD25^-$ gated T cells in whole blood pSTAT5 responses and NK cell proliferation) the V91K mutation reduced cynomolgus IL-2R signaling more substantially. In contrast, Fc.N88D shows reduced signaling in $CD25^+$ T cells in cynomolgus whole blood which is more similar to the signaling effect of Fc.V91K in T cells in human whole blood. The in vitro data summarized in Table 2 suggest that the therapeutic window observed with the weaker agonist, Fc.N88D, in cynomolgus monkeys will be predictive of the effects of Fc.V91K in human subjects.

TABLE 2

Summary of effects of the V91K or N88D mutations on in vitro responses of human and cyno cells

| | Whole blood pSTAT5 | | NK cell proliferation |
|---|---|---|---|
| | CD25+ T cells | CD25− T cells | |
| V91K on cyno | ∅ | ↓ | ↓ |
| V91K on human | ↓ | ↓↓ | ↓↓ |
| N88D on cyno | ↓ | ↓↓ | ↓↓ |
| N88D on human | ↓↓ | ↓↓ | ↓↓↓ |

Example-11

Figure 10A:
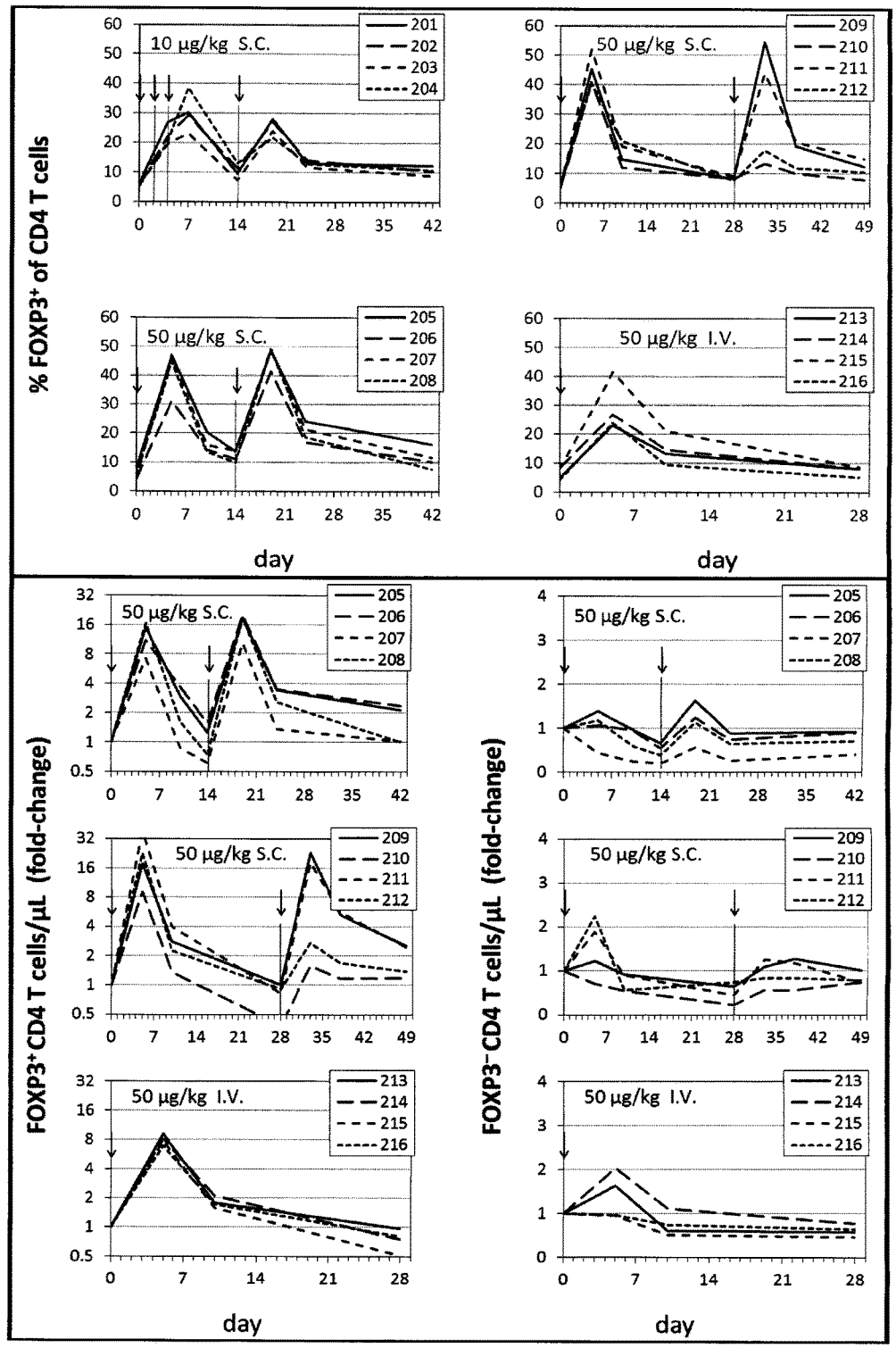
FIGS. 10A and B Comparison of two week and four week dosing intervals of Fc.V91K in cynomolgus monkeys, and comparison of IV and SC dosing routes.
Figure 10B:
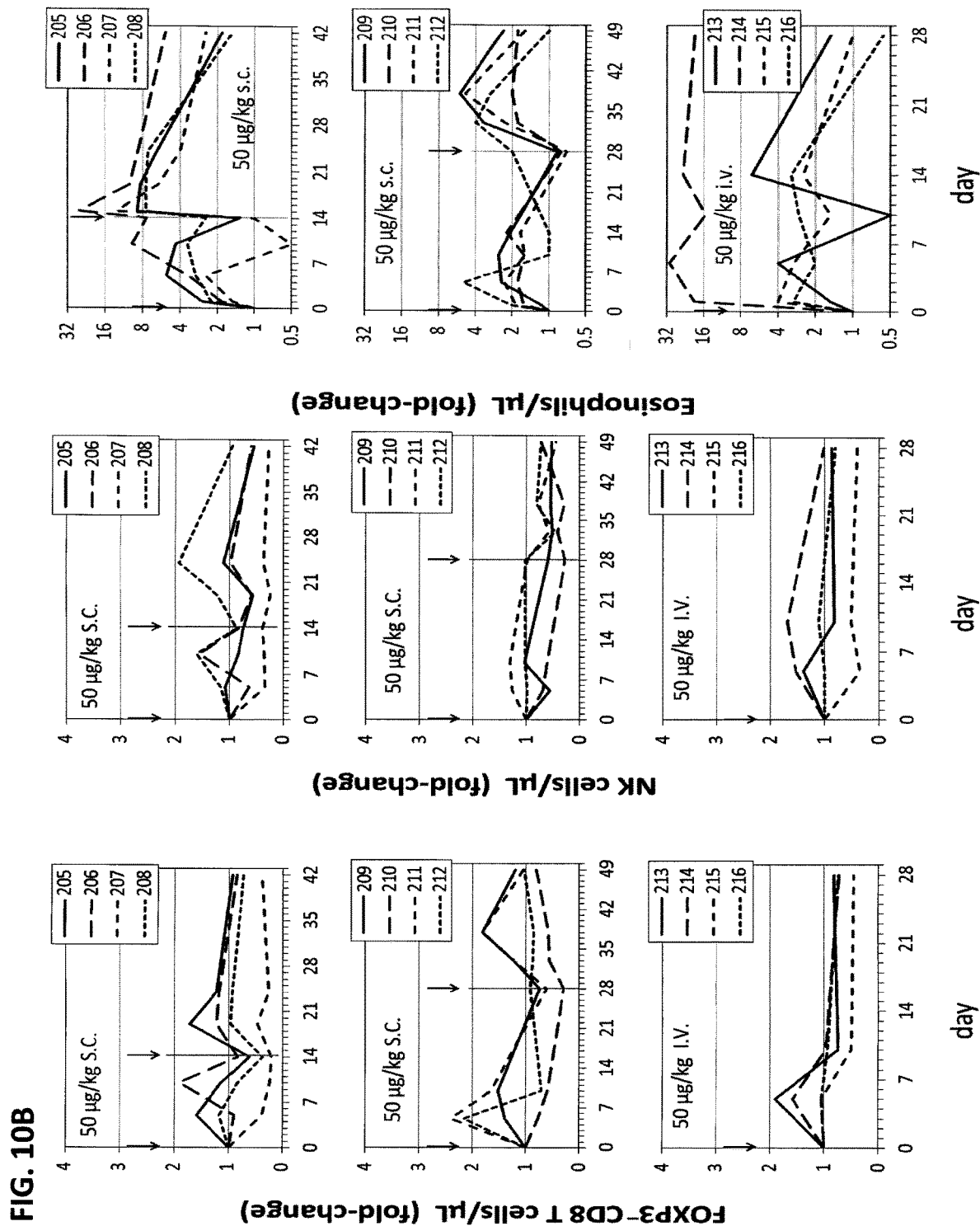
Figure 11A:
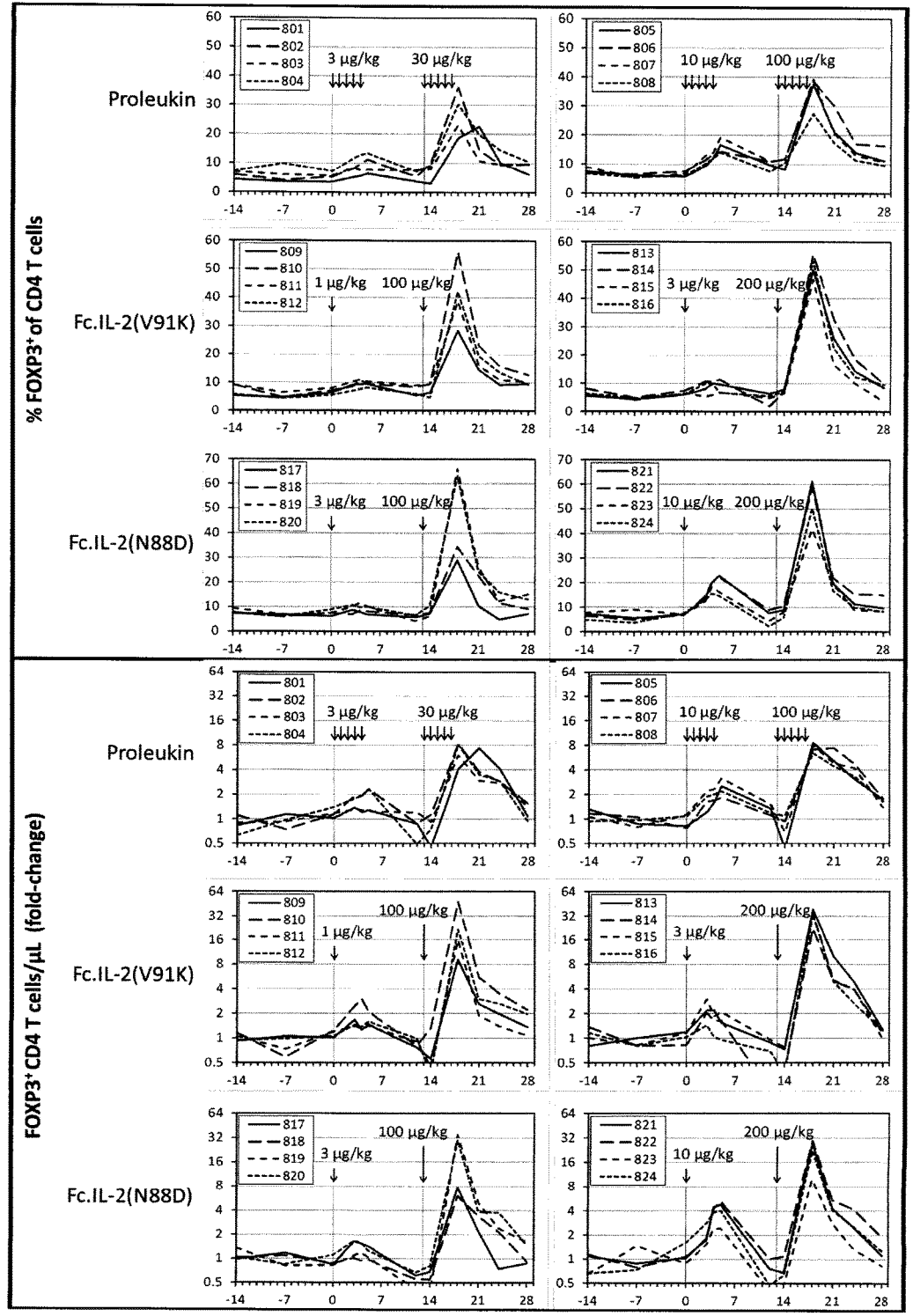
FIG. 11A-F Kinetics of cellular responses, body temperature, and serum CRP in cynolmogus monkeys treated with different dosing regimens of PROLEUKIN®, Fc.V91K, and Fc.N88D.
Figure 11B:
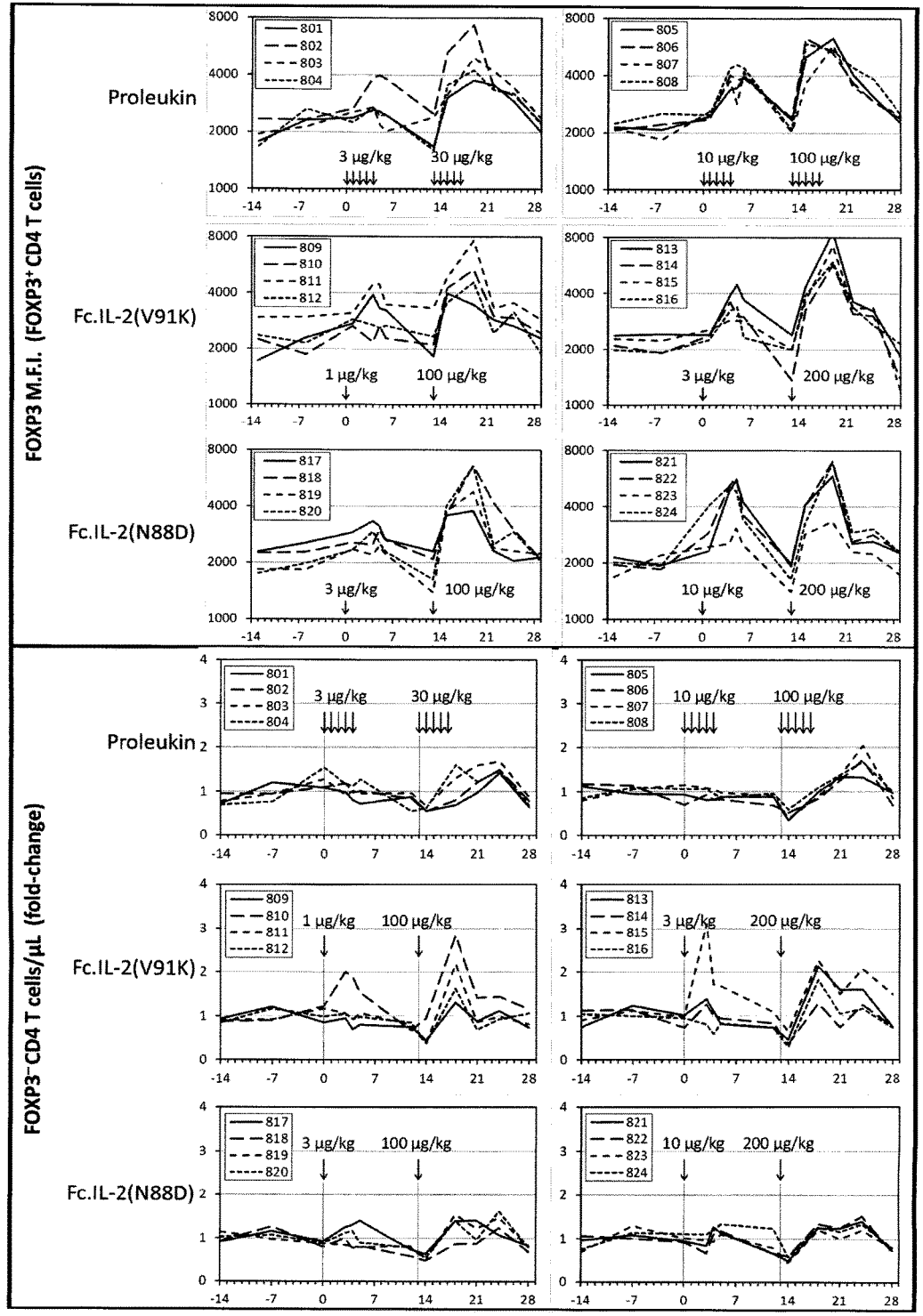
Figure 11C:
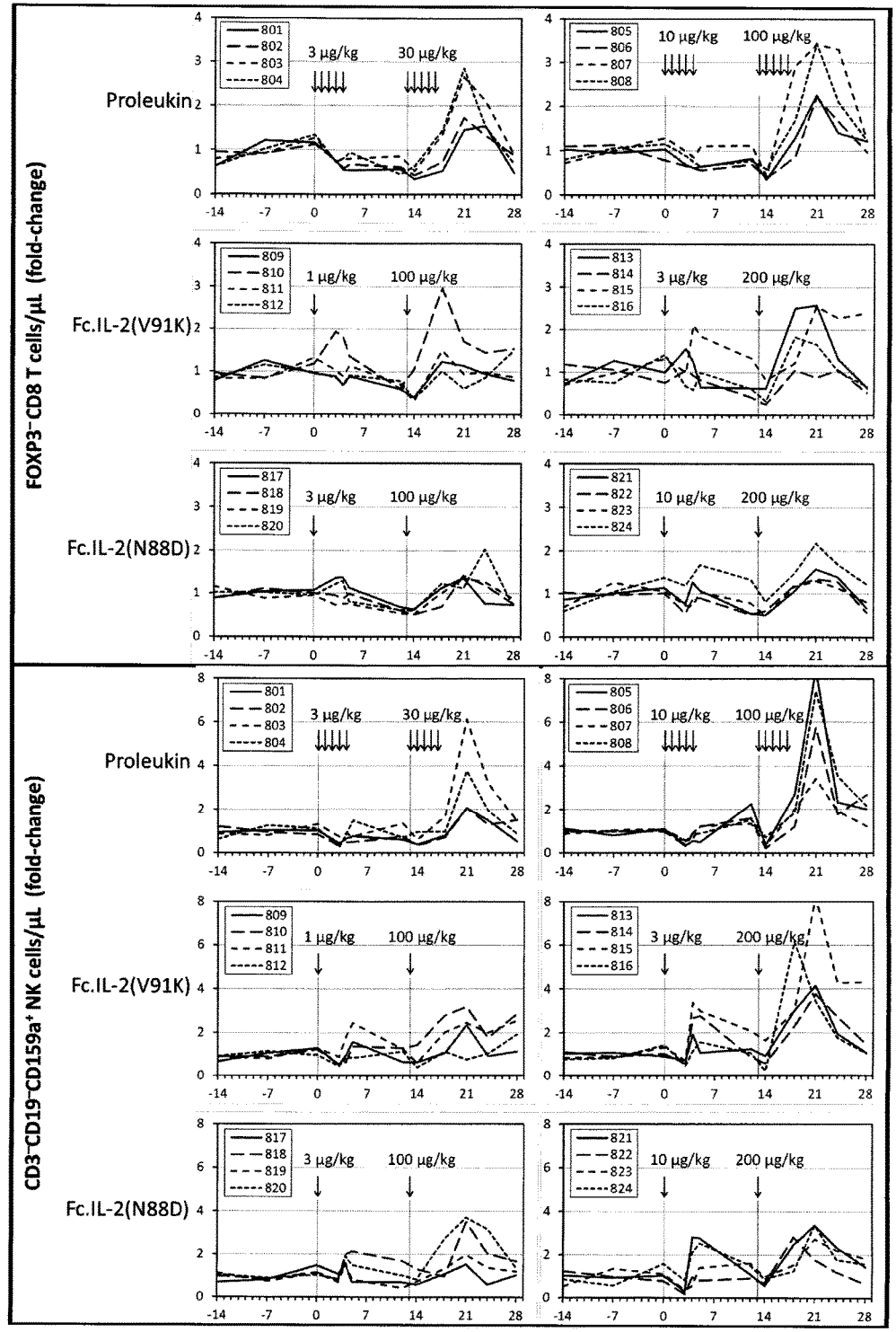
Figure 11D:
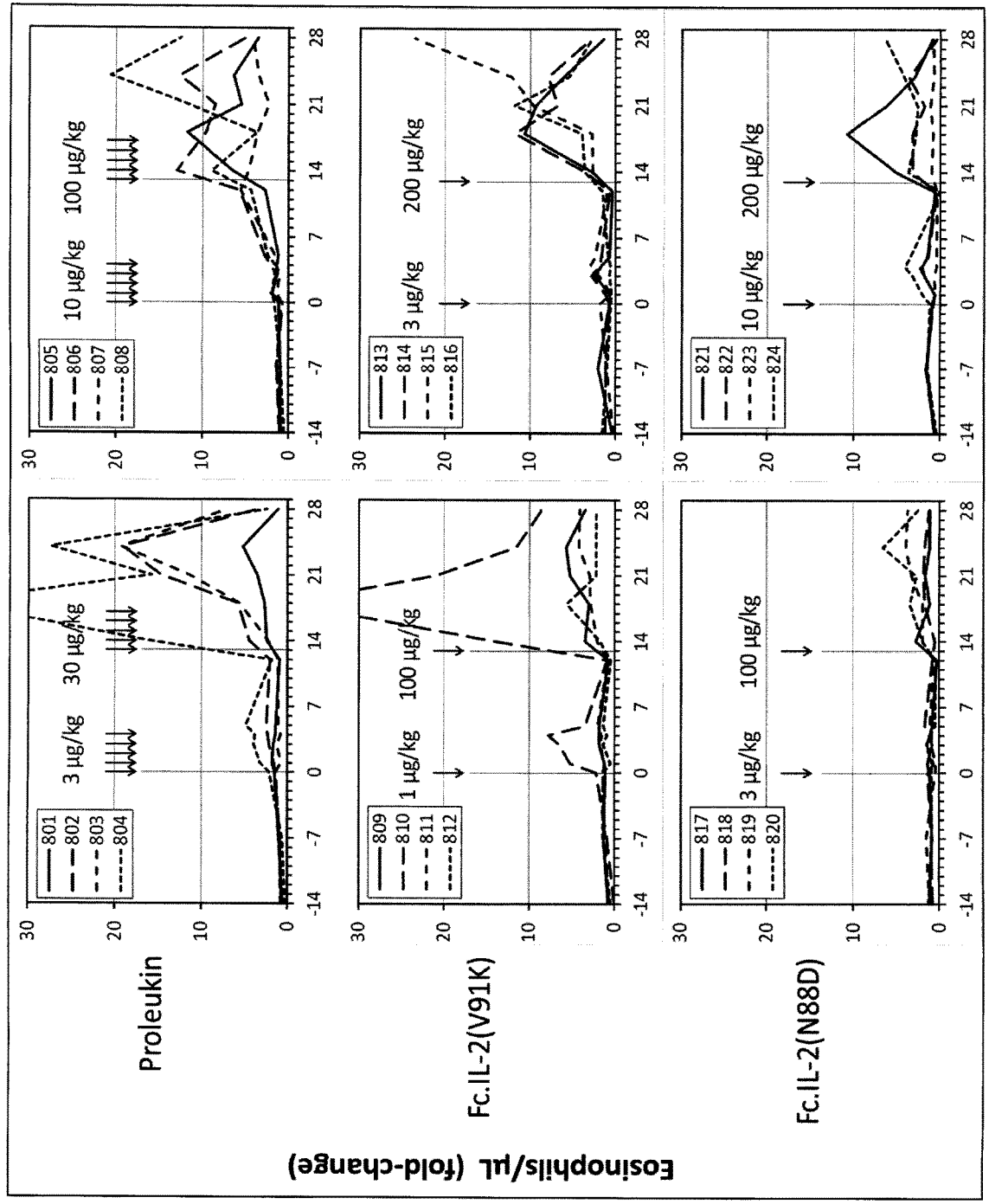
Figure 11E:
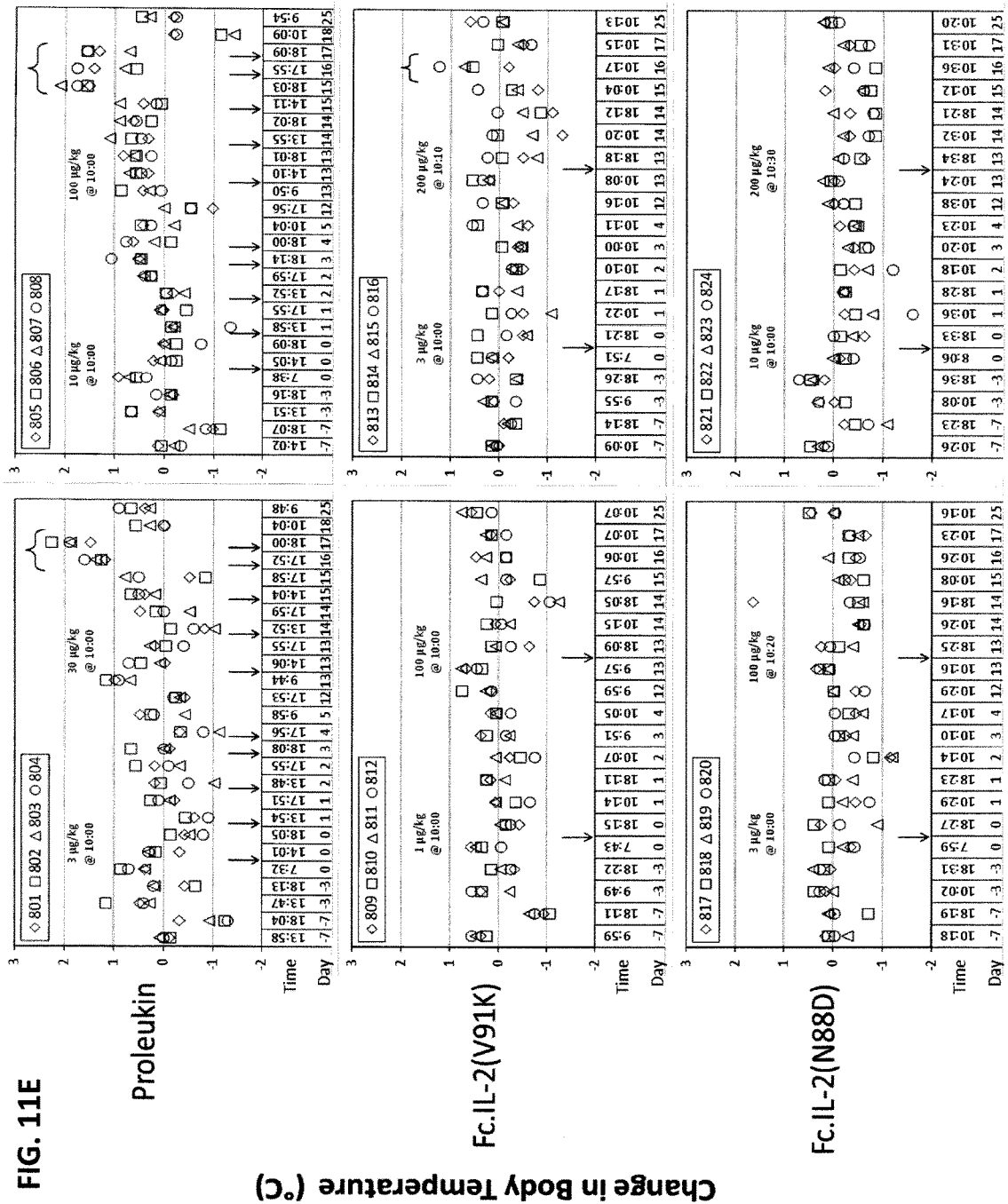
Figure 11F:
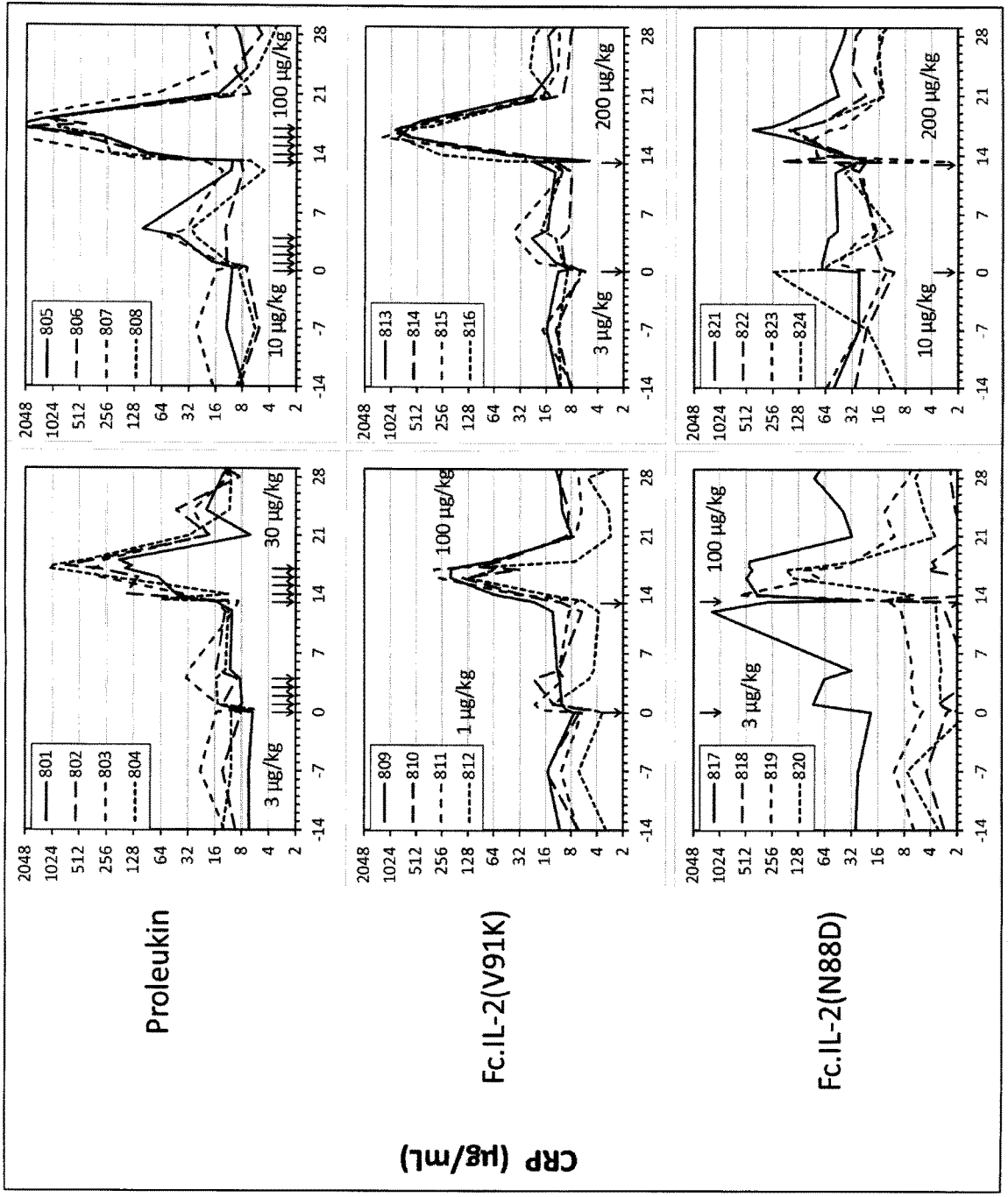

Two in vivo studies were performed in cynomolgus monkeys. The first cynomolgus monkey study was designed to compare two week and four week dosing intervals of Fc.V91K to determine if a complete or partial pharmacokinetic (PK) and pharmacodynamic (PD) trough altered the magnitude of response to a second dose (FIGS. 10A and B). A first dose, predicted to give a strong Treg response (50 µg/kg), and a second dose, to explore the lower limits of the therapeutic window (10 µg/kg), were used. Because it was not known whether 10 µg/kg was too low, doses were given on Days 1, 3, and 5 to increase the likelihood of a response. This dosing regimen gave the same exposure following Day 5 as achieved with the single 50 µg/kg subcutaneous (SC) dose, but with a lower C-max. A 50 µg/kg intravenous (IV) group was also included to investigate potential differences in PD depending on higher drug exposure in the lymph versus blood compartments. The results of this study established that each of the dose levels induced a strong Treg growth response without adverse events (AEs) or Teff or NK growth, and that responses to a second dose at either Day 14 or 28 were equivalent.

TABLE 3

Study Design for First Cynomolgus Monkey Study

| Group | # animals | Dosing (days) | Dose Fc.V91K |
|---|---|---|---|
| 1 | 4 | 1, 3, 5, 15 | 10 µg/kg SC |
| 2 | 4 | 1, 15 | 50 µg/kg SC |

TABLE 3-continued

Study Design for First Cynomolgus Monkey Study

| Group | # animals | Dosing (days) | Dose Fc.V91K |
|---|---|---|---|
| 3 | 4 | 1, 29 | 50 µg/kg SC |
| 4 | 4 | 1 | 50 µg/kg IV |

The second cynomolgus monkey study was designed to explore the margins of the therapeutic window with Fc.V91K doses of 1, 3, 100, 200 µg/kg (SC) and compare this with the weaker agonist Fc.N88D at doses of 3, 10, 100, 200 µg/kg (SC) and PROLEUKIN® at 3, 10, 30, 100 µg/kg (SC QD×5). PROLEUKIN® doses were selected based on published human and non-human primate studies (Hartemann et al., 2013, Lancet Diabetes Endocrin 1:295-305; Saadoun et al., 2011, NEJM 365:2067-77; Aoyama et al., 2012, Am J Transplantation 12:2532-37) and were administered QD×5 to mimic low-dose IL-2 clinical trials in HCV vasculitis and Type 1 diabetes (T1D).

TABLE 4

Study Design for Second Cynomolgus Monkey Study

| Group | # animals | Test Article | $1^{st}$ cycle treatment Treatment day: Dose (SC) | $2^{nd}$ cycle treatment Treatment day: Dose (SC) |
|---|---|---|---|---|
| 1 | 4 | PROLEUKIN® | Days 1-5: 3 µg/kg | Days 14-18: 30 µg/kg |
| 2 | 4 | PROLEUKIN® | Days 1-5: 10 µg/kg | Days 14-18: 100 µg/kg |
| 3 | 4 | Fc.V91K | Day 1: 1 µg/kg | Day 14: 100 µg/kg |
| 4 | 4 | Fc.V91K | Day 1: 3 µg/kg | Day 14: 200 µg/kg |
| 5 | 4 | Fc.N88D | Day 1: 3 µg/kg | Day 14: 100 µg/kg |
| 6 | 4 | Fc.N88D | Day 1: 10 µg/kg | Day 14: 200 µg/kg |

In FIGS. 11A-F, the kinetics of cellular responses, body temperature, and serum CRP are shown. The timeline on the x-axis starts with Day 0 rather than Day 1 as the day of first dose.

Figure 12A:
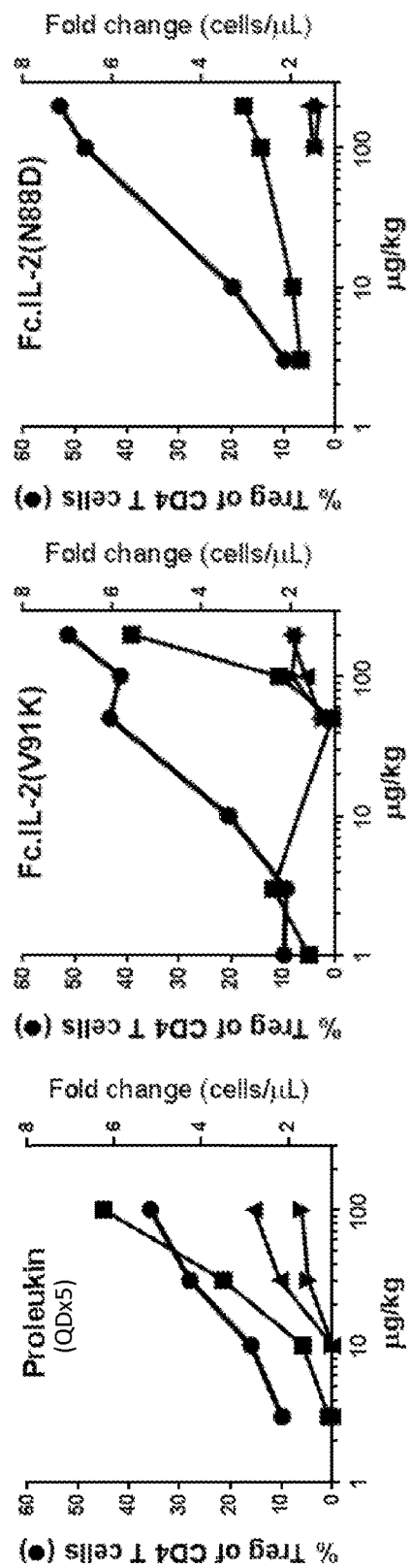
FIG. 12A Effect of increasing dosages of PROLEUKIN®, Fc.V91K, or Fc.N88D on levels of Treg cells, NK cells, CD4$^+$FOXP3$^-$ T cells, and CD8$^+$FOXP3$^-$ T cells in cynomolgus monkeys. Each data point represents the average peak responses of four animals.
Figure 12B:
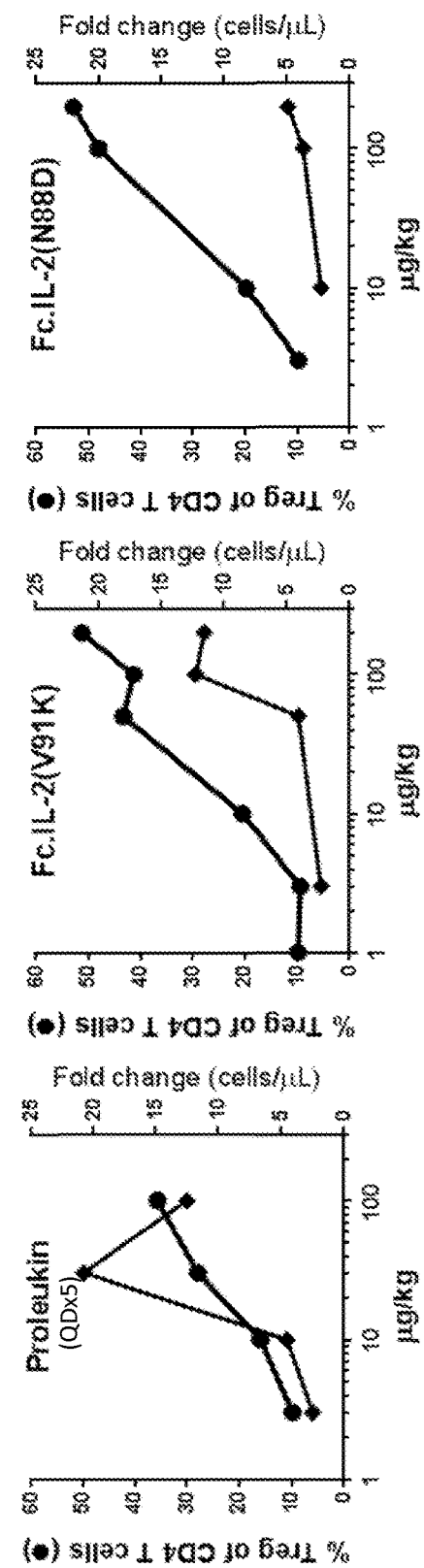
FIG. 12B Effect of increasing dosages of PROLEUKIN®, Fc.V91K, or Fc.N88D on levels of Treg cells and eosinophils in cynomolgus monkeys. Each data point represents the average peak responses of four animals.

In combination, the two cynomolgus monkey studies demonstrated that the IL-2 muteins induced greater Treg enrichment with a wider therapeutic window than achieved with PROLEUKIN® (FIGS. 12A and B). With PROLEUKIN®, Treg enrichment paralleled NK and eosinophil growth. Without being bound to any particular theory, eosinophil growth is a well-known response to IL-2 therapy and is likely a result of IL-2-induced IL-5 from CD25+ innate lymphoid cells. CD4 and CD8 Teff growth occurred at doses that increased Tregs to 25-35% of CD4 T cells. In contrast, Fc.V91K and Fc.N88D induced Treg growth with greater selectivity over NK cells and eosinophils, and doses that promoted Teff growth were above those that enriched Treg to >40% of CD4 T cells.

Figure 12C:
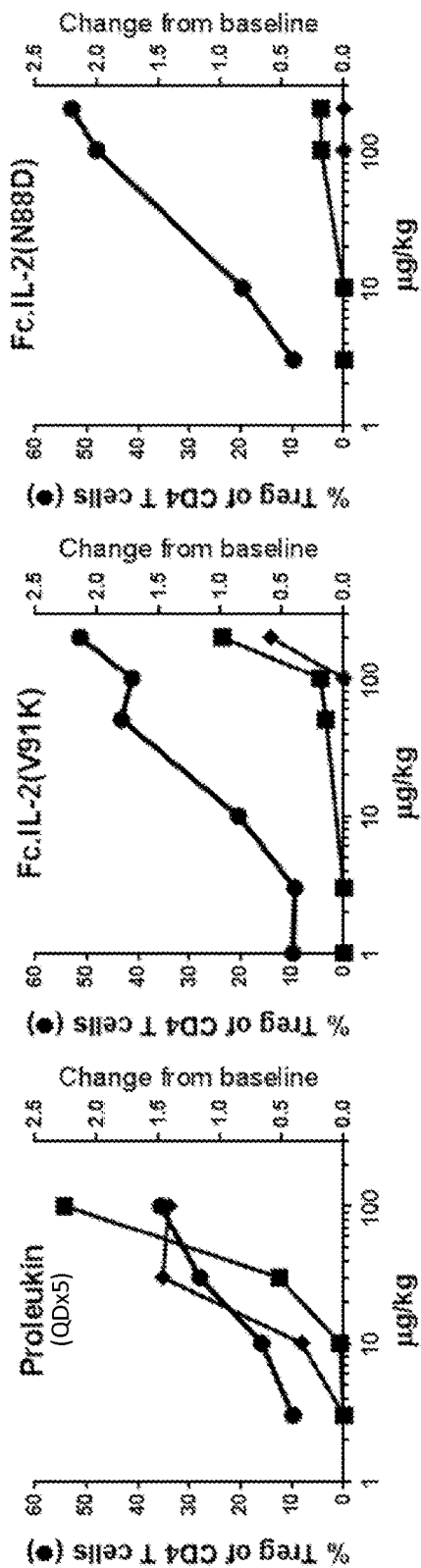
FIG. 12C Effect of increasing dosages of PROLEUKIN®, Fc.V91K, or Fc.N88D on levels of Treg cells and CRP and on body temperature in cynomolgus monkeys. Each data point represents the average peak responses of four animals.

In low-dose IL-2 clinical trials reported in the literature, the first AEs that occurred were flu-like symptoms and fever. Thus, in addition to comparing therapeutic windows, a goal of this study was to discover a biomarker that preceded fever. As shown in FIG. 12C, with the two higher doses of PROLEUKIN®, CRP levels were found to parallel body temperature. With Fc.V91K, a moderate elevation in body temperature was detected at the highest dose, and at the next lower dose a small increase in CRP was observed. Thus CRP can be used to monitor a subject's response to treatment with a molecule of the present invention and/or to define the upper limit of dose escalation in a patient.

Figure 12D:
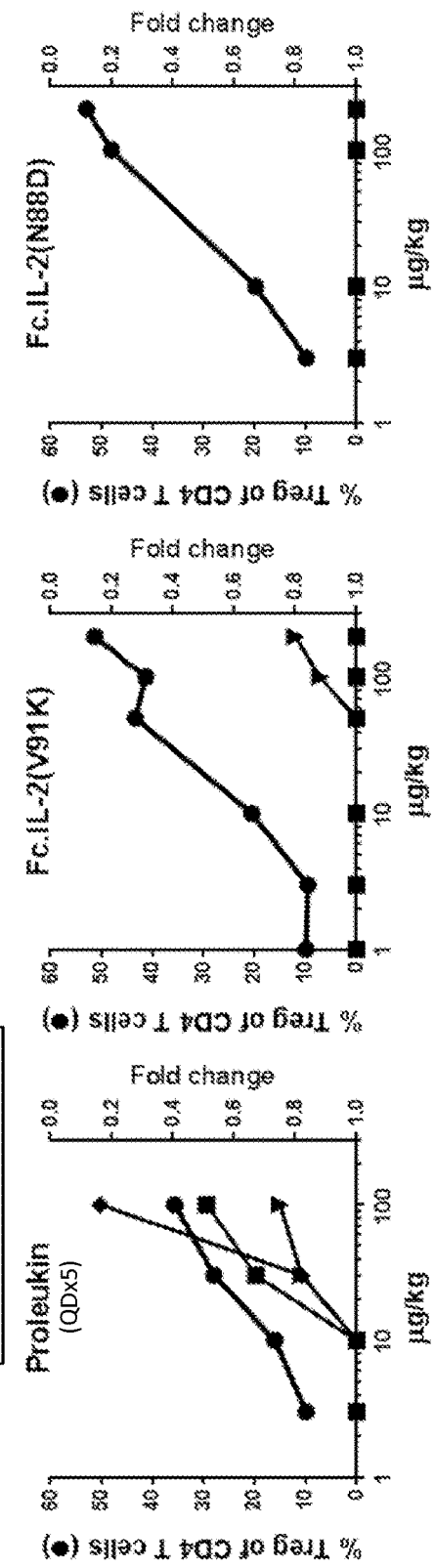
FIG. 12D Effect of increasing dosages of PROLEUKIN®, Fc.V91K, or Fc.N88D on levels of Treg cells, platelets, neutrophils, and albumin in cynomolgus monkeys. Each data point represents the average peak responses of four animals. The right y-axes are inverted to convey a fold-change decrease in platelets, neutrophils, or albumin relative to pre-dose samples.

Certain toxicities were also observed in the PROLEUKIN®-treated animals that were either less pronounced or not present in the Fc.V91K- or Fc.N88D-treated animals (FIG. 12D). Levels of platelets, neutrophils, and albumin were all found to be reduced by treatment with PROLEUKIN®, whereas doses of either Fc.V91K or Fc.N88D that resulted in similar or greater Treg enrichment produced little or no reductions in these parameters. Taken together, these data indicate that the therapeutic window for treatment of patients with either Fc.V91K- or Fc.N88D is expected to be significantly greater than with PROLEUKIN®.

Example-12

Figure 13:
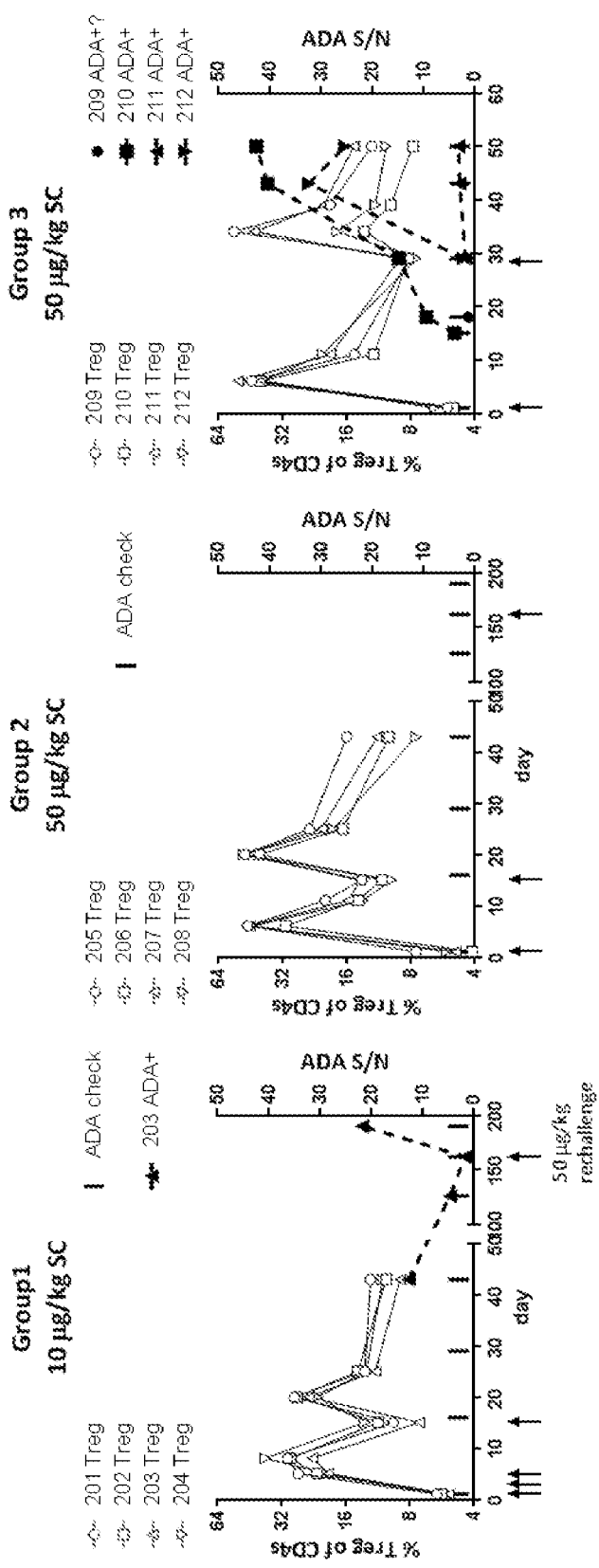
FIG. 13 Kinetics of the development of anti-drug antibodies (ADA) in cynomolgus monkeys treated with Fc.V91K.

At selected time points, sera from the first cynomolgus study of Example 11 were tested for anti-drug antibodies (ADA) (FIG. 13). ADA signal/noise data for samples where Fc.V91K specificity was confirmed by competition are shown. Time points where ADA were tested are shown with vertical lines above the x-axis. In Group 1, one animal generated ADA at least fifteen days after the last dose, in Group 2, no animals tested positive for ADA, and in Group 3, ADA consistently appeared in three animals fifteen or more days after the first dose. Upon repeat dosing of Groups 1 and 2 with 50 µg/kg on Day 162, no additional animals tested positive for ADA four weeks later (day 190). The two animals in Group 3 that generated the strongest ADA signals (210, 212) exhibited a reduced PD response, consistent with a reduced C-max observed after the second dose in these animals. No animals in a fourth group (50 µg/kg IV) tested positive for ADA. ADA were specific for both the IL-2 and Fc domains, which might be expected due to eight amino acid differences between cynomolgus IL-2 and human IL-2 (V91K,C125A). Neutralizing activity of the ADA was not tested.

Example 13

This example illustrates that the principles of the present invention can be used to design and identify IL-2 muteins that induce IL-2R signaling to a desired level.

To discover IL-2 mutations that partially attenuate IL-2Rβ binding and IL-2R signaling strength, a computational algorithm was applied to determine the degree to which IL-2 mutations decrease the energy of association between IL-2 and IL-2Rβ. The structure of the IL-2:IL-2Rα:IL-2Rβ:γc (PDB ID: 2B5I (Wang et al., 2005, Science 310(5751):1159-63)) was used as an input to computational algorithms to recommend sixty-four variants based on structure-guided computational energy calculations. In summary, the steps involve (i) preparing the structure of IL-2 in complex with its receptors for the energy calculations, (ii) identifying the interface residues at the IL-2:IL-2Rβ boundary for mutation to the other nineteen naturally-occurring amino acids, (iii) carrying out mutational energy calculations using two different computational algorithms, and (iv) selecting muteins using criteria that take advantage of the calculated energy values, conformation of amino acids, and previous experience and knowledge.

The IL-2:IL-2Rα:IL-2Rβ:γc structure was prepared via deletion of all water molecules, generation of coordinates of the missing atoms, and minimization of the energy of the complex structure in an implicit (GBIM) solvent model using CHARMm force field. The above steps were performed in the Discovery Studio software from ACCELRYS® (BIOVIA, San Diego, Calif.).

The following IL-2 residues at the IL-2: IL-2Rβ interface were identified from the complex structure and were chosen for in silico mutagenesis calculations: L12, Q13, E15, H16, L19, D20, M23, R81, D84, S87, N88, V91, I92, L94, and E95. The in silico mutagenesis was performed using the "Calculate Mutation Energy (Binding)" protocol of Discovery Studio software. This protocol computes the change in binding free energy, $\Delta\Delta G_{binding}$ (i.e. [binding free energy of mutant IL-2 to IL-2Rβ]–[binding free energy of wild-type IL-2 to IL-2Rβ]). The $\Delta\Delta G_{binding}$ values were calculated in an implicit solvent model (Generalized Born with Implicit Membrane). The numbering of residues within each mutein is relative to the sequence of wild-type human IL-2 (SEQ ID NO:1):

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
130
```

All of the selected IL-2 residues were mutated to the nineteen other amino acids leading to 299 single amino acid substitution variants. $\Delta\Delta G_{binding}$ for each of these variants was computed as described above. The calculated $\Delta\Delta G_{binding}$ are reported in FIG. 14. Variants were selected such that the selected mutation leads to a $\Delta\Delta G_{binding}$ value>1.5 kcal/mol and does not introduce a proline residue. To increase diversity, for positions where no mutation led to $\Delta\Delta G_{binding}$>1.5 kcal/mol (e.g., L12), mutations were selected with $\Delta\Delta G_{binding}$>1.0 kcal/mol.

The IL-2:IL-2Rα:IL-2Rβ:γc structure was prepared via deletion of all water molecules from the structure, generating coordinates of the missing atoms and minimization of the structure using OPLS 2005 force field (Banks et al., 2005, J Comp Chem 26:1752). The above steps were performed in BIOLUMINATE® software (Schrödinger, New York, N.Y.).

The following IL-2 residues in the IL-2: IL-2Rβ interface were identified from the complex structure and were chosen for in silico mutagenesis calculations: L12, Q13, E15, H16, L19, D20, M23, R81, D84, S87, N88, V91, I92, L94, E95. The in silico mutagenesis was performed using the "Residue Scanning" feature of BIOLUMINATE®. The calculated $\Delta\Delta G_{binding}$ are reported in FIG. 15.

Using the predicted $\Delta\Delta G_{binding}$, variants were selected according to the following criteria: the selected mutation does not introduce a proline reside; the selected mutation was not already recommended by the Discovery Studio software; the selected mutation leads to a $\Delta\Delta G_{binding}$ value>10 kcal/mol; the selected mutation does not introduce a histidine residue (the $\Delta\Delta G_{binding}$ values computed for mutation to histidine residues by BIOLUMINATE® were found to be unreliable).

Mutations D20E, V91D, and I92W were new variants suggested by BIOLUMINATE® and were added to the list of fifty-seven variants recommended by Discovery Studio software. Variants L12K, L12Q L19R and L19N were also included in the final analysis, resulting in the following list: D20A, D20E, D20F, D20G, D20W, D84A, D84E, D84G, D84I, D84M, D84Q, D84R, D84S, D84T, E15A, E15G, E15S, E95G, H16A, H16D, H16G, H16K, H16M, H16N, H16R, H16S, H16T, H16V, H16Y, I92K, I92R, L12G, L12K, L12Q, L12S, L19A, L19D, L19E, L19G, L19N, L19R, L19S, L19T, L19V, M23R, N88A, N88D, N88E, N88F, N88G, N88M, N88R, N88S, N88V, N88W, Q13G, R81A, R81G, R81S, R81T, S87R, V91D, V91E, V91G, V91K, and V91S. All IL-2 muteins also contained the C125A mutation for improved manufacturability.

A panel of sixty-six IL-2 muteins fused to the C-terminus of IgG1 Fc (N297G), separated by a G4S linker, was tested for IL-2R stimulation on pre-activated and rested human T cells (FIG. 16). As shown in FIG. 16A, 33 pM was a suboptimal concentration for all muteins, thus the activity of the muteins was ranked based on the pSTAT5 MFI at this concentration. This ranking is shown in FIG. 16B for two PBMC donors. Because Treg respond preferentially to such attenuated IL-2 muteins, as shown above, this panel can be used to define the upper and lower limits of IL-2R signaling that result in optimal Treg selectivity.

Example 14

From the initial pSTAT5 signaling data obtained with the supernatant fractions, a smaller panel of constructs was selected for expression, purification, and further evaluation. Each of these molecules comprised Fc.IL-2-G4S linker-IL-2 mutein, wherein each mutein comprised C125A and one of the following mutations: D20E, D20G, D20W, D84A, D84S, H16D, H16G, H16K, H16R, H16T, H16V, I92K, I92R, L12K, L19D, L19N, L19T, N88D, N88R, N88S, V91D, V91G, V91K, V91S, or no additional mutation ("WT"). These purified molecules were tested for their ability to activate STAT5 phosphorylation in pre-stimulated and rested human T cells (FIG. 17). The Fc.IL-2 muteins were also tested for their ability to stimulate proliferation of T cell subsets and to increase FOXP3 expression (FIG. 18) and for their ability to stimulate NK cell proliferation (FIG. 19).

Fc.IL-2 muteins were tested for their ability to bind CD25 (IL-2Rα) on the surface of T cells and to remain bound to cell surface CD25 at various time points (FIG. 20). The degree to which Fc.IL-2 muteins stimulated STAT5 phosphorylation in T cells (FIG. 17) bore a high negative correlation with cell surface retention (r=−0.87), indicating that the rate of internalization by signaling through IL-2Rβγ was closely linked to receptor agonism potency.

In a parallel experiment, the persistence of pSTAT5 signaling was observed by intracellular immunodetection of phospho-STAT5 at different time points. Phospho-STAT5 MFI for FOXP3+CD25+CD4+ T cells is shown in FIG. 21. These results demonstrated that certain muteins with intermediate signaling strength were more effective than Fc.WT IL-2 at maintaining pSTAT5 signaling at later timepoints (e.g., H16T, H16K, H16R, L19N, L19D, D20T, N88D, N88R, N88S, V91D, V91G, V91K, V91S). With the exception of the antagonist mutein (D20W), IL-2R signaling retention tended to correlate with cell surface retention; however, certain weak muteins that exhibited high surface retention were not the most effective at maintaining IL-2R signaling (e.g., D20G and D20T) (FIG. 22).

To determine how different Fc.IL-2 muteins increased Treg frequency in vivo, humanized mice (NSG mice reconstituted four months prior with CD34+ hematopoietic stem cells) were dosed with the indicated muteins, and Treg enrichment was measured in blood on day four (FIG. 23A). The degree of Treg enrichment was found to correlate most closely with the capacity to deliver an extended pSTAT5 signal (FIG. 23B), and substitutions at position V91 were particularly effective at Treg enrichment in vivo and increasing IL-2R signaling retention in vitro.

Example 15

A series of human anti-human IL-2 antibodies was generated in XENOMOUSE® (Amgen Inc., Thousand Oaks, Calif.) mice and selected on the basis of their ability to bind both human and cynomolgus monkey IL-2 in an ELISA assay. Their light and heavy chain variable domain amino acid and nucleic acid sequences are shown in FIGS. 26-29.

These antibodies were screened for their ability to inhibit IL-2 responses by DERL-2 cells (IL-2 receptor α/β/γ positive) and by NKL cells (IL-2 receptor α/β/γ positive). Antibodies that exhibited high inhibitory activity against DERL2 cells and moderate to low activity on NKL cells were selected for further analysis. Clones were sequenced to eliminate sister clones and those mAb that would be more difficult to manufacture satisfactorily. Binding cross-inhibition studies were conducted and antibodies were found to fall into eight bins. The tested XENOMOUSE® antibodies all fell into Bins A, B, C, D, E, and E.1. Antibodies in Bins B, C, E and E.1 were found to interfere with human IL-2 binding to human IL2Rα, while antibodies in Bins A and D did not. Bin F was defined by a control antibody whose binding to human IL-2 does not prevent the cytokine from binding to the IL-2 receptor α and Bin G was defined by control antibody 5344.111 (Cat. No. 555051, BD Biosciences, San Jose, Calif.). None of the tested XENOMOUSE® antibodies fell into Bin F or G.

The kinetic parameters $K_D$, $k_{on}$ and $k_{dis}$ were also defined for each of the antibodies using BIACORE® (GE Healthcare Bio-Sciences, Pittsburgh, Pa.) analysis. A subset of thirty-six antibodies was selected to represent a diversity of clones, including representatives of all of the Bins and a range of $K_D$ and $k_{dis}$ values. All of these clones were found to inhibit IL-2 signaling in human whole blood lymphocytes, generally with higher $IC_{50}$ values in regulatory T cells (Treg) than in non-Treg CD4 T cells (nTr), CD8 T cells (CD8) or natural killer (NK) cells (where a higher $IC_{50}$ indicates less effective inhibition).

All thirty-six antibodies were then tested as part of an anti-IL-2 antibody/hIL-2 immune complex (at a 1:2 molar ratio of antibody:hIL-2) in NSG SCID/Hu mice reconstituted with human stem cells for their ability to expand Treg vs nTr, NK and CD8 cells as compared to low dose wild type IL-2.Fc, a model IL-2 mutein N88D.Fc, 5344.111 mouse anti-human IL-2/hIL-2 complexes and PBS-treated control mice. Treg/NK and Tr/nTr ratios were used to assess the relative ability of the XENOMOUSE® antibodies to selectively expand Treg vs effector cells (ratios were normalized to the values observed for PBS-treated mice to allow comparability between and among the several runs needed to analyze all the antibodies). Twelve of the antibodies performed as well as or better than the 5344.111/IL-2 controls. Their properties are listed in Table 5 and shown in FIG. 30.

TABLE 5

| Antibody | Bin | Hu WB pSTAT5 $IC_{50}$ vs | | | |
|---|---|---|---|---|---|
| | | Treg | nonTreg CD4 | CD8 | NK |
| 9B10 | A | 200 | 38 | 23 | 79 |
| 14G7 | B | 61 | 64 | 44 | 54 |
| 26C12 | B | 302 | 224 | 283 | 370 |
| 26H7 | B | 25 | 22 | 16 | 259 |
| 2H11 | B | 106 | 42 | 49 | 18 |
| 9D6 | B | 29 | 21 | 16 | 23 |
| 18F3 | C | 42 | 25 | 21 | 181 |
| 2C3 | D | 184 | 132 | 79 | 152 |
| 8F10 | D | 158 | 30 | 20 | 24 |
| 14D7 | E | 668 | 244 | 144 | 293 |
| 21F8 | E | 61 | 64 | 44 | 54 |
| 22B9 | E.1 | 813 | 137 | 276 | — |

TABLE 6

Kinetic Properties of Anti-IL-2 Antibodies

| Antibody ID | Isotype | VH Germline | HC CDR3 | VL Germline | Epitope Bin | ~KD human | ~KD cyno |
|---|---|---|---|---|---|---|---|
| 14D7 | G2 | VH4\|4-31/D7\|7-27\|RF3/JH3 | DGWR------------------DAFDI | VK1\|O12/JK1 | E | 300 pM | 140 pM |
| 14G7 | G4 | VH5\|5-51/D4\|4-23\|RF2/JH6 | HRGGRS----------------YYYGMDV | VK1\|O18/JK3 | B | 280 pM | 130 pM |
| 18F3 | G4 | VH4\|4-31/D3\|3-3\|RF1/JH4 | EGRFGE---------------LGSYYFDY | VL3\|3p/JL2 | C | 50 pM* | 50 pM* |
| 21F8 | G2 | VH1\|1-08/D2\|2-21\|RF1/JH4 | SRQW------------------LVLDY | VK1\|A30/JK1 | E | 690 pM | 500 pM |
| 22B9 | G2 | VH1\|1-08/D2\|2-21\|RF1/JH4 | SRQW------------------LVLDY | VK1\|A30/JK1 | E.1 | 450 pM | 170 pM |
| 26C12 | G4 | VH5\|5-51/D3\|3-10\|RF2/JH6 | HGHGSSSG------------RTYYYGLDV | VK1\|O18/JK3 | B | 270 pM | 130 pM |
| 26H7 | G4 | VH5\|5-51/D5\|5-24\|RF3/JH6 | HGGYSGR--------------SYYYGMDV | VK1\|O18/JK3 | B | 1.3 pM | 310 pM |
| 2C3 | G2 | VH5\|5-51/D4\|4-11\|RF3/JH4 | QQVA------------------GMLDY | VK3\|A27/JK4 | D | 150 pM | 1.2 pM |
| 2H11 | G2/G4 | VH5\|5-51/D4\|4-17\|RF2/JH4 | DTG-------------------YFDY | VL3\|3p/JL2 | B | 30 pM | 8.0 pM |
| 8F10 | G2 | VH3\|3-33/D1\|1-26\|RF1/JH6 | GAVAGTGR------------ | VK2\|A19/JK4 | D | 1 pM* | 460 pM* |
| 9B10 | G2 | VH3\|3-30.3/D5\|5-18\|RF3/JH4 | GSYYDSSG------------YYFGEDFDY | VK2\|A23/JK4 | A | 110 pM | 160 pM |
| 9D6 | G2 | NH5\|5-51/D3\|3-9\|RF1/JH6 | QGRSF----------------YYYGMDV | VK2\|O11/JK4; | B | 41 pM | 16 pM |

What is claimed is:

1. A human interleukin-2 (IL-2) mutein comprising an amino acid sequence that is at least 95% identical to the amino acid sequence set forth in SEQ ID NO:1, wherein the IL-2 mutein has at least one mutation selected from H16A, H16G, H16K, H16M, H16R, H16S, H16T, H16V, and H16Y, and preferentially stimulates T regulatory cells relative to other T cells or NK cells.

2. The human IL-2 mutein of claim 1 further comprising a mutation at C125A.

3. An Fc-fusion protein comprising an Fc region and the human IL-2 mutein of claim 1.

4. The Fc-fusion protein of claim 3, wherein the Fc region is an IgG1 Fc comprising an N297G substitution.

5. The Fc-fusion protein of claim 4, further comprising a substitution or deletion of the C-terminal lysine of the human IgG1 Fc.

6. The Fc-fusion protein of claim 3, wherein a linker connects the Fc region and the human IL-2 mutein of the Fc-fusion protein, wherein the linker is GGGGS (SEQ ID NO: 5), GGNGT (SEQ ID NO: 6), or YGNGT (SEQ ID NO: 7).

7. The Fc-fusion protein of claim 3, wherein the human IL-2 mutein further comprises an amino acid addition, substitution, or deletion altering glycosylation of the Fc-fusion protein when expressed in mammalian cells, wherein the IL-2 mutein comprises a T3 substitution or an S5 substitution.

8. The Fc-fusion protein of claim 3, wherein the Fc-fusion protein comprises an Fc dimer.

9. The Fc-fusion protein of claim 8, wherein the Fc-fusion protein comprises two IL-2 muteins.

10. The Fc-fusion protein of claim 8, wherein the Fc-fusion protein comprises a single IL-2 mutein.

* * * * *